United States Patent
Jayasinghe et al.

(10) Patent No.: US 11,840,556 B2
(45) Date of Patent: Dec. 12, 2023

(54) MODIFIED NANOPORES, COMPOSITIONS COMPRISING THE SAME, AND USES THEREOF

(71) Applicant: Oxford Nanopore Technologies PLC, Oxford (GB)

(72) Inventors: Lakmal Jayasinghe, Oxford (GB); Elizabeth Jayne Wallace, Oxford (GB); Pratik Raj Singh, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 291 days.

(21) Appl. No.: 16/484,798

(22) PCT Filed: Feb. 12, 2018

(86) PCT No.: PCT/GB2018/050379
§ 371 (c)(1),
(2) Date: Aug. 8, 2019

(87) PCT Pub. No.: WO2018/146491
PCT Pub. Date: Aug. 16, 2018

(65) Prior Publication Data
US 2020/0010511 A1 Jan. 9, 2020

Related U.S. Application Data

(60) Provisional application No. 62/457,483, filed on Feb. 10, 2017.

(51) Int. Cl.
| | | |
|---|---|---|
| *A61K 39/02* | (2006.01) | |
| *C07K 14/195* | (2006.01) | |
| *C12Q 1/6869* | (2018.01) | |
| *B82Y 30/00* | (2011.01) | |

(52) U.S. Cl.
CPC .......... *C07K 14/195* (2013.01); *C12Q 1/6869* (2013.01); *B82Y 30/00* (2013.01)

(58) Field of Classification Search
None
See application file for complete search history.

(56) References Cited

U.S. PATENT DOCUMENTS

2013/0121915 A1* 5/2013 Paas ............. C07K 14/245
424/9.1

FOREIGN PATENT DOCUMENTS

| | | |
|---|---|---|
| EP | 2682460 A1 | 1/2014 |
| WO | WO 2000/028312 A1 | 5/2000 |
| WO | WO 2005/124888 A1 | 12/2005 |
| WO | WO 2006/100484 A2 | 9/2006 |
| WO | WO 2008/102120 A1 | 8/2008 |
| WO | WO 2008/102121 A1 | 8/2008 |
| WO | WO 2009/077734 A2 | 6/2009 |
| WO | WO 2010/004265 A1 | 1/2010 |
| WO | WO 2010/004273 A1 | 1/2010 |
| WO | WO 2010/086603 A1 | 8/2010 |
| WO | WO 2010/122293 A1 | 10/2010 |
| WO | WO 2011/061559 A1 | 5/2011 |
| WO | WO 2011/067559 A1 | 6/2011 |
| WO | WO 2011/125015 A2 | 10/2011 |
| WO | WO 2012/107778 A2 | 8/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/153359 A1 | 10/2013 |
| WO | WO 2014/064443 A2 | 5/2014 |
| WO | WO 2014/153625 A1 | 10/2014 |
| WO | WO 2015/055981 A2 | 4/2015 |
| WO | WO 2015/110777 A1 | 7/2015 |
| WO | WO 2015/124935 A1 | 8/2015 |
| WO | WO 2015/140535 A1 | 9/2015 |
| WO | WO 2015/166275 A1 | 11/2015 |
| WO | WO 2016/034591 A2 | 3/2016 |
| WO | WO 2016/055778 A1 | 4/2016 |
| WO | WO 2016/059427 A1 | 4/2016 |
| WO | WO 2016/166232 A1 | 10/2016 |
| WO | WO 2017/064444 A1 | 4/2017 |

OTHER PUBLICATIONS

Korotkov K V et al: "Crystal Structure of the N-Terminal Domain of the Secretin GspD from ETEC Determined with the Assistance of a Nanobody", Structure, Elsevier, Amsterdam, NL, vol. 17, No. 2, Feb. 13, 2009 , pp. 255-265. (Year: 2009).*
Korotkov et al. PLoS Patogens, vol. 7, No. 9, pp. 1-15 , 2011 (Year: 2011).*
International Search Report and Written Opinion for Application No. PCT/GB2018/050379, dated Apr. 9, 2018.
[No Author Listed] Database USPTO Proteins [Online], Sequence 1221 from U.S. Pat. No. 9,073,990. XP002779162, retrieved from EBI accession No. USPOP: AMF41126 Database accession No. AMF41126. Feb. 10, 2016. 1 page.
[No Author Listed] Peptide Cutter. The cleavage specificities of selected enzymes and chemicals. ExPASy Bioinformatics Resource Portal. Retrieved Nov. 8, 2019 from https://web.expasy.org/peptide_cutter/peptidecutter_enzymes.html. 8 pages.
Altschul et al., Basic local alignment search tool. J Mol Biol. Oct. 5, 1990;215(3):403-10.

(Continued)

*Primary Examiner* — Jana A Hines
*Assistant Examiner* — Khatol S Shahnan Shah
(74) *Attorney, Agent, or Firm* — Wolf, Greenfield & Sacks, P.C.

(57) ABSTRACT

Provided herein relate to modified or mutant forms of secretin and compositions comprising the same. In particular, the modified or mutant forms of secretin permits efficient capture and/or translocation of an analyte through the modified or mutant secretin nanopores. Methods for using unmodified secretin or the modified or mutant forms of secretin and compositions, for example, for characterizing an analyte, e.g., a target polynucleotide, are also provided.

17 Claims, 28 Drawing Sheets

Specification includes a Sequence Listing.

(56) References Cited

OTHER PUBLICATIONS

Altschul, A protein alignment scoring system sensitive at all evolutionary distances. J Mol Evol. Mar. 1993;36(3):290-300.
Braha et al., Designed protein pores as components for biosensors. Chem Biol. Jul. 1997;4(7):497-505.
Devereux et al., A comprehensive set of sequence analysis programs for the VAX. Nucleic Acids Res. Jan. 11, 1984;12(1 Pt 1):387-95.
GENBANK Submission: NIH/NCBI, Accession No. ANI31722. Hurst et al., Jun. 3, 2016. 1 page.
GENBANK Submission: NIH/NCBI, Accession No. KJO55878. Chavda, et al., Mar. 19, 2015. 2 pages.
GENBANK Submission: NIH/NCBI, Accession No. WP_000694679. Oct. 4, 2019. 1 page.
GENBANK Submission: NIH/NCBI, Accession No. WP_006122201. Oct. 4, 2019. 1 page.
GENBANK Submission: NIH/NCBI, Accession No. WP_016498773. Oct. 4, 2019. 1 page.
GENBANK Submission: NIH/NCBI, Accession No. WP_021564153. Oct. 4, 2019. 1 page.
GENBANK Submission: NIH/NCBI, Accession No. WP_024250244. Oct. 4, 2019. 1 page.
GENBANK Submission: NIH/NCBI, Accession No. WP_034249407. Oct. 4, 2019. 1 page.
GENBANK Submission: NIH/NCBI, Accession No. WP_036979259. Oct. 4, 2019. 1 page.
GENBANK Submission: NIH/NCBI, Accession No. WP_038392434. Lodge et al., Jul. 10, 2019. 2 pages.
GENBANK Submission: NIH/NCBI, Accession No. WP_043640872. Aug. 5, 2017. 1 page.
GENBANK Submission: NIH/NCBI, Accession No. WP_051238518. Oct. 4, 2019. 1 page.
GENBANK Submission: NIH/NCBI, Accession No. WP_052429256. Oct. 4, 2019. 1 page.
GENBANK Submission: NIH/NCBI, Accession No. WP_053215251. Oct. 4, 2019. 1 page.
GENBANK Submission: NIH/NCBI, Accession No. WP_059765897. Oct. 4, 2019. 1 page.
GENBANK Submission: NIH/NCBI, Accession No. WP_061203566. Oct. 4, 2019. 1 page.
GENBANK Submission: NIH/NCBI, Accession No. WP_070981539. Oct. 4, 2019. 1 page.
GENBANK Submission: NIH/NCBI, Accession No. WP_071651540. Lodge et al., Jul. 10, 2019. 1 page.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Heron et al., Simultaneous measurement of ionic current and fluorescence from single protein pores. J Am Chem Soc. Feb. 11, 2009;131(5):1652-3. doi: 10.1021/ja808128s.
Holden et al., Direct introduction of single protein channels and pores into lipid bilayers. J Am Chem Soc. May 11, 2005;127(18):6502-3.
Holden et al., Direct introduction of single channels and protein pores into lipid bilayers. Supporting Material. J Am Chem Soc. May 11, 2005;127(18):S1-2.
Holden et al., Functional bionetworks from nanoliter water droplets. J Am Chem Soc. Jul. 11, 2007;129(27):8650-5. Epub Jun. 16, 2007.
Holden et al., Functional bionetworks from nanoliter water droplets. Supplementary Info. J Am Chem Soc. Jul. 11, 2007;129(27):S1-S6. Epub Jun. 16, 2007.
Holden et al., Functional bionetworks from nanoliter water droplets. Supplementary Info. J Am Chem Soc. Jul. 11, 2007;129(27):S1-S3. Epub Jun. 16, 2007.
Humphrey et al., VMD: visual molecular dynamics. J Mol Graph. Feb. 1996;14(1):33-8.
Ivanov et al., DNA tunneling detector embedded in a nanopore. Nano Lett. Jan. 12, 2011;11(1):279-85. doi: 10.1021/nl103873a. Epub Dec. 6, 2010.
Johnson et al., Type II secretion: from structure to function. FEMS Microbiol Lett. Feb. 2006;255(2): 175-86.
Korotkov et al., Crystal structure of the N-terminal domain of the secretin GspD from ETEC determined with the assistance of a nanobody. Structure. Feb. 13, 2009; 17(2): 255-265. doi: 10.1016/j.str.2008.11.011.
Korotkov et al., Structural and functional studies on the interaction of GspC and GspD in the type II secretion system. PLoS Pathog. Sep. 2011;7(9):e1002228. doi: 10.1371/journal.ppat.1002228. Epub Sep. 8, 2011. 14 pages.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.
Miles et al., Properties of Bacillus cereus hemolysin II: A heptameric transmembrane pore. Protein Sci. Jul. 2002; 11(7): 1813-1824. doi: 10.1110/ps.0204002.
Philips et al., Scalable molecular dynamics with NAMD. J Comput Chem. Dec. 2005;26(16):1781-802.
RCSB Protein Data Bank No. 5WQ7. Yan et al., Nov. 23, 2016. 97 pages.
RCSB Protein Data Bank No. 5WQ8. Yan et al., Nov. 23, 2016. 99 pages.
Soni et al., Synchronous optical and electrical detection of biomolecules traversing through solid-state nanopores. Rev Sci Instrum. Jan. 2010;81(1):014301. doi: 10.1063/1.3277116. 7 pages.
Stoddart et al., Single-nucleotide discrimination in immobilized DNA oligonucleotides with a biological nanopore. PNAS. May 12, 2009;106(19):7702-7. doi: 10.1073/pnas.0901054106.
Stoddart et al., Single-nucleotide discrimination in immobilized DNA oligonucleotides with abiological nanopore. Supporting Information. PNAS. May 12, 2009;106(19):1-9. doi: 10.1073/pnas.0901054106.
UniProtKB Accession No. A0A1C6ZHG5. Capua et al., Nov. 2, 2016. 1 page.
UniProtKB Accession No. A0A1E4UJH6. Capua et al., Jan. 18, 2017. 2 pages.
UniProtKB Accession No. X5F782. Zhang et al., Jun. 11, 2014. 2 pages.
UniProtKB/Swiss-Prot Accession No. A0A181X688. Sep. 7, 2016. 5 pages.
UniProtKB/Swiss-Prot Accession No. A7ZRJ5. Oct. 23, 2007. 6 pages.
UniProtKB/Swiss-Prot Accession No. B7UMB3. Feb. 10, 2009. 5 pages.
UniProtKB/Swiss-Prot Accession No. D0ZWR9. Jarvik et al., Oct. 16, 2019. 2 pages.
UniProtKB/Swiss-Prot Accession No. P15644. d'Enfert et al., Sep. 18, 2019. 2 pages.
UniProtKB/Swiss-Prot Accession No. P31780. Howard. Sep. 18, 2019. 3 pages.
UniProtKB/Swiss-Prot Accession No. P35818. Akrim et al., Sep. 18, 2019. 5 pages.
UniProtKB/Swiss-Prot Accession No. P45758. Blattner et al., Oct. 16, 2019. 6 pages.
UniProtKB/Swiss-Prot Accession No. Q04641. Buchrieser et al., Oct. 16, 2019. 3 pages.
UniProtKB/Swiss-Prot Accession No. Q7BRZ9. Iriarte et al., Oct. 31, 2006. 1 page.
Worrall et al., Near-atomic-resolution cryo-EM analysis of the *Salmonella* T3S injectisome basal body. Nature. Dec. 22, 2016;540(7634):597-601. doi: 10.1038/nature20576. Epub Dec. 14, 2016.
Yan et al., Structural insights into the secretin translocation channel in the type II secretion system. Nat Struct Mol Biol. Feb. 2017;24(2):177-183. doi: 10.1038/nsmb.3350. Epub Jan. 9, 2017.
PCT/GB2018/050379, Apr. 9, 2018, International Search Report and Written Opinion.
Christensen C. Isolation and Use of the Aeromonas hydrophila Secretin ExeD for Nanopore Analysis (Doctoral dissertation, Department of Biochemistry, University of Saskatchewan). 2016, 118 pages. Accessible at https://harvest.usask.ca/bitstream/handle/10388/7517/CHRISTENSEN-THESIS-2016.pdf.

(56) References Cited

OTHER PUBLICATIONS

Nouwen et al., Secretin PulD: association with pilot PulS, structure, and ion-conducting channel formation. Proc Natl Acad Sci USA. Jul. 6, 1999;96(14):8173-7. doi: 10.1073/pnas.96.14.8173.

* cited by examiner

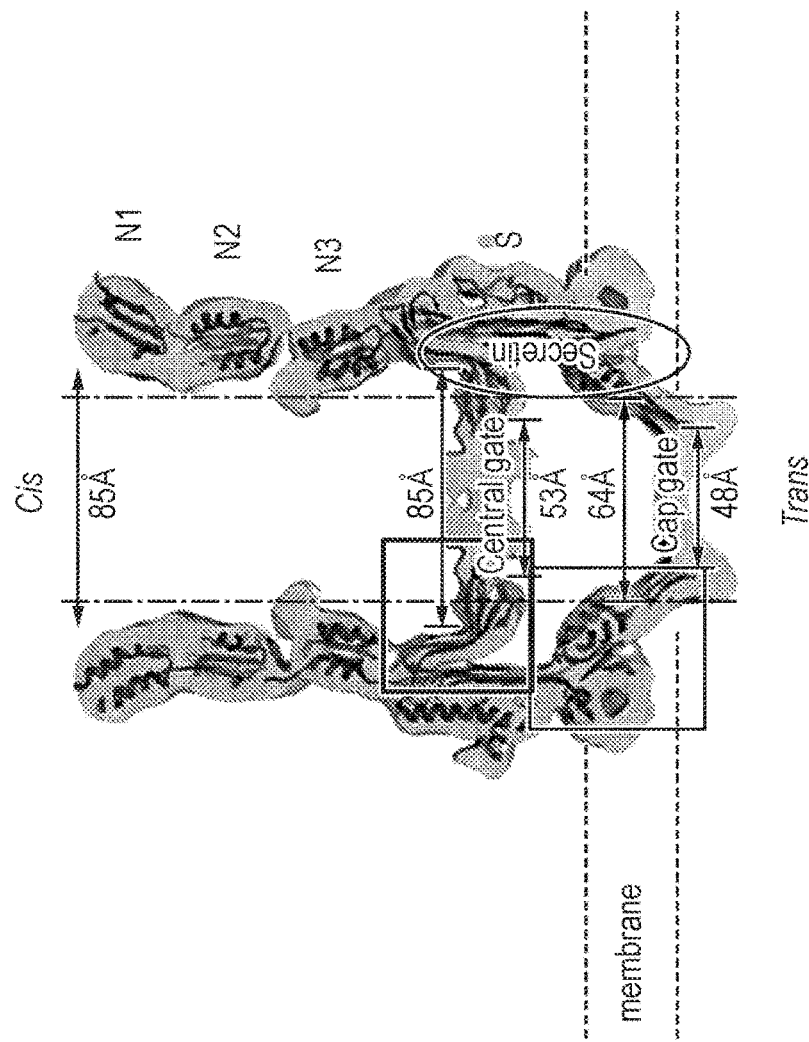
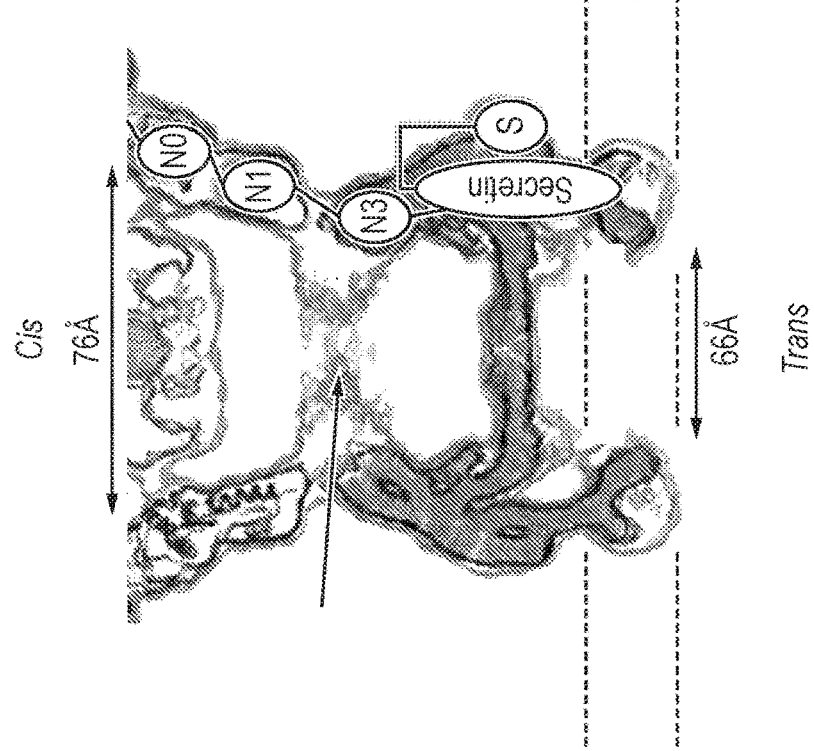
Fig. 1C

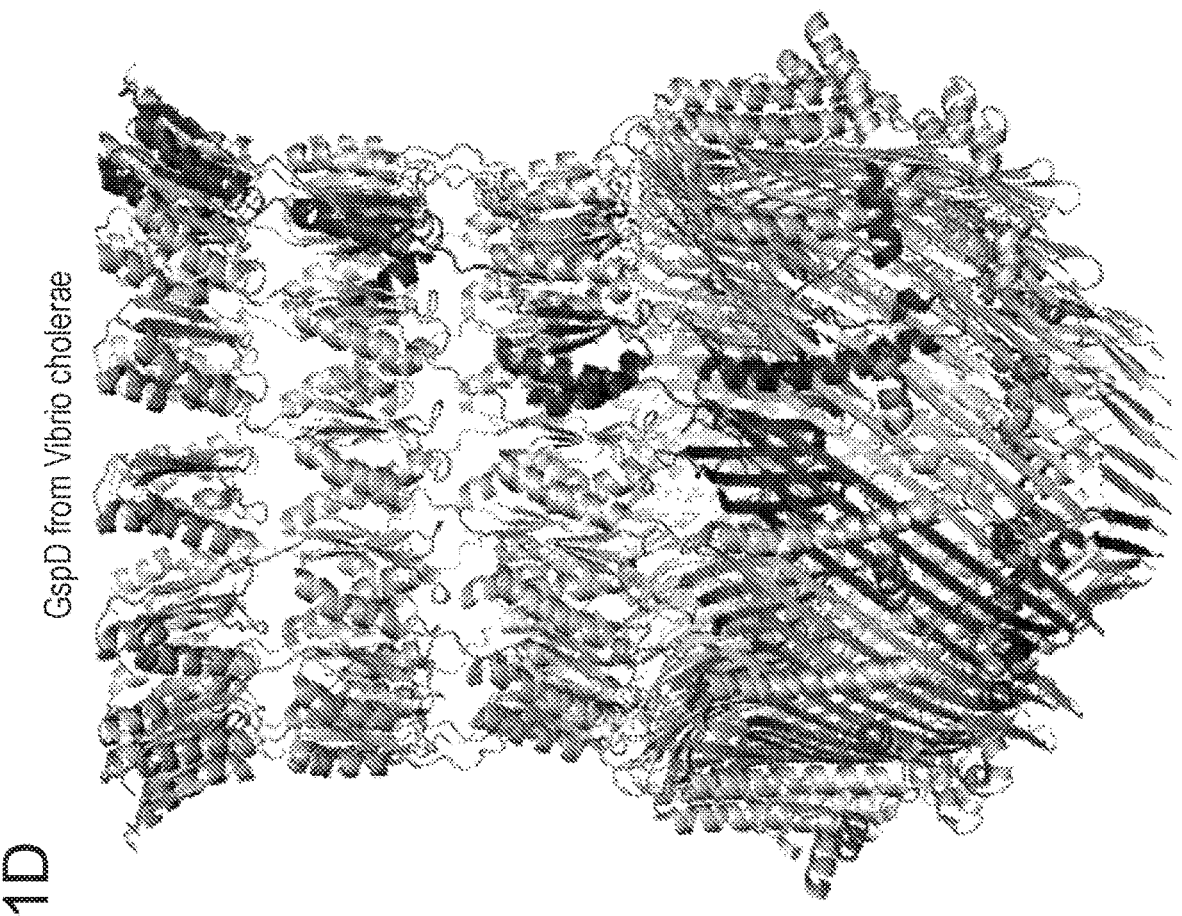
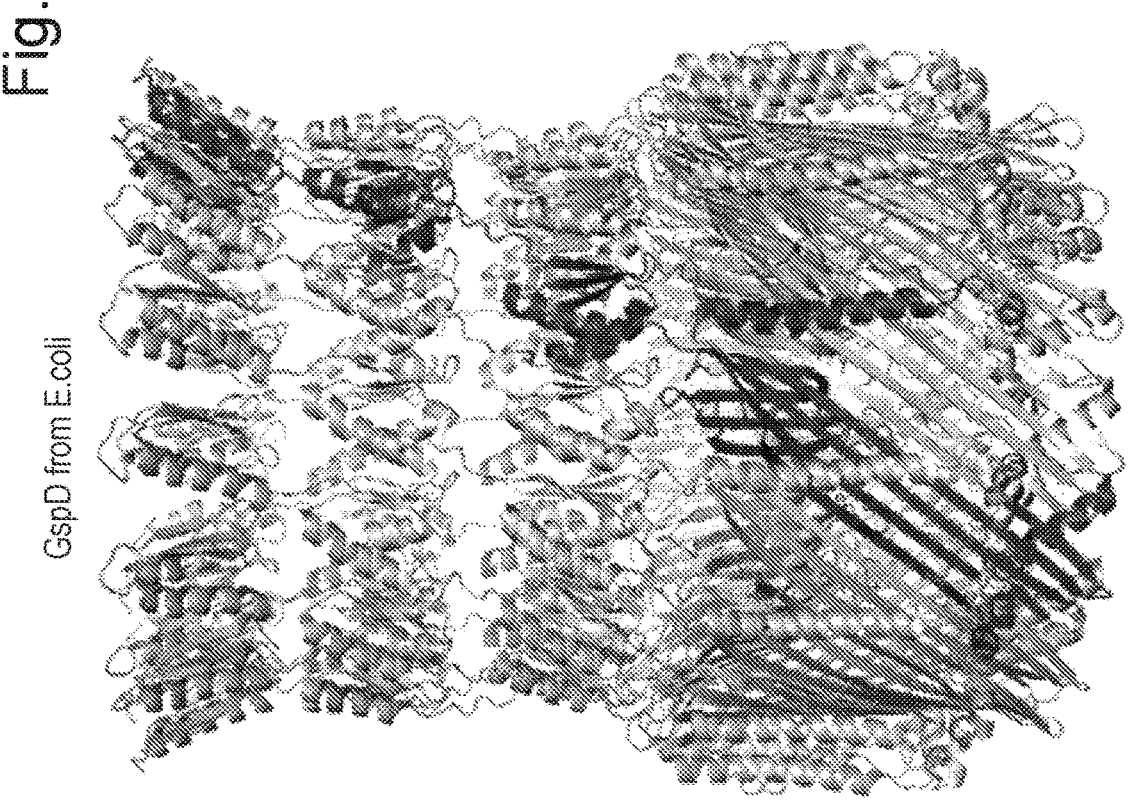
Fig. 1D

Fig. 2
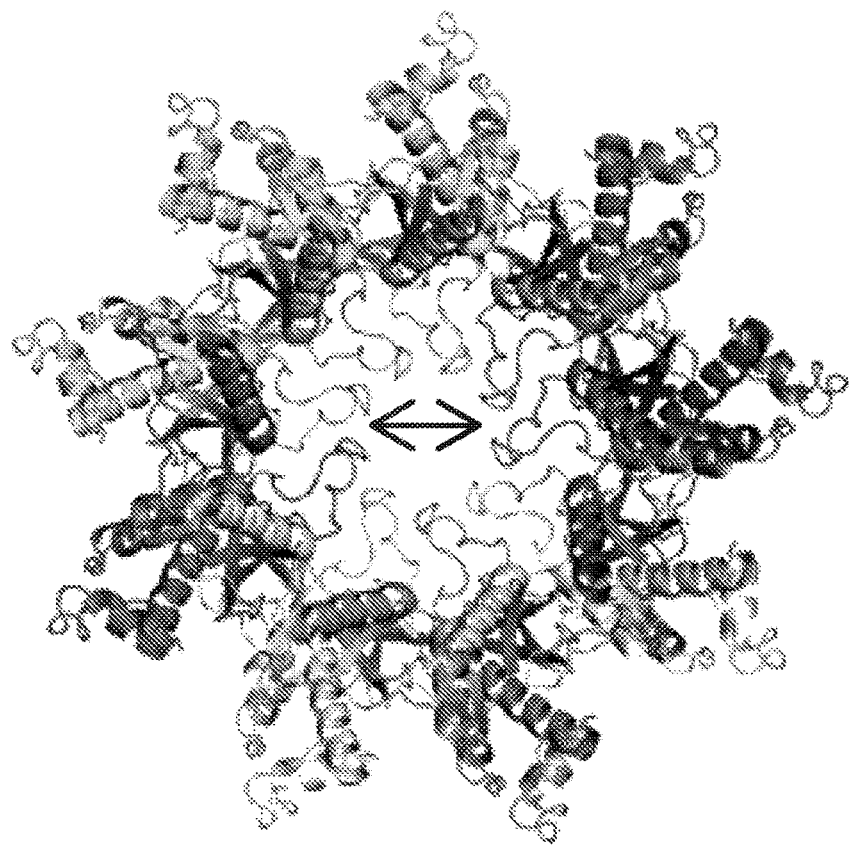
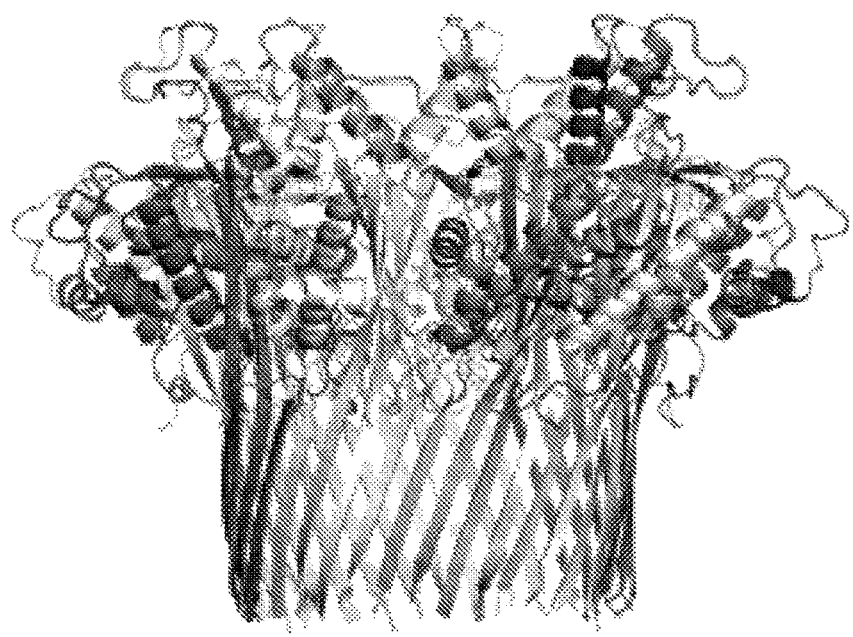
CsgG

Fig. 2 (Cont.)
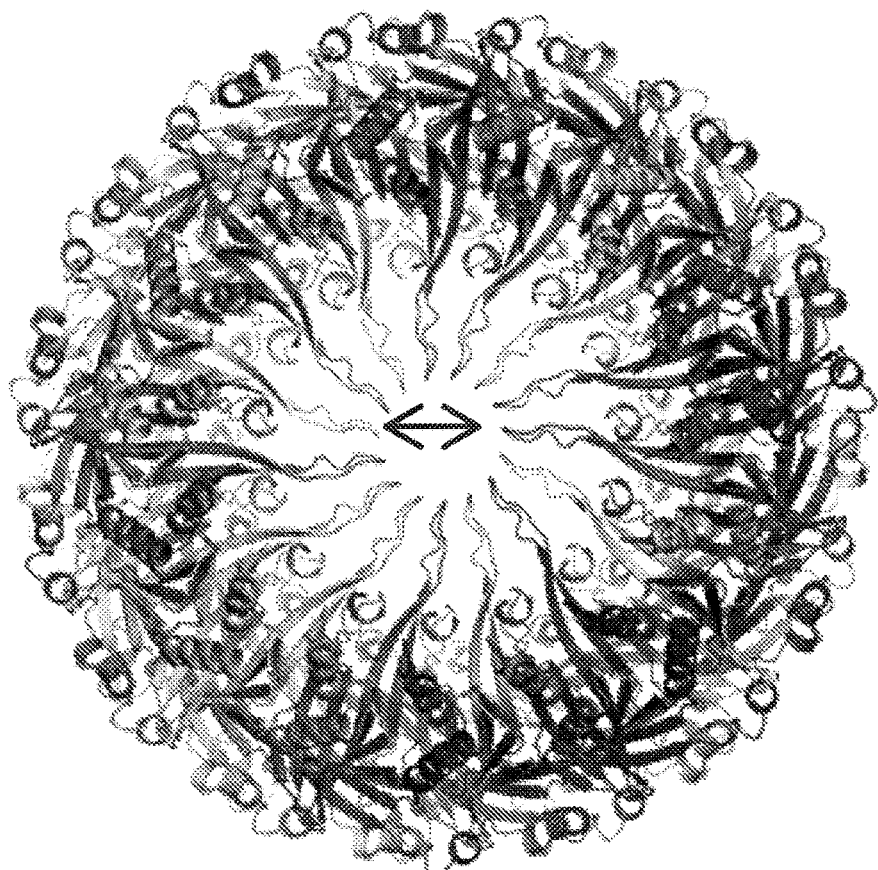
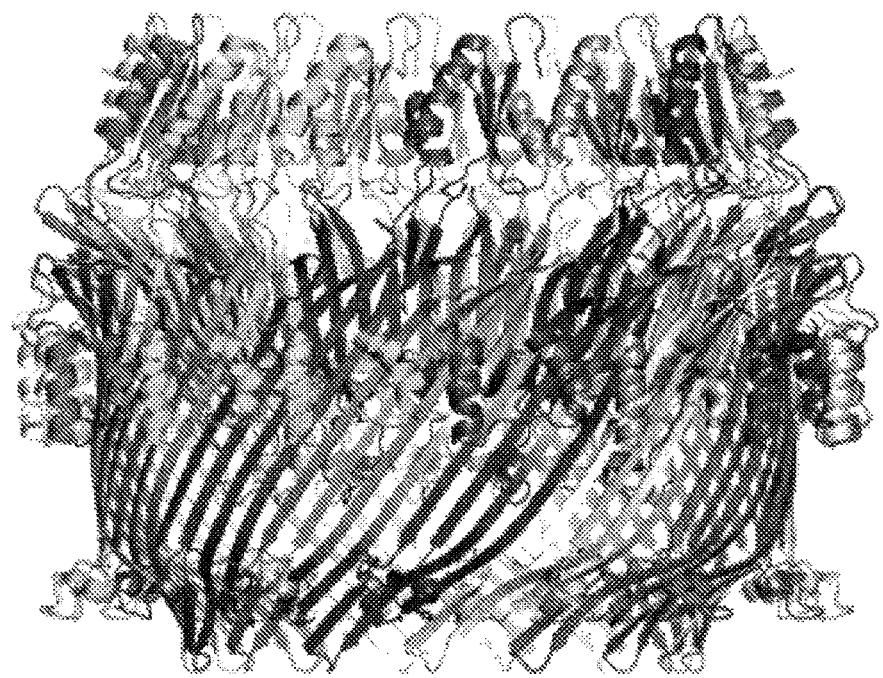
InvG

Fig. 3
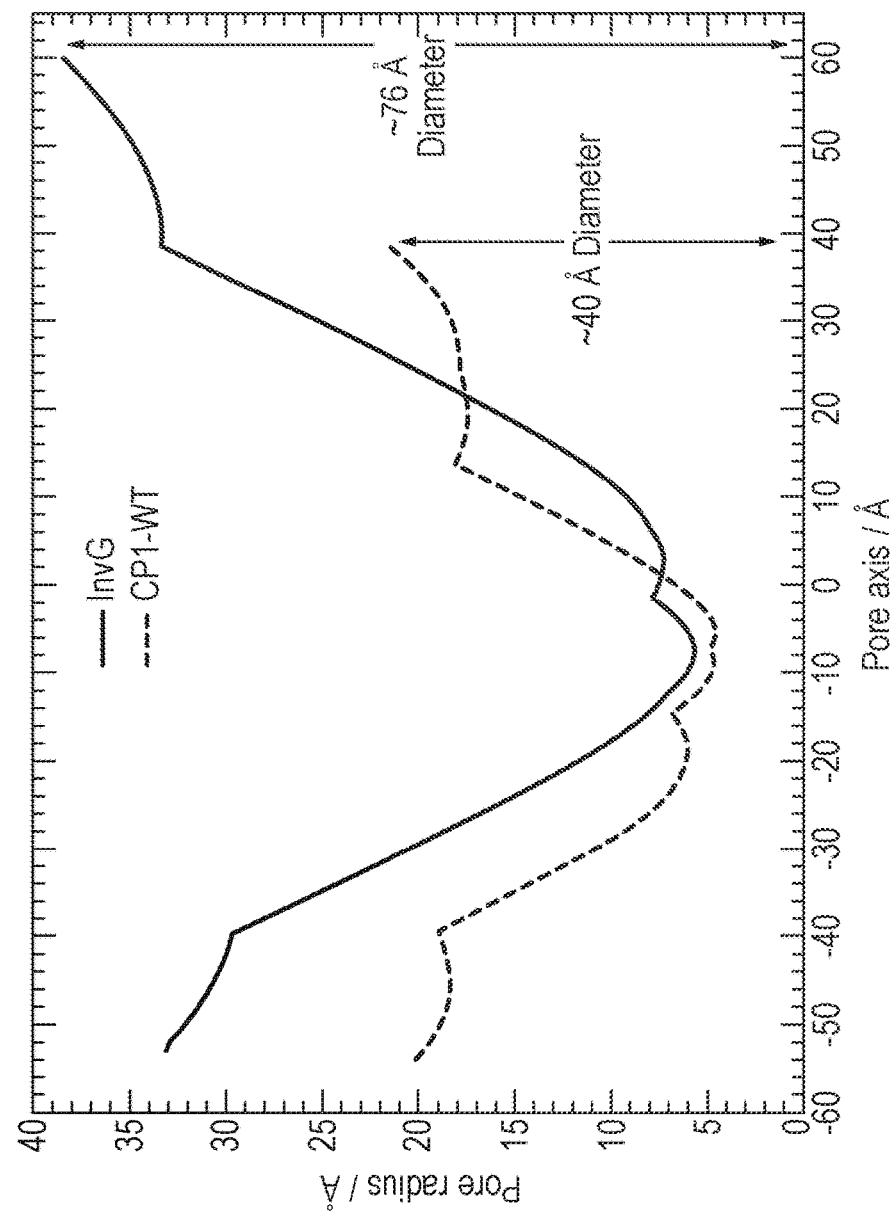
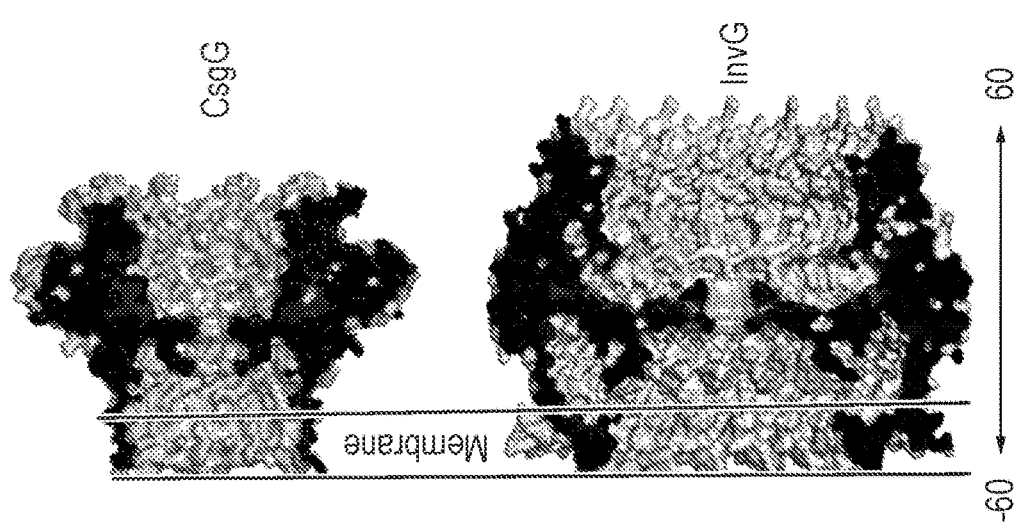

Fig. 4
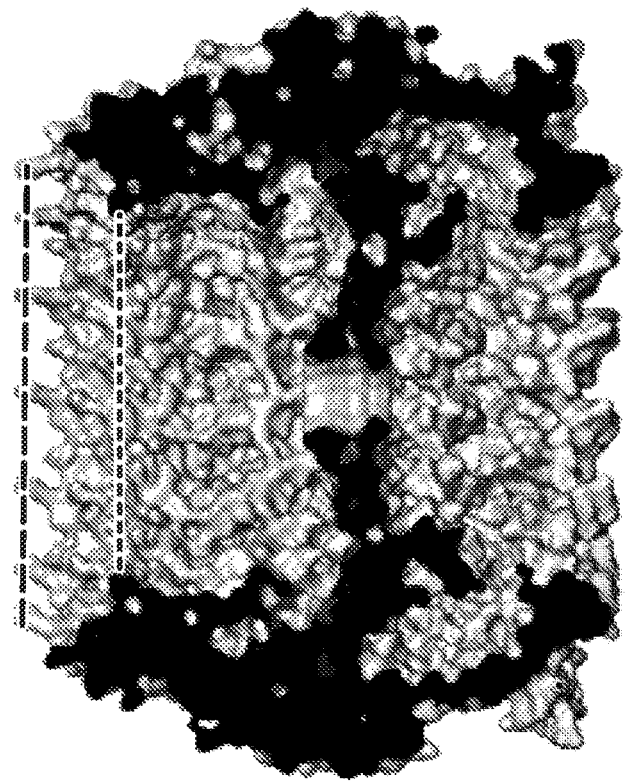
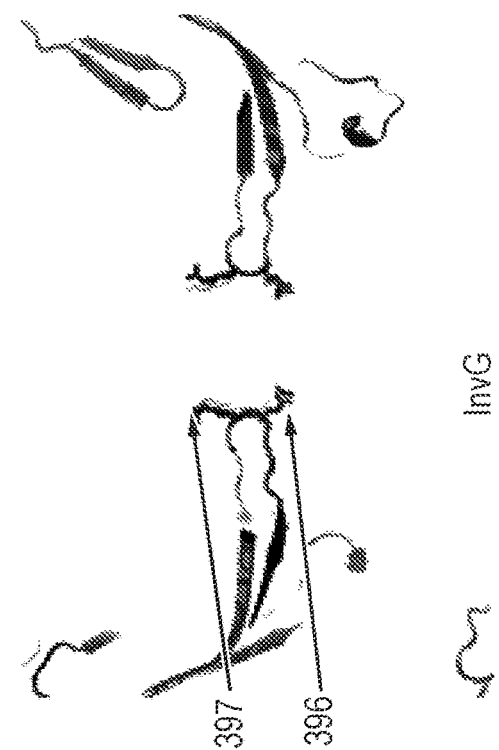
InvG
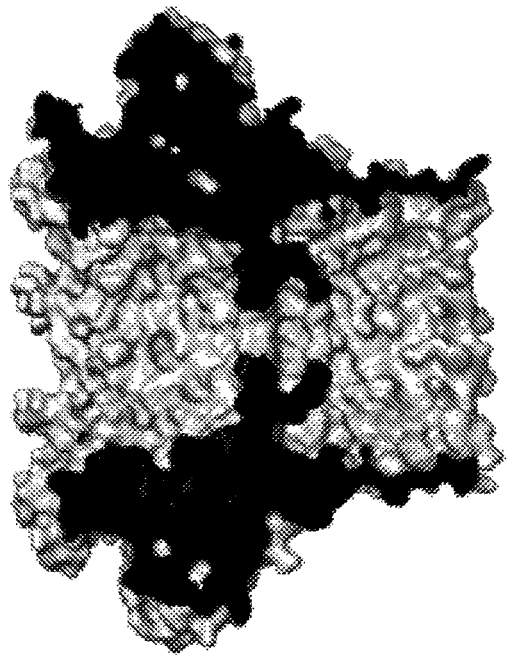
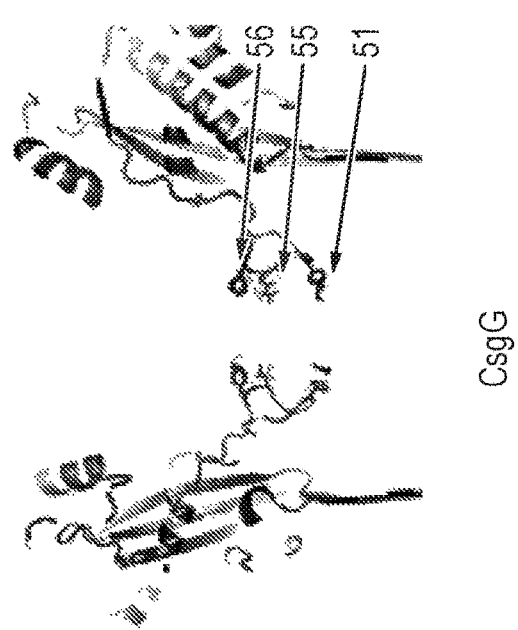
CsgG

Fig. 5
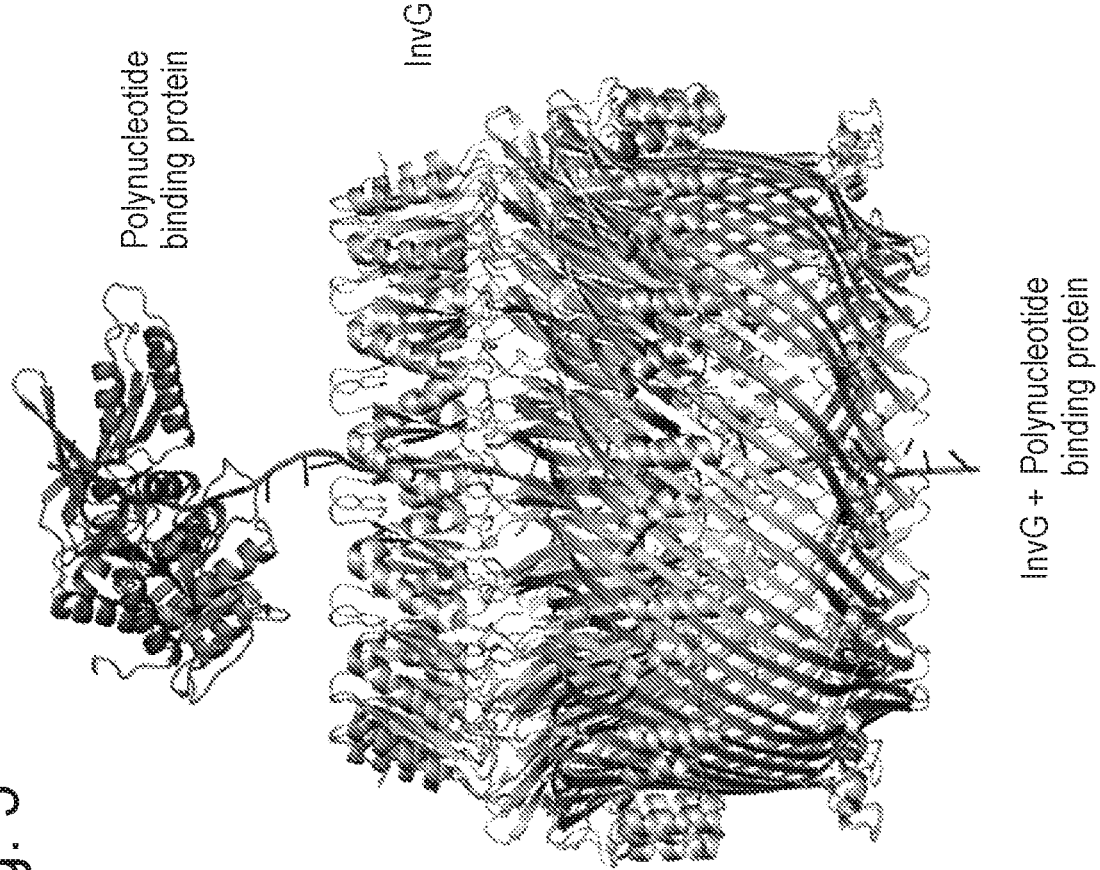
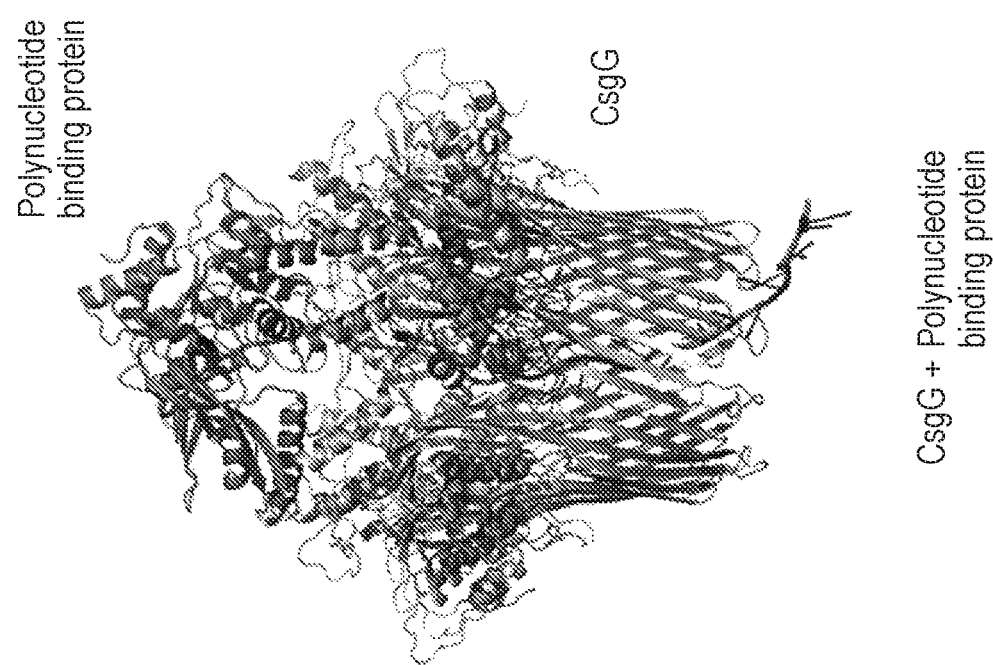

Fig. 7

Constriction

1. InvG-(WT-E396N/Q/T/A/S/G/P/H/F/Y/R/K)
2. InvG-(WT-R397N/Q/T/A/S/G/P/H/F/Y/K/V)
3. Combinations / permutations of 1 and 2
4. InvG-(Wt-Del-396)
5. InvG-(Wt-Del-396/397)

Capture

6. InvG-(WT-E402N/Q/T/A/S/G/P/H/R/K)
7. InvG-(WT-Q216R/K)
8. Combinations of 7 with 6
9. Combinations of 8 with 1-5
10. InvG-(WT-D199N/Q/T/S/G/R/K)
11. InvG-(WT-E212N/Q/T/S/G/R/K)
12. InvG-(WT-E285N/Q/T/S/G/R/K)
13. 10 – 12 with 9 (if too many combinations, this could be omitted)

Fig. 10

GspD sequences - *Vibrio Cholera*

PDB - 5WQ8:

NEFSASFKGTDIQEFINIVGRNLEKTIIVDPSVRGKVDVRSFDTLNEEQYYSFFLSVLEVYGFAVVEMDNGVLKVIKSKDAKTSAIPVLSGEERANGDEVITQVVAV
KNVSVRELSPLLRQLIDNAGAGNVVHYDPANIILITGRAAVVNRLAEIIRRVDQAGDKEIEVVELNNASAAEMVRIVEALNKTTDAQNTPEFLKPKFVADERTNS
ILISGDPKVRERLKRLIKQLDVEMAAKGNNRVVYLKYAKAEDLVEVLKGVSENLQAEKGTGQPTTSKRNEVMIAAHADTNSLVLTAPQDIMNAMLEVIGQLDIR
RAQVLIEALIVEMAEGDGINLGVQWGSLESGSVIQYGNTGASIGNVMIGLEEAKDTTQTKAVYDTNNNFLRNETTTTKGDYTKLASALSSIQGAAVSIAMGDW
TALINAVSNDSSSNILSSPSITVMDNGEASFIVGEEVPVITGSTAGSNNDNPFQTVDRKEVGIKLKVVPQINEGNSVQLNIEQEVSNVLGANGAVDVRFAKRQLN
TSVMVQDGQMLVLGGLIDERALESESKVPLLGDIPLLGQLFRSTSSQVEKKNLMVFIKPTIIRDGVTADGITQRKYNYIRAEQLFRAEKGLRLLDDASVPVLPKFG
DDRRHSPEIQAFIEQMEAKQ

The following regions are missing in the crystal structure:
N terminus N0 domain (1-96)
N1 and N2 domains (97-239)
Constriction loop (461-473)(GSTAGSNNDNPFQ)
Trans tip loop (370-379) (YDTNNNFLRN)
Gate loop in N3 (265-282) (NLQAEKGTGQPTTSKRNE)

Uniport - P45779 - GSPD_VIBCH Type II secretion system protein

MKYWLKKSSWLLAGSLLSTPLAMANEFSASFKGTDIQEFINIVGRNLEKTIIVDPSVRGKVDVRSFDTLNEEQYYSFFLSVLEVYGFAVVEMDNGVLKVIKSKDAK
TSAIPVLSGEERANGDEVITQVVAVKNVSVRELSPLLRQLIDNAGAGNVVHYDPANIILITGRAAVVNRLAEIIRRVDQAGDKEIEVVELNNASAAEMVRIVEALN
KTTDAQNTPEFLKPKFVADERTNSILISGDPKVRERLKRLIKQLDVEMAAKGNNRVVYLKYAKAEDLVEVLKGVSENLQAEKGTGQPTTSKRNEVMIAAHADTN
SLVLTAPQDIMNAMLEVIGQLDIRRAQVLIEALIVEMAEGDGINLGVQWGSLESGSVIQYGNTGASIGNVMIGLEEAKDTTQTKAVYDTNNNFLRNETTTTKG
DYTKLASALSSIQGAAVSIAMGDWTALINAVSNDSSSNILSSPSITVMDNGEASFIVGEEVPVITGSTAGSNNDNPFQTVDRKEVGIKLKVVPQINEGNSVQLNIE
QEVSNVLGANGAVDVRFAKRQLNTSVMVQDGQMLVLGGLIDERALESESKVPLLGDIPLLGQLFRSTSSQVEKKNLMVFIKPTIIRDGVTADGITQRKYNYIRAE
QLFRAEKGLRLLDDASVPVLPKFGDDRRHS PEIQAFIEQMEAKQ

Signal peptide (1-24) underlined.

GspD from Vibrio Cholera

Missing in Crystal structure:
- Constriction site: N265-E282
- Central gate: G461-Q473
- Cap gate: Y379-R387

Yan et.al. Nature structure and Molecular biology (2017)

Fig. 15C
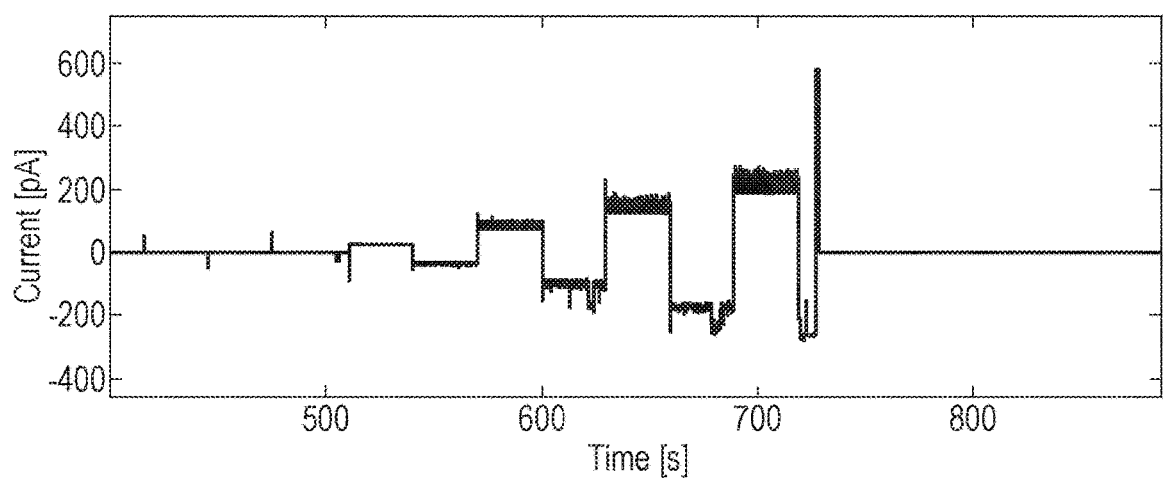
Fig. 15D
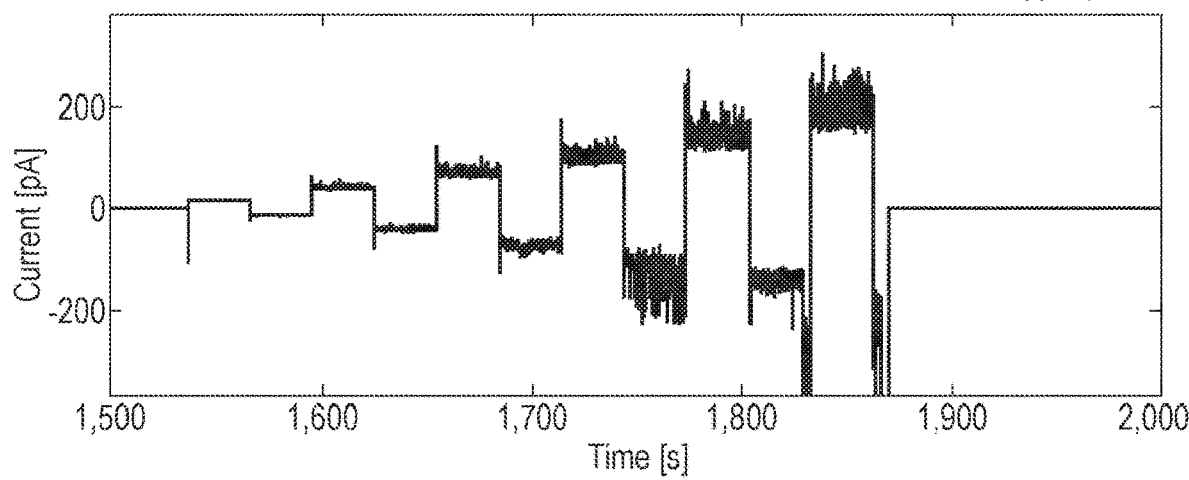
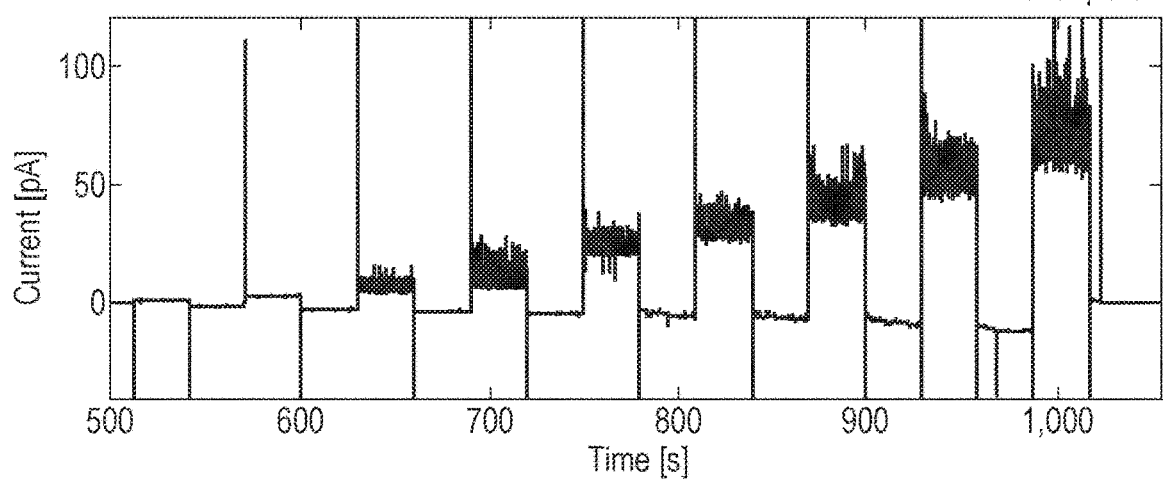

MODIFIED NANOPORES, COMPOSITIONS COMPRISING THE SAME, AND USES THEREOF

RELATED APPLICATIONS

This Application is a national stage filing under 35 U.S.C. 371 of International application number PCT/GB2018/050379, filed Feb. 12, 2018, which claims priority under 35 U.S.C. § 119(e) to U.S. Provisional application No. 62/457,483, filed Feb. 10, 2017, each of which is hereby incorporated herein by reference in its entirety.

TECHNICAL FIELD

Provided herein are modified or mutant forms of secretin and compositions comprising the same. Methods for using the modified or mutant forms of secretin and compositions, for example, for characterizing a target analyte, e.g., a target polynucleotide, are also provided. Also provided herein are compositions comprising secretin and an enzyme provided within the secretin lumen.

BACKGROUND

Transmembrane pores (e.g., nanopores) have been used to identify small molecules or folded proteins and to monitor chemical or enzymatic reactions at the single molecule level. The electrophoretic translocation of DNA across nanopores reconstituted into artificial membranes holds great promise for practical applications such as DNA sequencing, and biomarker recognition. However, translocation of double-stranded or single-stranded DNA through nanopores having internal surface facing negatively charged amino acids are not efficient.

SUMMARY

The disclosure relates generally to analyte detection using secretins as nanopores. The disclosure generally relates to modified nanopores. In some embodiments, the disclosure provides modified secretin nanopores and subunit polypeptides, compositions or apparatuses comprising the same, and uses thereof. In some embodiments, modified secretin nanopores provided herein are useful for analyte detection and analysis because they promote efficient capture and/or translocation of an analyte, e.g., a negatively-charged or hydrophobic biopolymer such as a polynucleotide or protein, across the nanopores. Accordingly, secretin nanopores, e.g. modified secretin nanopores as described herein can be used for characterizing an analyte, e.g., a target polynucleotide or polypeptide, and other suitable applications. Accordingly, in further embodiments, described herein are methods and compositions for characterizing an analyte, e.g., a target polynucleotide or polypeptide.

One aspect of the present disclosure features a modified secretin nanopore, for example, disposed in a membrane. The modified secretin nanopore comprises a lumenal surface defining a lumen that extends through the membrane between a cis-opening and a trans-opening, wherein the lumenal surface comprises one or more amino acid modifications. Examples of the amino acid modifications include, but are not limited to charge-altering modifications (e.g., substitutions of negatively-charged amino acids with positively-charged amino acids), amino acid modifications that change its hydrophobicity (e.g., substitutions of neutral amino acids with hydrophobic amino acids), amino acid modifications that change the size of an opening, e.g. a constriction or gate, in the secretin (e.g. substitution of one or more amino acid having a smaller or larger side group that the naturally occurring amino acid(s), or deletion of one or more amino acids that constrict an opening), amino acid modifications that inhibit or prevent gate opening (such as substitution of one or more flexible amino acid with more rigid amino acid(s)), and a combination thereof.

The cis-opening and trans-opening of the modified secretin nanopores may have a diameter of any size that suits the need of an application (e.g., detection and/or analysis of an analyte such as a target polynucleotide). In some embodiments, the cis-opening of the modified secretin nanopores may have a diameter in a range of 60 Å to 120 Å. In some embodiments, the trans-opening of the modified secretin nanopores may have a diameter in a range of 40 Å to 100 Å. In some embodiments, the constriction of the modified secretin nanopores may have a diameter of about 7.5 Å to 25 Å.

Any types of secretin may be used to produce the modified secretin nanopores described herein. For example, in some embodiments, the secretin may be of a type II secretion system (e.g., but not limited to GspD). In some embodiments, the secretin may be of a type III secretion system (e.g., but not limited to YscC and InvG). In some embodiments, the secretin may be of a type IV secretion system (e.g., but not limited to PilQ).

In some embodiments where the secretin is an InvG, the modified secretin nanopore may further comprise a subunit polypeptide having an amino acid sequence that is at least 95% identical to the amino acid sequence as set forth in SEQ ID NO: 1 (corresponding to the amino acid sequence of InvG without N1 or N0 domain). In these embodiments, the lumenal surface may further define a constriction within the lumen, the constriction having one or more amino acid modifications (e.g., charge-altering modifications) at amino acids D28, E225, R226, and/or E231 of SEQ ID NO: 1. Examples of such amino acid modifications include but are not limited to (i) D28N/Q/T/S/G/R/K; (ii) E225N/Q/T/A/S/G/P/H/F/Y/R/K; (iii) R226N/Q/T/A/S/G/P/H/F/Y/KN; (iv) Deletion of E225; (v) Deletion of R226; and (vi) E231N/Q/T/A/S/G/P/H/R/K. In some embodiments, the modified secretin nanopore, the lumenal surface may comprise a capture portion having one or more amino acid modifications at amino acids E41, Q45 or E114, examples of which include, but are not limited to (i) Q45R/K; (ii) E41N/Q/T/S/G/R/K; and (iii) E114N/Q/T/S/G/R/K.

The modified secretin nanopore can be homo-multimeric (e.g., all subunits within the nanopore are the same) or hetero-multimeric (e.g., at least one subunit is different from others within the nanopore). The modified secretin nanopore may comprise any number of subunit polypeptides that are sufficient to form a lumen large enough to permit a target analyte (e.g., polynucleotide) to pass through. In some embodiments, the modified secretin nanopore may comprise 9-20 subunit polypeptides, wherein at least one or more (e.g., 1, 2, 3, 4, 5, 6, 7, 8, 9, 10, 11, 12, 13, 14, 15, or up to all) of the subunit polypeptides comprises one or more of the amino acid modifications as described herein.

Accordingly, modified secretin nanopore subunit polypeptide and polynucleotides comprising nucleotide sequences encoding the modified secretin nanopore subunit polypeptides are also provided herein.

For example, in one aspect the modified GspD secretin nanopore comprises a subunit polypeptide comprising a secretin domain having an amino acid sequence that is at least 95% identical to the amino acid sequence of the secretin domain set forth in SEQ ID NO: 36.

The secretin domain of GspD from *Vibrio cholerae* and from *Escherichia coli* ETEC contains a cap gate. Other Type II secretion system secretin subunit polypeptides, including some GspD subunit polypeptides, such as *Escherichia coli* K12, do not comprise a cap gate. The modified secretin nanopore may, in one aspect be one that does not comprise a cap gate. The secretin domain set in out SEQ ID NO: 36 comprises a cap gate between positions 56 and 77. For example, the secretin domain set forth in SEQ ID NO: 36 may be modified to delete all or part of the cap gate, e.g. all or some of the amino acids from D55 or T56 to T77 of SEQ ID NO: 36 may be deleted or substituted. Alternatively, the modified GspD secretin nanopore may naturally lack a cap gate. The amino acids from D55 or T56 to T77 of SEQ ID NO: 36 correspond to the amino acids from D371 or T372 to T393 of SEQ ID NO: 32.

The central gate of GspD may be modified to replace an amino acid with an amino acid having a smaller side group and/or to replace a negatively charged amino acid with a neutral or positively charged amino acid. The secretin domain set in out SEQ ID NO: 36 comprises a central gate between positions 144 to 157, which correspond to positions 460 and 473 of SEQ ID NO: 32. The secretin domain of the modified GspD secretin nanopore may comprise a secretin domain having an amino acid sequence that is at least 95% identical to an amino acid sequence as set forth in SEQ ID NO: 36, wherein: (i) all or some of the amino acids from D55 or T56 to T77 are deleted or substituted, one or more of K60, D64, R71 and E73 is substituted with an uncharged amino acid and/or one or more of D55, T56, T77 and K78 is substituted with P; and/or (ii) F156 is substituted with a smaller amino acid, N151 and/or N152 is/are substituted with a smaller amino acid, D153 is substituted with an uncharged amino acid, G137 and G165 are each independently unmodified or substituted with A or V. For example, in the modified secretin GspD nanopore Y63 to R71 may deleted and/or substituted with GSG or SGS, F156 may be substituted with A, D153 may be substituted with S, and/or N151 and N152 may each independently be substituted with G or S. D55, T56, K60, Y63, D64, R71, E73, T77, K78, G137, N151, N152, D153, F156 and G165 of SEQ ID NO: 36 correspond to D371, T372, K376, Y379, D380, R387, E389, T393, K394, G453, N467, N468, D469, F472 and G481 of the full length GspD amino acid sequence set forth in SEQ ID NO: 32. The modified secretin GspD nanopore may in one aspect comprise a subunit polypeptide comprising an amino acid sequence that is at least 95% identical to the amino acid sequence as set forth in SEQ ID NO: 33, 34 and/or 35.

The secretin domain of the modified GspD secretin nanopore may comprise a secretin domain having an amino acid sequence that is at least 95% identical to an amino acid sequence as set forth in SEQ ID NO: 35, wherein: (i) all or some of the amino acids from D55 or T56 to T77 are deleted or substituted, one or more of K60, D64, R71 and E73 is substituted with an uncharged amino acid and/or one or more of D55, T56, T77 and K78 is substituted with P; and/or (ii) F156 is substituted with a smaller amino acid, N151 and/or N152 is/are substituted with a smaller amino acid, D153 is substituted with an uncharged amino acid, G137 and G165 are each independently unmodified or substituted with A or V. For example, in the modified secretin GspD nanopore Y63 to R71 may deleted and/or substituted with GSG or SGS, F156 may be substituted with A, D153 may be substituted with S, and/or N151 and N152 may each independently be substituted with G or S. D55, T56, K60, Y63, D64, R71, E73, T77, K78, G137, N151, N152, D153, F156 and G165 of SEQ ID NO: 35 correspond to D371, T372, K376, Y379, D380, R387, E389, T393, K394, G453, N467, N468, D469, F472 and G481 of the full length GspD amino acid sequence set forth in SEQ ID NO: 32.

The secretin domain of the modified GspD secretin nanopore may comprise a secretin domain having an amino acid sequence that is at least 95% identical to an amino acid sequence as set forth in SEQ ID NO: 34, wherein: (i) all or some of the amino acids from D117 or T118 to T139 are deleted or substituted, one or more of K122, D126, R133 and E135 is substituted with an uncharged amino acid and/or one or more of D117, T118, T139 and K140 is substituted with P; and/or (ii) F218 is substituted with a smaller amino acid, N213 and/or N214 is/are substituted with a smaller amino acid, D215 is substituted with an uncharged amino acid, G199 and G227 are each independently unmodified or substituted with A or V. For example, in the modified secretin GspD nanopore Y125 to R133 may deleted and/or substituted with GSG or SGS, F218 may be substituted with A, D215 may be substituted with S, and/or N213 and N214 may each independently be substituted with G or S. D117, T118, K122, Y125, D126, R133, E135, T139, K140, G199, N213, N214, D215, F218 and G227 of SEQ ID NO: 34 correspond to D371, T372, K376, Y379, D380, R387, E389, T393, K394, G453, N467, N468, D469, F472 and G481 of the full length GspD amino acid sequence set forth in SEQ ID NO: 32.

The secretin domain of the modified GspD secretin nanopore may comprise a secretin domain having an amino acid sequence that is at least 95% identical to an amino acid sequence as set forth in SEQ ID NO: 33, wherein: (i) all or some of the amino acids from D132 or T133 to T154 are deleted or substituted, one or more of K137, D141, R148 and E150 is substituted with an uncharged amino acid and/or one or more of D132, T133, T154 and K155 is substituted with P; and/or (ii) F233 is substituted with a smaller amino acid, N228 and/or N229 is/are substituted with a smaller amino acid, D230 is substituted with an uncharged amino acid, G214 and G242 are each independently unmodified or substituted with A or V. For example, in the modified secretin GspD nanopore Y140 to R148 may deleted and/or substituted with GSG or SGS, F233 may be substituted with A, D230 may be substituted with S, and/or N228 and N229 may each independently be substituted with G or S. D132, T133, K137, Y140, D141, R148, E150, T154, K155, G214, N228, N229, D230, F233 and G242 of SEQ ID NO: 33 correspond to D371, T372, K376, Y379, D380, R387, E389, T393, K394, G453, N467, N468, D469, F472 and G481 of the full length GspD amino acid sequence set forth in SEQ ID NO: 32.For example, in one aspect, a modified InvG nanopore subunit polypeptide comprises an amino acid sequence that is at least 95% identical to the amino acid sequence as set forth in SEQ ID NO: 1 (corresponding to the amino acid sequence of InvG without N1 or N0 domain), wherein the modified InvG nanopore subunit polypeptide comprises one or more amino acid modifications (e.g., charge-altering amino acid modifications) at amino acid(s) selected from D28, E41, E114, Q45, E225, R226, and E231 of SEQ ID NO: 1. The one or more amino acid modifications (e.g., charge-altering amino acid modifications) may comprise one or more of the following: (i) D28N/Q/T/S/G/R/K; (ii) E225N/Q/T/A/S/G/P/H/F/Y/R/K; (iii) R226N/Q/T/A/S/G/P/H/F/Y/K/V; (iv) Deletion of E225; (v) Deletion of R226; and (vi) E231N/Q/T/A/S/G/P/H/R/K. Other amino acid modifications may include, but are not limited to (i)

Q45R/K; (ii) E41N/Q/T/S/G/R/K; and/or (iii) E114N/Q/T/S/G/R/K. Such amino acid modifications may enhance capture of an analyte, e.g. a polynucleotide, by the nanopore (e.g. mutations at D28, E41, E114 and/or Q45) and/or improve the interaction of an analyte, e.g. a polynucleotide, with the constriction of the nanopore (e.g. mutations at E225 and/or R226). In another aspect, a modified InvG nanopore subunit polypeptide comprises an amino acid sequence that is at least 95% identical to the amino acid sequence as set forth in SEQ ID NO: 2 (corresponding to the amino acid sequence of WT InvG including N1 and N0 domains), wherein the modified InvG nanopore subunit polypeptide comprises one or more amino acid modifications (e.g., charge-altering amino acid modifications) at amino acid(s) selected from D199, E212, E285, Q216, E396, R397, and E402 of SEQ ID NO: 2. Non-limiting examples of such amino acid modifications include: (i) D199N/Q/T/S/G/R/K; (ii) E396N/Q/T/A/S/G/P/H/F/Y/R/K; (iii) R397N/Q/T/A/S/G/P/H/F/Y/K/V; (iv) Deletion of E396; (v) Deletion of R397; (vi) E402N/Q/T/A/S/G/P/H/R/K. Other amino acid modifications may include, but are not limited to (i) Q216R/K; (ii) E212N/Q/T/S/G/R/K; and (iii) E285N/Q/T/S/G/R/K. Such amino acid modifications may enhance capture of an analyte, e.g. a polynucleotide, by the nanopore (e.g. mutations at D199, E212, E285 and/or Q216) and/or improve the interaction of an analyte, e.g. a polynucleotide, with the constriction of the nanopore (e.g. mutations at E396 and/or R397).

A further aspect features a modified InvG nanopore subunit polypeptide that comprises an endopeptidase cleavage site. In this aspect, the modified InvG nanopore subunit polypeptide comprises an amino acid sequence that is at least 95% identical to the amino acid sequence as set forth in SEQ ID NO: 2 (corresponding to the amino acid sequence of WT InvG including N1 and N0 domains), wherein an endopeptidase cleavage site is inserted between positions 170 and 171 or 171 and 172 of SEQ ID NO: 2. In some embodiments, the modified InvG nanopore subunit polypeptide may further comprise one or more amino acid modifications (e.g., charge-altering amino acid modifications) at amino acid(s) selected from D199, E212, E285, Q216, E396, R397, and E402 of SEQ ID NO: 2. Non-limiting examples of such amino acid modifications include: (i) D199N/Q/T/S/G/R/K; (ii) E396N/Q/T/A/S/G/P/H/F/Y/R/K; (iii) R397N/Q/T/A/S/G/P/H/F/Y/KN; (iv) Deletion of E396; (v) Deletion of R397; (vi) E402N/Q/T/A/S/G/P/H/R/K. Other amino acid modifications may include, but are not limited to (i) Q216R/K; (ii) E212N/Q/T/S/G/R/K; and (iii) E285N/Q/T/S/G/R/K.

A further aspect of the present disclosure provides a composition comprising a secretin nanopore and an enzyme provided within the lumen of the nanopore. The composition may be disposed within a membrane.

Also within the scope of the present disclosure are apparatuses, for example, for use in characterizing a target analyte, e.g., a target polynucleotide. The apparatus may comprise a chamber housing an aqueous solution having disposed therein a membrane comprising any embodiment of the secretin nanopores described herein.

In some embodiments, the apparatus may further comprise an analyte present in the aqueous solution. Exemplary analytes include, but are not limited to polynucleotides, polypeptides, and/or ligands. In some embodiments where the apparatus comprises a polynucleotide in the aqueous solution, the apparatus can further comprise a polynucleotide binding protein, including, e.g., but not limited to a helicase, exonuclease, or polymerase, which is optionally bound to the polynucleotide. The polynucleotide binding protein may be on the cis-side or trans-side of the membrane, for example, being in contact (via, e.g., ionic and/or hydrophobic interactions) with or covalently attached to the cis-opening or trans-opening of the nanopore.

The modified secretin nanopores and apparatuses as described herein can be used for various biosensor or analyte detection applications, but not limited to polynucleotide sequencing and/or protein detection. Accordingly, methods for using the modified secretin nanopores and apparatuses are also provided herein. For example, the method comprises obtaining an embodiment of the apparatus as described herein and adding an analyte to the aqueous solution on the cis-side or the trans-side of the membrane disposed in the apparatus. In some embodiments, the method further comprises inducing ionic current flow through the nanopore by applying a voltage gradient across the membrane. In some embodiments, the method further comprises detecting ionic current flow through the nanopore under the applied voltage gradient, which can be used to determine the presence of the analyte.

Where the method is used for polynucleotide characterization, the method can further comprise adding a polynucleotide binding protein (e.g., a helicase, exonuclease, and/or polymerase) in the aqueous solution on the cis-side or the trans-side of the membrane. In some embodiments, the polynucleotide binding protein may be bound to the polynucleotide analyte and optionally interact with the cis-opening or trans-opening of the nanopore via, for example non-covalent interactions (e.g., ionic and/or hydrophobic interactions) and/or covalent attachment.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1C shows secondary structure topologies of a wild-type InvG secretin from *Salmonella enterica* (e.g., based on SEQ ID NO: 2) and a wild-type GspD secretin from *Vibrio cholerae* from positions 97-646 of SEQ ID NO: 10. The figure shows different domains and dimensions of the cis and trans openings of the InvG nanopore and GspD nanopore. The orientation of the nanopores is such that the OM region of the nanopores (as in the native state) is situated in the membrane as described herein.

FIG. 1D shows structures of GspD from *Vibrio cholerae* (PDB: 5wq8) and *E. coli* (PDB: 5wq7). One subunit of each GspD structure is colored in cyan.

FIG. 2 shows a comparison of a CsgG nanopore with an InvG nanopore. The top row shows the top view of CsgG and InvG nanopores, while the bottom row shows the side view of CsgG and InvG nanopores. A CsgG nanopore has 9 monomers or subunits and an InvG nanopore has 15 monomers or subunits. However, both CsgG and InvG nanopores have a constriction within the lumen that is roughly the same in diameter.

FIG. 3 shows the InvG and CsgG nanopore profiles. The X axis shows the internal pore radius profiles of InvG and CsgG nanopores: −60 (membrane side/trans opening) and +60 (cis opening) are arbitrary numbers for the height of the pore. 0 is the mid-point. The Y axis shows the actual radius of the lumen of the pore in angstrom for each position of the X axis.

FIG. 4 shows a comparison of the constrictions of CsgG and InvG nanopores. The top row shows the side view of the CsgG and InvG nanopores. The bottom row shows the amino acids present within the constriction of CsgG and InvG pores. While both CsgG and InvG nanopores have a constriction of roughly the same in diameter, the constriction of the CsgG nanopore has 3 amino acids at positions 51, 55, and 56 (based on the wild type sequence) and the InvG nanopore constriction has two amino acids at position 396 and 397 (based on SEQ ID NO: 2).

FIG. 5 shows the relative size of a polynucleotide binding protein (e.g., a DNA binding enzyme such as a helicase or polymerase) versus CsgG and InvG nanopores. Since the opening of the InvG nanopore is much wider than that of the CsgG nanopore, the polynucleotide binding protein (e.g., a DNA binding enzyme such as a helicase or polymerase) may interact with the InvG and CsgG nanopores in different orientations.

FIG. 7 shows exemplary combinations of mutations in InvG subunit polypeptide that can be used to form a nanopore. The amino acid positions indicated in the figure are based on SEQ ID NO: 2.

FIG. 10 shows the amino acid sequences of GspD from *Vibrio cholerae* and highlights the regions of amino acid sequence that are missing from the crystal structure, i.e. for which the crustal structure has not been determined in the art. The amino acid positions indicated in the figure are based on SEQ ID NO: 32.

BRIEF DESCRIPTION OF THE SEQUENCES

Figure 1A:
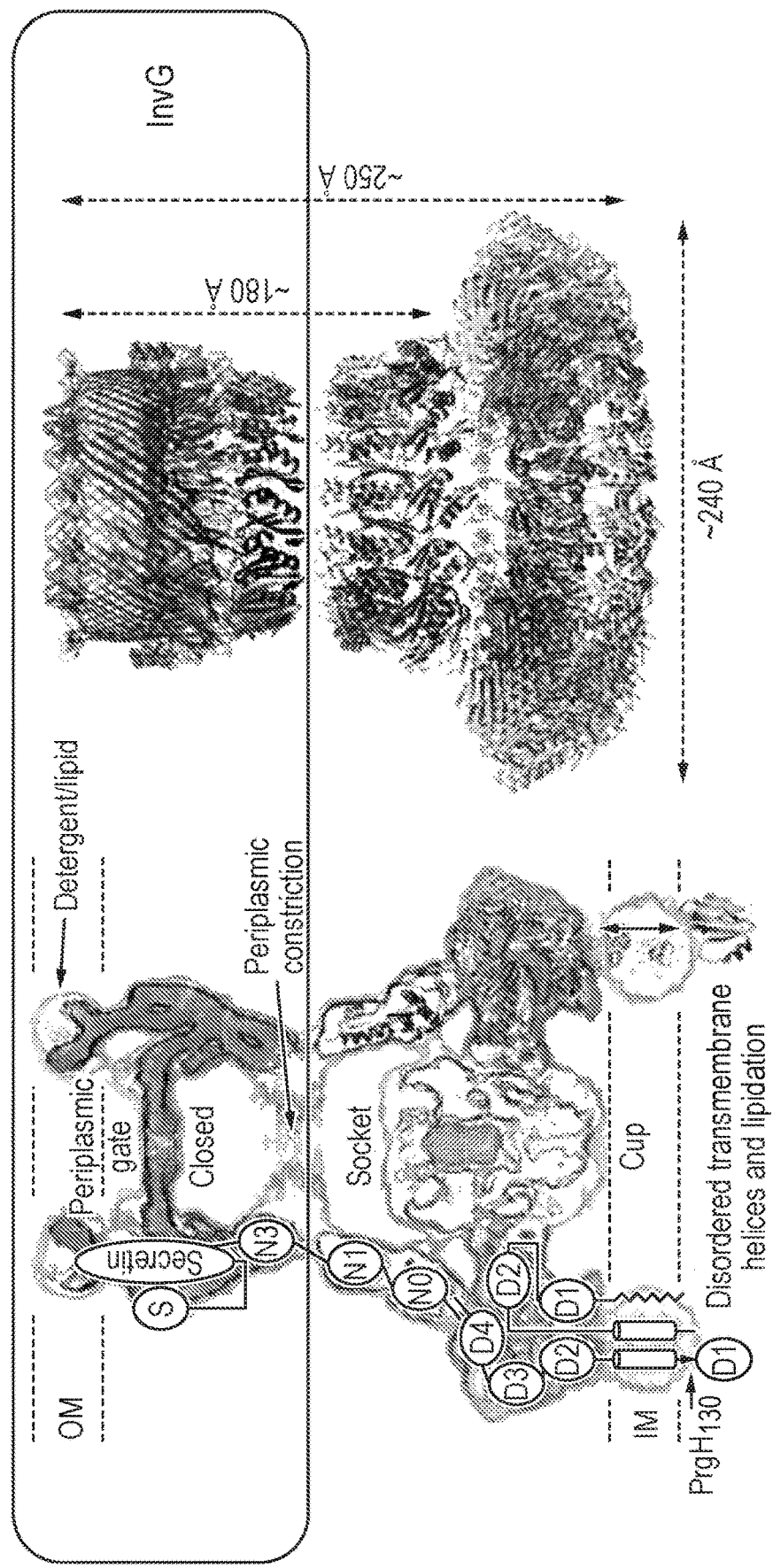
FIG. 1A shows Cry-EM structures of the injectisome basal body and isolated secretin. (Left panel) Central slice view of basal body reconstruction (dark-grey contoured as in a and light-grey contoured at lower level to highlight less-ordered features) and isolated secretin (blue). The domain annotation of PrgH, PrgK and InvG is overlaid on the left and the structures of the monomeric domains previously solved on the right. The PrgH cytoplasmic D1 domain (green, bottom left) is not present in the $PrgH_{130-392}$ mutant used in this study and its precise location with respect to the basal body is unclear. The transmembrane helices of PrgH (N-terminal) and PrgK (C-terminal) and the PrgK N-terminal lipidation are present but diffusely ordered. (Right panel) Refined structures for $InvG_{172-557}$ (blue), $PrgH_{171-364}$ (green), $PrgK_{20-203}$ (orange) and Rosetta-modeled $InvG_{34-171}$ (pale blue). One monomer encompassing $InvG_{34-557}$ is colored according to structural domains: medium blue, N0-N1 domains; cobalt blue, N3 domain; cyan, outer β-sheet; green, inner β-sheet; orange, secretin domain lip; red, S domain (note the displaced interaction with the β-sheet of the i+1 and i+2 promoters).

SEQ ID NO: 1 is the 391 amino acid sequence of truncated InvG from *Salmonella enterica* (Full length InvG without N0 and N1 domains).

SEQ ID NO: 2 is the 572 amino acid sequence of Wild-type InvG from *Salmonella enterica* (Full length InvG including N0 and N1 domains). The first 171 amino acids correspond to the N0 and N1 domains.

SEQ ID NO: 3 is the amino acid sequence of wild-type InvG from *Salmonella enterica* in which a TEV cleavage site (ENLYFQG) has been added at amino acids 172 to 178 after the N1 and N2 domains (the first 171 amino acids).

SEQ ID NO: 4 is the amino acid sequence of GspD from *Escherichia coli* (strain K12) (>sp|P45758|GSPD_ECOLI type II secretion system protein D OS=*Escherichia coli* (strain K12) GN=gspD PE=2 SV=2).

SEQ ID NO: 5 is the amino acid sequence of >tr|Q7BRZ9|Q7BRZ9_YEREN Secretin YscC OS=*Yersinia enterocolitica* GN=yscC PE=3 SV=1.

SEQ ID NO: 6 is the amino acid sequence of >sp|Q04641|MXID_SHIFL Outer membrane protein MxiD OS=*Shigella flexneri* GN=mxiD PE=1 SV=1.

SEQ ID NO: 7 is the amino acid sequence of >tr|A0A1C6ZHG5|A0A1C6ZHG5_PSEAI Type III secretion outer membrane protein PscC OS=*Pseudomonas aeruginosa* GN=pscC PE=3 SV=1.

SEQ ID NO: 8 is the amino acid sequence of >tr|B7UMB3|B7UMB3_ECO27 T3SS structure protein EscC OS=*Escherichia coli* O127:H6 (strain E2348/69/EPEC) GN=escC PE=1 SV=1.

SEQ ID NO: 9 is the amino acid sequence of >sp|D0ZWR9|SPIA_SALT1 Type III secretion system outer membrane protein SpiA OS=*Salmonella typhimurium* (strain 14028s/SGSC 2262) GN=spiA PE=2 SV=1.

SEQ ID NO: 10 is the amino acid sequence of >tr|A0A1E4UJH6|A0A1E4UJH6_VIBCL Type II secretion system protein GspD OS=*Vibrio cholerae* GN=BFX10_13405 PE=4 SV=1.

SEQ ID NO: 11 is the amino acid sequence of >sp|P15644|GSPD_KLEPN Type II secretion system protein D OS=*Klebsiella pneumoniae* GN=pulD PE=1 SV=1.

SEQ ID NO: 12 is the amino acid sequence of >tr|X5F782|X5F782_NEIME Type IV pilus assembly protein PilQ OS=*Neisseria meningitidis* GN=pilQ PE=3 SV=1.

SEQ ID NO: 13 is the amino acid sequence of >WP_071651540.1 EscC/YscC/HrcC family type III secretion system outer membrane ring protein [*Salmonella enterica*]—97% identity to SEQ ID NO: 2.

SEQ ID NO: 14 is the amino acid sequence of >WP_038392434.1 type III secretion system outer membrane pore InvG [*Salmonella bongori*]—94% identity to SEQ ID NO: 2.

SEQ ID NO: 15 is the amino acid sequence of >WP_043640872.1 type III secretion system outer membrane pore InvG [*Chromobacterium haemolyticum*]—69% identity to SEQ ID NO: 2.

SEQ ID NO: 16 is the amino acid sequence of >WP_059765897.1 type III secretion system outer membrane pore InvG [*Burkholderia ubonensis*]—67% identity to SEQ ID NO: 2.

SEQ ID NO: 17 is the amino acid sequence of >WP_036979259.1 type III secretion system outer membrane pore InvG [*Providencia alcalifaciens*]—64% identity to SEQ ID NO: 2.

SEQ ID NO: 18 is the amino acid sequence of >WP_051238518.1 type III secretion system outer membrane pore InvG [*Pseudogulbenkiania ferrooxidans*]—61% identity to SEQ ID NO: 2.

SEQ ID NO: 19 is the amino acid sequence of >WP_070981539.1 EscC/YscC/HrcC family type III secretion system outer membrane ring protein [*Chromobacterium vaccinii*]—61% identity to SEQ ID NO: 2.

SEQ ID NO: 20 is the amino acid sequence of >WP_052429256.1 type III secretion system outer membrane pore InvG [*Salmonella enterica*]—60% identity to SEQ ID NO: 2.

SEQ ID NO 21 is the amino acid sequence of >WP_021564153.1 EscC/YscC/HrcC family type III secretion system outer membrane ring protein [*Escherichia coli*]—59% identity to SEQ ID NO: 2.

SEQ ID NO: 22 is the amino acid sequence of >WP_024250244.1 type III secretion system outer membrane pore InvG [*Shigella dysenteriae*]—56% identity to SEQ ID NO: 2.

SEQ ID NO: 23 is the amino acid sequence of >WP_000694679.1 type III secretion system outer membrane pore InvG [*Escherichia coli*]—53% identity to SEQ ID NO: 2.

SEQ ID NO: 24 is the amino acid sequence of >WP_061203566.1 EscC/YscC/HrcC family type III secretion system outer membrane ring protein [*Stenotrophomonas rhizophila*]—52% identity to SEQ ID NO: 2.

SEQ ID NO: 25 is the amino acid sequence of >WP_016498773.1 EscC/YscC/HrcC family type III secretion system outer membrane ring protein [*Pseudomonas putida*]—52% identity to SEQ ID NO: 2.

SEQ ID NO: 26 is the amino acid sequence of >ANI31722.1 type III secretion system outer membrane pore InvG [*Yersinia entomophaga*]—50% identity to SEQ ID NO: 2.

SEQ ID NO: 27 is the amino acid sequence of >WP_053215251.1 EscC/YscC/HrcC family type III secretion system outer membrane ring protein [*Yersinia nurmii*]—49% identity to SEQ ID NO: 2.

SEQ ID NO: 28 is the amino acid sequence of >WP_034249407.1 EscC/YscC/HrcC family type III secretion system outer membrane ring protein [*Arsenophonus nasoniae*]—46% identity to SEQ ID NO: 2.

SEQ ID NO: 29 is the amino acid sequence of >WP_006122201.1 EscC/YscC/HrcC family type III secretion system outer membrane ring protein [*Pantoea stewartii*]—42% identity to SEQ ID NO: 2.

SEQ ID NO: 30 is the amino acid sequence of >KJO55878.1 type III secretion system protein [[*Enterobacter*] *aerogenes*]—41% identity to SEQ ID NO: 2.

SEQ ID NO: 31 is the amino acid sequence of GspD of *Vibrio cholerae*, including the leader sequence.

SEQ ID NO: 32 is the mature amino acid sequence of GspD of *Vibrio cholerae*.

SEQ ID NO: 33 is the sequence of the N3, secretin and S domains of GspD of *Vibrio cholerae* (amino acids 1 to 239 of SEQ ID NO: 32 deleted).

SEQ ID NO: 34 is the sequence of the N3, secretin and S domains of GspD of *Vibrio cholerae* in which the construction in the N3 domain has been removed by substituting amino acids Y379 to R387 of SEQ ID NO: 32 with the amino acids GSG.

SEQ ID NO: 35 is the sequence of the secretin and S domains of GspD of *Vibrio cholerae*.

SEQ ID NO: 36 is the sequence of the secretin domain of GspD of *Vibrio cholerae*.

SEQ ID NO: 37 is the sequence of >tr|A7ZRJ5|A7ZRJ5_ECO24 General secretion pathway protein D OS=*Escherichia coli* O139:H28 (strain E24377A/ETEC) GN=gspD PE=1 SV=1.

SEQ ID NO: 38 is the sequence of >sp|P31780|GSPD_AERHY Type II secretion system protein D OS=*Aeromonas hydrophila* GN=exeD PE=3 SV=2.

SEQ ID NO: 39 is the sequence of >sp|P35818|GSPD_PSEAE Type II secretion system protein D OS=*Pseudomonas aeruginosa* (strain ATCC 15692/DSM 22644/CIP 104116/JCM 14847/LMG 12228/1C/PRS 101/PAO1) GN=xcpQ PE=1 SV=1.

SEQ ID NO: 40 is the sequence of >tr|A0A181X688|A0A181X688_KLEOX General secretion pathway protein D OS=*Klebsiella oxytoca* GN=pulD PE=3 SV=1.

DETAILED DESCRIPTION OF THE INVENTION

Certain transmembrane pores (e.g., protein nanopores or solid state nanopores) are useful as sensors to detect or characterize a biopolymer. The structure of the transmembrane pore, particularly the lumen of the pore, affects the interaction between the biopolymer and the pore and hence the information that can be derived from a signal generated as the biopolymer interacts with the pore. Accordingly, there is a need to identify new transmembrane nanopores that are capable of capturing and translocating an analyte, e.g., a negatively-charged or hydrophobic biopolymer such as a polynucleotide or protein. The present disclosure provides, for the first time, that secretin nanopores are useful for practical applications such as polynucleotide mapping or sequencing, or protein detection.

While transmembrane pores (e.g., protein nanopores or solid state nanopores) are useful as sensors to detect or characterize a biopolymer, translocation of a biopolymer, e.g., a polynucleotide through certain nanopores could be challenging, e.g., because of a large electrostatic barrier for the entry of a biopolymer into the nanopore. Accordingly, there is a need to engineer transmembrane nanopores that permit more efficient capture and/or translocation of an analyte, e.g., a negatively-charged or hydrophobic biopolymer such as a polynucleotide or protein, across the nanopores, which can be useful for practical applications such as polynucleotide mapping or sequencing or protein detection.

The present disclosure relates to modified secretin nanopores and its subunit polypeptides, compositions or apparatuses comprising the same, and uses thereof. In some aspects, the present disclosure provides modified secretin nanopore subunit polypeptide (e.g., for forming a modified secretin nanopore) and nanopores comprising the same. The secretin nanopores and modified secretin nanopores as described herein can be used for various practical applications such as characterizing an analyte, e.g., a target polynucleotide or polypeptide. Accordingly, described herein are also methods and compositions for characterizing an analyte, e.g., a target polynucleotide or polypeptide.

In some embodiments of any aspects described herein, the cis and trans openings of the secretin nanopores are of a size such that an enzyme may be able to enter the lumenal cavity. The enzyme may be immobilized within the cavity, for example, by binding or attaching to the lumenal surface of the nanopore or otherwise provided within the lumenal cavity in a non-immobilized fashion. Thus, one aspect of the present disclosure also relates to compositions comprising a secretin nanopore and an enzyme provided within the lumen. The secretin nanopore may be of the wild type or a mutant or modified form as described in more detail below. The enzyme may be present in the cis vestibule or the trans vestibule of the nanopore, wherein the cis vestibule may be defined as the part of the lumen extending from the cis opening to the constriction of the nanopore and wherein the trans vestibule may be defined as the part of the lumen extending from the trans opening to the constriction of the nanopore. Such compositions may be used to detect small molecules that bind to or otherwise interact with the enzyme. The interaction of such small molecules with the enzyme may result in a change in ion current flow through the nanopore, for example by a change of conformation of the enzyme.

Modified Secretin Nanopore Subunit Polypeptides

Figure 8:
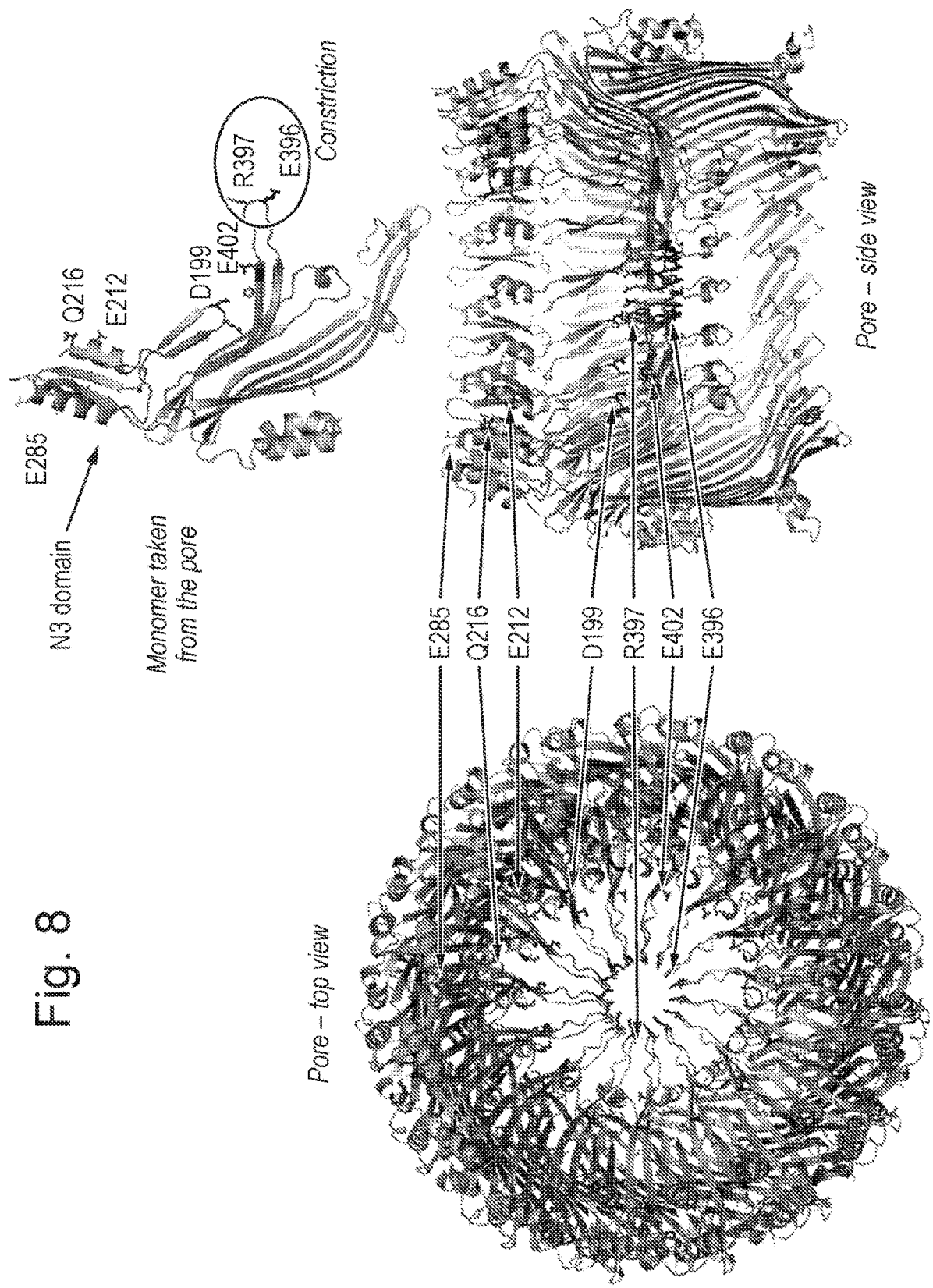
FIG. 8 shows the relative positions of the mutations as shown in FIG. 7 in an InvG nanopore. While the nanopore does not have N0 or N1 domains, the amino acid positions indicated in the figure are based on SEQ ID NO: 2.
Figure 9:
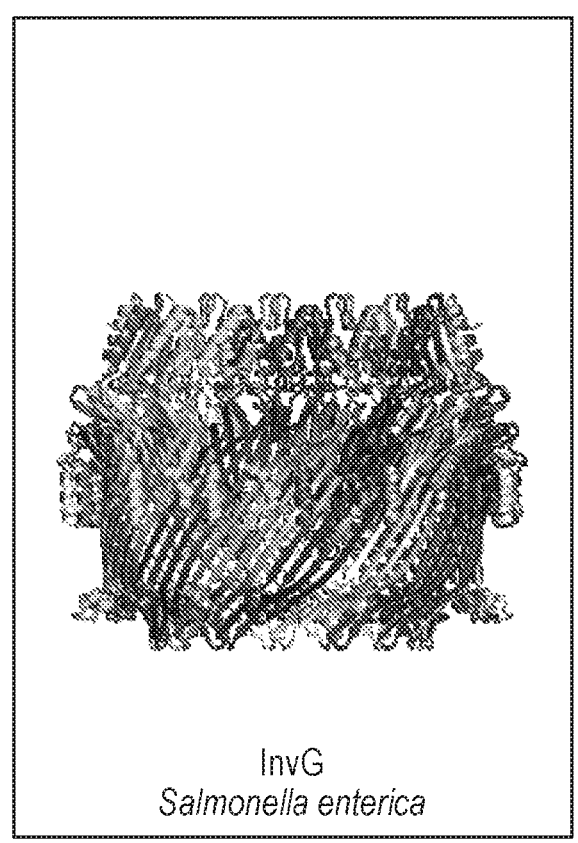
FIG. 9 shows the structural homology between GspD and InvG secretin nanopores.
Figure 9:
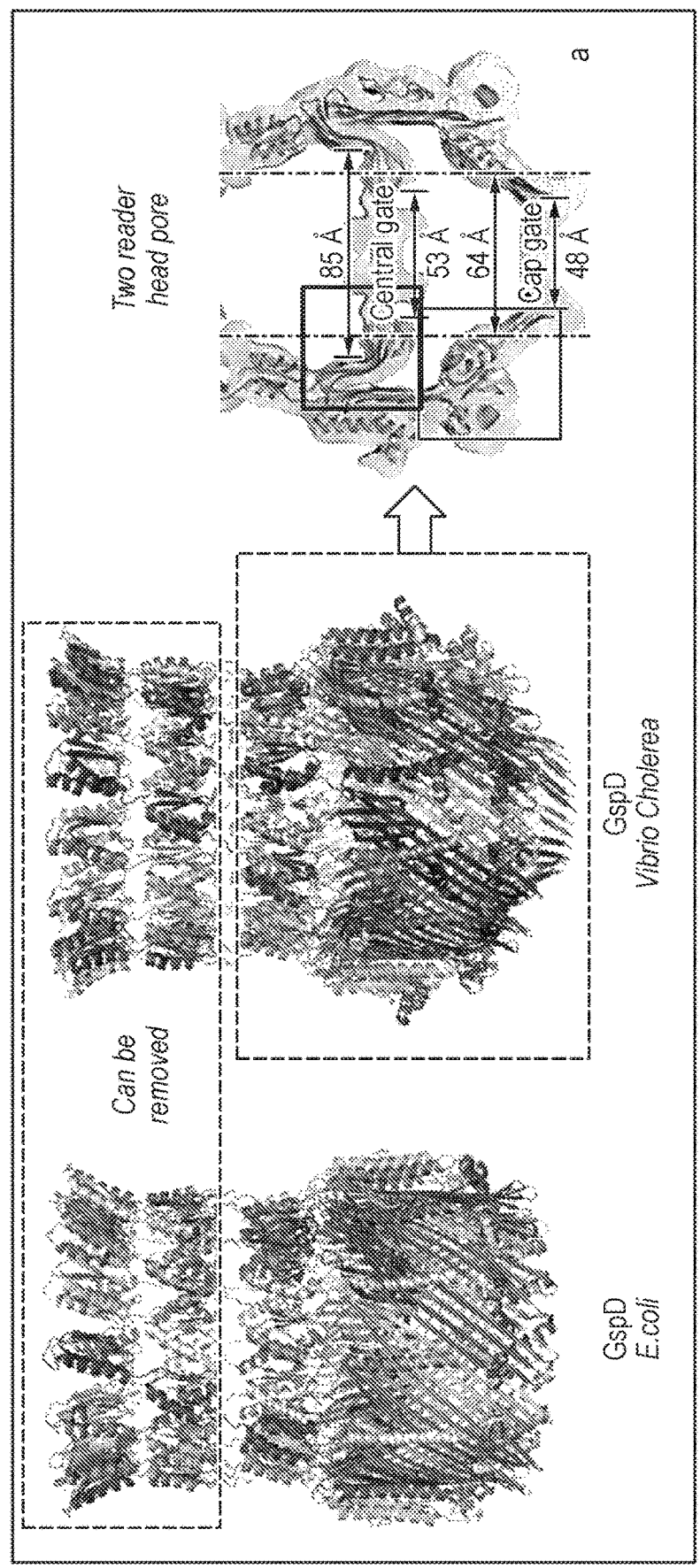

Some aspects of the present disclosure provide modified secretin nanopore subunit polypeptides. A modified secretin nanopore subunit polypeptide is a polypeptide whose sequence varies from that of a reference secretin amino acid sequence. The amino acid sequence of the modified secretin nanopore subunit polypeptide comprises (i) a cis opening-forming amino acid sequence, (ii) a lumen-forming amino acid sequence, and (iii) a trans opening-forming amino acid sequence. The cis opening-forming amino acid sequence is one or more portions of the amino acid sequence that forms part of a cis opening of a nanopore when the modified secretin nanopore subunit polypeptide interacts with other subunit polypeptides to form the nanopore in a membrane. The lumen-forming amino acid sequence is one or more portions of the amino acid sequence that forms part of a lumen of the nanopore when the modified secretin nanopore subunit polypeptides interacts with other subunit polypeptides to form the nanopore in a membrane. The trans opening-forming amino acid sequence is one or more portions of the amino acid sequence that forms part of a trans opening of a nanopore when the modified secretin nanopore subunit polypeptide interacts with other subunit polypeptides to form the nanopore in a membrane. Methods to identify portions of the secretin amino acid sequence that form the cis opening, lumen, and trans opening of a secretin nanopore are known in the art. For example, a nanopore, a portion of which is embedded into a membrane can be constructed by homology modelling from a known secretin structure using VMD, e.g., as described in Humphrey et al., "VMD: Visual Molecular Dynamics" J. Mol. Graphics (1996) 14: 33-38; and NAMD, e.g., as described in Phillips et al., "Scalable Molecular Dynamics with NAMD" J. Comput. Chem. (2005) 26: 1781-1802. See, e.g., FIG. 1D shows structures of GspD from *Vibrio cholerae* (PDB: 5wq8) and *E. coli* (PDB: 5wq7); and FIG. 8 shows a structure of an InvG nanopore and its different protein domains as well as the corresponding positions of example amino acid modifications within the lumen of the nanopore.

As used herein, the term "reference secretin amino acid sequence" refers to a known amino acid sequence of a secretin nanopore subunit. Various forms of secretin nanopore subunits are known in the art, including, e.g., but not limited to any secretin subunit of a type II, type III, or type IV secretion system. Non-limiting examples of a type II secretion system include GspD, PulD, and pIV. Examples of a type III secretion system include, but are not limited to InvG, MxiD, YscC, PscC, EscC, and SpiA. Non-limiting examples of a type IV secretion system include PilQ. A reference secretin amino acid sequence can be a known amino acid sequence of a member of a type II, type III, or type IV secretion system or a portion thereof. For example, a reference secretin amino acid sequence may be an amino acid sequence corresponding to at least a portion of wild type GspD, PulD, pIV, PilQ, InvG, MxiD, YscC, PscC, EscC, SpiA, ExeD or XcpQ wherein the portion comprises one or more of a secretin domain, a S domain, a N2 domain, a N3 domain and/or another related domain. For example, in some embodiments, the portion may comprise a secretin domain, a S domain, and a N3 domain. In some embodiments, the portion may comprise a secretin domain, a S domain, a N3 domain, and a N2 domain. In some embodiments, the portion may comprise a secretin domain and a S domain. Different domains of secretin nanopores are known in the art. For example, FIG. 1C shows different domains of an InvG from *Salmonella enterica* and GspD from *Vibrio cholerae*. In some embodiments, a reference secretin amino acid sequence may be an amino acid sequence corresponding to a full-length wild type GspD (e.g., as set forth in SEQ ID NO: 4, SEQ ID NO: 10, SEQ ID NO: 31 or SEQ ID NO: 37 (all including signal sequences), or SEQ ID NO: 32 (without leader peptide)), PulD (e.g., as set forth in SEQ ID NO: 11 or SEQ ID NO: 40), pIV, PilQ (e.g., as set forth in SEQ ID NO: 12), InvG (e.g., as set forth in SEQ ID Nos: 2 and 13-30), MxiD (e.g., as set forth in SEQ ID NO: 6), YscC (e.g., as set forth in SEQ ID NO: 5), PscC (e.g., as set forth in SEQ ID NO: 7), EscC (e.g., as set forth in SEQ ID NO: 8), SpiA (e.g., as set forth in SEQ ID NO: 9), ExeD (e.g. as set forth in SEQ ID NO: 38), or XcpQ (e.g. as set forth in SEQ ID NO: 39) as known in the art. In some embodiments, a reference secretin amino acid sequence may be an amino acid sequence as set forth in SEQ ID Nos. 1-40. In some embodiments, a reference secretin amino acid sequence may be an amino acid sequence of a wild-type InvG nanopore subunit polypeptide or a mutant thereof, e.g., as described in Worrall et al. "Near-Atomic-Resolution Cryo-EM analysis of the *Salmonella* T3S Injectisome Basal Body" Nature (2016) 540: 597-601. In some embodiments, a reference secretin amino acid sequence may be an amino acid sequence of a GspD nanopore subunit polypeptide or a mutant thereof, e.g., as described in Yan et al. "Structural insights into the secretin translocation channel in the type II secretion system" Nature Structural & Molecular Biology (2017) doi:10.1038/nsmb.3350. Any natural secretin sequences or variant thereof that are known in the art can be used as a reference secretin amino acid sequence.

In some embodiments, the reference secretin amino acid sequence may be an amino acid sequence corresponding to the secretin domain, secretin and S domains, or secretin, S and N3 domains of the secretin, such as wild type GspD (e.g., as set forth in SEQ ID NO: 36, SEQ ID NO: 35 or SEQ ID NO: 33) or an amino acid sequence corresponding to the secretin, S and N3 domains of GspD in which the constriction site in the N3 domain is deleted or substituted (e.g., as set forth in SEQ ID NO: 34). Any natural truncated secretin sequences or variants thereof that form a pore can be used as a reference secretin amino acid sequence.

Figure 1B:
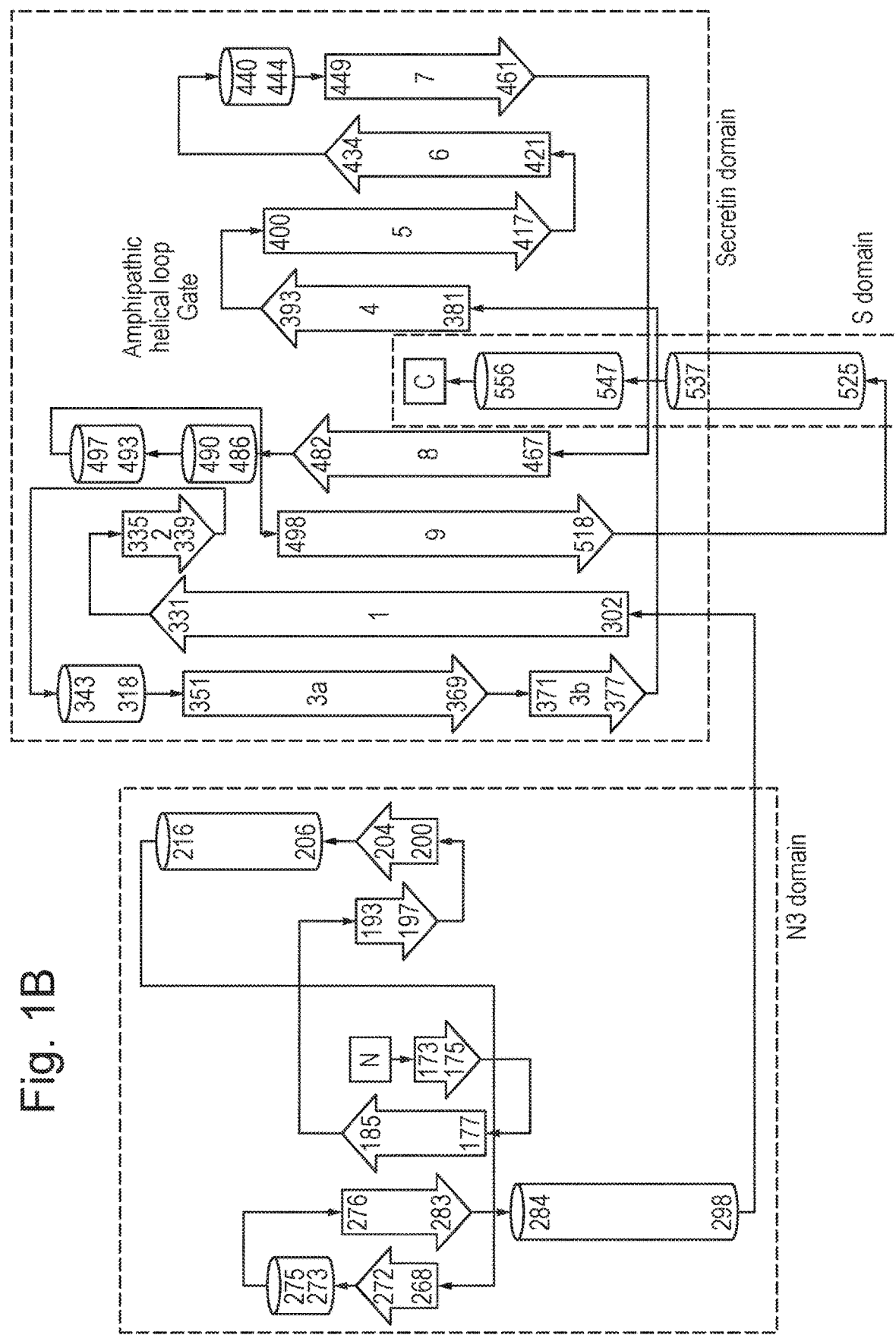
FIG. 1B shows secondary structure topology of a wild-type InvG$_{172-557}$ secretin. β-strands of the secretin domain are numbered, with 1, 3a/3b, 8 and 9 forming the outer β-barrel; 4-7 forming the inner β-barrel; and 1, 2 and 3a forming the lip of the β-barrel. Strand 3 is broken into 3a and 3b by the conserved residue Pro371. The numerical values indicated at both ends of each domain define the first and last amino acid positions of the domain based on SEQ ID NO: 2.

Accordingly, in some embodiments, a modified secretin nanopore subunit polypeptide has an amino acid sequence that is different from an amino acid sequence of any natural secretin, for example any of the reference secretin amino acid sequences (e.g., any of SEQ ID NOs: 1-40) and comprises one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications relative to the selected natural secretin, for example relative to any of the reference secretin amino acid sequence (e.g., relative to any one of SEQ ID NOs: 1-40). For example, a modified secretin nanopore subunit polypeptide may comprise an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to an amino acid sequence of a natural secretin, for example, any of the reference secretin amino acid sequence (e.g., any of SEQ ID Nos: 1-40) or any structural or functional fragment thereof (e.g., any fragment, portion, or domain of a secretin described herein, e.g., any fragment, portion, or domain as illustrated in FIG. 1A or 1B), and includes at least one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications relative to a natural secretin, for example relative to a reference secretin (e.g., relative to any one of SEQ ID NOs: 1-40) or any structural or functional fragment thereof (e.g., any fragment, portion, or domain of a secretin described herein, e.g., any fragment, portion, or domain as illustrated in FIG. 1A or 1B). The amino acid modification(s) can be selected, for example, to promote membrane integration, promote oligomerization, promote subunit synthesis, promote nanopore stability, promote analyte capture, promote analyte release, promote analyte translocation through a nanopore, improve analyte detection or signal quality, facilitate polymer analysis (e.g., polynucleotide sequences), etc. In some embodiments, the amino acid modification(s) may comprise modification(s) to promote analyte capture into a nanopore, to promote analyte translocation through a nanopore, and/or to improve analyte detection such as to improve signal quality. Examples of such amino acid modification(s) include but are not limited to positively-charged substitutions and hydrophobic amino acid substitutions as described herein.

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). Sequence identity may be determined by using a pairwise sequence alignment. Global alignment techniques such as the Needleman-Wunsch algorithm, or local alignment methods such as the Smith-Waterman algorithm may be used to determine sequence alignments. Various techniques exist to determine structural homology such as DALI, a distance matrix alignment for constructing structural alignments http://ekhidna.biocenter.helsinki.fi/dali_server/start or SSAP (sequential structure alignment program), a dynamic programming-based method of structural alignment. An example of the latter is CATH http://www.cathdb.info/.

In some embodiments, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence corresponding to at least a portion of wild-type InvG secretin comprising the secretin domain, S domain, and N3 domain. In some embodiments, the InvG secretin can be obtained from any species, including, e.g., but not limited to bacteria such as *Salmonella, Chromobacterium, Burkholderia, Providencia, Pseudogulbenkiania, Escherichia, Shigella, Stenotrophomonas, Pseudomonas, Yersinia, Arsenophonus, Pantoea*, and *Enterobacter*. The amino acid sequences of a full-length InvG secretin (including N0 and N1 domains) from different species are set forth in SEQ ID Nos: 2 and 13-32 and 37-40. In one embodiment, the InvG secretin can be obtained from *Salmonella*. For example, in some embodiments, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 1, which corresponds to the wild-type InvG secretin from *Salmonella* without N1 or N0 domain; and includes at least one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications (e.g., as described herein) relative to the amino acid sequence as set forth in SEQ ID NO: 1. Alternatively, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 2, which corresponds to the wild-type full-length InvG secretin; and includes at least one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications (e.g., as described herein) relative to the amino acid sequence as set forth in SEQ ID NO: 2. Without wishing to be bound by theory, removing the N1 and N0 domain of InvG secretin can improve signal-to-noise ratio of the modified secretin nanopores when they are used for detecting or characterizing an analyte, e.g., a target polynucleotide or polypeptide.

In some embodiments, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence corresponding to at least a portion of a wild-type GspD secretin comprising the secretin domain, S domain, and N3 domain. In some embodiments, the GspD secretin can be obtained from any species, including, e.g., but not limited to bacteria such as *Vibrio, Escherichia, Aeromonas, Pseudomonas*, and *Klebsiella*. The amino acid sequences of a full-length GspD secretin (including N0 and N1 domains) from different species are set forth in SEQ ID Nos: 4, 10, 31, 32 and 37). In one embodiment, the GspD secretin can be obtained from *Vibrio cholerae*. For example, in some embodiments, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 32, 33, 34, 35 or 36. The modified secretin nanopore may comprise a subunit polypeptide having an amino acid sequence that corresponds to the amino acid sequence as set forth in SEQ ID NO: 32, 33, 34, 35 or 36 and includes at least one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications (e.g., as described herein) relative to the amino acid sequence as set forth in SEQ ID NO: 32, 33, 34, 35 or 36. Alternatively, the GspD secretin can be obtained from *E. coli*, or the type II secretin can be PulD, e.g. from *Klebsiella oxytoca*, XcpQ, e.g. from *Pseudomonas aeruginosa*, or ExeD, e.g. from *Aeromonas hydrophila*. For example, in some embodiments, the modified secretin nanopore may comprise a subunit polypeptide having an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in the mature portion of SEQ ID NO: 37, 38, 39 or 40, the N3, secretin and S domains of the amino acid sequences set forth in SEQ ID NO: 37, 38, 39 or 40, the secretin and S domains of the amino acid sequences set forth in SEQ ID NO: 37, 38, 39 or 40, or the secretin domain of the amino acid sequences set forth in SEQ ID NO: 37, 38, 39 or 40. The modified secretin nanopore may comprise a subunit polypeptide having an amino acid sequence that corresponds to the amino acid sequence as set forth in SEQ ID NO: 32, 33, 34, 35 or 36 and includes at least one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40) amino acid modifications (e.g., as described herein) relative to the amino acid sequence as set forth in SEQ ID NO: 37, 38, 39 or 40, the N3, the secretin and S domains of the amino acid sequences set forth in SEQ ID NO: 37, 38, 39 or 40, the secretin and S domains of the amino acid sequences set forth in SEQ ID NO: 37, 38, 39 or 40, or the secretin domain of the amino acid sequences set forth in SEQ ID NO: 37, 38, 39 or 40. The amino acids of the N3, secretin and S domains in these SEQ ID NOs can be determined by aligning the sequence with SEQ ID NO: 31 (as in the supplementary notes to Yan et al. "Structural insights into the secretin translocation channel in the type II secretion system" Nature Structural & Molecular Biology (2017) doi:10.1038/nsmb.3350).

FIG. 1B shows the secondary structure topology of the wild-type InvG secretin from positions 172-557 of SEQ ID NO: 2, where the numbered domains correspond to β-strands and the regions between two numbered domains (shown as a line with an arrowhead in FIG. 1B) correspond to loop regions. By way of example only, domain 4 (amino acids 381-393) and domain 5 (amino acids 400-417) correspond to β strands, and the region (amino acids 393-400) between the domains 4 and 5 corresponds to a loop region.

FIG. 1I shows the secondary structure topology of the wild-type GspD secretin (SEQ ID NO: 32), showing the β-strands, α-helicies and loop regions.

FIG. 1C shows the secondary structure topologies of a wild-type InvG secretin and a wild-type GspD secretin from *Vibrio cholerae* (from positions 97-646 of SEQ ID NO: 10, or from SEQ D NO: 32). In the *Vibrio cholerae* GspD amino acid sequence shown in SEQ ID NO: 32, amino acids 1 to 99 form the N0 domain, amino acids 100 to 163 form the N1 domain, amino acids 164 to 238 form the N2 domain, amino acids 239 to 314 form the N3 domain, amino acids 317 to 588 form the secretin domain and amino acids 589 to 650 form the S domain.

Figure 11:
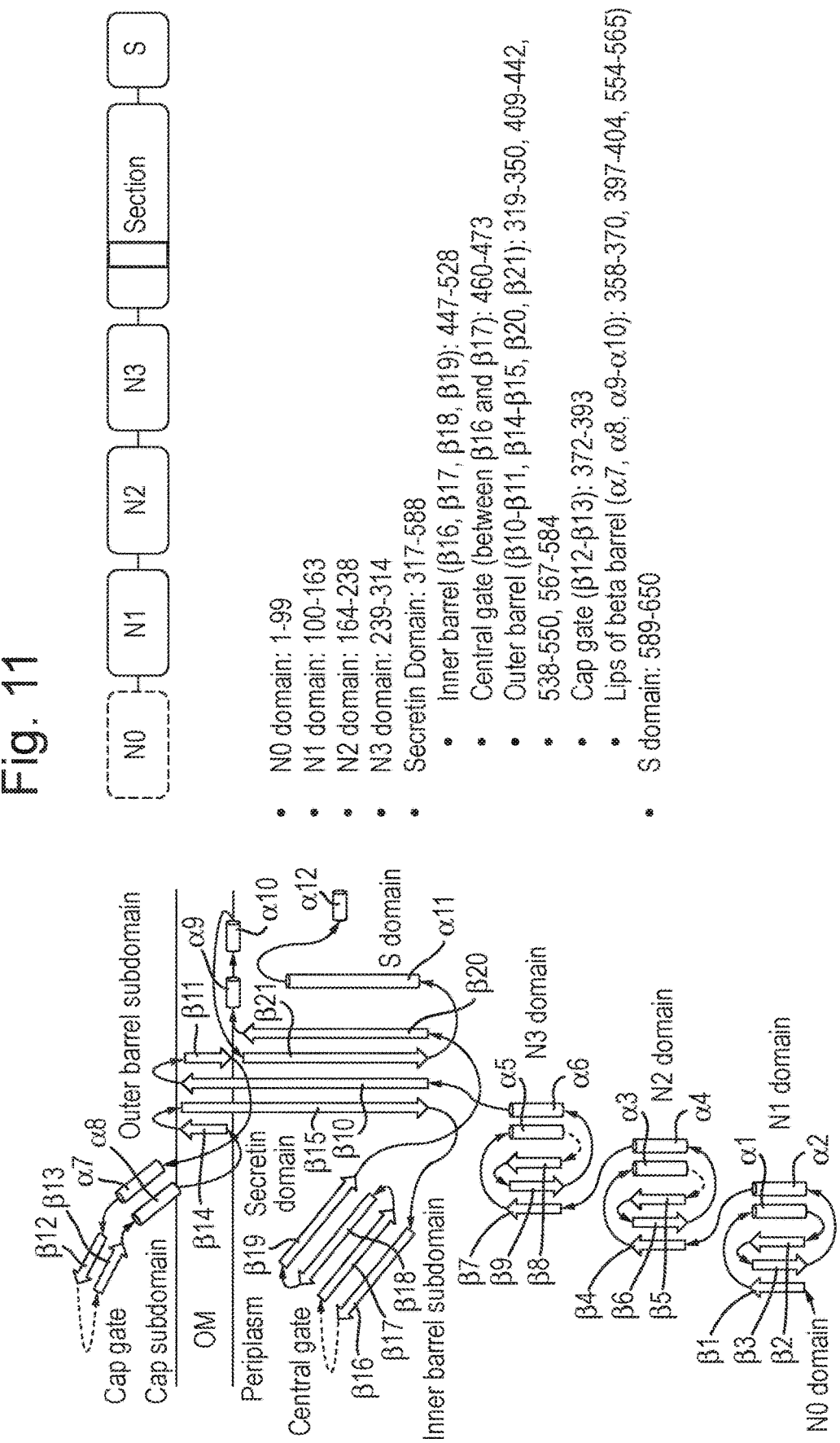
FIG. 11 shows the domain structure of GspD from *Vibrio cholerae*. The amino acid positions indicated in the figure are based on SEQ ID NO: 32.
Figure 12:
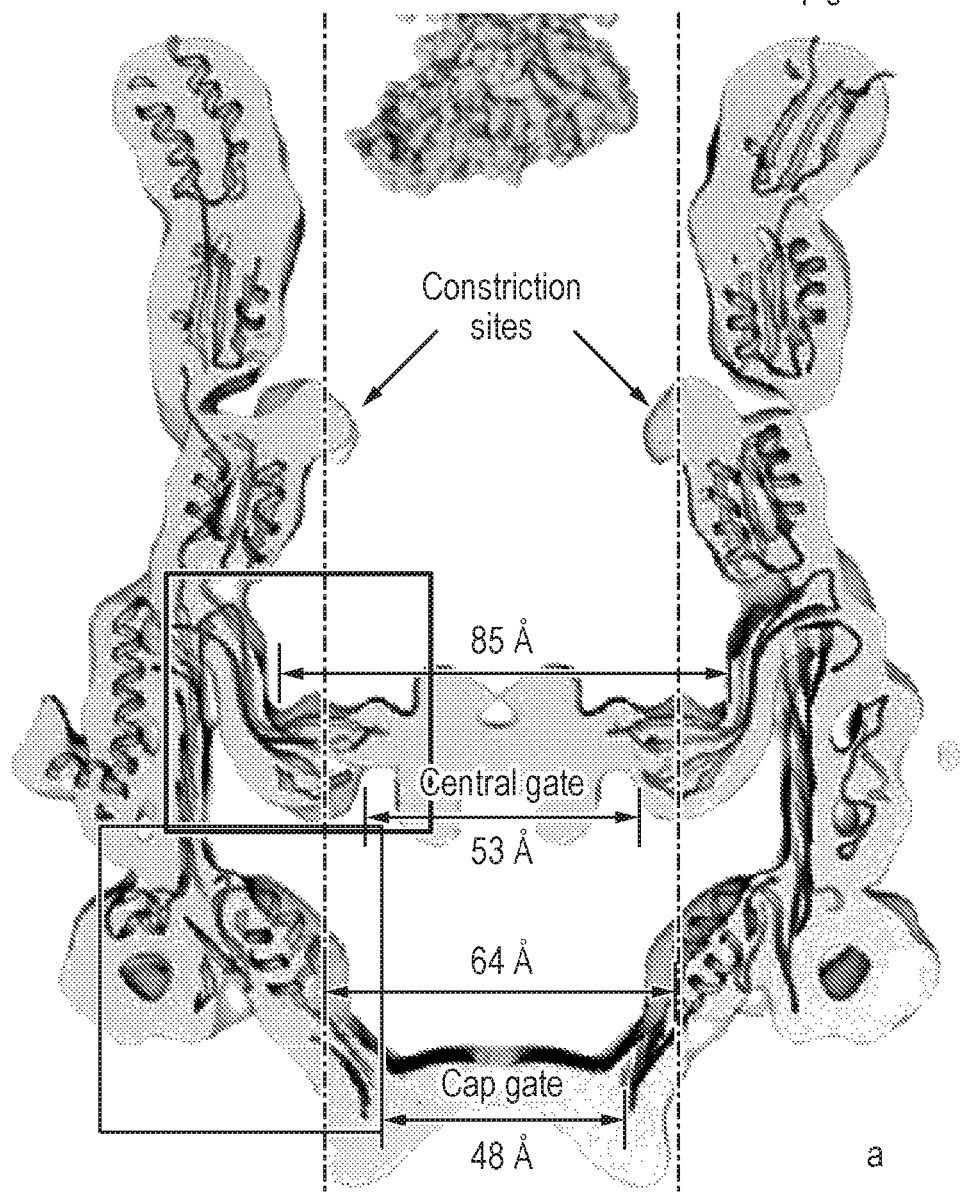
FIG. 12 shows the structure of GspD from *Vibrio cholerae* and highlights the positions of the N3 constriction site and the cap and central gates. The amino acid positions indicated in the figure are based on SEQ ID NO: 32.
Figure 13:
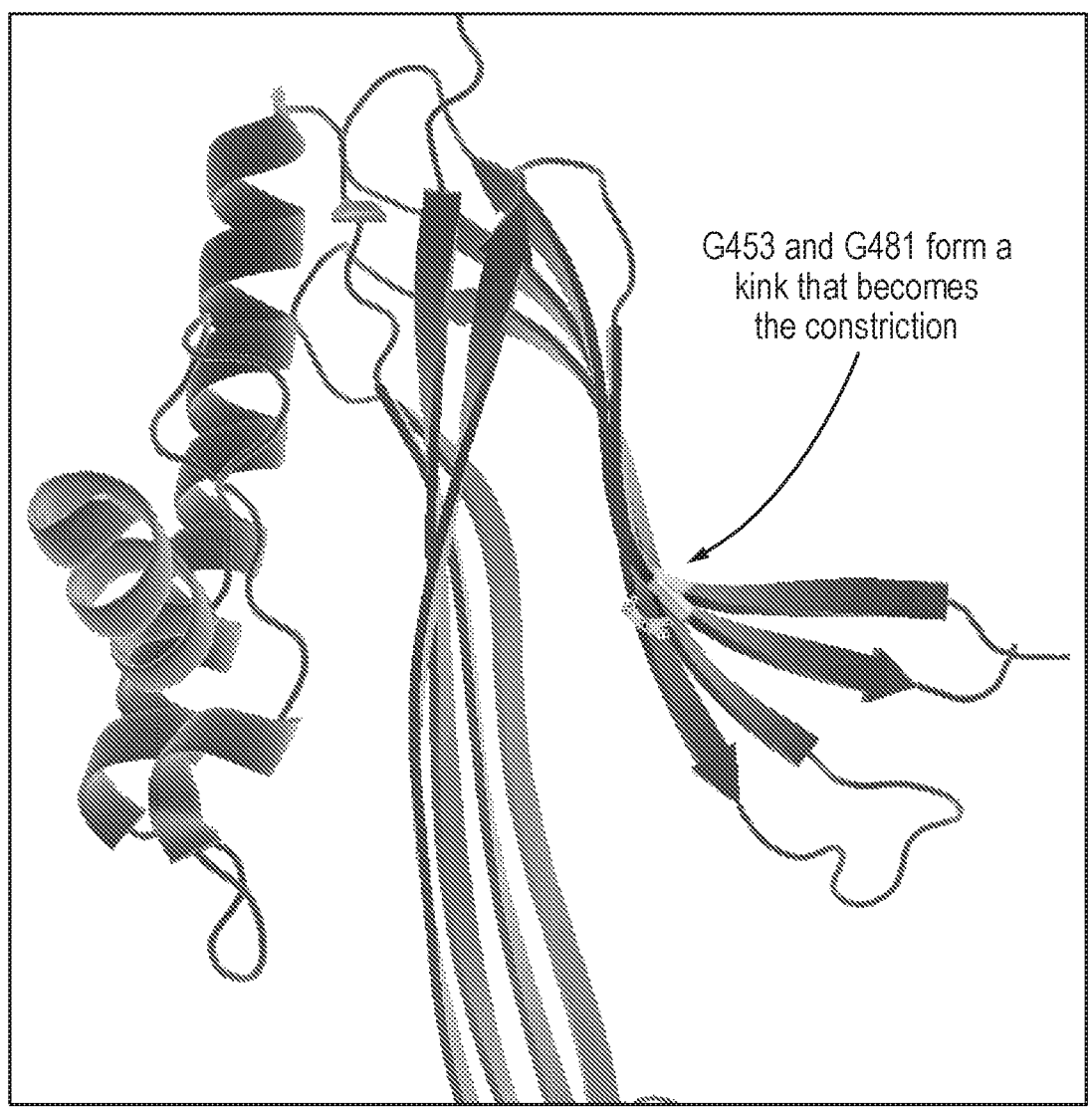
FIG. 13 shows the kink formed by G453 and G481 in the amino acid sequence of GspD from *Vibrio cholerae*.
Figure 14A:
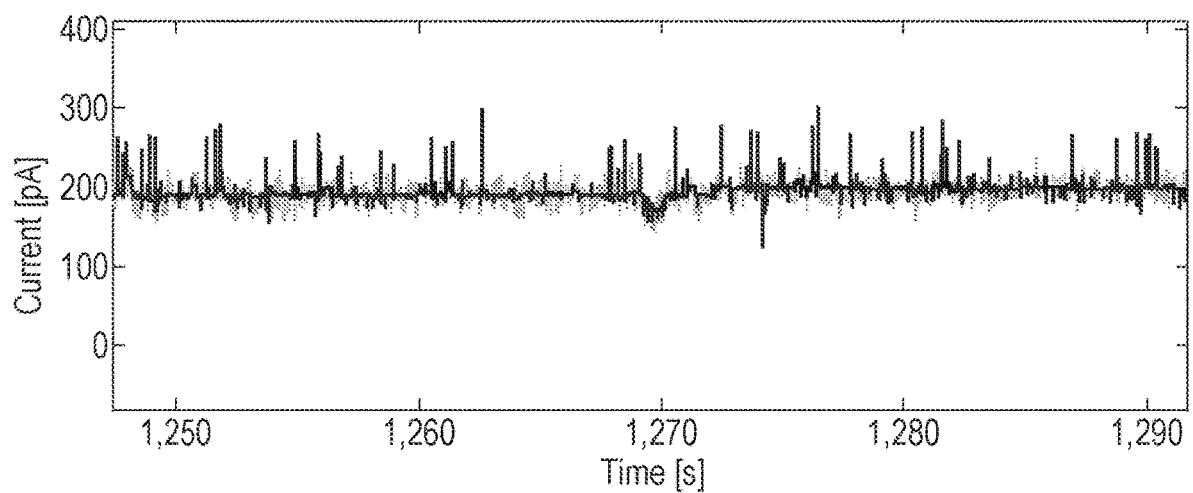
FIG. 14 shows electrophysiological characteristics of the GspD-Vch-(WT-del(1-239)/(265-282)-H6(C) mutant which was used as a baseline. A) Open pore current at −180 mV in 500 mM KCl, 25 mM Phosphate buffer, pH 7. B) IV curve ranging from −25 mV to −200 mV and 25 mV to 200 mV in 25 mV alternating potential steps.
Figure 14B:
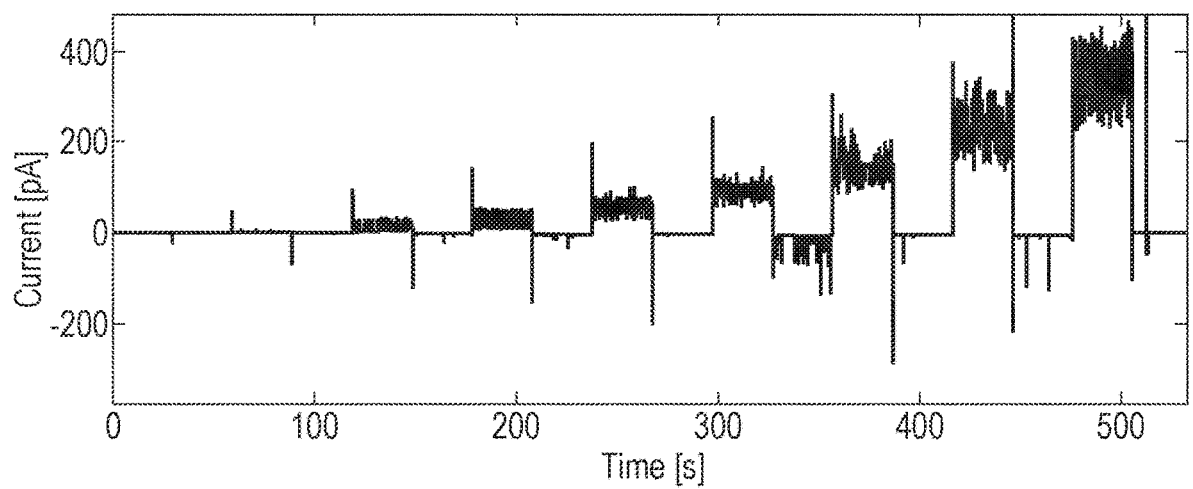
Figure 15A:
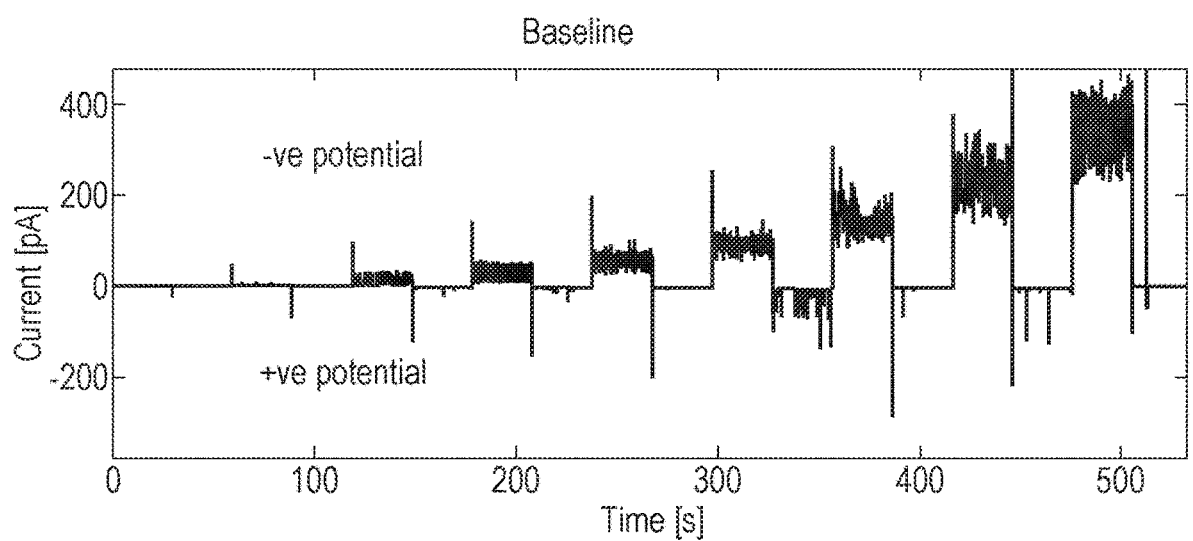
FIG. 15 shows IV characteristics of different GspD mutants ranging from −25 mV to −200 mV and 25 mV to 200 mV in 25 mV alternating potential steps. A) GspD-Vch-(WT-del(1-239)/(265-282)-H6(C). B) GspD-Vch-(WT-Del((N1-K239)/(N265-SGS-E282)/(Y379-GSG-R387)). C) GspD-Vch-(WT-F472A-Del((N1-K239)/(N265-SGS-E282))). D) GspD-Vch-(WT-D469S-Del((N1-K239)/(N265-SGS-E282))). E) GspD-Vch-(WT-N467G/N468S-Del((N1-K239)/(N265-SGS-E282))). F) GspD-Vch-(WT-N467S/N468G-Del((N1-K239)/(N265-SGS-E282))). G) GspD-Vch-(WT-N467G/N468S/D469S-Del((N1-K239)/(N265-SGS-E282))).
Figure 15B:
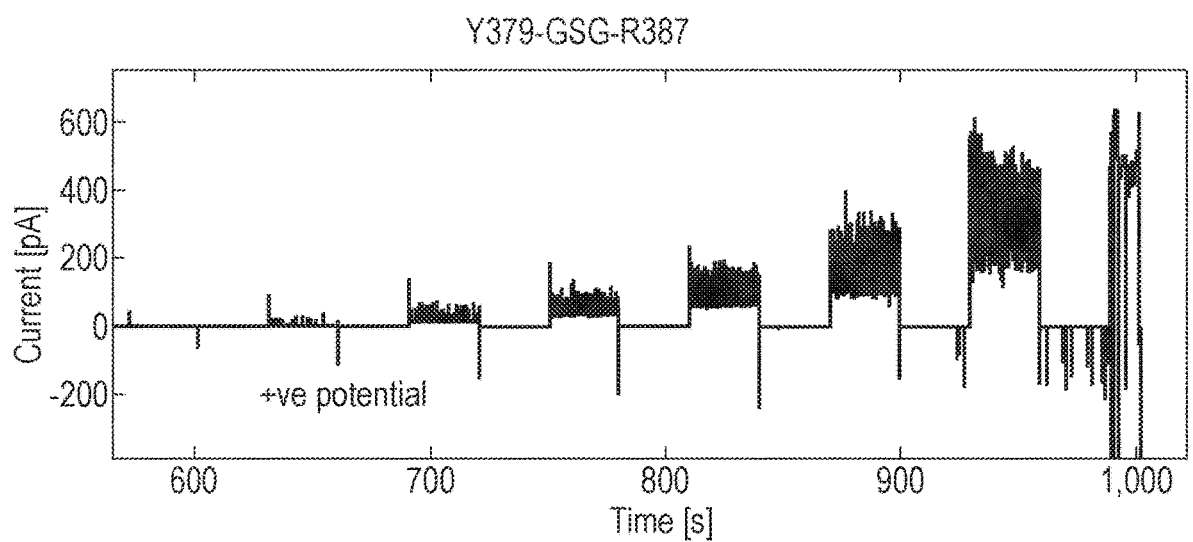
Figure 15E:
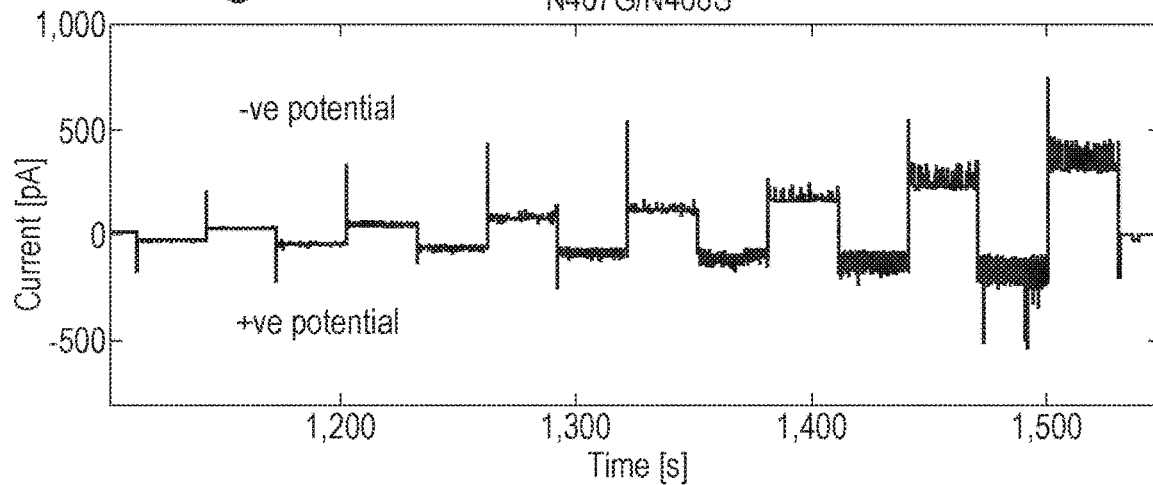
Figure 15F:
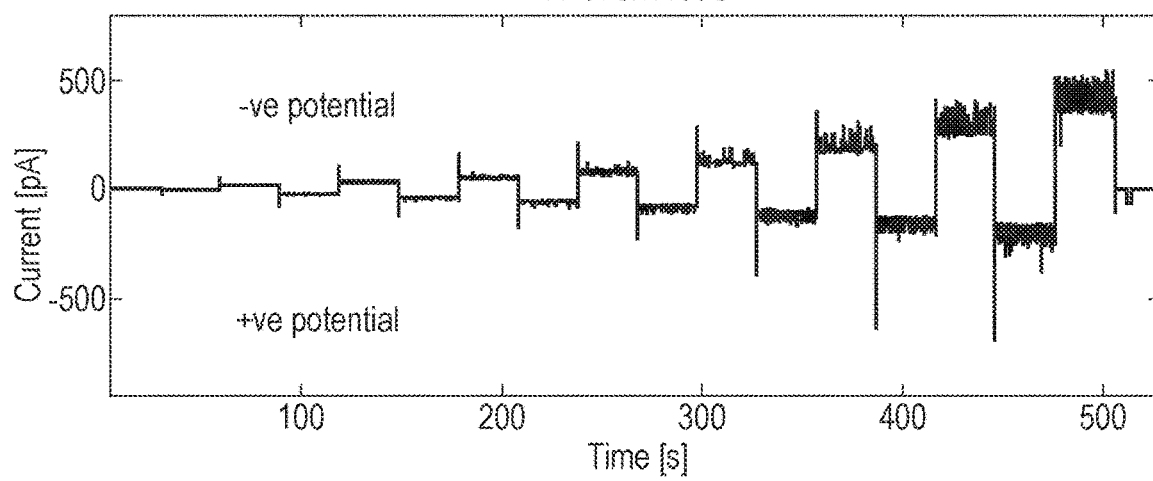
Figure 15G:
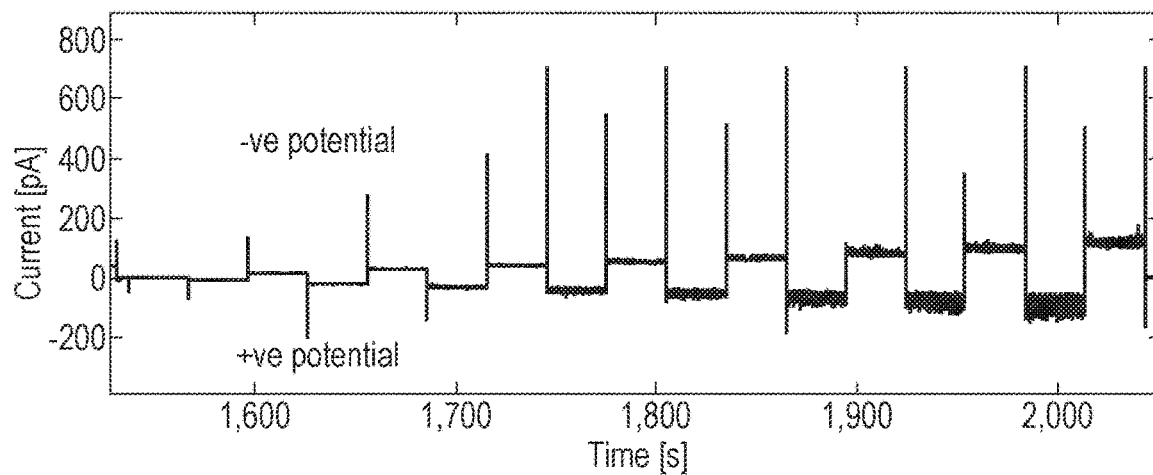
Figure 16A:
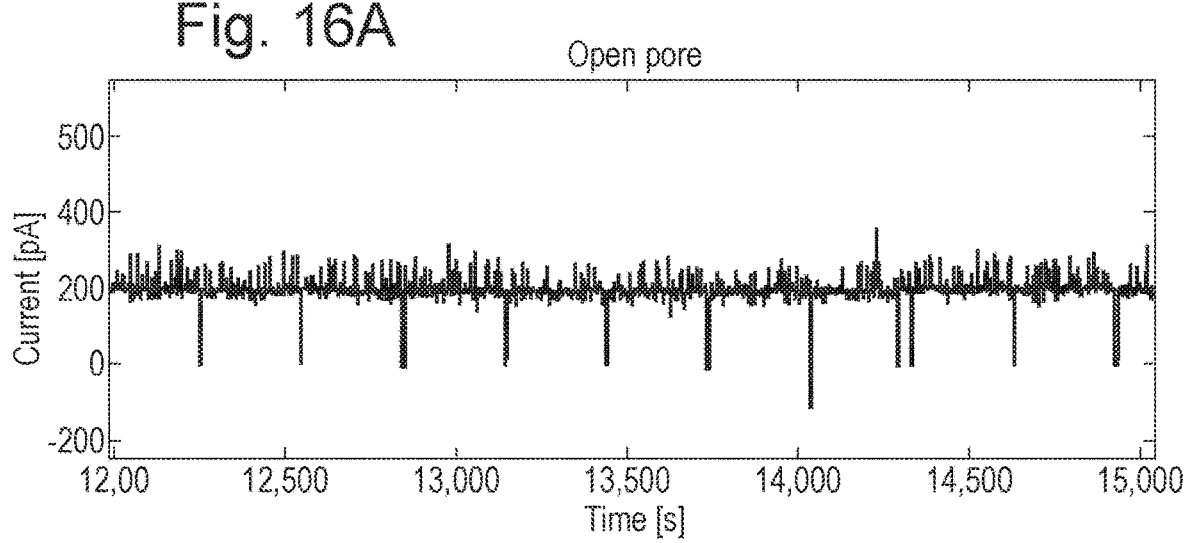
FIG. 16 shows DNA translocation through the GspD-Vch-(WT-del(1-239)/(265-282)-H6(C) mutant. A) Open pore current at −180 mV in 470 mM KCL, 25 mM HEPES, 11 mM ATP and 10 mM MgCl$_2$, pH8.0. B) Addition of Lambda 3.6 kb DNA ligated to adapter shows clear noisy patterns in the current trace. There is an increase in current spikes when DNA is inside the pore. C) Zoomed in image of the noisy pattern show a drop in open pore current which is the DNA translocating through the pore.
Figure 16B:
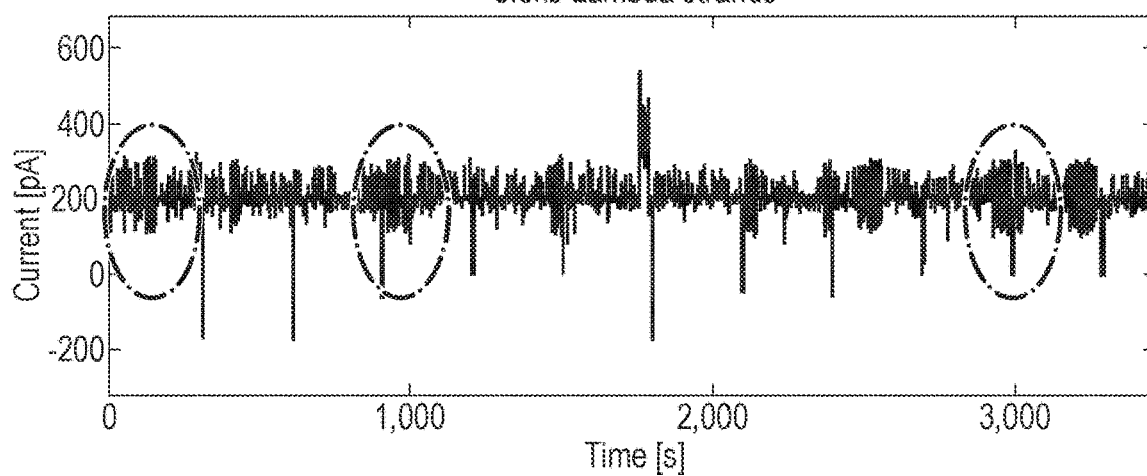
Figure 16C:
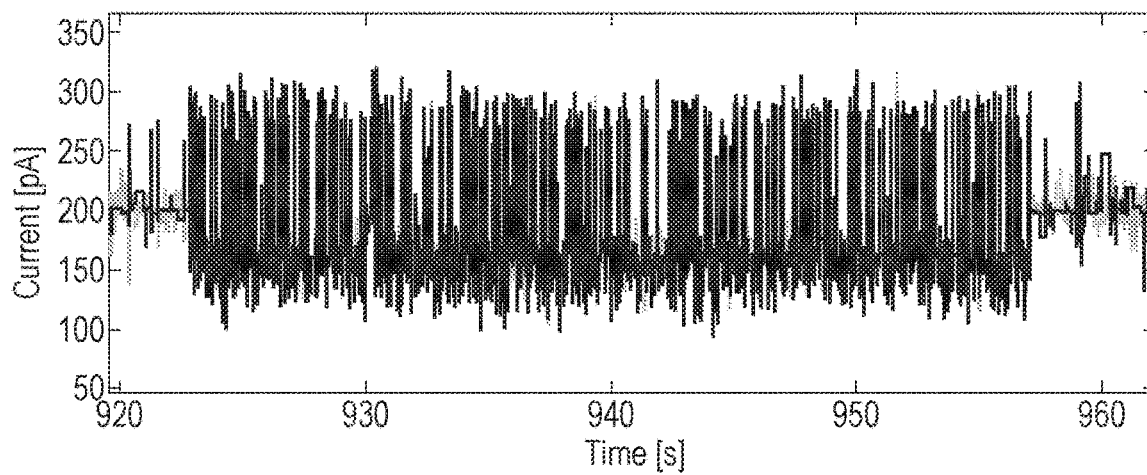
Figure 17A:
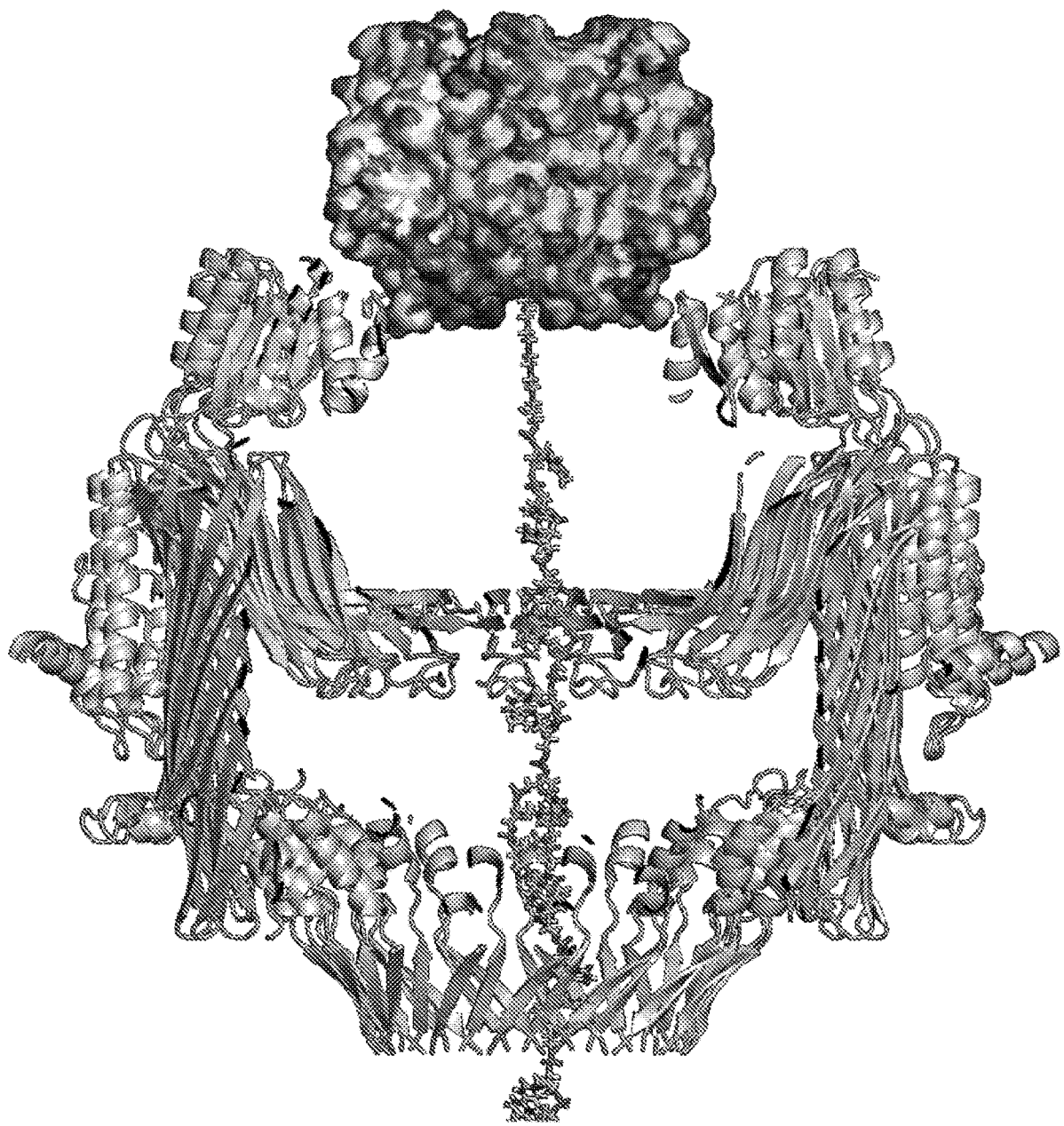
FIG. 17 is a model of biotinylated static strands bound monovalent streptavidin inside the GspD pore. A) Streptavidin molecule in top of the pore. B) Streptavidin molecule inside the pore above the constriction gate.
Figure 17B:
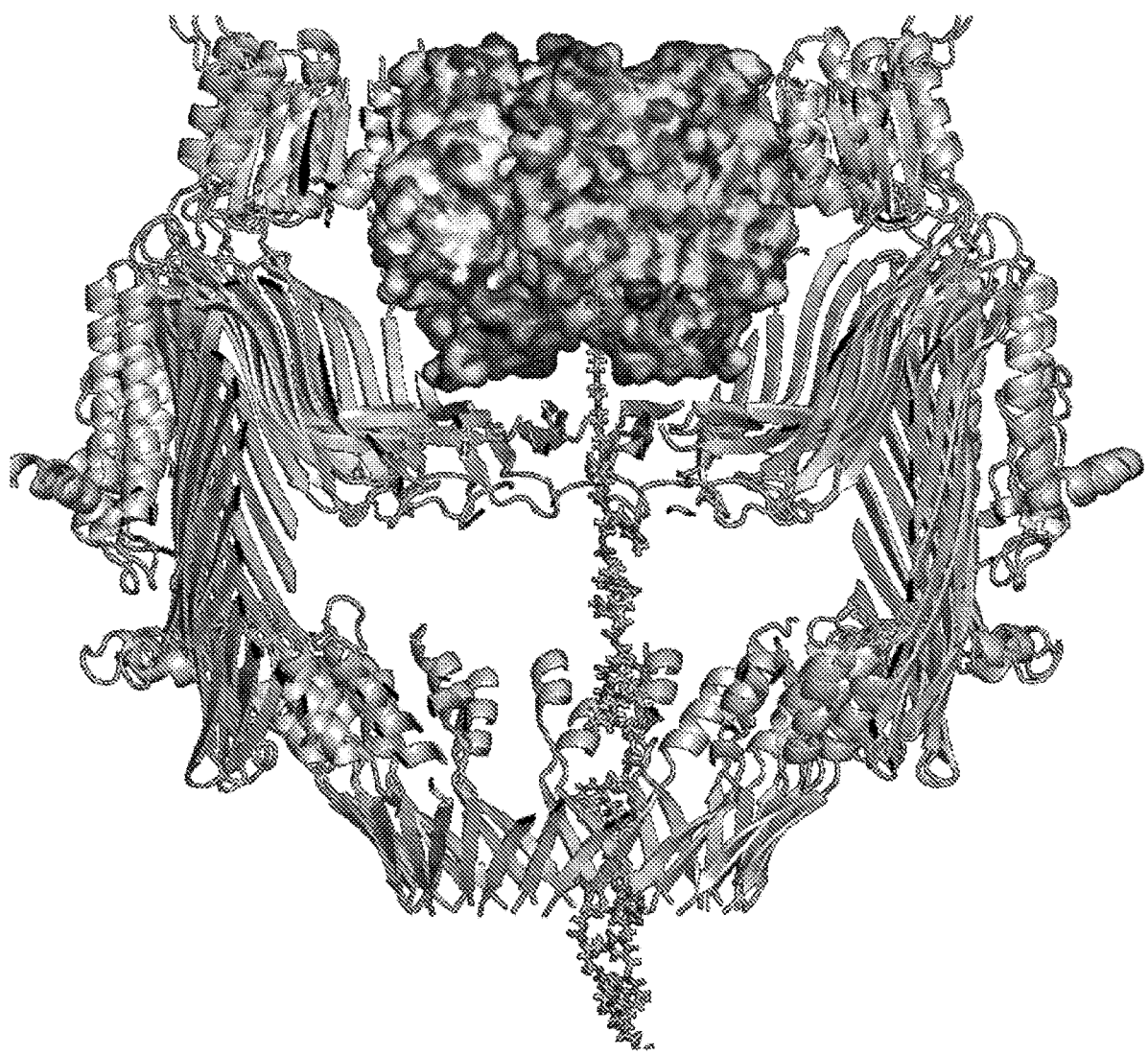
Figure 18A:
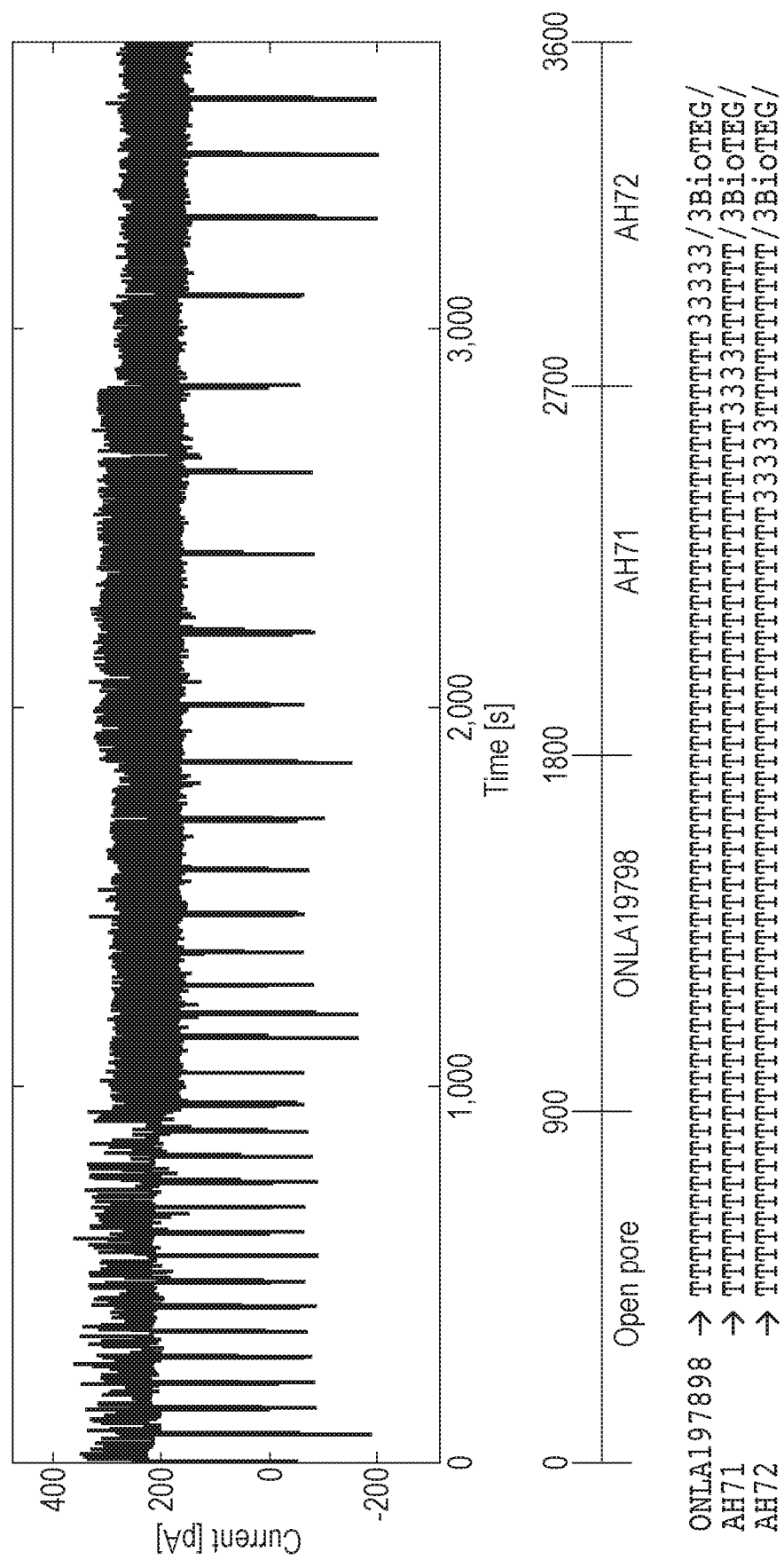
FIG. 18 shows the capture of streptavidin bound biotinylated static strands by the GspD-Vch-(WT-N467G/N468S-Del ((N1-K239)/(N265-SGS-E282))). A) Static strands experiment run for 1 hour in single GspD pore starting with control open pore experiment for 15 minutes and flushing three static strands, ONLA19798, AH71 and AH72 respectively after 15 minutes through the chip. B) Open pore control trace with current around 250 pA. C) Addition of ONLA19798 shows the capture of static strand from the open pore instantly. D) Addition of AH71 shows the capture of static strand from the open pore. E) Addition of AH72 also shows the capture of static strand.
Figure 18B:
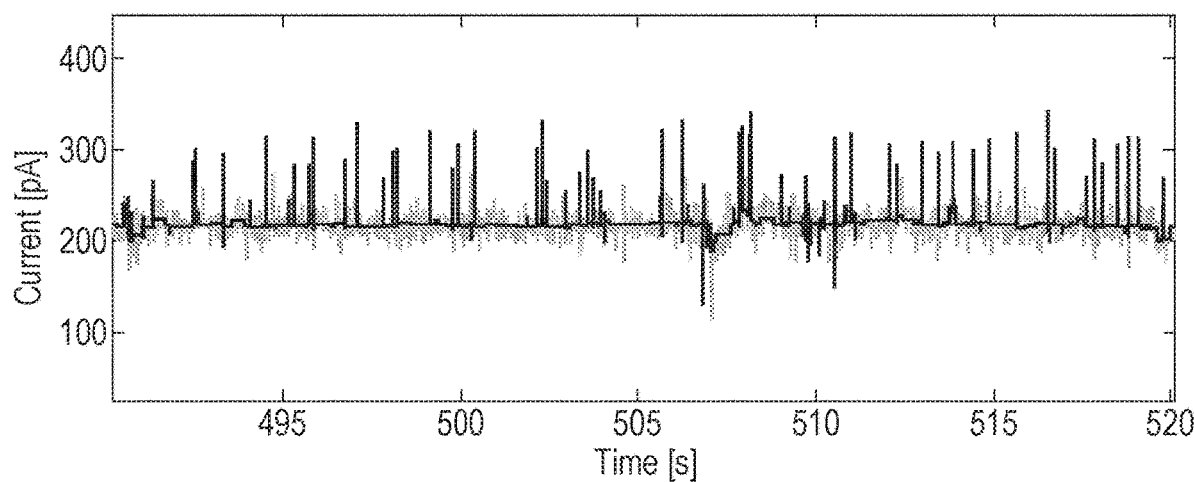
Figure 18C:
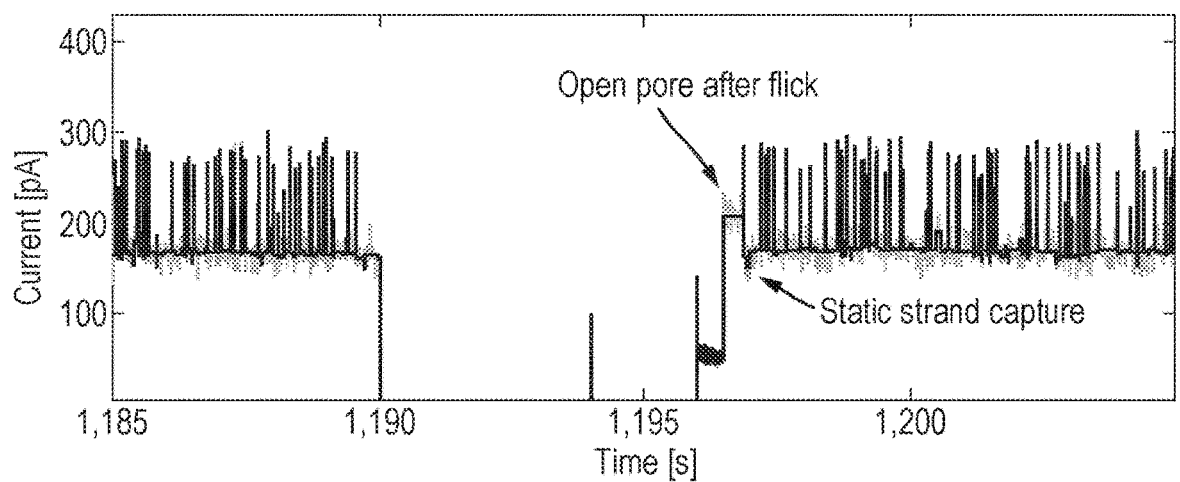
Figure 18D:
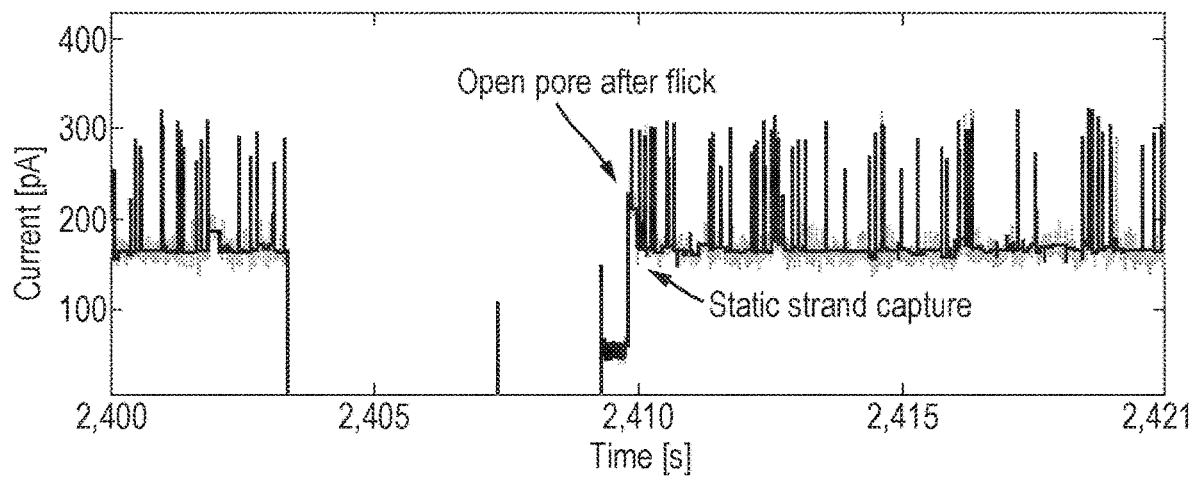
Figure 18E:
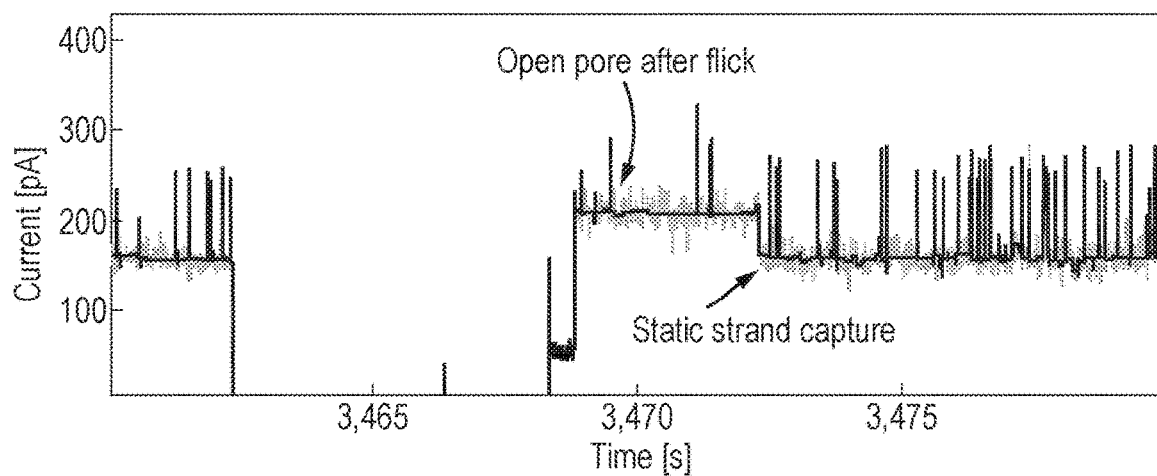

In some embodiments, one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, 3, or 4) β-strands of the secretin domains that form the outer β-barrel ("outer β-barrel-forming domains"), e.g., domains numbered 1, 3a/3b, 8, and 9 as shown in FIG. 1B, or β10, β11, β14, β15, β20 and β21 as shown in FIG. 11. In some embodiments, one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, 3, or 4) loop regions between the outer β-barrel-forming domains, for example, as shown in FIG. 1B or FIG. 11. In some embodiments, at least one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, 3, or 4) β-strands of the secretin domains that form the inner β-barrel, ("inner β-barrel-forming domains"), e.g., domains numbered 4, 5, 6, and 7 as shown in FIG. 1B, or β16, β17, β18 and β19 as shown in FIG. 11. In some embodiments, one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, 3, or 4) loop regions between the inner β-barrel-forming domains. For example, in some embodiments, one or more amino acid modifications (e.g., 1, 2, 3, 4, 5, 6, 7, or 8 amino acid modifications) can be made to the loop region between the inner β-barrel-forming domains 4 and 5 as shown in FIG. 1B. For example, in some embodiments, one or more amino acid modifications (e.g., 1, 2, 3, 4, 5, 6, 7, or 8 amino acid modifications) can be made to the loop region between the inner β-barrel-forming β16 and β17 that forms the central gate as shown in FIG. 11.

In some embodiments, at least one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, or 3) domains that form the lips of the β-barrel ("β-barrel lip-forming domains"), e.g., domains numbered 1, 2, and 3a as shown in FIG. 1B, or β12, β13, α7, α8 in FIG. 11, which correspond to the β-strands that form the trans-opening portion of the modified secretin nanopore described herein. In some embodiments, one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more (e.g., 1, 2, 3, or 4) loop regions between the β-barrel lip-forming domains. For example, in some embodiments, one or more amino acid modifications (e.g., 1, 2, 3, 4, or 5 amino acid modifications) can be made to the loop region (amino acids 331-335) between the β-barrel lip-forming domains 1 and 2 as shown in FIG. 1B or the loop between β12 and β13 (cap gate) in FIG. 11, which forms at least part of the trans-opening of the modified secretin nanopore described herein.

In some embodiments, one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more β-strands and/or loop regions within the N3 domain as defined in FIG. 1B or FIG. 11. For example, in some embodiments, one or more amino acid modifications (e.g., 1, 2, 3, 4, or 5 amino acid modifications) can be made to the loop region defined by amino acids 216-268 of SEQ ID NO: 2. For example, in some embodiments, one or more amino acid modifications (e.g., 1, 2, 3, 4, or 5 amino acid modifications) can be made to the constriction site in the N3 domain of GspD (e.g. amino acids N265 to E282 in SEQ ID NO: 32).

In some embodiments, at least one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) can be made to one or more β-strands and/or loop regions within the S domain as defined in FIG. 1B or FIG. 11.

Accordingly, in some embodiments, the modified nanopore secretin nanopore may comprise a subunit polypeptide having (i) outer β-barrel-forming domains of InvG or GspD secretin and/or loop regions there between; (ii) inner β-barrel-forming domains of InvG or GspD secretin and/or loop regions there between; (iii) β-barrel lip-forming domains of InvG or GspD secretin and/or loop regions there between, (iv) S domain of InvG or GspD secretin and/or loop regions there between; and (v) N3 domain of InvG or GspD secretin and/or loop regions there between, in which the β-strands and/or loop regions may have different numbers and/or types of amino acid modifications, e.g., depending on their locations within the nanopore and/or its degree of interaction with an analyte and/or an enzyme. For example, the amino acid sequence of each of the outer β-barrel-forming domains and/or loop regions there between may be each independently at least about 50% (including, e.g., at least about 55%, at least about 60%, at least about 65%, at least about 70%, at least about 75%, at least about 80%, at least about 85%, at least about 90%, at least about 95%, or higher, including 100%) identical to the amino acid sequence of the corresponding domain as set forth in SEQ ID NO: 2, or SEQ ID NO: 4, 32 or 37. The amino acid sequence of each of the inner β-barrel-forming domains and/or loop regions there between may be each independently at least about 50% (including, e.g., at least about 55%, at least about 60%, at least about 65%, at least about 70%, at least about 75%, at least about 80%, at least about 85%, at least about 90%, at least about 95%, or higher, including 100%) identical to the amino acid sequence of the corresponding domain as set forth in SEQ ID NO: 2, or SEQ ID NO: 4, 32 or 37. The amino acid sequence of each of the β-barrel lip-forming domains and/or loop regions there between may be each independently at least about 50% (including, e.g., at least about 55%, at least about 60%, at least about 65%, at least about 70%, at least about 75%, at least about 80%, at least about 85%, at least about 90%, at least about 95%, or higher, including 100%) identical to the amino acid sequence of the corresponding domain as set forth in SEQ ID NO: 2, or SEQ ID NO: 4, 32 or 37. The amino acid sequence of each domain within the S domain and/or loop regions there between may be at least about 50% (including, e.g., at least about 55%, at least about 60%, at least about 65%, at least about 70%, at least about 75%, at least about 80%, at least about 85%, at least about 90%, at least about 95%, or higher, including 100%) identical to the amino acid sequence of the corresponding domain as set forth in SEQ ID NO: 2, or SEQ ID NO: 4, 32 or 37. The amino acid sequence of each domain within the N3 domain and/or loop regions there between may be at least about 50% (including, e.g., at least about 55%, at least about 60%, at least about 65%, at least about 70%, at least about 75%, at least about 80%, at least about 85%, at least about 90%, at least about 95%, or higher, including 100%) identical to the amino acid sequence of the corresponding domain as set forth in SEQ ID NO: 2, or SEQ ID NO: 4, 32 or 37. Each domain may have different percentages of amino acid identity provided that the resulting modified domain does not adversely affect the capture and/or translocation of an analyte through the lumen of the modified nanopore. For example, in some embodiments, the outer β-barrel forming domains may permit a larger number of amino acid mutations that result in less than 80% or lower (including, e.g., less than 70%, less than 60%, less than 50%, less than 40%, less than 30%, or lower) amino acid identity to the amino acid sequence of the corresponding domain as set forth in SEQ ID NO: 2, or SEQ ID NO: 4, 32 or 37, while the inner β-barrel forming domains maintain a higher amino acid identity, for example, the amino acid sequence of the inner β-barrel forming domains may be each independently at least about 80% or higher (including at least about 85%, at least about 90%, at least about 95% or higher, including 100%). In some embodiments, at least one loop region of the N3 domain (e.g., a loop region defined by amino acids 216-268 of SEQ ID NO: 2, or SEQ ID NO: 4, 32 or 37) may permit a larger number of amino acid mutations (e.g., to improve enzyme/nanopore interaction) that result in less than 80% or lower (including, e.g., less than 70%, less than 60%, less than 50%, less than 40%, less than 30%, or lower) amino acid identity to the amino acid sequence of the corresponding domain as set forth in SEQ ID NO: 2, or SEQ ID NO: 4, 32 or 37, while the inner β-barrel forming domains maintain a higher amino acid identity, for example, the amino acid sequence of the inner β-barrel forming domains may be each independently at least about 80% or higher (including at least about 85%, at least about 90%, at least about 95% or higher, including 100%).

One of ordinary skill in the art will readily recognize that various types of modifications to the secretin nanopores as described herein (e.g., but not limited to amino acid modifications to different domains of secretin nanopores) can be applied to any other secretin nanopores that have a high structural homology to secretin nanopores as described herein. By way of example only, SEQ ID Nos: 4 and 37, and 10, 31 and 32 relate to GspD from *Escherichia coli* and *Vibrio cholerae*, respectively. The sequence identity between SEQ ID NO: 4 and SEQ ID NO: 10, for example, is 41.6%, the sequence identity between the secretin domains of SEQ ID NO: 4 and SEQ ID NO: 10, for example, is 44.2% and the similarity is 62.7% as calculated by pairwise alignment using the EMBOSS Needle nucleotide alignment algorithm provided by EMBL-EBI http://www.ebi.ac.uk/Tools/psa/emboss_needle/nucleotide.html. While the sequence identities between the two structures may be low, they share a high structural homology because they both have similar structural domains, including, e.g., secretin domain, S domain, N3 domain, N2 domain, and N1 domain.

Truncated secretin subunit polypeptides that lack the N-terminal domains are capable of forming pores. Therefore the modified secretin nanopore of the invention is, in some embodiments, a truncated secretin nanopore. The truncated secretin nanopore may typically comprise an N3 domain, a secretin domain and an S domain, a secretin domain and an S domain, or a secretin domain.

Thus, in some embodiments, the secretin nanopore subunit polypeptide comprises a secretin domain comprising a beta barrel forming domain comprising an inner barrel forming subdomain and an outer barrel forming subdomain, each subdomain being composed of β-sheets, the outer barrel typically comprising about six β-sheets and/or the inner barrel typically comprising about four β-sheets. The outer beta barrel may further comprise two α-helices, typically between two of the β-sheets, for example as shown in FIG. 11. In a secretin nanopore, the outer barrel typically spans the membrane and the inner barrel typically abuts the lumen of the pore. The inner barrel typically comprises a central gate. The central gate is typically a loop between two β-sheets that form the inner barrel. The central gate typically extends into the pore to narrow the size of the pore. The central gate can be modified by altering amino acids present in the central gate loop as described herein to alter the properties of the pore. The central gate may be flexible, for example the central gate may be capable of opening. The central gate may be rigid to maintain a constant constriction size, e.g. the central gate loop may be closed or partially closed. The beta barrel of the secretin nanopore may also comprise lips, wherein a first lip protrudes from the membrane on the opposite side of the membrane to the inner beta barrel. The second lip may be on the other side of the inner beta barrel to the first lip. The first lip of the beta barrel is typically composed of two α-helicies and two β-sheets. The β-sheets may be joined by a loop region that forms a cap gate, or the loop joining the β-sheets may be short and not form a gate. The cap gate may be flexible, for example the cap gate may be capable of opening. The cap gate may be rigid to maintain a constant constriction size, e.g. the cap gate may be closed or partially closed. In some embodiments, the first lip of the beta barrel may comprise no β-sheets and comprise two α-helicies that are joined by a loop. In these embodiments the subunit polypeptide forms a nanopore which does not comprise a cap gate. The second lip of the beta barrel may comprise two α-helicies.

In some embodiments, the secretin nanopore subunit polypeptide may, in addition to the secretin domain, comprise an S domain. The S-domain may comprise two α-helices. One of the α-helices typically interacts with the beta-barrel of the secretin nanopore. The S-domain is typically located on the outside of the pore (i.e. away from the lumen of the pore).

Figure 6:
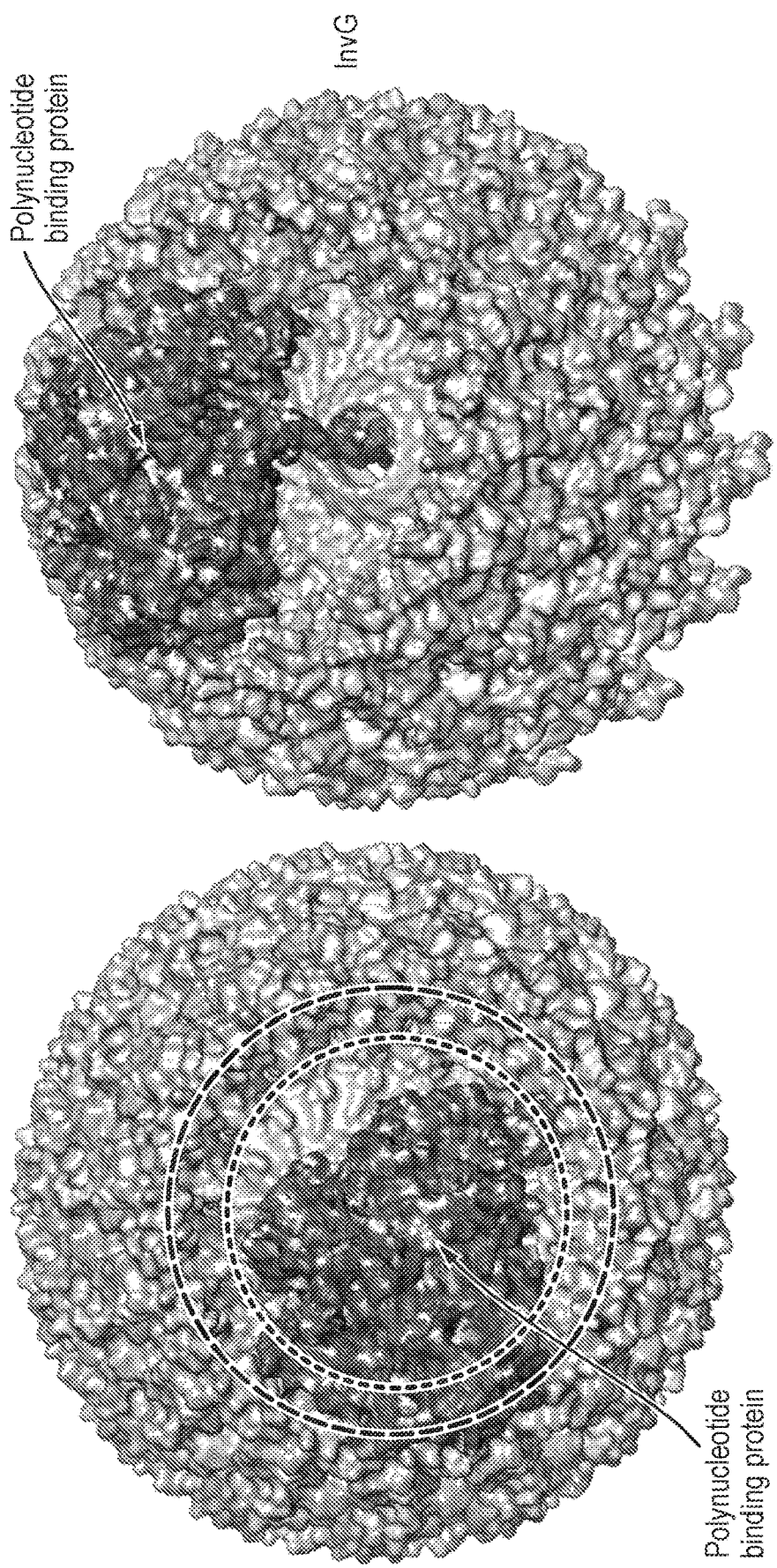
FIG. 6 shows the top views (from different perspectives) of a polynucleotide binding protein (e.g., a DNA binding enzyme such as a helicase or polymerase) interacting with an InvG nanopore. In the left panel, the inner dotted line corresponds to the lower dotted line in the InvG (right panel) of FIG. 4 and the outer dotted line corresponds to the upper dotted line in the InvG (right panel) of FIG. 4.

In some embodiments, the secretin nanopore subunit polypeptide may, in addition to the secretin domain, and optionally the S domain, comprise an N3 domain. The N3 domain is typically composed of β-barrels and α-helicies, e.g. from 3 to 6 β-barrels and from 2 to 3 α-helicies, such as 3 β-barrels and 2 α-helicies as shown in FIG. 11 or 6 β-barrels and 3 α-helicies as shown in FIG. 1B. The N3 domain may form a constriction in the lumen of the pore. The N3 domain may be modified so that it does not constrict the pore. The N3 domain may be modified to increase or decrease the size of the constriction.

In some embodiments, the amino acid sequence of the modified secretin nanopore subunit polypeptide comprises one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) at positions within the lumen-forming amino acid sequence. The amino acid modifications are selected to provide improved frequency of capture and/or translocation of an analyte (e.g., a polynucleotide such as double stranded or single stranded DNA) through the nanopore, as compared to a reference secretin amino acid sequence.

In some embodiments, the amino acid modifications may be charge-altering modifications. In some embodiments, the amino acid modification is a positively-charged amino acid substitution. The term "positively-charged amino acid substitution" as used herein refers to a modification to a reference amino acid that increases the net positive charge, or decreases the net negative charge, of the reference amino acid, e.g., as detected at pH 7.0-8.0 (e.g., at pH 8.0) and at room temperature, e.g., at 20-25° C. For example, a positively-charged amino acid substitution can include, but is not limited to, (i) replacement of a negatively-charged amino acid with a less negatively charged amino acid, neutral amino acid, or positively-charged amino acid, (ii) replacement of a neutral amino acid with a positively-charged amino acid, or (iii) replacement of a positively charged amino acid with a more positively-charged amino acid. In some embodiments, a positively-charged amino acid substitution may include deletion of a negatively-charged amino acid or addition of a positively-charged amino acid. In some embodiments, a positively-charged amino acid substitution may include one or more chemical modifications of one or more negatively charged amino acids which neutralize their negative charge. For instance, the one or more negatively charged amino acids may be reacted with a carbodiimide.

A positively-charged amino acid is an amino acid having an isoelectric point (pI) that is higher than the pH of a solution so that the amino acid in the solution carries a net positive charge. For example, examples of a positively-charged amino acid as detected at pH 7.0-8.0 (e.g., at pH 8.0) and at room temperature, e.g., at 20-25° C., include, but are not limited to arginine (R), histidine (H), and lysine (K). A negatively-charged amino acid is an amino acid having a pI that is lower than the pH of a solution so that the amino acid in the solution carries a net negative charge. Examples of a negatively-charged amino acid as detected at pH 7.0-8.0 (e.g., at pH 8.0) and at room temperature, e.g., at 20-25° C., include, but are not limited to aspartic acid (D), glutamic acid (E), serine (S), glutamine (Q). A neutral amino acid is an amino acid having an isoelectric point (pI) that is same as the pH of a solution so that the amino acid in the solution carries no net charge. A neutral amino acid can be a polar, non-polar, or hydrophobic amino acid. The pI values of amino acids are known in the art. By comparing the pI value of an amino acid of interest to the pH of a solution, one of ordinary skill in the art will readily determine whether the amino acid present in the solution is a positively charged amino acid, a neutral amino acid, or a negatively-charged amino acid. An amino acid can be a naturally-occurring or synthetic amino acid.

In some embodiments, the amino acid modification may be a modification to change the hydrophobicity of the amino acid. Such a modification includes a modification to a reference amino acid that changes its hydrophobicity, e.g., as detected at pH 7.0-8.0 (e.g., at pH 8.0) and at room temperature, e.g., at 20-25° C. For example, the amino acid modification may be a substitution of a reference amino acid with a hydrophobic amino acid, e.g., an amino acid with a hydrophobic side chain. Examples of hydrophobic amino acids include glycine (G), alanine (A), valine (V), leucine (L), isoleucine (I), proline (P), phenylalanine (F), methionine (M), tyrosine (Y), and tryptophan (W). For example, the amino acid modification may be a substitution of a neutral amino acid with a hydrophobic amino acid. The hydropathy index of amino acids are known in the art. Hydrophobicity scales are values that define relative hydrophobicity of amino acid residues. The more positive the value, the more hydrophobic are the amino acids located in that region of the protein. An amino acid can be an naturally-occurring or synthetic amino acid.

In some embodiments, the amino acid modification may be a modification to change the size of the amino acid. Such a modification includes a modification to a reference amino acid that changes its size, e.g., the size of the side chain. For example, the amino acid modification may be a substitution of a reference amino acid having a large side chain with an amino acid having a smaller side chain. Examples of very large amino acids include phenylalanine (F), tryptophan (W) and tyrosine (Y). Examples of large amino acids include isoleucine (I), leucine (L), methionine (M), lysine (K) and arginine(R). Examples of medium sized amino acids include valine (V), histidine (H), glutamic acid (E) and glutamine (Q). Examples of small amino acids include cysteine (C), proline (P), threonine (T), aspartic acid (D) and asparagine (N). Examples of very small amino acids include serine (S), glycine (G) and alanine (A). For example, the amino acid modification may be a substitution of a very large amino acid with a large, medium, small or very small amino acid. For example, the amino acid modification may be a substitution of a large amino acid with a medium, small or very small amino acid. For example, the amino acid modification may be a substitution of a medium amino acid with a small or very small amino acid. The smaller amino acid can be an naturally-occurring or synthetic amino acid.

In some embodiments, the modified secretin nanopore subunit polypeptide is a modified InvG nanopore subunit polypeptide comprising an amino acid sequence that is at least about 40% (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 1 (corresponding to the amino acid sequence of InvG without N1 or N0 domain), wherein the modified InvG nanopore subunit polypeptide comprises one or more amino acid modifications (e.g., 1, 2, 3, 4, 5, 6, or 7 amino acid modifications) at amino acid(s) selected from D28, E41, E114, Q45, E225, R226, and E231 of SEQ ID NO: 1. The amino acid modification can be a positively-charged amino acid substitution or a modification to change the hydrophobicity of a reference amino acid. In some embodiments, the amino acid modification may comprises one or more (e.g., 1, 2, 3, 4, 5, or 6) of the following: (i) D28N/Q/T/S/G/R/K; (ii) E225 N/Q/T/A/S/G/P/H/F/Y/R/K; (iii) R226N/Q/T/A/S/G/P/H/F/Y/K/V; (iv) deletion of E225; (v) deletion of R226; and (vi) E231N/Q/T/A/S/G/P/H/R/K. In some embodiments, the modified InvG nanopore subunit polypeptide may comprise one or more amino acid modifications at amino acid(s) selected from Q45, E41, and E114 of SEQ ID NO: 1. For example, the modified InvG nanopore subunit polypeptide may comprise one or more (e.g., 1, 2, or 3) of the following amino acid modifications: (i) Q45R/K; (ii) E41N/Q/T/S/G/R/K; and (iii) E114N/Q/T/S/G/R/K of SEQ ID NO: 1. The "/" symbol between amino acids X and Y means that a reference amino acid may be modified to amino acid X or amino acid Y. It should be understood that the amino acid positions based on SEQ ID NO: 1 will shift accordingly if modifications (e.g., amino acid addition or deletion) are made to the N-terminus of or within the amino acid sequence as set forth in SEQ ID NO: 1. By way of example only, SEQ ID NO: 2 differs from SEQ ID NO: 1 in that the N-terminus of SEQ ID NO: 2 contains additional 171 amino acids that correspond to the N0 and N1 domains of an InvG nanopore, which are missing from the N-terminus of SEQ ID NO: 1. Thus, one of ordinary skill in the art will readily recognize that the amino acid positions D28, E41, E114, Q45, E225, R226, and E231 in SEQ ID NO: 1 correspond to amino acid positions D199, E212, E285, Q216, E396, R397, and E402 in SEQ ID NO: 2.

In some embodiments, the modified InvG nanopore subunit polypeptide comprises an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 1 and one or any combinations of the amino acid modifications as shown in FIG. 7. For example, in some embodiments, the modified InvG nanopore subunit polypeptide may comprise amino acid substitution E225N/Q/T/A/S/G/P/H/F/Y/R/K and deletion of R226 of SEQ ID NO: 1. In some embodiments, the modified InvG nanopore subunit polypeptide may comprise a deletion of E225 amino acid and amino acid substitutions E231N/Q/T/A/S/G/P/H/R/K and Q45R/K. It should be noted that the amino acid positions as shown in FIG. 7 (based on SEQ ID NO: 2) are adjusted to correspond to the amino acid positions in SEQ ID NO: 1. Methods of aligning two amino acid sequences are known in the art. Thus, one of ordinary skill in the art can readily identify the corresponding amino acid positions in SEQ ID NO: 1 based on the amino acid positions provided in SEQ ID NO: 2.

In some embodiments, the modified InvG nanopore subunit polypeptide comprises an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 2 and one or any combinations of the amino acid modifications as shown in FIG. 7.

In another aspect, provided herein is a modified secretin nanopore subunit polypeptide comprising an amino acid sequence that is at least 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence of a secretin nanopore subunit polypeptide, e.g., the amino acid sequence as set forth in SEQ ID NOs: 2, or 4-30 (corresponding to the amino acid sequence of wild-type (WT) secretin including N1 and N0 domains), wherein an endopeptidase cleavage site is inserted upstream of the N3 domain of the secretin nanopore subunit polypeptide. In some embodiments, the endopeptidase cleavage site is inserted between the N1 domain and N3 domain of the secretin nanopore subunit polypeptide (e.g., an InvG nanopore subunit polypeptide). In other embodiments, the endopeptidase cleavage site is inserted between the N1 domain and N2 domain (e.g., a GspD or PulD nanopore subunit polypeptide). Such a modified secretin nanopore subunit polypeptide allows removal of N1 and/or N0 domains using an endopeptidase that targets the corresponding endopeptidase cleavage site after expression of the polypeptide. For example, cleavage of N0 and N1 domains can be done by treating full length protein that are expressed and purified with an appropriate endopeptidase.

As used herein, the term "endopeptidase cleavage site" refers to a peptide sequence that is recognized and cleaved by an endopeptidase, which is a proteolytic enzyme that breaks or cleaves bonds of nonterminal amino acids (e.g., within the molecule). Various endopeptidases and their corresponding cleavage sites are known in the art. For example, such information can be assessed online at web.expasy.org/peptide_cutter/peptidecutter_enzymes.html. Non-limiting examples of endopeptidases include, but are not limited to, Trypsin, Chymotrypsin, Elastase, Thermolysin, Pepsin, Glutamyl endopeptidase, Neprilysin, Caspase 1-10, CNBr, Enterokinase, Proteinase K, Factor Xa Protease, Bovine Alpha Thrombin, and Tobacco Etch Virus (TEV) protease. In one embodiment, the endopeptidase cleavage site inserted into the modified secretin nanopore subunit polypeptide may be recognized by a TEV protease. TEV protease recognizes a linear epitope of the general form E-Xaa-Xaa-T-Xaa-Q-(G/S), with cleavage occurring between Q and G or Q and S. An exemplary TEV protease cleavage sequence may be ENLYFQG. In one embodiment, the endopeptidase cleavage site inserted into the modified secretin nanopore subunit polypeptide may be recognized by a Factor Xa Protease. Factor Xa cleaves after the arginine residue in its preferred cleavage site Ile-(Glu or Asp)-Gly-Arg. It will sometimes cleave at other basic residues, depending on the conformation of the protein substrate. In another embodiment, the endopeptidase cleavage site inserted into the modified secretin nanopore subunit polypeptide may be recognized by a bovine alpha thrombin. Thrombin recognizes the consensus sequence Leu-Val-Pro-Arg-Gly-Ser, cleaving the peptide bond between Arg and Gly.

In one aspect, provided herein is a modified InvG nanopore subunit polypeptide comprising an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 2 (corresponding to the amino acid sequence of WT InvG including N1 and N0 domains), wherein an endopeptidase cleavage site is inserted between positions 170 and 171 or 171 and 172 of SEQ ID NO: 2. In one embodiment, an endopeptidase cleavage site is inserted between D171 and G172 of SEQ ID NO: 2. Such a modified InvG nanopore subunit polypeptide allows removal of N1 and N0 domains using an endopeptidase that targets the corresponding endopeptidase cleavage site after expression of the polypeptide. Any appropriate endopeptidase cleavage site (e.g., as described herein) can be used. In one embodiment, the endopeptidase cleavage site inserted into the modified InvG nanopore subunit polypeptide may be recognized by a TEV protease. An exemplary TEV protease cleavage sequence may be ENLYFQG. Example 2 provides an exemplary method for expression and purification of a modified secretin nanopore subunit polypeptide comprising a TEV protease cleavage site.

In some embodiments, the modified InvG nanopore subunit polypeptide comprising an endopeptidase cleavage site may comprise one or more (e.g., 1, 2, 3, 4, 5, 6, or 7) of the amino acid modifications as shown in FIG. 7. For example, in some embodiments, the modified InvG nanopore subunit polypeptide may comprise amino acid substitution E396N/Q/T/A/S/G/P/H/F/Y/R/K and deletion of R397 of SEQ ID NO: 2. In some embodiments, the modified InvG nanopore subunit polypeptide may comprise a deletion of E396 amino acid and amino acid substitutions E402N/Q/T/A/S/G/P/H/R/K and Q216R/K.

For example, in one aspect the modified GspD secretin nanopore comprises a subunit polypeptide comprising a secretin domain having an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence of the secretin domain set forth in SEQ ID NO: 36.

The secretin domain of GspD from *Vibrio cholerae* and from *Escherichia coli* ETEC contain a cap gate. Other Type II secretion system subunit polypeptides, including some GspD secretin subunit polypeptides, such as *Escherichia coli* K12, do not comprise a cap gate. The modified GspD secretin nanopore may, in one aspect be one that does not comprise a cap gate. The secretin domain set in out SEQ ID NO: 36 comprises a cap gate between positions 56 and 77. For example, the secretin domain set forth in SEQ ID NO:

36 may be modified to delete all or part of the cap gate, e.g. all or some of the amino acids from D55 or T56 to T77 of SEQ ID NO: 36 may be deleted or substituted. Alternatively, the modified GspD secretin nanopore may naturally lack a cap gate.

The central gate of GspD may be modified to replace an amino acid with an amino acid having a smaller side group and/or to replace a negatively charged amino acid with a neutral or positively charged amino acid. The secretin domain set in out SEQ ID NO: 36 comprises a central gate between positions 144 to 157, which correspond to positions 460 and 473 of SEQ ID NO: 32. The secretin domain of the modified GspD secretin nanopore may comprise a secretin domain having an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to an amino acid sequence as set forth in SEQ ID NO: 36, wherein: (i) all or some of the amino acids from D55 or T56 to T77 are deleted or substituted, one or more of K60, D64, R71 and E73 is substituted with an uncharged amino acid and/or one or more of D55, T56, T77 and K78 is substituted with P; and/or (ii) F156 is substituted with a smaller amino acid, N151 and/or N152 is/are substituted with a smaller amino acid, D153 is substituted with an uncharged amino acid, G137 and G165 are each independently unmodified or substituted with A or V. For example, in the modified secretin GspD nanopore Y63 to R71 may deleted and/or substituted with GSG or SGS, F156 may be substituted with A, D153 may be substituted with S, and/or N151 and N152 may each independently be substituted with G or S. D55, T56, K60, Y63, D64, R71, E73, T77, K78, G137, N151, N152, D153, F156 and G165 of SEQ ID NO: 36 correspond to D371, T372, K376, Y379, D380, R387, E389, T393, K394, G453, N467, N468, D469, F472 and G481 of the full length GspD amino acid sequence set forth in SEQ ID NO: 32.

The modified secretin GspD nanopore may comprise a modified secretin domain as defined above with reference to SEQ ID NO 36, an N3 domain and an S domain. The modified secretin GspD nanopore may in one aspect comprises a subunit polypeptide comprising an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to the amino acid sequence as set forth in SEQ ID NO: 33, 34 and/or or 35. SEQ ID NO: 35 comprises a secretin domain and an S domain. SEQ ID NO: 34 comprises a secretin domain, an S domain and a modified N3 domain. SEQ ID NO: 34 comprises a secretin domain, an S domain and an N3 domain. The amino acid modifications referred to with reference to SEQ ID NO: 36 may be made at the corresponding positions of any one of SEQ ID NOs: 31 to 35. The amino acid modifications referred to with reference to SEQ ID NO: 36 may also be made at the corresponding positions of any one of SEQ ID NOs: 4 and 37 to 40, or to a truncated subunit polypeptide comprising a portion of any one of SEQ ID NOs: 4 and 37 to 40, e.g. a truncated subunit polypeptide comprising the secretin domain, secretin and S domains or secretin, S and N3 domains of any one of SEQ ID NOs: 4 and 37 to 40.

For example, the secretin domain of the modified GspD secretin nanopore may comprise a secretin domain having an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to an amino acid sequence as set forth in SEQ ID NO: 34, wherein: (i) all or some of the amino acids from D117 or T118 to T139 are deleted or substituted, one or more of K122, D126, R133 and E135 is substituted with an uncharged amino acid and/or one or more of D117, T118, T139 and K140 is substituted with P; and/or (ii) F218 is substituted with a smaller amino acid, N213 and/or N214 is/are substituted with a smaller amino acid, D215 is substituted with an uncharged amino acid, G199 and G227 are each independently unmodified or substituted with A or V. For example, in the modified secretin GspD nanopore Y125 to R133 may deleted and/or substituted with GSG or SGS, F218 may be substituted with A, D215 may be substituted with S, and/or N213 and N214 may each independently be substituted with G or S. D117, T118, K122, Y125, D126, R133, E135, T139, K140, G199, N213, N214, D215, F218 and G227 of SEQ ID NO: 34 correspond to D371, T372, K376, Y379, D380, R387, E389, T393, K394, G453, N467, N468, D469, F472 and G481 of the full length GspD amino acid sequence set forth in SEQ ID NO: 32.

For example, the secretin domain of the modified GspD secretin nanopore may comprise a secretin domain having an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to an amino acid sequence as set forth in SEQ ID NO: 35, wherein: (i) all or some of the amino acids from D55 or T56 to T77 are deleted or substituted, one or more of K60, D64, R71 and E73 is substituted with an uncharged amino acid and/or one or more of D55, T56, T77 and K78 is substituted with P; and/or (ii) F156 is substituted with a smaller amino acid, N151 and/or N152 is/are substituted with a smaller amino acid, D153 is substituted with an uncharged amino acid, G137 and G165 are each independently unmodified or substituted with A or V. For example, in the modified secretin GspD nanopore Y63 to R71 may deleted and/or substituted with GSG or SGS, F156 may be substituted with A, D153 may be substituted with S, and/or N151 and N152 may each independently be substituted with G or S. D55, T56, K60, Y63, D64, R71, E73, T77, K78, G137, N151, N152, D153, F156 and G165 of SEQ ID NO: 35 correspond to D371, T372, K376, Y379, D380, R387, E389, T393, K394, G453, N467, N468, D469, F472 and G481 of the full length GspD amino acid sequence set forth in SEQ ID NO: 32.

For example, the secretin domain of the modified GspD secretin nanopore may comprise a secretin domain having an amino acid sequence that is at least about 40% or higher (including, e.g., at least about 50%, at least about 55%, at least about 60%, at least about 65%, at least about 70%, at least about 75%, at least about 80%, at least about 85%, at least about 90%, at least about 95%, or higher) identical to an amino acid sequence as set forth in SEQ ID NO: 33, wherein: (i) all or some of the amino acids from D132 or T133 to T154 are deleted or substituted, one or more of K137, D141, R148 and E150 is substituted with an uncharged amino acid and/or one or more of D132, T133, T154 and K155 is substituted with P; and/or (ii) F233 is substituted with a smaller amino acid, N228 and/or N229 is/are substituted with a smaller amino acid, D230 is substituted with an uncharged amino acid, G214 and G242 are each independently unmodified or substituted with A or V. For example, in the modified secretin GspD nanopore Y140 to R148 may deleted and/or substituted with GSG or SGS, F233 may be substituted with A, D230 may be substituted with S, and/or N228 and N229 may each independently be substituted with G or S. D132, T133, K137, Y140, D141, R148, E150, T154, K155, G214, N228, N229, D230, F233 and G242 of SEQ ID NO: 33 correspond to D371, T372, K376, Y379, D380, R387, E389, T393, K394, G453, N467, N468, D469, F472 and G481 of the full length GspD amino acid sequence set forth in SEQ ID NO: 32.

In any aspects of the modified secretin nanopore subunit polypeptide described herein, additional amino acid substitutions (other than the amino acid modifications described above), may be made to a reference secretin amino acid sequence, for example up to 1, 2, 3, 4, 5, 6, 7, 8, 9, 10, 15, 20, or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |

TABLE 2-continued

Hydropathy scale

| Side Chain | Hydropathy |
|---|---|
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the reference amino acid sequence (e.g., as set forth in SEQ ID Nos: 1-10) may additionally be deleted from the polypeptides described above. Up to 1, 2, 3, 4, 5, 10, 20 or 30 residues may be deleted, or more. One or more amino acids may be alternatively or additionally added to the polypeptides described above. An extension may be provided at the amino terminal or carboxy terminal of the reference amino acid sequence (e.g., as set forth in SEQ ID NO: 1 or 2) or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence, e.g., an amino acid sequence of a modified secretin nanopore subunit polypeptide. Other fusion proteins are discussed in more detail below.

Methods for modifying amino acids (e.g., by substitution, addition, or deletion) are well known in the art. For instance, a reference amino acid may be substituted with a target amino acid by replacing the codon for the reference amino acid with a codon for the target amino acid at the relevant position in a polynucleotide encoding the modified secretin nanopore subunit polypeptide. The polynucleotide can then be expressed as discussed below. If the amino acid is a non-naturally-occurring amino acid, it may be introduced by including synthetic aminoacyl-tRNAs in the IVTT system used to express the modified secretin nanopore subunit polypeptide. Alternatively, it may be introduced by expressing the modified secretin nanopore subunit polypeptide in *E. coli* that are auxotrophic for specific amino acids in the presence of synthetic (i.e., non-naturally-occurring) analogues of those specific amino acids. They may also be produced by naked ligation if the modified secretin nanopore subunit polypeptide is produced using partial peptide synthesis.

The modified secretin nanopore subunit polypeptides described herein may be used to form a homo-multimeric nanopore or hetero-multimeric nanopore as described herein. Accordingly, in some embodiments, the modified secretin nanopore subunit polypeptide retains the ability to form a nanopore with other subunit polypeptides. Methods for assessing the ability of modified monomers to form nanopores are well-known in the art. For instance, a modified secretin nanopore subunit polypeptide may be inserted into an amphiphilic layer along with other appropriate subunits and its ability to oligomerize to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484), the contents of which are incorporated herein by reference.

The modified secretin nanopore subunit polypeptides may contain non-specific modifications as long as they do not interfere with nanopore formation. A number of non-specific side chain modifications are known in the art and may be made to the side chains of the amino acids. Such modifications include, for example, reductive alkylation of amino acids by reaction with an aldehyde followed by reduction with NaBH4, amidination with methylacetimidate or acylation with acetic anhydride.

The modified secretin nanopore subunit polypeptides can be produced using standard methods known in the art. The modified secretin nanopore subunit polypeptides may be made synthetically or by recombinant means. Exemplary methods for expression and purification of the modified secretin nanopore subunit polypeptides according to some embodiments described herein are provided in Examples 1 and 2. Alternatively, the modified secretin nanopore subunit polypeptides may be synthesized by in vitro translation and transcription (IVTT). Suitable methods for producing pores and modified secretin nanopore subunit polypeptides are discussed in International Application Nos. PCT/GB09/001690 (published as WO 2010/004273), PCT/GB09/001679 (published as WO 2010/004265) or PCT/GB10/000133 (published as WO 2010/086603), the contents of each of which are incorporated herein by reference.

The modified secretin nanopore subunit polypeptides as described herein may be produced using D-amino acids. For instance, the modified secretin nanopore subunit polypeptides as described herein may comprise a mixture of L-amino acids and D-amino acids. This is conventional in the art for producing such proteins or peptides.

In some embodiments, the modified secretin nanopore subunit polypeptides may be chemically modified. The modified secretin nanopore subunit polypeptides can be chemically modified in any way and at any site. For instance, the modified secretin nanopore subunit polypeptides may be chemically modified by attachment of a dye or a fluorophore. In some embodiments, the modified secretin nanopore subunit polypeptide may be chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art.

In some embodiments, the modified secretin nanopore subunit polypeptide may be chemically modified with a molecular adaptor that facilitates the interaction between a nanopore comprising the modified secretin nanopore subunit polypeptide and a target nucleotide or target polynucleotide sequence. The presence of the adaptor improves the host-guest chemistry of the nanopore and the nucleotide or polynucleotide sequence and thereby improves the sequencing ability of pores formed from the modified secretin nanopore subunit polypeptides. The principles of host-guest chemistry are well-known in the art. The adaptor has an effect on the physical or chemical properties of the nanopore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

In some embodiments, the molecular adaptor may be a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

In some embodiments, the molecular adaptor can be covalently attached to the modified secretin nanopore subunit polypeptide. The adaptor can be covalently attached to the nanopore using any method known in the art. The adaptor is typically attached via chemical linkage. If the molecular adaptor is attached via cysteine linkage, one or more cysteines can be introduced to the modified secretin nanopore subunit polypeptide by substitution.

In other embodiment, the modified secretin nanopore subunit polypeptide may be attached or coupled to an enzyme such as a polynucleotide binding protein, e.g., helicases, exonucleases, and polymerases. In some embodiments, the modified secretin nanopore subunit polypeptide may be attached or coupled to a helicase, e.g., a DNA helicase. Examples of helicases, exonucleases, and polymerases that are suitable for use in nanopore sequencing are known in the art. In some embodiments, the modified secretin nanopore subunit polypeptide may be attached or coupled to a helicase, e.g., a DNA helicase, a Hel308 helicase (e.g., as described in WO 2013/057495), a RecD helicase (e.g., as described in WO2013/098562), a XPD helicase (e.g., as described in WO201/098561), or a Dda helicase (e.g., as described in WO2015/055981). This forms a modular sequencing system that may be used in the methods of characterizing a target polynucleotide. Polynucleotide binding proteins are discussed below. The translocation speed control may be determined by the type of polynucleotide binding protein and/or amount of fuel (ATP) added to the system. For example, the rate of translocation of the double stranded DNA analyte may be controlled by a double stranded DNA translocase such as FtsK. Depending upon the fuel (ATP) added to the system, the translocation speed of a target polynucleotide can be between about 30 B/s and 1000 B/s or about 30 B/s and 2000 B/s.

In some embodiments, the polynucleotide binding protein can be covalently attached to the modified secretin nanopore subunit polypeptide. The polynucleotide binding protein can be covalently attached to the modified secretin nanopore subunit polypeptide using any method known in the art. The modified secretin nanopore subunit polypeptide and the polynucleotide binding protein may be chemically fused or genetically fused. The modified secretin nanopore subunit polypeptide and the polynucleotide binding protein are genetically fused if the whole construct is expressed from a single polynucleotide sequence. Genetic fusion of a modified secretin nanopore subunit polypeptide to a polynucleotide binding protein is discussed in International Application No. PCT/GB09/001679 (published as WO 2010/004265), the contents of which are incorporated herein by reference.

The modified secretin nanopore subunit polypeptide may be chemically modified with a molecular adaptor and a polynucleotide binding protein.

Any of the proteins described herein, such as the modified secretin nanopore subunit polypeptides and nanopores described herein, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the modified secretin nanopore subunit polypeptide and nanopores described herein, may be labelled with a detectable label. The detectable label may be any suitable label which allows the protein to be detected. Suitable labels include, but are not limited to, fluorescent molecules, radioisotopes, e.g., 125I, 35S, enzymes, antibodies, antigens, polynucleotides and ligands such as biotin.

Any of the proteins described herein, including the modified secretin nanopore subunit polypeptide described herein, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Polynucleotides Encoding the Modified Secretin Nanopore Subunit Polypeptides

Provided herein are also polynucleotide sequences encoding any one of the modified secretin nanopore subunit polypeptides as described herein.

Polynucleotide sequences may be derived and replicated using standard methods in the art. Chromosomal DNA encoding wild-type secretin may be extracted from a pore producing organism, such as *Salmonella typhi*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding any one of the modified secretin nanopore subunit polypeptides can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, N.Y.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art.

Another aspect of the disclosure includes a method of producing a modified secretin nanopore subunit polypeptide or a construct described herein. The method comprises expressing a polynucleotide encoding any embodiment of the modified secretin nanopore subunit polypeptides in a suitable host cell. The polynucleotide is preferably part of a vector and is preferably operably linked to a promoter.

Modified Secretin Nanopores

One aspect of the present disclosure features a modified secretin nanopore, for example, that is disposed in a membrane and permits capture of an analyte, e.g., a target polynucleotide or polypeptide, into the modified secretin nanopore and/or translocation of the analyte through the modified secretin nanopore. The modified secretin nanopore, e.g., as disposed in a membrane, comprises a lumenal surface defining a lumen that extends, e.g., through the membrane, between a cis-opening and a trans-opening, in which the lumenal surface comprises one or more amino acid modifications. As used herein, the term "lumenal surface" refers to the internal surface of a nanopore, which surface comprises a set of amino acids of multiple nanopore subunits, that defines a lumen that is exposed to a solution.

In some embodiments, the secretin nanopore comprises a secretin domain comprising a beta barrel comprising an inner barrel subdomain and an outer barrel subdomain, each composed of β-sheets, with each subunit typically contributing about six β-sheets and/or the inner barrel typically comprising about four β-sheets to the outer barrel. Each subunit may further contribute two α-helices, typically between two of the β-sheets, to the outer beta barrel, for example as shown in FIG. 11. The outer barrel typically spans the membrane. The inner barrel typically abuts the lumen of the pore. The inner barrel typically comprises a central gate. The central gate is typically formed from loops between two β-sheets that form the inner barrel in each subunit. The central gate typically extends into the pore to narrow the size of the pore. The central gate can be modified by altering amino acids present in the central gate loop as described herein to alter the properties of the pore. The central gate may be flexible, for example the central gate may be capable of opening. The central gate may be rigid to maintain a constant constriction size, e.g. the central gate loop may be closed or partially closed. The beta barrel of the secretin nanopore wherein a first lip protrudes from the membrane on the opposite side of the membrane to the inner beta barrel. The lips of the beta barrel are typically composed of two α-helicies and two β-sheets from each subunit polypeptide. The β-sheets in each subunit may be joined by a loop region and the loop regions form a cap gate. Alternatively, the loop joining the β-sheets may be short and not form a gate. The cap gate may be flexible, for example the cap gate may be capable of opening. The cap gate may be rigid to maintain a constant constriction size, e.g. the cap gate may be closed or partially closed. In some embodiments, the first lip of the beta barrel may comprise no β-sheets and comprise from each subunit two α-helicies that are joined by a loop. In these embodiments the nanopore does not comprise a cap gate. The second lip may be on the other side of the inner beta barrel to the first lip. The second lip of the beta barrel may comprise two α-helicies in each subunit.

In some embodiments, the secretin nanopore may in addition to the secretin domain, comprise an S domain. The S-domain may comprise two α-helices. One of the α-helices typically interacts with the beta-barrel of the secretin nanopore. The S-domain is typically located on the outside of the pore (i.e. away from the lumen of the pore).

In some embodiments, the secretin nanopore may, in addition to the secretin domain, and optionally the S domain, comprises an N3 domain. The N3 domain is typically composed of β-barrels and α-helicies, e.g. from 3 to 6 β-barrels and from 2 to 3 α-helicies, such as 3 β-barrels and 2 α-helicies as shown in FIG. 11 or 6 β-barrels and 3 α-helicies as shown in FIG. 1B. The N3 domain may form a constriction in the lumen of the pore. The N3 domain may be modified so that it does not constrict the pore. The N3 domain may be modified to increase or decrease the size of the constriction.

When used as a nanopore to detect or characterize an analyte, the central gate, cap gate and/or N3 constriction may function as an read-head, i.e. interaction of the analyte with one, two or all of the central gate, cap gate and N3 constriction may alter the signal obtained as an analyte interacts with the pore and thus enable information about the analyte to be derived. Accordingly, the secretin nanopore may comprise one, two or three read-heads.

The amino acid modifications can be selected to improve translocation of an analyte through the modified secretin nanopore, to improve capture of an analyte into the modified secretin nanopore, and/or improve signal quality during detection of an analyte as it moves through the nanopore. Examples of the amino acid modifications are described in detail in the section "Modified secretin nanopore subunit polypeptide" above. While a modified secretin nanopore generally comprises one or more amino acid modifications (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more and up to 40 amino acid modifications) of a lumenal surface, it should be appreciated that a modified secretin nanopores may have any of a variety of different modifications. For example, a modified secretin nanopore may have amino acid modifications (lumenal or non-lumenal) (e.g., 1, 2, 3, 4, 5, 6, 7, 8, 9, 10, 15, 20, 25, 30, 40, 50, 60, 70, or more and up to 100 amino acid modifications) that promote membrane integration, promote oligomerization, promote subunit synthesis, promote nanopore stability, promote analyte capture, promote analyte release, improve analyte detection, facilitate polymer analysis (e.g., polynucleotide sequences), etc.

By way of example only, FIG. 5 shows that an enzyme may interact with CsgG and InvG nanopores in different orientations due to the larger cis-opening of the InvG nanopore. Without wishing to be bound by theory, due to the size difference of the enzyme and the nanopore opening (also see FIG. 6), the enzyme may wedge into the nanopore. Similar to CsgG nanopores of which the cis-opening was engineered to improve its interaction with an enzyme such as a polynucleotide binding problem, in some embodiments, the modified secretin nanopores described herein (e.g., the cis-opening or capture portion as described herein) can be engineered to facilitate a preferred orientation of an enzyme (e.g., a polynucleotide binding protein) such that it reduces the noise and improves the signal and accuracy.

In some embodiments, the cis-opening may have a diameter of at least about 30 Å, at least about 40 Å, at least about 50 Å, at least about 60 Å, at least about 70 Å, at least about 80 Å, at least about 90 Å, at least about 100 Å, or higher. In some embodiments, the cis-opening may have a diameter of no more than about 150 Å, no more than about 140 Å, no more than about 130 Å, no more than about 120 Å, no more than about 110 Å, no more than about 100 Å, no more than about 90 Å, no more than about 80 Å, no more than about 70 Å, no more than about 60 Å, no more than about 50 Å, or lower. Combinations of the above-referenced ranges are also possible. For example, in some embodiments, the cis-opening may have a diameter in a range of about 30 Å to about 120 Å. In some embodiments, the cis-opening may have a diameter in a range of about 60 Å to about 120 Å. In some embodiments, the cis-opening may have a diameter in a range of about 60 Å to about 100 Å. In some embodiments, the cis-opening may have a diameter in a range of about 30 Å to about 80 Å. In one embodiment, the trans-opening may have a diameter of about 80 Å.

In some embodiments, the trans-opening may have a diameter of at least about 30 Å, at least about 40 Å, at least about 50 Å, at least about 60 Å, at least about 70 Å, at least about 80 Å, at least about 90 Å, at least about 100 Å, or higher. In some embodiments, the trans-opening may have a diameter of no more than about 150 Å, no more than about 140 Å, no more than about 130 Å, no more than about 120 Å, no more than about 110 Å, no more than about 100 Å, no more than about 90 Å, no more than about 80 Å, no more than about 70 Å, no more than about 60 Å, no more than about 50 Å, or lower. Combinations of the above-referenced ranges are also possible. For example, in some embodiments, the trans-opening may have a diameter in a range of about 30 Å to about 100 Å. In some embodiments, the trans-opening may have a diameter in a range of about 40 Å to about 100 Å. In some embodiments, the trans-opening may have a diameter in a range of about 60 Å to about 100 Å. In some embodiments, the trans-opening may have a diameter in a range of about 30 Å to about 80 Å. In one embodiment, the trans-opening may have a diameter of about 80 Å.

In some embodiments, the lumenal surface may further define a constriction within the lumen. The diameter of the lumen can vary along an axis that extends between the cis-opening and trans-opening of the nanopore. As an illustration only, FIG. 3 shows the radius profile of the lumen of an InvG nanopore along the nanopore axis (extending between the cis-opening and trans-opening), in which the lumen comprises a constriction. As used herein, the term "constriction" refers to a portion of the lumen having a diameter that is smaller than the diameter of both the cis-opening and the trans-opening. For example, the constriction may have a diameter that is about 5%-20% (inclusive) of the diameter of the cis-opening and/or the diameter of the trans-opening. For example, in some embodiments, the constriction may have a diameter of at least about 5 Å, at least about 6 Å, at least about 7 Å, at least about 8 Å, at least about 9 Å, at least about 10 Å, at least about 15 Å, at least about 20 Å, at least about 25 Å, or higher. In some embodiments, the constriction may have a diameter of no more than about 30 Å, no more than about 25 Å, no more than about 20 Å, no more than about 15 Å, no more than about 10 Å, or lower. Combinations of the above-referenced ranges are also possible. For example, in some embodiments, the constriction may have a diameter in a range of about 5 Å to about 25 Å. In some embodiments, the constriction may have a diameter in a range of about 7 Å to about 25 Å. In some embodiments, the constriction may have a diameter in a range of about 10 Å to about 25 Å. In one embodiment, the constriction may have a diameter of about 15 Å.

The constriction may be located about halfway between the cis-opening and trans-opening. In some embodiments, the constriction may be located at a distance of about 30 Å to about 60 Å away from the cis-opening. In some embodiments, the constriction may be located at a distance of about 30 Å to about 60 Å away from the trans-opening.

In some embodiments, the modified secretin nanopores described herein may comprise a lumenal surface defining a lumen that exhibits the radius profile of a natural secretin nanopore, for example, as shown in FIG. 3.

Any forms of secretin found in a microorganism (e.g., bacteria) may be used to produce the modified secretin nanopore described herein. In some embodiments, the secretin may be any member of a type II, type III, or type IV secretion system. Non-limiting examples of a type II secretion system include GspD, PulD, and pIV. Examples of a type III secretion system include, but are not limited to InvG, MxiD, YscC, PscC, EscC, and SpiA. An exemplary type IV secretion system includes, but is not limited to PilQ. Accordingly, in some embodiments, the modified secretin nanopore may comprise any embodiment of a modified secretin subunit polypeptide described herein, e.g., in the section "Modified secretin nanopore subunit polypeptide" above.

In some embodiments, one or more (e.g., 1, 2, 3, 4, 5, 6, 7, 8, 9, 10, or more) of the amino acid modifications described herein (e.g., but not limited to a positively-charged amino acid substitution and/or hydrophobic amino acid substitution) may be present in a portion of the lumenal surface that defines the constriction. For example, one or more (e.g., 1, 2, 3, 4, 5, 6, 7, 8, 9, 10, or more) of the amino acid modifications described herein (e.g., but not limited to a positively-charged amino acid substitution and/or hydrophobic amino acid substitution) may be present in the portion of the lumenal surface that defines the constriction of a modified secretin nanopore, e.g., a modified InvG nanopore. As an example only, FIG. 1A shows the location of a constriction (labelled as "periplasmic gate" in the figure) of a wild-type InvG nanopore. In some embodiments, the constriction of the modified InvG secretin nanopore may have one or more amino acid modifications for improving translocation of an analyte through the nanopore and/or improving detection signal quality as the analyte moves through the nanopore. For example, the constriction of the modified InvG secretin nanopore may comprise amino acid modifications at amino acids D28, E225, R226, and/or E231 of SEQ ID NO: 1. In some embodiments, the constriction of the modified InvG secretin nanopore may comprise one or more (e.g., 1, 2, 3, 4, 5, or 6) of the following amino acid modifications: (i) D28N/Q/T/S/G/R/K; (ii) E225N/Q/T/A/S/G/P/H/F/Y/R/K; (iii) R226N/Q/T/A/S/G/P/H/F/Y/K/V; (iv) deletion of E225; (v) deletion of R226; and (vi) E231N/Q/T/A/S/G/P/H/R/K.

In some embodiments, the lumenal surface may further comprise a capture portion (e.g., an analyte capture portion (e.g., a polynucleotide capture portion)). As used herein, the term "capture portion" refers to a portion of a lumenal surface of a nanopore that favourably interacts, via one or more amino acids of one or more pore subunits, with a target analyte to permit or facilitate binding of the analyte to, and/or translocation of the analyte through, the nanopore. The capture portion may be located between the cis-opening and the constriction of the modified secretin nanopore. In some embodiments, the capture portion may correspond to a N3 domain of a secretin nanopore (e.g., a type II, III, or IV secretion system). For example, the capture portion may correspond to a N3 domain of an InvG nanopore, e.g., as shown in FIG. 1A, or a portion of such a domain. FIG. 1B shows the peptide domains (with corresponding amino acid positions in SEQ ID NO: 2) that encompass the N3 domain of an InvG nanopore. In some embodiments, a capture portion of a lumenal surface comprises one or more amino acids of one or more pore subunits (e.g., 1, 2, 3, 4, 5, 6, 7, 8, 9, 10, 11, 12, 13, 14, 15, 16, 17, or more amino acids) on a cis-opening side of a constriction.

In some embodiments, the capture portion may correspond to a N3 domain of an InvG nanopore, e.g., as shown in FIG. 1A, or a portion of such a domain and include a "periplasmic constriction" as shown in FIG. 1A, which may act like a second constriction. Thus, in some embodiments, the modified secretin nanopore (e.g., a modified InvG nanopore) may comprise two constrictions—one located about halfway between the cis-opening and trans-opening as described above and another located close to the cis-opening of the nanopore. Such a modified secretin nanopore may act like a two reader nanopore in which an analyte (e.g., a polynucleotide) interacts with the pore lumen at the two constriction sites that are distant from each other.

In some embodiments, the capture portion of the lumenal surface may comprise one or more amino acid modifications (e.g., 1, 2, 3, 4, 5, 6, 7, 8, 9, 10, 11, 12, 13, 14, 15, 16, 17, or more and up to 25 amino acid modifications) for improving capture of a target analyte, e.g., a target polynucleotide. By way of example only, the capture portion of the modified InvG secretin nanopore may comprise amino acid modifications at amino acids E41, Q45, and/or E114 of SEQ ID NO: 1. In some embodiments, the capture portion of the modified InvG secretin nanopore may comprise one or more (e.g., 1, 2, or 3) of the following amino acid modifications: (i) Q45R/K; (ii) E41N/Q/T/S/G/R/K; and (iii) E114N/Q/T/S/G/R/K.

Any of the modified secretin nanopores described herein can be homo-multimeric (e.g., all subunits within the nanopore are the same) or hetero-multimeric (e.g., at least one subunit is different from others within the nanopore). The modified secretin nanopore may comprise any number of subunit polypeptides that are sufficient to form a lumen large enough to permit a target polymer (e.g., polynucleotide) pass through. In some embodiments, the modified secretin nanopore may comprise about 9 to about 20 subunit polypeptides (e.g., 9, 10, 11, 12, 13, 14, 15, 16, 17, 18, 19, 20 subunit polypeptides), wherein at least one or more of the subunit polypeptides comprises one or more amino acid substitutions (e.g., positively-charged amino acid substitutions and/or hydrophobic amino acid modifications) as described herein.

The modified secretin nanopores may be isolated, substantially isolated, purified or substantially purified. The modified secretin nanopores can be isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, one or more of the modified secretin nanopores may be present in a membrane. Suitable membranes are discussed below.

The modified secretin nanopore may be present as an individual or single pore. Alternatively, the modified secretin nanopores may be present in a homologous or heterologous population of two or more pores. In some embodiments, the modified secretin nanopores may be arranged in an array, e.g., each nanopore disposed in a membrane present in a microwell. In some embodiments, the array may comprise the modified secretin nanopores and at least one or more non-secretin nanopore known in the art, e.g., but not limited to CsgG nanopores (e.g., as described in WO 2016/034591); a-hemolysin nanopores (e.g., as described in WO 2010/004273); lysenin nanopores (e.g., as described in WO 2013/

153359); Msp nanopores (e.g., as described in WO 2012/107778; WO 2015/166275; and WO 2016/055778).

The modified secretin nanopores described herein can provide improved analyte detection and/or analysis. For illustration only, FIG. 4 shows that while both CsgG and InvG nanopores have a constriction of approximately the same in diameter, the constriction of the CsgG nanopore has 3 amino acids at positions 51, 55, and 56 (based on wild type sequence), respectively, and the InvG nanopore constriction has two amino acids at position 396 and 397 (based on SEQ ID NO: 2), respectively. Further, the amino acid 51 at the constriction of the CsgG nanopore is also a little far from amino acid 55. In contrast, the amino acids 396 and 397 at the constriction of the InvG nanopore are located next to each other, thus providing a sharper reader head. Therefore, in some embodiments, the modified secretin nanopores can provide a sharper reader head for analyte detection and/or analysis.

Homo-Multimeric Secretin Nanopores

Homo-multimeric nanopores comprising identical modified secretin nanopore subunit polypeptides are also provided herein. The homo-multimeric nanopore may comprise any embodiment of the modified secretin nanopore subunit polypeptides described herein. The homo-multimeric nanopore can be used for characterizing an analyte, e.g., a target polynucleotide and/or a target polypeptide. The homo-multimeric nanopore described herein may have any of the advantages discussed above.

The homo-multimeric pore may contain any number of modified secretin nanopore subunit polypeptides. The pore typically comprises at least 9, at least 10, at least 11, at least 12, at least 13, at least 14, at least 15, at least 16, at least 17, at least 18, at least 19, at least 20 identical modified secretin nanopore subunit polypeptides, such as 9, 10, 11, 12, 13, 14, 15, 16, 17, 18, 19, or 20 identical modified secretin nanopore subunit polypeptides.

Hetero-Multimeric Secretin Nanopores

Hetero-multimeric nanopores comprising at least one modified secretin nanopore subunit polypeptides are also provided herein. The hetero-multimeric nanopores can be used for characterizing a target analyte, e.g., a target polynucleotide and/or a target polypeptide. Hetero-multimeric nanopores can be made using methods known in the art (e.g., Protein Sci. 2002 July; 11(7):1813-24).

The hetero-multimeric pore contains sufficient subunit polypeptide to form the pore. The subunit polypeptides may be of any type. The pore typically comprises at least 9, at least 10, at least 11, at least 12, at least 13, at least 14, at least 15, at least 16, at least 17, at least 18, at least 19, at least 20 subunit polypeptides, such as 9, 10, 11, 12, 13, 14, 15, 16, 17, 18, 19, or 20 subunit polypeptides.

In some embodiments, all of the subunit polypeptides (such as 9, 10, 11, 12, 13, 14, 15, 16, 17, 18, 19, or 20 subunit polypeptides) are modified secretin nanopore subunit polypeptides and at least one of them differs from the others.

In some embodiments, at least one of the subunit polypeptides is not a modified secretin nanopore subunit polypeptide as described herein. In this embodiment, the remaining monomers may be any one of the modified secretin nanopore subunit polypeptides described herein. Hence, the pore may comprise 19, 18, 17, 16, 15, 14, 13, 12, 11, 10, 9, 8, 7, 6, 5, 4, 3, 2, or 1 modified secretin nanopore subunit polypeptide(s). The modified secretin nanopore subunit polypeptide(s) that form the nanopore can be the same or different.

Exemplary Uses of the Secretin Nanopores Described Herein

The modified secretin nanopores can be used for characterizing or detecting an analyte, e.g., a target polynucleotide (e.g., a double stranded polynucleotide and/or a single stranded polynucleotide) and/or a target polypeptide. Accordingly, methods for detecting and/or characterizing an analyte in a sample are also provided herein. The method comprises: providing an aqueous solution comprising any embodiment of the modified secretin nanopores described herein and a membrane, wherein the modified secretin nanopore is disposed in the membrane; and adding an analyte to the aqueous solution on the cis-side or trans-side of the membrane. In some embodiments, an enzyme such as a polynucleotide binding protein, e.g., helicases, exonucleases, and/or polymerase, can also be added to the aqueous solution on the cis-side or trans-side of the membrane. The enzyme such as a polynucleotide binding protein may enter the lumen or be in contact (via, e.g., but not limited to ionic and/or hydrophobic interactions) or covalently attached to the cis-opening or trans-opening, of the modified secretin nanopores. In some embodiments, the analyte may bind to the enzyme such as a polynucleotide binding protein. An analyte may be a target polynucleotide, polypeptide, ligand, or hydrophobic molecule.

In some embodiments, the secretin nanopores may be used to detect molecules that bind to or otherwise interact with an enzyme provided within the cis or trans vestibule that give rise to a change in conformation of the enzyme. The change in conformation can give rise to a change in ion current flow through the nanopore. Examples of such molecules are drugs, antibodies, peptides, polynucleotides and so on. Examples of enzymes that interact with small molecules such as drugs include but are not limited to Cytochrome p450 enzymes.

In some embodiments, the method may further comprise applying a potential across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. The method may be carried out with a voltage applied across the membrane and nanopore. The voltage used may vary from +5 V to −5 V, such as from +4 V to −4 V, +3 V to −3 V or +2 V to −2 V. In some embodiments, the voltage used may be from −600 mV to +600 mV or −400 mV to +400 mV. In some embodiments, the voltage used may be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. In some embodiments, the voltage used may be in the range of 100 mV to 240 mV or in the range of 120 mV to 220 mV. It is possible to increase discrimination between different nucleotides by a pore by using an increased applied potential.

In some embodiments, the method may further comprise, upon application of a potential across the membrane, detecting a signal in response to an analyte passing through the nanopore. The signal may be an electrical measurement and/or an optical measurement. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore. Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET. In some embodiments, the method may further comprise, upon application of a potential across the membrane, detecting an ionic current flow through the nanopore as an analyte (e.g., but not limited to a target polynucleotide) interacts and/or moves through the nanopore. In some embodiments, the methods may be carried out using a patch clamp or a voltage clamp. In some embodiments, the methods may be carried out using a voltage clamp. Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

In alternative embodiments, the method may further comprise, upon application of a potential across the membrane, detecting an analyte by measuring the movement or conformational change of an enzyme (e.g., a polynucleotide binding protein or a ligand binding protein) upon binding to the analyte. In some embodiments, at least a portion of the enzyme may reside within the lumen of the modified secretin nanopore when the analyte is bound to the enzyme. In these embodiments, an ionic current passing through the nanopore may vary with the movement or conformational change of the enzyme bound to an analyte, as compared to an enzyme with no analyte bound thereto. Thus, the presence and/or type of an analyte can be detected by measuring changes in the level of the ionic current and/or current signature generated across the nanopore.

In any of the methods described herein, the aqueous solution in which the modified secretin nanopore and the membrane are disposed may comprise any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed herein, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide may be used. The charge carriers may be asymmetric across the membrane. For instance, the type and/or concentration of the charge carriers may be different on each side of the membrane.

In any of the methods described herein, the aqueous solution in which the modified secretin nanopore and the membrane are disposed may comprise salt. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

In some embodiments, the aqueous solution may be a low ionic strength solution. As used herein, the term "low ionic strength solution" refers to a solution with an ionic strength of less than 2 M, including, e.g., less than 1 M, less than 900 mM, less than 800 mM, less than 700 mM, less than 600 mM, less than 500 mM, less than 400 mM, less than 300 mM, less than 200 mM, less than 150 mM, or lower. In some embodiments, a lower ionic strength solution has an ionic strength of at least about 50 mM, at least about 100 mM, at least about 150 mM, at least about 200 mM, at least about 300 mM, at least about 400 mM, at least about 500 mM, at least about 600 mM, at least about 700 mM, at least about 800 mM, at least about 900 mM, at least about 1 M, or higher. Combinations of the above-references ranges are also encompassed. For example, a low ionic strength solution may have an ionic strength of about 100 mM to about 600 mM, or about 150 mM to about 300 mM. Any salt can be used to yield a solution with appropriate ionic strength. In some embodiments, alkaline salt (e.g., but not limited to potassium chloride or sodium chloride) can be used in the low ionic strength solution.

The methods described herein are typically carried out in the presence of a buffer. In the exemplary apparatus discussed herein, the buffer is present in the aqueous solution in the chamber. Any buffer may be used in the methods described herein. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5 or 8.0.

The methods described herein may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

In some embodiments, the methods described herein can be used to discriminate between different nucleotides under a range of conditions, which is further described in detail in the section "Polynucleotide characterization" below. For example, the methods described herein can be used to discriminate between nucleotides under conditions that are favourable to the characterizing, such as sequencing, of nucleic acids. The extent to which the modified secretin nanopores used in the methods can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The modified secretin nanopores may also be used to identify polynucleotide polymers from the interaction with one or more monomers rather than on a nucleotide by nucleotide basis. In some embodiments, the modified secretin nanopores can also be used to distinguish modified bases, e.g., between methylated and unmethylated nucleotides.

FIG. 2 shows that while a CsgG nanopore has 9 monomers or subunits and an InvG nanopore has 15 monomers or subunits, both nanopores have a constriction of approximately the same in diameter. Unlike CsgG nanopores (e.g., as described in WO 2016/034591), in some embodiments, the modified secretin nanopores (e.g., but not limited to InvG nanopores) can be used to sequence DNA and/or RNA.

In some embodiments, the methods described herein can be used to characterize and/or detect or characterize a molecule or a ligand. For example, the modified secretin nanopores used in the methods described herein may be used for characterizing ligand-enzyme interactions (e.g., nucleic acid-protein interactions or protein-protein interactions). In some embodiments, the nanopores can be used interrogate ligand-enzyme interactions (e.g., protein-nucleic acid interaction or protein-protein interaction) using different sensing modes such as, for example, by scanning and mapping the locations of binding sites along a ligand (e.g., nucleic acid or polypeptide) and/or by probing the strength of interactions between a ligand and an enzyme (e.g., between a protein and nucleic acid or between a protein and a protein). In some embodiments, native charges of a nucleic acid or protein may be leveraged to apply an electrophoretic force to a nucleic acid-protein complex or a protein-protein complex. For example, in some embodiments, DNA-protein interactions may be evaluated using voltage-driven threading of single DNA molecules through a protein nanopore. In such embodiments, electrical force applied to an individual DNA protein complex (e.g., a DNA-exonuclease I complex, a DNA-helicase complex, a DNA-clamp complex) may pull the two molecules apart, while at the same time ion current changes may be used to evaluate the dissociation rate of the complex. In some embodiments, modified secretin nanopores provided herein may be used for detection and characterization of nucleic acid-protein interactions involving nucleic acid and other nucleic acid binding proteins such as transcription factors, enzymes, DNA packaging proteins and others. In some embodiments, modified secretin nanopores provided herein may be used for detection and characterization of protein-protein interactions involving a ligand and other ligand binding proteins.

In some embodiments, at least a portion of an enzyme (e.g., but not limited to polynucleotide binding protein) can enter the lumen of the modified secretin nanopores, for example, as shown in FIG. 6. Localization of the enzyme inside the nanopore may restrict undesirable movements of the enzyme and thus result in improved signals. For example, as shown with ClyA nanopores (e.g., as described in International Patent Application Publications WO 2014/153625 and WO 2016/166232), the modified secretin nanopores as described herein, in some embodiments, can be used to detect an analyte by measuring the movement of its binding to an enzyme, at least a portion of which is present inside the nanopore. Since the constriction of secretin nanopores such as InvG nanopores is much smaller than that of ClyA nanopores, signal generating from such an event may be more pronounced with secretin nanopores such as InvG nanopores. Thus, in some embodiments, the modified secretin nanopores and the methods described herein can provide a new area of molecular testing.

Polynucleotide Characterization

Another aspect of the present disclosure provides a method of characterizing a target polynucleotide. The method comprises: (a) providing in an aqueous solution a modified secretin nanopore according to any embodiment described herein and a membrane, wherein the modified secretin nanopore is present in the membrane; (b) adding in the aqueous solution of step (a) the target polynucleotide; and (c) measuring, during application of a potential across the nanopore, ion flow through the modified secretin nanopore, wherein the ion flow measurements are indicative of one or more characteristics of the target polynucleotide. In some embodiments, the target polynucleotide is added to the cis side of the aqueous solution. In some embodiments, the target polynucleotide is added to the trans side of the aqueous solution. In some embodiments, the aqueous solution is present in an embodiment of an apparatus described herein.

The target polynucleotide may also be called the template polynucleotide or the polynucleotide of interest.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e., lack a nucleobase). A nucleotide may also lack a nucleobase and a sugar.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method described herein may concern characterizing 2, 3, 4, 5, 6, 7, 8, 9, 10, 20, 30, 50, 100 or more polynucleotides. If two or more polynucleotides are characterized, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

The polynucleotide may comprise an attached species such as a protein or analyte. The polynucleotide may comprise a hybridized probe.

Characterization

The method for polynucleotide characterization may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the methods described herein, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The target polynucleotide is contacted with any one of the modified secretin nanopores described herein. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in International Application No. PCT/GB08/000562 (published as WO 2008/102120), the contents of which are incorporated herein by reference.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore. Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method can be carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This may be described as strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method may involve the measuring of a current passing through the pore as the polynucleotide moves with respect to the pore. Suitable conditions for measuring ionic currents through transmembrane protein pores are known in the art and also provided herein.

Enzymes Such as Polynucleotide Binding Protein

In some embodiments, the method for characterizing an analyte (e.g., a target polynucleotide or polypeptide) may include adding an enzyme such as a polynucleotide binding protein in an aqueous solution comprising an analyte such that the enzyme binds to the analyte (e.g., target polynucleotide or polypeptide). In some embodiments, the binding of the analyte (e.g., target polynucleotide) to the enzyme such as a polynucleotide binding protein controls the movement of the analyte (e.g., target polynucleotide) through the modified secretin nanopore, thereby characterizing the analyte (e.g., target polynucleotide). In some embodiments, the movement of an analyte (e.g., target polypeptide or ligand) binding to an enzyme such as a ligand-binding protein can be measured to detect the analyte and/or characterize the interaction of the analyte with the enzyme.

Polynucleotide binding protein: The polynucleotide binding protein may be any protein that is capable of binding to the polynucleotide and controlling its movement through the pore. Examples of the polynucleotide binding proteins include, but are not limited to helicases, polymerases, exonucleases, DNA clamps, etc. The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein.

Helicase(s) and Molecular Brake(s).

In one embodiment, the method comprises:

(a) providing the polynucleotide with one or more helicases and one or more molecular brakes attached to the polynucleotide;

(b) adding the polynucleotide in the low ionic strength solution that comprises a modified secretin nanopore present in a membrane, and applying a potential across the pore such that the one or more helicases and the one or more molecular brakes are brought together and both control the movement of the polynucleotide through the pore;

(c) measuring, during application of a potential across the nanopore, ion flow through the modified secretin nanopore, as the polynucleotide moves with respect to the pore wherein the ion flow measurements are indicative of one or more characteristics of the polynucleotide and thereby characterizing the polynucleotide. This type of method is discussed in detail in International Application No. PCT/GB2014/052737 (published as WO 2015/110777), the contents of which are incorporated herein by reference.

Membrane

The modified secretin nanopores described herein may be present in a membrane. In the method of characterizing an analyte (e.g., a target polynucleotide, polypeptide, or a ligand), the analyte (e.g., a target polynucleotide, polypeptide, or a ligand) is typically contacted with a modified secretin nanopore in a membrane. Any membrane may be used. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic or lipophilic, whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in International Application No. PCT/GB2013/052766 (published as WO 2014/064443) or PCT/GB2013/052767 (published as WO 2014/064444), the contents of each of which are incorporated herein by reference.

The amphiphilic molecules may be chemically-modified or functionalized to facilitate coupling of the analyte (e.g., a target polynucleotide, polypeptide, or a ligand).

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s$^{-1}$. This means that the pore and coupled analyte (e.g., a target polynucleotide, polypeptide, or a ligand) can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484), the contents of each of which are incorporated herein by reference.

In some embodiments, the analyte (e.g., a target polynucleotide, polypeptide, or a ligand) can be coupled to the membrane comprising any one of the modified secretin nanopores described herein. The method may comprise coupling the analyte (e.g., a target polynucleotide, polypeptide, or a ligand) to the membrane comprising any one of the modified secretin nanopores described herein. The analyte (e.g., a target polynucleotide, polypeptide, or a ligand) is preferably coupled to the membrane using one or more anchors. The analyte (e.g., a target polynucleotide, polypeptide, or a ligand) may be coupled to the membrane using any known method.

Double Stranded Polynucleotide Sequencing

In some embodiments, the polynucleotide may be double stranded. If the polynucleotide is double stranded, the method may further comprises before the contacting step ligating a hairpin adaptor to one end of the polynucleotide. The two strands of the polynucleotide may then be separated as or before the polynucleotide is contacted or interacted with a modified secretin nanopore as described herein. The two strands may be separated as the polynucleotide movement through the pore is controlled by a polynucleotide binding protein, such as a helicase, or molecular brake. This is described in International Application No. PCT/GB2012/051786 (published as WO 2013/014451), the contents of which are incorporated herein by reference. Linking and interrogating both strands on a double stranded construct in this way increases the efficiency and accuracy of characterization.

Round the Corner Sequencing

In a preferred embodiment, a target double stranded polynucleotide is provided with a hairpin loop adaptor at one end and the method comprises contacting the polynucleotide with any one of the modified secretin nanopores described herein such that both strands of the polynucleotide move through the pore and taking one or more measurements as the both strands of the polynucleotide move with respect to the pore wherein the measurements are indicative of one or more characteristics of the strands of the polynucleotide and thereby characterizing the target double stranded polynucleotide. Any of the embodiments discussed above equally apply to this embodiment.

Leader Sequence

Before the contacting step, the method preferably comprises attaching to the polynucleotide a leader sequence which preferentially threads into the pore. The leader sequence facilitates any of the methods described herein. The leader sequence is designed to preferentially thread into any one of the modified secretin nanopores described herein and thereby facilitate the movement of polynucleotide through the nanopore. The leader sequence can also be used to link the polynucleotide to the one or more anchors as discussed above.

Modified Polynucleotides

Before characterization, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in International Application No. PCT/GB2015/050483, the contents of which are incorporated herein by reference. Any of the polymerases discussed herein may be used.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. A primer or a 3' hairpin is typically used as the nucleation point for polymerase extension.

Characterization, such as sequencing, of a polynucleotide using a transmembrane pore typically involves analyzing polymer units made up of k nucleotides where k is a positive integer (i.e., "k-mers"). This is discussed in International Application No. PCT/GB2012/052343 (published as WO 2013/041878), the contents of which are incorporated herein by reference. While it is desirable to have clear separation between current measurements for different k-mers, it is common for some of these measurements to overlap. Especially with high numbers of polymer units in the k-mer, i.e., high values of k, it can become difficult to resolve the measurements produced by different k-mers, to the detriment of deriving information about the polynucleotide, for example an estimate of the underlying sequence of the polynucleotide. Various algorithms may be employed to characterize the sequence, such as use of a Hidden Markov Model or recurrent neural network. The sequence may be aligned to a reference sequence using methods such as disclosed in International Patent Application Nos. PCT/GB2015/050776 (published as WO 2015/140535) and PCT/GB2015/053083 (published as WO 2016/059427), the contents of each of which are incorporated herein by reference.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterize the target polynucleotide. In some instances, the modified polynucleotide itself may be easier to characterize. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Other Characterization Method

In another embodiment, a polynucleotide is characterized by detecting labelled species that are released as a polymerase incorporates nucleotides into the polynucleotide. The polymerase uses the polynucleotide as a template. Each labelled species is specific for each nucleotide. The polynucleotide is contacted with a modified secretin nanopore described herein, a polymerase and labelled nucleotides such that phosphate labelled species are sequentially released when nucleotides are added to the polynucleotide(s) by the polymerase, wherein the phosphate species contain a label specific for each nucleotide. The polymerase may be any of those discussed above. The phosphate labelled species are detected using the pore and thereby characterizing the polynucleotide. This type of method is disclosed in European Application No. 13187149.3 (published as EP 2682460). Any of the embodiments discussed above equally apply to this method.

Sample

Any suitable sample comprising an analyte to be detected or characterized may be subjected to any of the methods described herein. The methods described herein can be carried out on two or more samples that are known to contain or suspected to contain the analytes. Alternatively, the method may be carried out on two or more samples to confirm the identity of two or more analytes whose presence in the samples is known or expected. In some embodiments, the method may be carried out on samples to distinguish double stranded polynucleotides from single-stranded polynucleotides.

The first sample and/or second sample may be a biological sample. The methods described herein may be carried out in vitro using at least one sample obtained from or extracted from any organism or microorganism. The first sample and/or second sample may be a non-biological sample. The non-biological sample can be a fluid sample. Examples of non-biological samples include surgical fluids, water such as drinking water, sea water or river water, and reagents for laboratory tests.

The first sample and/or second sample is typically processed prior to being used in the methods described herein, for example by centrifugation or by passage through a membrane that filters out unwanted molecules or cells, such as red blood cells. The first sample and/or second sample may be measured immediately upon being taken. The first sample and/or second sample may also be typically stored prior to assay, preferably below −70° C.

Kits

Another aspect of the present disclosure also provides a kit, for example, for characterizing a target analyte such as a target polynucleotide, polypeptide, or ligand. The kit comprises any one of the modified secretin nanopores described herein and the components of a membrane. The membrane is preferably formed from the components. The modified secretin nanopore is preferably present in the membrane. The kit may comprise components of any of the membranes disclosed above, such as an amphiphilic layer or a triblock copolymer membrane.

The kit may further comprise an enzyme such as a polynucleotide binding protein or a ligand binding protein.

The kit may further comprise one or more anchors for coupling the analyte (e.g., polynucleotide, polypeptide, or ligand) to the membrane.

The kit may additionally comprise one or more other reagents or instruments which enable any of the embodiments mentioned above to be carried out. Such reagents or instruments may include one or more of the following: suitable buffer(s) (aqueous solutions), means to obtain a sample, e.g., from a subject (such as a vessel or an instrument comprising a needle), means to amplify polynucleotides and/or express proteins or polypeptides, or voltage or patch clamp apparatus. Reagents may be present in the kit in a dry state such that a fluid sample resuspends the reagents. The kit may also, optionally, comprise instructions to enable the kit to be used in any one of the methods described herein or details regarding for which organism the method may be used.

Apparatus

Another aspect described herein also provides an apparatus, for example, for characterizing a target analyte such as a polynucleotide, polypeptide, or ligand. The apparatus comprises a plurality of modified secretin nanopores as described herein and a plurality of membranes. In some embodiments, the plurality of the modified secretin nanopores are present in the plurality of membranes. In some embodiments, the numbers of modified secretin nanopores and membranes are equal. In one embodiment, a single modified secretin nanopore is present in each membrane.

In some embodiments, an apparatus comprises a chamber (e.g., a microwell) containing an aqueous solution having disposed therein a membrane comprising a modified secretin nanopore as described herein. In some embodiments, an apparatus may comprise an array of chambers (e.g., an array of microwells), each of which contains an aqueous solution having disposed therein a membrane comprising a modified secretin nanopore as described herein. In some embodiments, an apparatus may comprise an array of chambers (e.g., an array of microwells), each of which contains an aqueous solution having disposed therein a membrane comprising a nanopore. In these embodiments, at least one nanopore is a modified secretin nanopore as described herein, and the remaining nanopores may be a non-secretin nanopore known in the art, e.g., but not limited to CsgG nanopores (e.g., as described in WO 2016/034591); α-hemolysin nanopores (e.g., as described in WO 2010/004273); lysenin nanopores (e.g., as described in WO 2013/153359); Msp nanopores (e.g., as described in WO 2012/107778; WO 2015/166275; and WO 2016/055778). Thus, more than one type of nanopores can be present in such an array.

In some embodiments, the apparatus may further comprise an analyte in the aqueous solution. In some embodiments where the analyte is a polynucleotide, the apparatus may further comprise a polynucleotide binding protein, e.g., a helicase, exonuclease, or polymerase. The polynucleotide binding protein may be bound to the polynucleotide. In some embodiments, the polynucleotide binding protein may be on the cis-side of the membrane and the polynucleotide binding protein may be in contact (via e.g., ionic and/or hydrophobic interactions) with or covalently attached to the cis-opening of the nanopore. In some embodiments, the polynucleotide binding protein may be on the trans-side of the membrane and the polynucleotide binding protein may be in contact (via e.g., ionic and/or hydrophobic interactions) with or covalently attached to the trans-opening of the nanopore.

The apparatus can further comprises instructions for carrying out any of the methods as described herein. The apparatus may be any conventional apparatus for polynucleotide analysis, such as an array or a chip. Any of the embodiments discussed above with reference to the methods, e.g., for characterizing a target polynucleotide, are equally applicable to the apparatus described herein. The apparatus may further comprise any of the features present in the kit described herein.

In some embodiments, the apparatus is set up to carry out any of the methods described herein, e.g., for characterizing a target analyte such as a target polynucleotide.

In one embodiment, the apparatus comprises: (a) a sensor device that is capable of supporting the plurality of modified secretin nanopores and membranes and that is operable to perform polynucleotide characterization using the nanopores and membranes; and (b) at least one port for delivery of material for performing the characterization.

Alternatively, the apparatus may comprise: (a) a sensor device that is capable of supporting the plurality of modified secretin nanopores and membranes and that is operable to perform polynucleotide characterization using the nanopores and membranes; and (b) at least one reservoir for holding material for performing the characterization.

In another embodiment, the apparatus may comprise: (a) a sensor device that is capable of supporting the membrane and plurality of modified secretin nanopores and membranes and that is operable to perform polynucleotide characterizing using the pores and membranes; (b) at least one reservoir for holding material for performing the characterizing; (c) a fluidics system configured to controllably supply material from the at least one reservoir to the sensor device; and (d) one or more containers for receiving respective samples, the fluidics system being configured to supply the samples selectively from one or more containers to the sensor device.

The apparatus may be any of those described in International Application No. No. PCT/GB08/004127 (published as WO 2009/077734), PCT/GB10/000789 (published as WO 2010/122293), International Application No. PCT/GB10/002206 (published as WO 2011/067559) or International Application No. PCT/US99/25679 (published as WO 00/28312), the contents of each of which are incorporated herein by reference.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLE 1

Exemplary Method for Expression and Purification of a Modified Secretin Nanopore Subunit Polypeptide, e.g., a Modified InvG Nanopore Subunit Polypeptide Ampicillin-resistant pT7 vector containing the gene encoding a modified secretin nanopore subunit polypeptide (e.g., an amino acid sequence as set forth in SEQ ID NO: 1 or 2 with one or more (e.g., 1, 2, 3, 4, 5, 6, 7, 8, 9, 10, 15, 20, 25, 30, or more and up to 50 amino acid modifications described herein)) with a C terminal hexa-histidine (His) tag and kanamycin-resistant pRham vector containing the gene encoding InvH protein (20 Kd protein that would enhance the expression of InvG) were co-transformed into C43 DE3 pLysS cells and plated out on agar plates containing both Ampicillin (100 µg/ml) and Kanamycin (30 µg/ml) and grown overnight at 37° C. A single colony was used to inoculate a 100 ml starter culture of TB media containing both Ampicillin (100 µg/ml) and Kanamycin (30 µg/ml). The culture was grown at 250 rpm at 37° C. for 18 hours. 15 ml of starter culture was used to inoculate 500 ml of TB media containing both Ampicillin (100 µg/ml) and Kanamycin (30 µg/ml), and the culture was grown at 250 rpm at 37° C. until OD at 600 nm reached 0.6. The temperature was reduced to 18° C. and the culture was allowed to equilibrate to the reduced temperature for 1 hour. IPTG was added to the final concentration of 0.5 mM, and Rhamnose was added to 0.2% to induce protein production. The culture was allowed to incubate for 18 hrs at 250 rpm at 18° C. The culture was harvested by centrifugation at 6000 g for 20 minutes. The cell pellet was lysed by resuspending in 7.5 ml per 1 g pellet of 25 mM HEPES, 500 mM NaCl, 15 mM Imidazole, Protease inhibitors, 25 unit/ml Benzonase Nuclease, 0.01% DDM pH7.5 and mixed to homogeneity. The resuspended pellet was then lysed by sonication (15 cycles of 20 seconds on/20 seconds off for 15 cycles). The lysate was separated by centrifugation at 50,000 g for 1 hour. The supernatant was filtered through a 0.22 µm filter and applied to a 1 mL His trap crude column. The protein was purified by the AKTA system as per manufacturer's instructions, using 25 mM HEPES, 500 mM NaCl, 15 mM Imidazole, 0.01% DDM pH7.5 as the loading buffer; 25 mM HEPES, 500 mM NaCl, 75 mM Imidazole, 0.01% DDM pH7.5 as the wash buffer; and 25 mM HEPES, 500 mM NaCl, 500 mM Imidazole, 0.01% DDM pH7.5 as the elution buffer.

SDS Page was carried out to ascertain that the correct protein was present. Eluted fractions were then pooled and concentrated, for example, via 30 kD MWCO Amicon spin column. The protein was carried forward for SEC chromatography of S200 increase column, as per manufacturer's instructions, using 25 mM HEPES, 500 mM NaCl, 0.001% DDM pH7.5 as buffer A. The protein of interest was eluted as a single peak in an appropriate molecular weight fraction. For example, a modified InvG nanopore subunit polypeptide may have a molecular weight of about 40 kDa to about 70 kDa (which can vary depending on the elution conditions of the SEC chromatography). The elution fractions were pooled and incubated with lecithin liposomes for 3 hours at 37° C. with gentle mixing in a thermoshaker. The sample was then spun at 20,000G for 20 minutes, the supernatant discarded, and the pellet resuspended in 25 mM HEPES, 500 mM NaCl, 0.1% SDS pH7.5. Following resuspension, the sample was heated at 60° C. for 15 minutes and spun at 20,000 g for 10 minutes. The supernatant was carried forward for SEC on SW TOSOH G4000 column as per manufactures instructions to select for oligomer.

EXAMPLE 2

Exemplary Method for Expression and Purification of a Modified Secretin Nanopore Subunit Polypeptide Comprising an Endopeptidase Cleavage Site Ampicillin-resistant pT7 vector containing the gene encoding a modified secretin nanopore subunit polypeptide that comprises an endopeptidase cleavage site such as Tobacco Etch Virus (TEV) protease cleavage site (e.g., an amino acid sequence as set forth in SEQ ID NO: 3 with one or more (e.g., 1, 2, 3, 4, 5, 6, 7, 8, 9, 10, 15, 20, 25, 30, or more and up to 50 amino acid modifications described herein)) with a C terminal hexa-histidine tag was transformed into C43 DE3 pLysS cells and plated out on agar plates containing Ampicillin (100 µg/ml). A single colony was used to inoculate a 100 ml starter culture of TB media containing Ampicillin (100 µg/ml). The culture was grown at 250 rpm at 37° C. for 18 hours. 15 ml of starter culture was used to inoculate 500 ml of TB media containing Ampicillin (100 µg/ml) and the culture was grown at 250 rpm at 37° C. until the OD at 600 nm reached 0.6. The temperature was reduced to 18° C. and the culture was allowed to equilibrate to the reduced temperature for 1 hour. IPTG was added to the final concentration of 0.5 mM to induce protein production. The culture was allowed to incubate for 18 hrs at 250 rpm at 18° C. and harvested by centrifugation at 6000 g for 20 minutes. The cell pellet was lysed by resuspending in 7.5 ml per 1 g pellet of 25 mM HEPES, 500 mM NaCl, 15 mM Imidazole, Protease inhibitors, 25 unit/ml Benzonase Nuclease, and 0.01% DDM pH 7.5, and mixed to homogeneity. The resuspended pellet was then lysed by sonication (15 cycles of 20 seconds on/20 seconds off for 15 cycles). The lysate was separated by centrifugation at 50,000 g for 1 hour. The supernatant was filtered through 0.22 µm filter and applied to a 1 ml His trap crude column. The protein was purified by the AKTA system as per manufacturer's instructions, using 25 mM HEPES, 500 mM NaCl, 15 mM Imidazole, and 0.01% DDM pH 7.5 as the loading buffer; 25 mM HEPES, 500 mM NaCl, 75 mM Imidazole, and 0.01% DDM pH 7.5 as the wash buffer, and 25 mM HEPES, 500 mM NaCl, 500 mM Imidazole, and 0.01% DDM pH 7.5 as the elution buffer.

SDS Page was carried out to ascertain that the correct protein was present. Eluted fractions were then pooled and concentrated via a 30 kD MWCO Amicon spin column. The protein was carried forward for SEC chromatography of S200 increase column as per manufacturer's instructions using 25 mM HEPES, 500 mM NaCl, and 0.001% DDM pH 7.5 as buffer A. The protein of interest was eluted as a single peak in an appropriate molecular weight fraction. For example, a modified InvG nanopore subunit polypeptide may have a molecular weight of about 40 kDa to about 70 kDa (which can vary depending on the elution conditions of the SEC chromatography). The elution fractions were pooled. His-tagged TEV Protease was added to a final concentration of 0.2 mg/ml and the sample was allowed to incubate at 4° C. for 18 hours to remove peptide domains that were located upstream of the endopeptidase cleavage site within the vector sequence (e.g., N0 and N1 domains of an InvG protein) from the rest of the modified secretin nanopore subunit. The sample was reapplied to a trap column and the flow-through was collected. Flow-through fractions were incubated with lecithin liposomes for 3 hours at 37° C. with gentle mixing in a thermoshaker. The sample was then spun at 20,000G for 20 minutes, the supernatant discarded, and the pellet resuspended in 25 mM HEPES, 500 mM NaCl, and 0.1% SDS pH 7.5. Following resuspension, the sample was heated at 60° C. for 15 minutes and spun at 20,000 g for 10 minutes. The supernatant was carried forward for SEC on a SW TOSOH G4000 column as per manufacturer's instructions to select for the oligomer.

EXAMPLE 3

Design, Expression and Purification of GspD Mutants

GspD mutants were designed as shown in the Tables below using the *Vibrio cholerae* GspD sequence shown in SEQ ID NO: 32 as the starting sequence

TABLE 1

DNA Capture Mutants

| Mutation | Mutant Position |
| --- | --- |
| GspD-Vch-(WT-E253Q/E257Q/E264Q/D290N-Del((N1-K239)/(N265-SGS-E282))) | N3 Domain |
| GspD-Vch-(WT-E253Q/E257Q/E264K/D290N-Del((N1-K239)/(N265-SGS-E282))) | N3 Domain |
| GspD-Vch-(WT-E253Q/E257K/E264Q-Del((N1-K239)/(N265-SGS-E282))) | N3 Domain |
| GspD-Vch-(WT-E257K/E264K-Del((N1-K239)/(N265-SGS-E282))) | N3 Domain |
| GspD-Vch-(WT-E253R/E257K/E264Q-Del((N1-K239)/(N265-SGS-E282))) | N3 Domain |
| GspD-Vch-(WT-E454Q/D469S/E479K-Del((N1-K239)/(N265-SGS-E282))) | Central Gate |
| GspD-Vch-(WT-E454Q/E455N/D469S/E479K-Del((N1-K239)/(N265-SGS-E282))) | Central Gate |
| GspD-Vch-(WT-E455N/D469S/E479K-Del((N1-K239)/(N265-SGS-E282))) | Central Gate |
| GspD-Vch-(WT-E454Q/D469S/E479T-Del((N1-K239)/(N265-SGS-E282))) | Central Gate |
| GspD-Vch-(WT-E253Q/E257Q/E264Q/D290N/E454Q/E479K)-Del((N1-K239)/(N265-SGS-E282))) | Central Gate and N3 Domain |
| GspD-Vch-(WT-E253R/E257K/E264Q/E454Q/E479K-Del((N1-K239V(N265-SGS-E282))) | Central Gate and N3 Domain |
| GspD-Vch-(WT-E253Q/E257K/E264Q/D290N/E454Q/E455N-Del((N1-K239)/(N265-SGS-E282))) | Central Gate and N3 Domain |
| GspD-Vch-(WT-E253Q/E257Q/E264Q/D290N/E454Q/E455N/D469S/E479K-Del((N1-K239)/(N265-SGS-E282))) | Central Gate and N3 Domain |
| GspD-Vch-(WT-E253Q/E257K/E264K/D290N/E454Q/E455N/D469S/E479K-Del((N1-K239)/(N265-SGS-E282))) | Central Gate and N3 Domain |

TABLE 2

Increasing constriction size of central gate

| Mutation | Mutant Position |
| --- | --- |
| GspD-Vch-(WT-F472A-Del((N1-K239)/(N265-SGS-E282))) | Central Gate |
| GspD-Vch-(WT-Q473S-Del((N1-K239)/(N265-SGS-E282))) | Central Gate |
| GspD-Vch-(WT-N467S/N468G-Del(( TABLE 4-continued Stabilizing cap gate: charge removal

| Mutation | Mutant Position |
| --- | --- |
| GspD-Vch-(WT-R387N/N467G/N468S-Del(N1-K239)/(N265-SGS-E282))) | Cap Gate |
| GspD-Vch-(WT-D380S/R387S/N467G/N468S-Del(N1-K239)/(N265-SGS-E282))) | Cap Gate |
| GspD-Vch-(WT-D380N/R387S/N467G/N468S-Del(N1-K239)/(N265-SGS-E282))) | Cap Gate |
| GspD-Vch-(WT-D380N/N467G/N468S/D469S-Del(N1-K239)/(N265-SGS-E282))) | Cap Gate |
| GspD-Vch-(WT-D380S/N467G/N468S/D469S-Del(N1-K239)/(N265-SGS-E282))) | Cap Gate |
| GspD-Vch-(WT-R387S/N467G/N468S/D469S-Del(N1-K239)/(N265-SGS-E282))) | Cap Gate |
| GspD-Vch-(WT-R387N/N467G/N468S/D469S-Del(N1-K239)/(N265-SGS-E282))) | Cap Gate |
| GspD-Vch-(WT-D380S/R387S/N467G/N468S/D469S-Del(N1-K239)/(N265-SGS-E282))) | Cap Gate |
| GspD-Vch-(WT-D380N/R387S/N467G/N468S/D469S-Del(N1-K239)/(N265-SGS-E282))) | Cap Gate |
| GspD-Vch-(WT-E367Q/N467G/N468S/D469S-Del(N1-K239)/(N265-SGS-E282))) | Cap Gate |
| GspD-Vch-(WT-E368Q/N467G/N468S/D469S-Del(N1-K239)/(N265-SGS-E282))) | Cap Gate |
| GspD-Vch-(WT-D396N/N467G/N468S/D469S-Del(N1-K239)/(N265-SGS-E282))) | Cap Gate |
| GspD-Vch-(WT-K376S/D380S/R387S/E389Q/N467G/N468S/D469S-Del(N1-K239)/(N265-SGS-E282))) | Cap Gate |
| GspD-Vch-(WT-D371N/K376S/D380S/R387S/E389Q/K394S/N467G/N468S/D469S-Del(N1-K239)/(N265-SGS-E282))) | Cap Gate |

TABLE 5

Stabilizing cap gate

| Mutation | Mutant position |
| --- | --- |
| GspD-Vch-(WT-N467G/N468S/D469S-Del((N1-K239)/(N265-SGS-E282)/(D371-SGS-K394))) | Cap Gate deletion |
| GspD-Vch-(WT-N467G/N468S/D469S-Del((N1-K239)/(N265-SGS-E282)/(T372-SGS-T393))) | Cap Gate deletion |
| GspD-Vch-(WT-D371P/N467G/N468S/D469S-Del(N1-K239)/(N265-SGS-E282))) | Cap Gate: Proline substitution |
| GspD-Vch-(WT-K394P/N467G/N468S/D469S-Del(N1-K239)/(N265-SGS-E282))) | Cap Gate: Proline substitution |
| GspD-Vch-(WT-D371P/K394P/N467G/N468S/D469S-Del(N1-K239)/(N265-SGS-E282))) | Cap Gate: Proline substitution |
| GspD-Vch-(WT-T372P/T393P/N467G/N468S/D469S-Del(N1-K239)/(N265-SGS-E282))) | Cap Gate: Proline substitution |
| GspD-Vch-(WT-D371P/T372P/T393P/K394P/N467G/N468S/D469S-Del(N1-K239)/(N265-SGS-E282))) | Cap Gate: Proline substitution |

TABLE 6

Constriction and Cap extreme mutants

| Mutation | Mutant position |
| --- | --- |
| GspD-Vch-(WT-N467G/N468S/D469S-Del((N1-K239)/(N265-SGS-E282)/(D371-T393)))15 | Cap Gate deletion |
| GspD-Vch-(WT-G453A/N467G/N468S/D469S-Del((N1-K239)/(N265-SGS-E282)/(D371-T393)))15 | Cap Gate deletion and Central gate mutation |
| GspD-Vch-(WT-G453A/N467G/N468S/D469S-Del((N1-K239)/(N265-SGS-E282)/(T372-SGS-T393)))15 | Cap Gate deletion and Central gate mutation |
| GspD-Vch-(WT-N467G/N468S/D469S-Del((N1-K239)/(N265-SGS-E282)/(T372-SGS-T393)/(T463-QTT-S466)))15 | Cap Gate deletion and Central gate mutation |

TABLE 6-continued

Constriction and Cap extreme mutants

| Mutation | Mutant position |
|---|---|
| GspD-Vch-(WT-N467G-Del((N1-K239)/(N265-SGS-E282)/(T372-SGS-T393)/(N468-D469)))15 | Cap Gate deletion and Central gate mutation |
| GspD-Vch-(WT-Del((N1-K239)/(N265-SGS-E282)/(T372-SGS-T393)/(N467-D469)))15 | Cap Gate deletion and Central gate mutation |
| GspD-Vch-(WT-Del((N1-K239)/(N265-SGS-E282)/(T372-SGS-T393)/(T463-N470)))15 | Central gate deletion |

GspD mutants were expressed and purified in vitro using NEB pure express Kit. The reaction was setup as shown below.

TABLE 7

Reaction Mixture

| Component | Volume (μL) |
|---|---|
| Solution A | 10 |
| Solution B | 7.5 |
| 35S methionine | 1 |
| Rifampicin | 0.8 |
| Water | 4 |
| Lecithin vesicles | 20 μl (spun as pellet) |
| DNA | 1.5 |

The volume of the initial reaction mix was 25 μL. The reaction mixture was incubated for 3 hours at 37° C. in a thermomixer. After incubation, the tube was centrifuged for 10 min at 22000 g, of Which the supernatant was discarded. The protein present in the pellet was re-suspended in 1×laemmli buffer and run in 5% Tris-HCl gel overnight at 55V. The gel was then dried and exposed to Carestream® Kodak® BioMax® MR film overnight. The film was then processed and the protein in the gel visualized. The Oligomeric band of the protein was cut from the gel and re-suspended in 100 mM Tris, 50 mM NaCl, 0.1% zwittergent, pH 8.

EXAMPLE 4

Electrophysiology Setup

Setting up the experiment involved two separate steps, i) preparing the chips containing multiple wells of bulk co-polymer membrane to have single GspD mutant nanopores inserted and ready for sequencing and ii) DNA sample prep, which is added to the chip for sequencing. Materials and methods for both the steps are explained below.

GspD mutants were expressed and purified in-vitro and stored in buffer with 100 mM Tris, 50 mM NaCl, 0.1% zwittergent, pH 8. These mutant pores were diluted to 1:1000 using the 25 mM K Phosphate, 150 mM Potassium Ferrocyanide (II), 150 mM Potassium Ferricyanide (III), pH 8.0 buffer and added to the chips to obtain single pores in each wells. After pore insertion, the chips were washed with 1 mL, 25 mM K Phosphate buffer, 150 mM Potassium Ferrocyanide (II), 150 mM Potassium Ferricyanide (III), pH 8.0 buffer to remove excess GspD pores. IV curve measurement were performed when required using a script which records current at different potentials, ranging from −25 mV to −200 mV and 25 mV to 200 mV in 25 mV alternating potential steps. The chips was flushed twice with 500 mL of sequencing mix containing 470 mM KCL, 25 mM HEPES, 11 mM ATP and 10 mM MgCl2, pH8.0. The chip is now ready for sequencing.

Meanwhile, for 3.6 kb experiment, DNA sample was prepped for sequencing. 1 μg of DNA analyte was incubated with the 40 nM of Adapter mix (containing E8 helicase enzyme prebound to the adapter) and blunt TA ligase for 10 minutes. The ligation mixture was then purified of unligated free adapter using Spri purification. The final ligated mixture was eluted in 25 μL elution buffer containing 40 mM CAPS pH10, 40 mM KCl, 400 nM cholesterol tether. For each chip, 6 μl of DNA-adapter ligated mix was mixed with the sequencing mix (final volume of 75 μL) and added to chip for sequencing. The experiment was then run for 6 hours at 180 mV.

For the static strands experiment, Biotinylated static strands were incubated with monovalent streptavidin in ratio 1:1 for 10 minutes. The static strands were made to 1 mM final concentration in 470 mM KCL, 25 mM HEPES, pH8. 150 μl of strand was then added to the chip for static strand experiment. The pore used for the static strand experiment was GspD-Vch-(WT-N467G/N468S-Del((N1-K239)/(N265-SGS-E282))).

The results are shown in the Tables below and in FIGS. 14 to 18. The baseline pore is GspD-Vch-(WT-del(N1-K239)/(N265-SGS-E282))). This pore was chosen as a baseline. This pore expresses in IVTT even after deletion of two domains (1-238) as well as the constriction site 265-282 from the N3 domain. It is an open pore at −180 mV around 200 pA in C13 buffer, although frequent spikes in increases in open pore current are visible. It has an asymmetric IV-curve asymmetric, such that the pore remains open in negative potential and closed in positive potential. It has a non-linear IV curve with increasing open pore current with increasing potential.

TABLE 8

Characteristics of Mutant GspD Pores

| Mutant (Mutation from baseline, using numbering of SEQ ID NO: 32) | Location of Mutant | Change in characteristic |
|---|---|---|
| Baseline | Removal of top constriction and N0, N1 Domain | Open pore around 200 pA at −100 mV. Asymmetric IV curve with pore open at negative potential and closed at positive. |
| Y379-GSG-R387 | Removal of cap gate | Increases the open pore current (400-500 pA in −180 mV) at high voltages. However, the pore still has asymmetric IV which was open in negative potential and closed in positive potential. |
| F472A | Mutating larger residues to smaller ones in the central gate | Increase in open pore current. Makes the pore open at both negative and positive potential. |
| D469S | Removing charge in central gate | Small pores with open pore around 60 pA at −180 mV. However, some large pores with asymmetric IV curves were also seen. |
| G453 and G481 | Central Gate | Important for protein expression and oligomerization and does not express when mutated to other residues apart from A and V. |
| N467G/N468S* | Mutating larger residues to smaller ones in the central gate | Slight increase in open pore current slightly from 200 pA to 300 pA at −180 mV. Pore start to open even at positive potential. |
| N467S/N468G | Mutating larger residues to smaller ones in the central gate | Slight increases open pore current slightly from 200 pA to 300 pA at −180 mV. Pore start to open even at positive potential. |
| N467G/N468S/D469S* | Mutating larger residues to smaller ones in the central gate and removal of Charge in the central gate | Decrease in open pore current to 80 pA at −180 mV. Pores are symmetrical which are open in both negative and positive potential. |

*Selected as backgrounds for further mutant designs

TABLE 9

Characteristics of Mutant GspD Pores

| Mutant (Mutation from baseline) | Comparing IV curves and Current levels |
|---|---|
| Baseline | 100 pA at −150 mV. Open in negative potential and close in positive. |
| Y379-GSG-R387 | 80 p at −150 mV but open pore spikes up to 200 pA (due to the increased cap gate diameter). Still has assymetric IV curve which is open in negative potential and close in positive. |
| F472A | Triggers saturation in IV curve at higher potential. Current is around 200 pA at −100 mV. Open in both negative and positive potential. |
| D469S | Small pore with 40 pA current at −150 mV has asymmetric IV. Larger pore has symmetric IV and current of 200 pA at −150 mV. |
| N467G/N468S* | Mutating larger residues to smaller ones in the central gate |
| N467S/N468G | Mutating larger residues to smaller ones in the central gate |
| N467G/N468S/D469S* | Mutating larger residues to smaller ones in the central gate and removal of Charge in the central gate |

*Selected as backgrounds for further mutant designs

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A nanopore sequencing apparatus comprising a chamber housing an aqueous solution having disposed therein a membrane comprising a modified secretin nanopore disposed in the membrane, the modified secretin nanopore comprising a lumenal surface defining a lumen that extends through the membrane between a cis-opening and a trans-opening, wherein the lumenal surface comprises one or more amino acid modifications relative to a wild-type secretin nanopore.

2. The nanopore sequencing apparatus of claim 1, wherein the one or more amino acid modifications comprise a charge-altering modification and the charge-altering modification is a substitution of a negatively-charged amino acid with a positively-charged amino acid or the one or more amino acid modifications comprise a substitution of a neutral amino acid with a hydrophobic amino acid.

3. The nanopore sequencing apparatus of claim 1, wherein the cis-opening has a diameter in a range of 60 Å to 120 Å, the trans-opening has a diameter in a range of 40 Å to 100 Å and the secretin nanopore comprises a constriction having a diameter of about 7.5 Å to 25 Å.

4. The nanopore sequencing apparatus of claim 1, wherein the secretin is of a type II, type III or type IV secretion system, optionally wherein the modified secretin is GspD, YscC, InvG or PilQ.

5. The nanopore sequencing apparatus of claim 1, which comprises a subunit polypeptide having an amino acid sequence that is at least 95% identical to the amino acid sequence as set forth in SEQ ID NO: 33, SEQ ID NO: 34, SEQ ID NO: 35, SEQ ID NO: 36, SEQ ID NO: 1, or SEQ ID NO: 2.

6. The nanopore sequencing apparatus of claim 1 wherein the secretin is GaspD and wherein the central gate of GspD is modified to replace an amino acid with an amino acid having a smaller side group and/or to replace a negatively charged amino acid with a neutral or positively charged amino acid.

7. The nanopore sequencing apparatus of claim 1 wherein the secretin is GspD and which comprises a subunit polypeptide comprising a secretin domain having an amino acid sequence that is at least 95% identical to an amino acid sequence as set forth in SEQ ID NO: 36, wherein: (i) all or some of the amino acids from D55 or T56 to T77 are deleted or substituted, one or more of K60, D64, R71 and E73 is substituted with an uncharged amino acid and/or one or more of D55, T56, T77 and K78 is substituted with P; and/or (ii) F156 is substituted with a smaller amino acid, N151 and/or N152 is/are substituted with a smaller amino acid, D153 is substituted with an uncharged amino acid, G137 and G165 are each independently unmodified or substituted with A or V; and/or (iii) Y63 to R71 are deleted and/or substituted with GSG or SGS, F156 is substituted with A, D153 is substituted with S, and/or N151 and N152 are each independently substituted with G or S.

8. The nanopore sequencing apparatus of claim 1, wherein the secretin is InvG or which comprises a subunit polypeptide having an amino acid sequence that is at least 95% identical to the amino acid sequence as set forth in SEQ ID NO: 1, wherein the lumenal surface further defines a constriction within the lumen, the constriction having one or more amino acid modifications at amino acids D28, E225, R226, and/or E231 of SEQ ID NO: 1, optionally comprising one or more of the following:
   i. D28N/Q/T/S/G/R/K;
   ii. E225N/Q/T/A/S/G/P/H/F/Y/R/K;
   iii. R226N/Q/T/A/S/G/P/H/F/Y/K/V;
   iv. Deletion of E225;
   v. Deletion of R226; and
   vi. E231N/Q/T/A/S/G/P/H/R/K.

9. The nanopore sequencing apparatus of claim 1, wherein the secretin is InvG or which comprises a subunit polypeptide having an amino acid sequence that is at least 95% identical to the amino acid sequence as set forth in SEQ ID NO: 1, wherein the lumenal surface comprises a capture portion having one or more amino acid modifications at amino acids E41, Q45 or E114, optionally comprising one or more of the following amino acid modifications:
   i. Q45R/K;
   ii. E41N/Q/T/S/G/R/K; and
   iii. E114N/Q/T/S/G/R/K.

10. The nanopore sequencing apparatus of claim 1, further comprising an analyte present in the aqueous solution.

11. The nanopore sequencing apparatus of claim 10, wherein the analyte is a polynucleotide.

12. The nanopore sequencing apparatus of claim 11, further comprising a polynucleotide binding protein bound to the polynucleotide.

13. The nanopore sequencing apparatus of claim 12, wherein the polynucleotide binding protein is a helicase, exonuclease, or polymerase.

14. The nanopore sequencing apparatus of claim 12, wherein the polynucleotide binding protein is on the cis-side of the membrane.

15. The nanopore sequencing apparatus of claim 14, wherein the polynucleotide binding protein is in contact with or covalently attached to the cis-opening of the nanopore.

16. The nanopore sequencing apparatus of claim 12, wherein the polynucleotide binding protein is on the trans-side of the membrane.

17. The nanopore sequencing apparatus of claim 16, wherein the polynucleotide binding protein is in contact with or covalently attached to the trans-opening of the nanopore.

* * * * *

SEQUENCE LISTING

```
<160> NUMBER OF SEQ ID NOS: 40

<210> SEQ ID NO 1
<211> LENGTH: 391
<212> TYPE: PRT
<213> ORGANISM: Salmonella enterica

<400> SEQUENCE: 1

Gly Ile Glu Leu Gly Arg Gln Lys Ile Gly Val Met Arg Leu Asn Asn
1               5                   10                  15

Thr Phe Val Gly Asp Arg Thr Tyr Asn Leu Arg Asp Gln Lys Met Val
            20                  25                  30

Ile Pro Gly Ile Ala Thr Ala Ile Glu Arg Leu Leu Gln Gly Glu Glu
        35                  40                  45

Gln Pro Leu Gly Asn Ile Val Ser Ser Glu Pro Pro Ala Met Pro Ala
```

```
        50                  55                  60
    Phe Ser Ala Asn Gly Glu Lys Gly Lys Ala Ala Asn Tyr Ala Gly Gly
    65                  70                  75                  80

Met Ser Leu Gln Glu Ala Leu Lys Gln Asn Ala Ala Gly Asn Ile
                    85                  90                  95

Lys Ile Val Ala Tyr Pro Asp Thr Asn Ser Leu Val Lys Gly Thr
                    100                 105                 110

Ala Glu Gln Val His Phe Ile Glu Met Leu Val Lys Ala Leu Asp Val
                    115                 120                 125

Ala Lys Arg His Val Glu Leu Ser Leu Trp Ile Val Asp Leu Asn Lys
                    130                 135                 140

Ser Asp Leu Glu Arg Leu Gly Thr Ser Trp Ser Gly Ser Ile Thr Ile
    145                 150                 155                 160

Gly Asp Lys Leu Gly Val Ser Leu Asn Gln Ser Ser Ile Ser Thr Leu
                    165                 170                 175

Asp Gly Ser Arg Phe Ile Ala Ala Val Asn Ala Leu Glu Glu Lys Lys
                    180                 185                 190

Gln Ala Thr Val Val Ser Arg Pro Val Leu Leu Thr Gln Glu Asn Val
                    195                 200                 205

Pro Ala Ile Phe Asp Asn Asn Arg Thr Phe Tyr Thr Lys Leu Ile Gly
    210                 215                 220

Glu Arg Asn Val Ala Leu Glu His Val Thr Tyr Gly Thr Met Ile Arg
    225                 230                 235                 240

Val Leu Pro Arg Phe Ser Ala Asp Gly Gln Ile Glu Met Ser Leu Asp
                    245                 250                 255

Ile Glu Asp Gly Asn Asp Lys Thr Pro Gln Ser Asp Thr Thr Thr Ser
                    260                 265                 270

Val Asp Ala Leu Pro Glu Val Gly Arg Thr Leu Ile Ser Thr Ile Ala
                    275                 280                 285

Arg Val Pro His Gly Lys Ser Leu Leu Val Gly Gly Tyr Thr Arg Asp
                    290                 295                 300

Ala Asn Thr Asp Thr Val Gln Ser Ile Pro Phe Leu Gly Lys Leu Pro
    305                 310                 315                 320

Leu Ile Gly Ser Leu Phe Arg Tyr Ser Ser Lys Asn Lys Ser Asn Val
                    325                 330                 335

Val Arg Val Phe Met Ile Glu Pro Lys Glu Ile Val Asp Pro Leu Thr
                    340                 345                 350

Pro Asp Ala Ser Glu Ser Val Asn Asn Ile Leu Lys Gln Ser Gly Ala
                    355                 360                 365

Trp Ser Gly Asp Asp Lys Leu Gln Lys Trp Val Arg Val Tyr Leu Asp
                    370                 375                 380

Arg Gly Gln Glu Ala Ile Lys
    385                 390

<210> SEQ ID NO 2
<211> LENGTH: 562
<212> TYPE: PRT
<213> ORGANISM: Salmonella enterica

<400> SEQUENCE: 2

Met Lys Thr His Ile Leu Leu Ala Arg Val Leu Ala Cys Ala Ala Leu
1               5                   10                  15

Val Leu Val Thr Pro Gly Tyr Ser Ser Glu Lys Ile Pro Val Thr Gly
                20                  25                  30
```

-continued

```
Ser Gly Phe Val Ala Lys Asp Asp Ser Leu Arg Thr Phe Asp Ala
         35                  40                  45

Met Ala Leu Gln Leu Lys Glu Pro Val Ile Val Ser Lys Met Ala Ala
 50                  55                  60

Arg Lys Lys Ile Thr Gly Asn Phe Glu Phe His Asp Pro Asn Ala Leu
 65                  70                  75                  80

Leu Glu Lys Leu Ser Leu Gln Leu Gly Leu Ile Trp Tyr Phe Asp Gly
                 85                  90                  95

Gln Ala Ile Tyr Ile Tyr Asp Ala Ser Glu Met Arg Asn Ala Val Val
            100                 105                 110

Ser Leu Arg Asn Val Ser Leu Asn Glu Phe Asn Asn Phe Leu Lys Arg
            115                 120                 125

Ser Gly Leu Tyr Asn Lys Asn Tyr Pro Leu Arg Gly Asp Asn Arg Lys
    130                 135                 140

Gly Thr Phe Tyr Val Ser Gly Pro Pro Val Tyr Val Asp Met Val Val
145                 150                 155                 160

Asn Ala Ala Thr Met Met Asp Lys Gln Asn Asp Gly Ile Glu Leu Gly
                165                 170                 175

Arg Gln Lys Ile Gly Val Met Arg Leu Asn Asn Thr Phe Val Gly Asp
            180                 185                 190

Arg Thr Tyr Asn Leu Arg Asp Gln Lys Met Val Ile Pro Gly Ile Ala
        195                 200                 205

Thr Ala Ile Glu Arg Leu Leu Gln Gly Glu Glu Gln Pro Leu Gly Asn
    210                 215                 220

Ile Val Ser Ser Glu Pro Pro Ala Met Pro Ala Phe Ser Ala Asn Gly
225                 230                 235                 240

Glu Lys Gly Lys Ala Ala Asn Tyr Ala Gly Gly Met Ser Leu Gln Glu
                245                 250                 255

Ala Leu Lys Gln Asn Ala Ala Ala Gly Asn Ile Lys Ile Val Ala Tyr
            260                 265                 270

Pro Asp Thr Asn Ser Leu Leu Val Lys Gly Thr Ala Glu Gln Val His
        275                 280                 285

Phe Ile Glu Met Leu Val Lys Ala Leu Asp Val Ala Lys Arg His Val
    290                 295                 300

Glu Leu Ser Leu Trp Ile Val Asp Leu Asn Lys Ser Asp Leu Glu Arg
305                 310                 315                 320

Leu Gly Thr Ser Trp Ser Gly Ser Ile Thr Ile Gly Asp Lys Leu Gly
                325                 330                 335

Val Ser Leu Asn Gln Ser Ser Ile Ser Thr Leu Asp Gly Ser Arg Phe
            340                 345                 350

Ile Ala Ala Val Asn Ala Leu Glu Glu Lys Lys Gln Ala Thr Val Val
        355                 360                 365

Ser Arg Pro Val Leu Leu Thr Gln Glu Asn Val Pro Ala Ile Phe Asp
    370                 375                 380

Asn Asn Arg Thr Phe Tyr Thr Lys Leu Ile Gly Glu Arg Asn Val Ala
385                 390                 395                 400

Leu Glu His Val Thr Tyr Gly Thr Met Ile Arg Val Leu Pro Arg Phe
                405                 410                 415

Ser Ala Asp Gly Gln Ile Glu Met Ser Leu Asp Ile Glu Asp Gly Asn
            420                 425                 430

Asp Lys Thr Pro Gln Ser Asp Thr Thr Ser Val Asp Ala Leu Pro
        435                 440                 445

Glu Val Gly Arg Thr Leu Ile Ser Thr Ile Ala Arg Val Pro His Gly
```

```
                  450                 455                 460
Lys Ser Leu Leu Val Gly Gly Tyr Thr Arg Asp Ala Asn Thr Asp Thr
465                 470                 475                 480

Val Gln Ser Ile Pro Phe Leu Gly Lys Leu Pro Leu Ile Gly Ser Leu
                485                 490                 495

Phe Arg Tyr Ser Ser Lys Asn Lys Ser Asn Val Val Arg Val Phe Met
            500                 505                 510

Ile Glu Pro Lys Glu Ile Val Asp Pro Leu Thr Pro Asp Ala Ser Glu
        515                 520                 525

Ser Val Asn Asn Ile Leu Lys Gln Ser Gly Ala Trp Ser Gly Asp Asp
    530                 535                 540

Lys Leu Gln Lys Trp Val Arg Val Tyr Leu Asp Arg Gly Gln Glu Ala
545                 550                 555                 560

Ile Lys

<210> SEQ ID NO 3
<211> LENGTH: 569
<212> TYPE: PRT
<213> ORGANISM: Salmonella enterica

<400> SEQUENCE: 3

Met Lys Thr His Ile Leu Leu Ala Arg Val Leu Ala Cys Ala Ala Leu
1               5                   10                  15

Val Leu Val Thr Pro Gly Tyr Ser Ser Glu Lys Ile Pro Val Thr Gly
                20                  25                  30

Ser Gly Phe Val Ala Lys Asp Asp Ser Leu Arg Thr Phe Phe Asp Ala
            35                  40                  45

Met Ala Leu Gln Leu Lys Glu Pro Val Ile Val Ser Lys Met Ala Ala
        50                  55                  60

Arg Lys Lys Ile Thr Gly Asn Phe Glu Phe His Asp Pro Asn Ala Leu
65                  70                  75                  80

Leu Glu Lys Leu Ser Leu Gln Leu Gly Leu Ile Trp Tyr Phe Asp Gly
                85                  90                  95

Gln Ala Ile Tyr Ile Tyr Asp Ala Ser Glu Met Arg Asn Ala Val Val
                100                 105                 110

Ser Leu Arg Asn Val Ser Leu Asn Glu Phe Asn Asn Phe Leu Lys Arg
            115                 120                 125

Ser Gly Leu Tyr Asn Lys Asn Tyr Pro Leu Arg Gly Asp Asn Arg Lys
        130                 135                 140

Gly Thr Phe Tyr Val Ser Gly Pro Pro Val Tyr Val Asp Met Val Val
145                 150                 155                 160

Asn Ala Ala Thr Met Met Asp Lys Gln Asn Asp Glu Asn Leu Tyr Phe
                165                 170                 175

Gln Gly Gly Ile Glu Leu Gly Arg Gln Lys Ile Gly Val Met Arg Leu
                180                 185                 190

Asn Asn Thr Phe Val Gly Asp Arg Thr Tyr Asn Leu Arg Asp Gln Lys
            195                 200                 205

Met Val Ile Pro Gly Ile Ala Thr Ala Ile Glu Arg Leu Leu Gln Gly
        210                 215                 220

Glu Glu Gln Pro Leu Gly Asn Ile Val Ser Ser Glu Pro Pro Ala Met
225                 230                 235                 240

Pro Ala Phe Ser Ala Asn Gly Glu Lys Gly Lys Ala Ala Asn Tyr Ala
                245                 250                 255

Gly Gly Met Ser Leu Gln Glu Ala Leu Lys Gln Asn Ala Ala Ala Gly
```

```
            260                 265                 270
Asn Ile Lys Ile Val Ala Tyr Pro Asp Thr Asn Ser Leu Leu Val Lys
            275                 280                 285

Gly Thr Ala Glu Gln Val His Phe Ile Glu Met Leu Val Lys Ala Leu
290                 295                 300

Asp Val Ala Lys Arg His Val Glu Leu Ser Leu Trp Ile Val Asp Leu
305                 310                 315                 320

Asn Lys Ser Asp Leu Glu Arg Leu Gly Thr Ser Trp Ser Gly Ser Ile
                325                 330                 335

Thr Ile Gly Asp Lys Leu Gly Val Ser Leu Asn Gln Ser Ser Ile Ser
                340                 345                 350

Thr Leu Asp Gly Ser Arg Phe Ile Ala Ala Val Asn Ala Leu Glu Glu
                355                 360                 365

Lys Lys Gln Ala Thr Val Val Ser Arg Pro Val Leu Leu Thr Gln Glu
            370                 375                 380

Asn Val Pro Ala Ile Phe Asp Asn Asn Arg Thr Phe Tyr Thr Lys Leu
385                 390                 395                 400

Ile Gly Glu Arg Asn Val Ala Leu Glu His Val Thr Tyr Gly Thr Met
                405                 410                 415

Ile Arg Val Leu Pro Arg Phe Ser Ala Asp Gly Gln Ile Glu Met Ser
            420                 425                 430

Leu Asp Ile Glu Asp Gly Asn Asp Lys Thr Pro Gln Ser Asp Thr Thr
            435                 440                 445

Thr Ser Val Asp Ala Leu Pro Glu Val Gly Arg Thr Leu Ile Ser Thr
450                 455                 460

Ile Ala Arg Val Pro His Gly Lys Ser Leu Leu Val Gly Gly Tyr Thr
465                 470                 475                 480

Arg Asp Ala Asn Thr Asp Thr Val Gln Ser Ile Pro Phe Leu Gly Lys
                485                 490                 495

Leu Pro Leu Ile Gly Ser Leu Phe Arg Tyr Ser Ser Lys Asn Lys Ser
            500                 505                 510

Asn Val Val Arg Val Phe Met Ile Glu Pro Lys Glu Ile Val Asp Pro
            515                 520                 525

Leu Thr Pro Asp Ala Ser Glu Ser Val Asn Asn Ile Leu Lys Gln Ser
530                 535                 540

Gly Ala Trp Ser Gly Asp Asp Lys Leu Gln Lys Trp Val Arg Val Tyr
545                 550                 555                 560

Leu Asp Arg Gly Gln Glu Ala Ile Lys
                565

<210> SEQ ID NO 4
<211> LENGTH: 650
<212> TYPE: PRT
<213> ORGANISM: Escherichia coli

<400> SEQUENCE: 4

Met Lys Gly Leu Asn Lys Ile Thr Cys Cys Leu Leu Ala Ala Leu Leu
1               5                   10                  15

Met Pro Cys Ala Gly His Ala Glu Asn Glu Gln Tyr Gly Ala Asn Phe
            20                  25                  30

Asn Asn Ala Asp Ile Arg Gln Phe Val Glu Ile Val Gly Gln His Leu
        35                  40                  45

Gly Lys Thr Ile Leu Ile Asp Pro Ser Val Gln Gly Thr Ile Ser Val
    50                  55                  60
```

```
Arg Ser Asn Asp Thr Phe Ser Gln Gln Glu Tyr Tyr Gln Phe Phe Leu
 65                  70                  75                  80

Ser Ile Leu Asp Leu Tyr Gly Tyr Ser Val Ile Thr Leu Asp Asn Gly
                 85                  90                  95

Phe Leu Lys Val Val Arg Ser Ala Asn Val Lys Thr Ser Pro Gly Met
            100                 105                 110

Ile Ala Asp Ser Ser Arg Pro Gly Val Gly Asp Glu Leu Val Thr Arg
        115                 120                 125

Ile Val Pro Leu Glu Asn Val Pro Ala Arg Asp Leu Ala Pro Leu Leu
    130                 135                 140

Arg Gln Met Met Asp Ala Gly Ser Val Gly Asn Val Val His Tyr Glu
145                 150                 155                 160

Pro Ser Asn Val Leu Ile Leu Thr Gly Arg Ala Ser Thr Ile Asn Lys
                165                 170                 175

Leu Ile Glu Val Ile Lys Arg Val Asp Val Ile Gly Thr Glu Lys Gln
                180                 185                 190

Gln Ile Ile His Leu Glu Tyr Ala Ser Ala Glu Asp Leu Ala Glu Ile
        195                 200                 205

Leu Asn Gln Leu Ile Ser Glu Ser His Gly Lys Ser Gln Met Pro Ala
210                 215                 220

Leu Leu Ser Ala Lys Ile Val Ala Asp Lys Arg Thr Asn Ser Leu Ile
225                 230                 235                 240

Ile Ser Gly Pro Glu Lys Ala Arg Gln Arg Ile Thr Ser Leu Leu Lys
                245                 250                 255

Ser Leu Asp Val Glu Glu Ser Glu Glu Gly Asn Thr Arg Val Tyr Tyr
            260                 265                 270

Leu Lys Tyr Ala Lys Ala Thr Asn Leu Val Glu Val Leu Thr Gly Val
            275                 280                 285

Ser Glu Lys Leu Lys Asp Glu Lys Gly Asn Ala Arg Lys Pro Ser Ser
        290                 295                 300

Ser Gly Ala Met Asp Asn Val Ala Ile Thr Ala Asp Glu Gln Thr Asn
305                 310                 315                 320

Ser Leu Val Ile Thr Ala Asp Gln Ser Val Gln Glu Lys Leu Ala Thr
                325                 330                 335

Val Ile Ala Arg Leu Asp Ile Arg Arg Ala Gln Val Leu Val Glu Ala
            340                 345                 350

Ile Ile Val Glu Val Gln Asp Gly Asn Gly Leu Asn Leu Gly Val Gln
        355                 360                 365

Trp Ala Asn Lys Asn Val Gly Ala Gln Gln Phe Thr Asn Thr Gly Leu
    370                 375                 380

Pro Ile Phe Asn Ala Ala Gln Gly Val Ala Asp Tyr Lys Lys Asn Gly
385                 390                 395                 400

Gly Ile Thr Ser Ala Asn Pro Ala Trp Asp Met Phe Ser Ala Tyr Asn
                405                 410                 415

Gly Met Ala Ala Gly Phe Phe Asn Gly Asp Trp Gly Val Leu Leu Thr
            420                 425                 430

Ala Leu Ala Ser Asn Asn Lys Asn Asp Ile Leu Ala Thr Pro Ser Ile
        435                 440                 445

Val Thr Leu Asp Asn Lys Leu Ala Ser Phe Asn Val Gly Gln Asp Val
    450                 455                 460

Pro Val Leu Ser Gly Ser Gln Thr Thr Ser Gly Asp Asn Val Phe Asn
465                 470                 475                 480

Thr Val Glu Arg Lys Thr Val Gly Thr Lys Leu Lys Val Thr Pro Gln
```

```
                        485                 490                 495
Val Asn Glu Gly Asp Ala Val Leu Leu Glu Ile Glu Gln Glu Val Ser
                    500                 505                 510

Ser Val Asp Ser Ser Asn Ser Thr Leu Gly Pro Thr Phe Asn Thr
                515                 520                 525

Arg Thr Ile Gln Asn Ala Val Leu Val Lys Thr Gly Glu Thr Val Val
            530                 535                 540

Leu Gly Gly Leu Leu Asp Asp Phe Ser Lys Glu Gln Val Ser Lys Val
545                 550                 555                 560

Pro Leu Leu Gly Asp Ile Pro Leu Val Gly Gln Leu Phe Arg Tyr Thr
                565                 570                 575

Ser Thr Glu Arg Ala Lys Arg Asn Leu Met Val Phe Ile Arg Pro Thr
                580                 585                 590

Ile Ile Arg Asp Asp Val Tyr Arg Ser Leu Ser Lys Glu Lys Tyr
            595                 600                 605

Thr Arg Tyr Arg Gln Glu Gln Gln Arg Ile Asp Gly Lys Ser Lys
            610                 615                 620

Ala Leu Val Gly Ser Glu Asp Leu Pro Val Leu Asp Glu Asn Thr Phe
625                 630                 635                 640

Asn Ser His Ala Pro Ala Pro Ser Ser Arg
                645                 650

<210> SEQ ID NO 5
<211> LENGTH: 607
<212> TYPE: PRT
<213> ORGANISM: Yersinia enterocolitica

<400> SEQUENCE: 5

Met Ala Phe Pro Leu His Ser Phe Phe Lys Arg Val Leu Thr Gly Thr
1               5                   10                  15

Leu Leu Leu Leu Ser Ser Tyr Ser Trp Ala Gln Glu Leu Asp Trp Leu
                20                  25                  30

Pro Ile Pro Tyr Val Tyr Val Ala Lys Gly Glu Ser Leu Arg Asp Leu
            35                  40                  45

Leu Thr Asp Phe Gly Ala Asn Tyr Asp Ala Thr Val Val Val Ser Asp
        50                  55                  60

Lys Ile Asn Asp Lys Val Ser Gly Gln Phe Glu His Asp Asn Pro Gln
65                  70                  75                  80

Asp Phe Leu Gln His Ile Ala Ser Leu Tyr Asn Leu Val Trp Tyr Tyr
                85                  90                  95

Asp Gly Asn Val Leu Tyr Ile Phe Lys Asn Ser Glu Val Ala Ser Arg
            100                 105                 110

Leu Ile Arg Leu Gln Glu Ser Glu Ala Ala Glu Leu Lys Gln Ala Leu
        115                 120                 125

Gln Arg Ser Gly Ile Trp Glu Pro Arg Phe Gly Trp Arg Pro Asp Ala
    130                 135                 140

Ser Asn Arg Leu Val Tyr Val Ser Gly Pro Pro Arg Tyr Leu Glu Leu
145                 150                 155                 160

Val Glu Gln Thr Ala Ala Ala Leu Glu Gln Gln Thr Gln Ile Arg Ser
                165                 170                 175

Glu Lys Thr Gly Ala Leu Ala Ile Glu Ile Phe Pro Leu Lys Tyr Ala
            180                 185                 190

Ser Ala Ser Asp Arg Thr Ile His Tyr Arg Asp Asp Glu Val Ala Ala
        195                 200                 205
```

-continued

Pro Gly Val Ala Thr Ile Leu Gln Arg Val Leu Ser Asp Ala Thr Ile
210                 215                 220

Gln Gln Val Thr Val Asp Asn Gln Arg Ile Pro Gln Ala Ala Thr Arg
225                 230                 235                 240

Ala Ser Ala Gln Ala Arg Val Glu Ala Asp Pro Ser Leu Asn Ala Ile
            245                 250                 255

Ile Val Arg Asp Ser Pro Glu Arg Met Pro Met Tyr Gln Arg Leu Ile
            260                 265                 270

His Ala Leu Asp Lys Pro Ser Ala Arg Ile Glu Val Ala Leu Ser Ile
            275                 280                 285

Val Asp Ile Asn Ala Asp Gln Leu Thr Glu Leu Gly Val Asp Trp Arg
290                 295                 300

Val Gly Ile Arg Thr Gly Asn Asn His Gln Val Val Ile Lys Thr Thr
305                 310                 315                 320

Gly Asp Gln Ser Asn Ile Ala Ser Asn Gly Ala Leu Gly Ser Leu Val
            325                 330                 335

Asp Ala Arg Gly Leu Asp Tyr Leu Leu Ala Arg Val Asn Leu Leu Glu
            340                 345                 350

Asn Glu Gly Ser Ala Gln Val Val Ser Arg Pro Thr Leu Leu Thr Gln
            355                 360                 365

Glu Asn Ala Gln Ala Val Ile Asp His Ser Glu Thr Tyr Tyr Val Lys
370                 375                 380

Val Thr Gly Lys Glu Val Ala Glu Leu Lys Gly Ile Thr Tyr Gly Thr
385                 390                 395                 400

Met Leu Arg Met Thr Pro Arg Val Leu Thr Gln Gly Asp Lys Ser Glu
            405                 410                 415

Ile Ser Leu Asn Leu His Ile Glu Asp Gly Asn Gln Lys Pro Asn Ser
            420                 425                 430

Ser Gly Ile Glu Gly Ile Pro Thr Ile Ser Arg Thr Val Val Asp Thr
            435                 440                 445

Val Ala Arg Val Gly His Gly Gln Ser Leu Ile Ile Gly Gly Ile Tyr
450                 455                 460

Arg Asp Glu Leu Ser Val Ala Leu Ser Lys Val Pro Leu Leu Gly Asp
465                 470                 475                 480

Ile Pro Tyr Ile Gly Ala Leu Phe Arg Arg Lys Ser Glu Leu Thr Arg
            485                 490                 495

Arg Thr Val Arg Leu Phe Ile Ile Glu Pro Arg Ile Ile Asp Glu Gly
            500                 505                 510

Ile Ala His His Leu Ala Leu Gly Asn Gly Gln Asp Leu Arg Thr Gly
            515                 520                 525

Ile Leu Thr Val Asp Glu Ile Ser Asn Gln Ser Thr Thr Leu Asn Lys
530                 535                 540

Leu Leu Gly Gly Ser Gln Cys Gln Pro Leu Asn Lys Ala Gln Glu Val
545                 550                 555                 560

Gln Lys Trp Leu Ser Gln Asn Asn Lys Ser Ser Tyr Leu Thr Gln Cys
            565                 570                 575

Lys Met Asp Lys Ser Leu Gly Trp Arg Val Val Glu Gly Ala Cys Thr
            580                 585                 590

Pro Ala Gln Ser Trp Cys Val Ser Ala Pro Lys Arg Gly Val Leu
            595                 600                 605

<210> SEQ ID NO 6
<211> LENGTH: 566
<212> TYPE: PRT

<213> ORGANISM: Shigella flexneri

<400> SEQUENCE: 6

| | | | | | | | | | | | | | | |
|---|---|---|---|---|---|---|---|---|---|---|---|---|---|---|
| Met | Lys | Lys | Phe | Asn | Ile | Lys | Ser | Leu | Thr | Leu | Leu | Ile | Val | Leu |
| 1 | | | | 5 | | | | | 10 | | | | | 15 |
| Pro | Leu | Ile | Val | Asn | Ala | Asn | Asn | Ile | Asp | Ser | His | Leu | Leu | Glu | Gln |
| | | | 20 | | | | | 25 | | | | | 30 | | |
| Asn | Asp | Ile | Ala | Lys | Tyr | Val | Ala | Gln | Ser | Asp | Thr | Val | Gly | Ser | Phe |
| | | | 35 | | | | | 40 | | | | | 45 | | |
| Phe | Glu | Arg | Phe | Ser | Ala | Leu | Leu | Asn | Tyr | Pro | Ile | Val | Val | Ser | Lys |
| | 50 | | | | | 55 | | | | | 60 | | | | |
| Gln | Ala | Ala | Lys | Lys | Arg | Ile | Ser | Gly | Glu | Phe | Asp | Leu | Ser | Asn | Pro |
| 65 | | | | | 70 | | | | | 75 | | | | | 80 |
| Glu | Glu | Met | Leu | Glu | Lys | Leu | Thr | Leu | Leu | Val | Gly | Leu | Ile | Trp | Tyr |
| | | | | 85 | | | | | 90 | | | | | 95 | |
| Lys | Asp | Gly | Asn | Ala | Leu | Tyr | Ile | Tyr | Asp | Ser | Gly | Glu | Leu | Ile | Ser |
| | | | 100 | | | | | 105 | | | | | 110 | | |
| Lys | Val | Ile | Leu | Leu | Glu | Asn | Ile | Ser | Leu | Asn | Tyr | Leu | Ile | Gln | Tyr |
| | | | 115 | | | | | 120 | | | | | 125 | | |
| Leu | Lys | Asp | Ala | Asn | Leu | Tyr | Asp | His | Arg | Tyr | Pro | Ile | Arg | Gly | Asn |
| | 130 | | | | | 135 | | | | | 140 | | | | |
| Ile | Ser | Asp | Lys | Thr | Phe | Tyr | Ile | Ser | Gly | Pro | Pro | Ala | Leu | Val | Glu |
| 145 | | | | | 150 | | | | | 155 | | | | | 160 |
| Leu | Val | Ala | Asn | Thr | Ala | Thr | Leu | Leu | Asp | Lys | Gln | Val | Ser | Ser | Ile |
| | | | | 165 | | | | | 170 | | | | | 175 | |
| Gly | Thr | Asp | Lys | Val | Asn | Phe | Gly | Val | Ile | Lys | Leu | Lys | Asn | Thr | Phe |
| | | | 180 | | | | | 185 | | | | | 190 | | |
| Val | Ser | Asp | Arg | Thr | Tyr | Asn | Met | Arg | Gly | Glu | Asp | Ile | Val | Ile | Pro |
| | | | 195 | | | | | 200 | | | | | 205 | | |
| Gly | Val | Ala | Thr | Val | Val | Glu | Arg | Leu | Leu | Asn | Asn | Gly | Lys | Ala | Leu |
| | 210 | | | | | 215 | | | | | 220 | | | | |
| Ser | Asn | Arg | Gln | Ala | Gln | Asn | Asp | Pro | Met | Pro | Pro | Phe | Asn | Ile | Thr |
| 225 | | | | | 230 | | | | | 235 | | | | | 240 |
| Gln | Lys | Val | Ser | Glu | Asp | Ser | Asn | Asp | Phe | Ser | Phe | Ser | Ser | Val | Thr |
| | | | | 245 | | | | | 250 | | | | | 255 | |
| Asn | Ser | Ser | Ile | Leu | Glu | Asp | Val | Ser | Leu | Ile | Ala | Tyr | Pro | Glu | Thr |
| | | | 260 | | | | | 265 | | | | | 270 | | |
| Asn | Ser | Ile | Leu | Val | Lys | Gly | Asn | Asp | Gln | Gln | Ile | Gln | Ile | Ile | Arg |
| | | | 275 | | | | | 280 | | | | | 285 | | |
| Asp | Ile | Ile | Thr | Gln | Leu | Asp | Val | Ala | Lys | Arg | His | Ile | Glu | Leu | Ser |
| | 290 | | | | | 295 | | | | | 300 | | | | |
| Leu | Trp | Ile | Ile | Asp | Ile | Asp | Lys | Ser | Glu | Leu | Asn | Asn | Leu | Gly | Val |
| 305 | | | | | 310 | | | | | 315 | | | | | 320 |
| Asn | Trp | Gln | Gly | Thr | Ala | Ser | Phe | Gly | Asp | Ser | Phe | Gly | Ala | Ser | Phe |
| | | | | 325 | | | | | 330 | | | | | 335 | |
| Asn | Met | Ser | Ser | Ser | Ala | Ser | Ile | Ser | Thr | Leu | Asp | Gly | Asn | Lys | Phe |
| | | | 340 | | | | | 345 | | | | | 350 | | |
| Ile | Ala | Ser | Val | Met | Ala | Leu | Asn | Gln | Lys | Lys | Lys | Ala | Asn | Val | Val |
| | | | 355 | | | | | 360 | | | | | 365 | | |
| Ser | Arg | Pro | Val | Ile | Leu | Thr | Gln | Glu | Asn | Ile | Pro | Ala | Ile | Phe | Asp |
| | 370 | | | | | 375 | | | | | 380 | | | | |
| Asn | Asn | Arg | Thr | Phe | Tyr | Val | Ser | Leu | Val | Gly | Glu | Arg | Asn | Ser | Ser |
| 385 | | | | | 390 | | | | | 395 | | | | | 400 |

```
Leu Glu His Val Thr Tyr Gly Thr Leu Ile Asn Val Ile Pro Arg Phe
                    405                 410                 415

Ser Ser Arg Gly Gln Ile Glu Met Ser Leu Thr Ile Glu Asp Gly Thr
                420                 425                 430

Gly Asn Ser Gln Ser Asn Tyr Asn Tyr Asn Asn Glu Asn Thr Ser Val
            435                 440                 445

Leu Pro Glu Val Gly Arg Thr Lys Ile Ser Thr Ile Ala Arg Val Pro
        450                 455                 460

Gln Gly Lys Ser Leu Leu Ile Gly Gly Tyr Thr His Glu Thr Asn Ser
465                 470                 475                 480

Asn Glu Ile Ile Ser Ile Pro Phe Leu Ser Ser Ile Pro Val Ile Gly
                485                 490                 495

Asn Val Phe Lys Tyr Lys Thr Ser Asn Ile Ser Asn Ile Val Arg Val
                500                 505                 510

Phe Leu Ile Gln Pro Arg Glu Ile Lys Glu Ser Ser Tyr Tyr Asn Thr
            515                 520                 525

Ala Glu Tyr Lys Ser Leu Ile Ser Glu Arg Gly Ile Gln Lys Thr Thr
        530                 535                 540

Gln Ile Ile Pro Ser Glu Thr Thr Leu Leu Glu Asp Glu Lys Ser Leu
545                 550                 555                 560

Val Ser Tyr Leu Asn Tyr
                565

<210> SEQ ID NO 7
<211> LENGTH: 600
<212> TYPE: PRT
<213> ORGANISM: Pseudomonas aeruginosa

<400> SEQUENCE: 7

Met Arg Arg Leu Leu Ile Gly Gly Leu Leu Ala Leu Leu Pro Gly Ala
1               5                   10                  15

Val Leu Arg Ala Gln Pro Leu Asp Trp Pro Ser Leu Pro Tyr Asp Tyr
                20                  25                  30

Val Ala Gln Gly Glu Ser Leu Arg Asp Val Leu Ala Asn Phe Gly Ala
            35                  40                  45

Asn Tyr Asp Ala Ser Val Ile Val Ser Asp Lys Val Asn Asp Gln Val
    50                  55                  60

Ser Gly Arg Phe Asp Leu Glu Ser Pro Gln Ala Phe Leu Gln Leu Met
65                  70                  75                  80

Ala Ser Leu Tyr Asn Leu Gly Trp Tyr Tyr Asp Gly Thr Val Leu Tyr
                85                  90                  95

Val Phe Lys Thr Thr Glu Met Gln Ser Arg Leu Val Arg Leu Glu Gln
                100                 105                 110

Val Gly Glu Ala Glu Leu Lys Arg Ala Leu Thr Ala Ala Gly Ile Trp
            115                 120                 125

Glu Pro Arg Phe Gly Trp Arg Ala Asp Pro Ser Gly Arg Leu Val His
        130                 135                 140

Val Ser Gly Pro Gly Arg Tyr Leu Glu Leu Val Glu Gln Thr Ala Gln
145                 150                 155                 160

Val Leu Glu Gln Gln Tyr Thr Leu Arg Ser Glu Lys Thr Gly Asp Leu
                165                 170                 175

Ser Val Glu Ile Phe Pro Leu Arg Tyr Ala Val Ala Glu Asp Arg Lys
                180                 185                 190

Ile Glu Tyr Arg Asp Asp Glu Ile Glu Ala Pro Gly Ile Ala Ser Ile
            195                 200                 205
```

Leu Ser Arg Val Leu Ser Asp Ala Asn Val Ala Val Gly Asp Glu
210                 215                 220

Pro Gly Lys Leu Arg Pro Gly Gln Ser Ser His Ala Val Val Gln
225                 230                 235                 240

Ala Glu Pro Ser Leu Asn Ala Val Val Arg Asp His Lys Asp Arg
                245                 250                 255

Leu Pro Met Tyr Arg Arg Leu Ile Glu Ala Leu Asp Arg Pro Ser Ala
                260                 265                 270

Arg Ile Glu Val Gly Leu Ser Ile Ile Asp Ile Asn Ala Glu Asn Leu
                275                 280                 285

Ala Gln Leu Gly Val Asp Trp Ser Ala Gly Ile Arg Leu Gly Asn Asn
290                 295                 300

Lys Ser Ile Gln Ile Arg Thr Thr Gly Gln Asp Ser Glu Glu Gly Gly
305                 310                 315                 320

Gly Ala Gly Asn Gly Ala Val Gly Ser Leu Val Asp Ser Arg Gly Leu
                325                 330                 335

Asp Phe Leu Leu Ala Lys Val Thr Leu Leu Gln Ser Gln Gly Gln Ala
                340                 345                 350

Gln Ile Gly Ser Arg Pro Thr Leu Leu Thr Gln Glu Asn Thr Gln Ala
                355                 360                 365

Val Leu Asp Gln Ser Glu Thr Tyr Tyr Val Arg Val Thr Gly Glu Arg
370                 375                 380

Val Ala Glu Leu Lys Ala Ile Thr Tyr Gly Thr Met Leu Lys Met Thr
385                 390                 395                 400

Pro Arg Val Val Thr Leu Gly Asp Thr Pro Glu Ile Ser Leu Ser Leu
                405                 410                 415

His Ile Glu Asp Gly Ser Gln Lys Pro Asn Ser Ala Gly Leu Asp Lys
                420                 425                 430

Ile Pro Thr Ile Asn Arg Thr Val Ile Asp Thr Ile Ala Arg Val Gly
                435                 440                 445

His Gly Gln Ser Leu Leu Ile Gly Gly Ile Tyr Arg Asp Glu Leu Ser
450                 455                 460

Gln Ser Gln Arg Lys Val Pro Trp Leu Gly Asp Ile Pro Tyr Leu Gly
465                 470                 475                 480

Ala Leu Phe Arg Thr Thr Ala Asp Thr Val Arg Arg Ser Val Arg Leu
                485                 490                 495

Phe Leu Ile Glu Pro Arg Leu Ile Asp Asp Gly Val Gly His Tyr Leu
                500                 505                 510

Ala Leu Asn Asn Arg Arg Asp Leu Arg Gly Gly Leu Leu Glu Val Asp
                515                 520                 525

Glu Leu Ser Asn Gln Ser Leu Ser Leu Arg Lys Leu Leu Gly Ser Ala
530                 535                 540

Arg Cys Gln Ala Leu Ala Pro Ala Arg Ala Glu Gln Glu Arg Leu Arg
545                 550                 555                 560

Gln Ala Gly Gln Gly Ser Phe Leu Thr Pro Cys Arg Met Gly Ala Gln
                565                 570                 575

Glu Gly Trp Arg Val Thr Asp Ser Ala Cys Pro Lys Asp Gly Ala Trp
                580                 585                 590

Cys Val Gly Ala Glu Arg Gly Asn
                595                 600

<210> SEQ ID NO 8
<211> LENGTH: 512

<212> TYPE: PRT
<213> ORGANISM: Escherichia coli

<400> SEQUENCE: 8

Met Lys Lys Ile Ser Phe Phe Ile Phe Thr Ala Leu Phe Cys Cys Ser
1               5                   10                  15

Ala Gln Ala Ala Pro Ser Ser Leu Glu Lys Arg Leu Gly Lys Asn Glu
            20                  25                  30

Tyr Phe Ile Ile Thr Lys Ser Ser Pro Val Arg Ala Ile Leu Asn Asp
                35                  40                  45

Phe Ala Ala Asn Tyr Ser Ile Pro Val Phe Ile Ser Ser Ser Val Asn
        50                  55                  60

Asp Asp Phe Ser Gly Glu Ile Lys Asn Glu Lys Pro Val Lys Val Leu
65                  70                  75                  80

Glu Lys Leu Ser Lys Leu Tyr His Leu Thr Trp Tyr Tyr Asp Glu Asn
                85                  90                  95

Ile Leu Tyr Ile Tyr Lys Thr Asn Glu Ile Ser Arg Ser Ile Ile Thr
            100                 105                 110

Pro Thr Tyr Leu Asp Ile Asp Ser Leu Leu Lys Tyr Leu Ser Asp Thr
        115                 120                 125

Ile Ser Val Asn Lys Asn Ser Cys Asn Val Arg Lys Ile Thr Thr Phe
130                 135                 140

Asn Ser Ile Glu Val Arg Gly Val Pro Glu Cys Ile Lys Tyr Ile Thr
145                 150                 155                 160

Ser Leu Ser Glu Ser Leu Asp Lys Glu Ala Gln Ser Lys Ala Lys Asn
                165                 170                 175

Lys Asp Val Val Lys Val Phe Lys Leu Asn Tyr Ala Ser Ala Thr Asp
            180                 185                 190

Ile Thr Tyr Lys Tyr Arg Asp Gln Asn Val Val Pro Gly Val Val
        195                 200                 205

Ser Ile Leu Lys Thr Met Ala Ser Asn Gly Ser Leu Pro Ser Thr Gly
210                 215                 220

Lys Gly Ala Val Glu Arg Ser Gly Asn Leu Phe Asp Asn Ser Val Thr
225                 230                 235                 240

Ile Ser Ala Asp Pro Arg Leu Asn Ala Val Val Lys Asp Arg Glu
            245                 250                 255

Ile Thr Met Asp Ile Tyr Gln Gln Leu Ile Ser Glu Leu Asp Ile Glu
        260                 265                 270

Gln Arg Gln Ile Glu Ile Ser Val Ser Ile Ile Asp Val Asp Ala Asn
            275                 280                 285

Asp Leu Gln Gln Leu Gly Val Asn Trp Ser Gly Thr Leu Asn Ala Gly
        290                 295                 300

Gln Gly Thr Ile Ala Phe Asn Ser Ser Thr Ala Gln Ala Asn Ile Ser
305                 310                 315                 320

Ser Ser Val Ile Ser Asn Ala Ser Asn Phe Met Ile Arg Val Asn Ala
            325                 330                 335

Leu Gln Gln Asn Ser Lys Ala Lys Ile Leu Ser Gln Pro Ser Ile Ile
        340                 345                 350

Thr Leu Asn Asn Met Gln Ala Ile Leu Asp Lys Asn Val Thr Phe Tyr
        355                 360                 365

Thr Lys Val Ser Gly Glu Lys Val Ala Ser Leu Glu Ser Ile Thr Ser
    370                 375                 380

Gly Thr Leu Leu Arg Val Thr Pro Arg Ile Leu Asp Asp Ser Ser Asn
385                 390                 395                 400

-continued

Ser Leu Thr Gly Lys Arg Arg Glu Arg Val Arg Leu Leu Asp Ile
            405                 410                 415

Gln Asp Gly Asn Gln Ser Thr Asn Gln Ser Asn Ala Gln Asp Ala Ser
            420                 425                 430

Ser Thr Leu Pro Glu Val Gln Asn Ser Glu Met Thr Thr Glu Ala Thr
            435                 440                 445

Leu Ser Ala Gly Glu Ser Leu Leu Gly Gly Phe Ile Gln Asp Lys
450                 455                 460

Glu Ser Ser Ser Lys Asp Gly Ile Pro Leu Leu Ser Asp Ile Pro Val
465                 470                 475                 480

Ile Gly Ser Leu Phe Ser Ser Thr Val Lys Gln Lys His Ser Val Val
            485                 490                 495

Arg Leu Phe Leu Ile Lys Ala Thr Pro Ile Lys Ser Ala Ser Ser Glu
            500                 505                 510

<210> SEQ ID NO 9
<211> LENGTH: 497
<212> TYPE: PRT
<213> ORGANISM: Salmonella typhimurium

<400> SEQUENCE: 9

Met Val Val Asn Lys Arg Leu Ile Leu Ile Leu Phe Ile Leu Asn
1               5                   10                  15

Thr Ala Lys Ser Asp Glu Leu Ser Trp Lys Gly Asn Asp Phe Thr Leu
            20                  25                  30

Tyr Ala Arg Gln Met Pro Leu Ala Glu Val Leu His Leu Leu Ser Glu
        35                  40                  45

Asn Tyr Asp Thr Ala Ile Thr Ile Ser Pro Leu Ile Thr Ala Thr Phe
    50                  55                  60

Ser Gly Lys Ile Pro Pro Gly Pro Val Asp Ile Leu Asn Asn Leu
65              70                  75                  80

Ala Ala Gln Tyr Asp Leu Leu Thr Trp Phe Asp Gly Ser Met Leu Tyr
                85                  90                  95

Val Tyr Pro Ala Ser Leu Leu Lys His Gln Val Ile Thr Phe Asn Ile
            100                 105                 110

Leu Ser Thr Gly Arg Phe Ile His Tyr Leu Arg Ser Gln Asn Ile Leu
        115                 120                 125

Ser Ser Pro Gly Cys Glu Val Lys Glu Ile Thr Gly Thr Lys Ala Val
130                 135                 140

Glu Val Ser Gly Val Pro Ser Cys Leu Thr Arg Ile Ser Gln Leu Ala
145                 150                 155                 160

Ser Val Leu Asp Asn Ala Leu Ile Lys Arg Lys Asp Ser Ala Val Ser
                165                 170                 175

Val Ser Ile Tyr Thr Leu Lys Tyr Ala Thr Ala Met Asp Thr Gln Tyr
            180                 185                 190

Gln Tyr Arg Asp Gln Ser Val Val Pro Gly Val Val Ser Val Leu
        195                 200                 205

Arg Glu Met Ser Lys Thr Ser Val Pro Thr Ser Ser Thr Asn Asn Gly
210                 215                 220

Ser Pro Ala Thr Gln Ala Leu Pro Met Phe Ala Ala Asp Pro Arg Gln
225                 230                 235                 240

Asn Ala Val Ile Val Arg Asp Tyr Ala Ala Asn Met Ala Gly Tyr Arg
                245                 250                 255

Lys Leu Ile Thr Glu Leu Asp Gln Arg Gln Gln Met Ile Glu Ile Ser

```
                260                 265                 270
Val Lys Ile Ile Asp Val Asn Ala Gly Asp Ile Asn Gln Leu Gly Ile
            275                 280                 285

Asp Trp Gly Thr Ala Val Ser Leu Gly Gly Lys Lys Ile Ala Phe Asn
    290                 295                 300

Thr Gly Leu Asn Asp Gly Ala Ser Gly Phe Ser Thr Val Ile Ser
305                 310                 315                 320

Asp Thr Ser Asn Phe Met Val Arg Leu Asn Ala Leu Glu Lys Ser Ser
                325                 330                 335

Gln Ala Tyr Val Leu Ser Gln Pro Ser Val Val Thr Leu Asn Asn Ile
            340                 345                 350

Gln Ala Val Leu Asp Lys Asn Ile Thr Phe Tyr Thr Lys Leu Gln Gly
        355                 360                 365

Glu Lys Val Ala Lys Leu Glu Ser Ile Thr Thr Gly Ser Leu Leu Arg
    370                 375                 380

Val Thr Pro Arg Leu Leu Asn Asp Asn Gly Thr Gln Lys Ile Met Leu
385                 390                 395                 400

Asn Leu Asn Ile Gln Asp Gly Gln Gln Ser Asp Thr Gln Ser Glu Thr
                405                 410                 415

Asp Pro Leu Pro Glu Val Gln Asn Ser Glu Ile Ala Ser Gln Ala Thr
            420                 425                 430

Leu Leu Ala Gly Gln Ser Leu Leu Gly Gly Phe Lys Gln Gly Lys
        435                 440                 445

Gln Ile His Ser Gln Asn Lys Ile Pro Leu Leu Gly Asp Ile Pro Val
    450                 455                 460

Val Gly His Leu Phe Arg Asn Asp Thr Thr Gln Val His Ser Val Ile
465                 470                 475                 480

Arg Leu Phe Leu Ile Lys Ala Ser Val Val Asn Asn Gly Ile Ser His
                485                 490                 495

Gly

<210> SEQ ID NO 10
<211> LENGTH: 675
<212> TYPE: PRT
<213> ORGANISM: Vibrio cholerae

<400> SEQUENCE: 10

Met Lys Tyr Trp Leu Lys Lys Ser Ser Trp Leu Leu Ala Gly Ser Leu
1               5                   10                  15

Leu Ser Thr Pro Leu Ala Met Ala Asn Glu Phe Ser Ala Ser Phe Lys
            20                  25                  30

Gly Thr Asp Ile Gln Glu Phe Ile Asn Ile Val Gly Arg Asn Leu Glu
        35                  40                  45

Lys Thr Ile Ile Val Asp Pro Ser Val Arg Gly Lys Val Asp Val Arg
    50                  55                  60

Ser Phe Asp Thr Leu Asn Glu Glu Gln Tyr Tyr Ser Phe Phe Leu Ser
65                  70                  75                  80

Val Leu Glu Val Tyr Gly Phe Ala Val Val Glu Met Asp Asn Gly Val
                85                  90                  95

Leu Lys Val Ile Lys Ser Lys Asp Ala Lys Thr Ser Ala Ile Pro Val
            100                 105                 110

Leu Ser Gly Glu Glu Arg Ala Asn Gly Asp Glu Val Ile Thr Gln Val
        115                 120                 125

Val Ala Val Lys Asn Val Ser Val Arg Glu Leu Ser Pro Leu Leu Arg
```

```
            130                 135                 140
Gln Leu Ile Asp Asn Ala Gly Ala Gly Asn Val Val His Tyr Asp Pro
145                 150                 155                 160

Ala Asn Ile Ile Leu Ile Thr Gly Arg Ala Ala Val Val Asn Arg Leu
                165                 170                 175

Ala Glu Ile Ile Arg Arg Val Asp Gln Ala Gly Asp Lys Glu Ile Glu
                180                 185                 190

Val Val Glu Leu Asn Asn Ala Ser Ala Ala Glu Met Val Arg Ile Val
            195                 200                 205

Glu Ala Leu Asn Lys Thr Thr Asp Ala Gln Asn Thr Pro Glu Phe Leu
        210                 215                 220

Lys Pro Lys Phe Val Ala Asp Glu Arg Thr Asn Ser Ile Leu Ile Ser
225                 230                 235                 240

Gly Asp Pro Lys Val Arg Glu Arg Leu Lys Arg Leu Ile Lys Gln Leu
                245                 250                 255

Asp Val Glu Met Ala Ala Lys Gly Asn Asn Arg Val Val Tyr Leu Lys
                260                 265                 270

Tyr Ala Lys Ala Glu Asp Leu Val Glu Val Leu Lys Gly Val Ser Glu
        275                 280                 285

Asn Leu Gln Ala Glu Lys Gly Thr Gly Gln Pro Thr Thr Ser Lys Arg
        290                 295                 300

Asn Glu Val Met Ile Ala Ala His Ala Asp Thr Asn Ser Leu Val Leu
305                 310                 315                 320

Thr Ala Pro Gln Asp Ile Met Asn Ala Met Leu Glu Val Ile Gly Gln
                325                 330                 335

Leu Asp Ile Arg Arg Ala Gln Val Leu Ile Glu Ala Leu Ile Val Glu
                340                 345                 350

Met Ala Glu Gly Asp Gly Ile Asn Leu Gly Val Gln Trp Gly Ser Leu
            355                 360                 365

Glu Ser Gly Ser Val Ile Gln Tyr Gly Asn Thr Gly Ala Ser Ile Gly
        370                 375                 380

Asn Val Met Ile Gly Leu Glu Glu Ala Lys Asp Thr Thr Glu Lys Lys
385                 390                 395                 400

Pro Ile Arg Asn Ser Glu Thr Gly Glu Ile Lys Tyr Tyr Glu Glu Thr
                405                 410                 415

Thr Thr Lys Gly Asp Tyr Ser Lys Leu Ala Ser Ala Leu Ser Gly Leu
                420                 425                 430

Gln Gly Ala Ala Val Ser Ile Ala Met Gly Asp Trp Thr Ala Leu Ile
            435                 440                 445

Asn Ala Val Ser Asn Asp Ser Ser Asn Ile Leu Ser Ser Pro Ser
        450                 455                 460

Ile Thr Val Met Asp Asn Gly Glu Ala Ser Phe Ile Val Gly Glu Glu
465                 470                 475                 480

Val Pro Val Ile Thr Gly Ser Thr Ala Gly Ser Asn Asn Asp Asn Pro
                485                 490                 495

Phe Gln Thr Val Asp Arg Lys Glu Val Gly Ile Lys Leu Lys Val Val
            500                 505                 510

Pro Gln Ile Asn Glu Gly Asn Ser Val Gln Leu Asn Ile Glu Gln Glu
        515                 520                 525

Val Ser Asn Val Leu Gly Ala Asn Gly Ala Val Asp Val Arg Phe Ala
        530                 535                 540

Lys Arg Gln Leu Asn Thr Ser Val Met Val Gln Asp Gly Gln Met Leu
545                 550                 555                 560
```

```
Val Leu Gly Gly Leu Ile Asp Glu Arg Ala Leu Glu Ser Glu Ser Lys
                565                 570                 575

Val Pro Leu Leu Gly Asp Ile Pro Leu Leu Gly Gln Leu Phe Arg Ser
                580                 585                 590

Thr Ser Ser Gln Val Glu Lys Lys Asn Leu Met Val Phe Ile Lys Pro
            595                 600                 605

Thr Ile Ile Arg Asp Gly Val Thr Ala Asp Gly Ile Thr Gln Arg Lys
            610                 615                 620

Tyr Asn Tyr Ile Arg Ala Glu Gln Leu Phe Arg Ala Glu Lys Gly Leu
625                 630                 635                 640

Arg Leu Leu Asp Asp Ala Ser Val Pro Val Leu Pro Lys Phe Gly Asp
                645                 650                 655

Asp Arg Arg His Ser Pro Glu Ile Gln Ala Phe Ile Glu Gln Met Glu
                660                 665                 670

Ala Lys Gln
        675

<210> SEQ ID NO 11
<211> LENGTH: 660
<212> TYPE: PRT
<213> ORGANISM: Klebsiella pneumoniae

<400> SEQUENCE: 11

Met Ile Ile Ala Asn Val Ile Arg Ser Phe Ser Leu Thr Leu Leu Ile
1               5                   10                  15

Phe Ala Ala Leu Leu Phe Arg Pro Ala Ala Glu Glu Phe Ser Ala
                20                  25                  30

Ser Phe Lys Gly Thr Asp Ile Gln Glu Phe Ile Asn Thr Val Ser Lys
            35                  40                  45

Asn Leu Asn Lys Thr Val Ile Ile Asp Pro Ser Val Arg Gly Thr Ile
50                  55                  60

Thr Val Arg Ser Tyr Asp Met Leu Asn Glu Glu Gln Tyr Tyr Gln Phe
65                  70                  75                  80

Phe Leu Ser Val Leu Asp Val Tyr Gly Phe Ala Val Ile Asn Met Asn
                85                  90                  95

Asn Gly Val Leu Lys Val Val Arg Ser Lys Asp Ala Lys Thr Ala Ala
                100                 105                 110

Val Pro Val Ala Ser Asp Ala Ala Pro Gly Ile Gly Asp Glu Val Val
            115                 120                 125

Thr Arg Val Val Pro Leu Thr Asn Val Ala Ala Arg Asp Leu Ala Pro
            130                 135                 140

Leu Leu Arg Gln Leu Asn Asp Asn Ala Gly Val Gly Ser Val Val His
145                 150                 155                 160

Tyr Glu Pro Ser Asn Val Leu Leu Met Thr Gly Arg Ala Ala Val Ile
                165                 170                 175

Lys Arg Leu Leu Thr Ile Val Glu Arg Val Asp Asn Ala Gly Asp Arg
            180                 185                 190

Ser Val Val Thr Val Pro Leu Ser Trp Ala Ser Ala Ala Asp Val Val
            195                 200                 205

Lys Leu Val Thr Glu Leu Asn Lys Asp Thr Ser Lys Ser Ala Leu Pro
            210                 215                 220

Gly Ser Met Val Ala Asn Val Ala Asp Glu Arg Thr Asn Ala Val
225                 230                 235                 240

Leu Val Ser Gly Glu Pro Asn Ser Arg Gln Arg Ile Ile Ala Met Ile
```

```
            245                 250                 255
Lys Gln Leu Asp Arg Gln Gln Ala Thr Gln Gly Asn Thr Lys Val Ile
            260                 265                 270

Tyr Leu Lys Tyr Ala Lys Ala Ser Asp Leu Val Glu Val Leu Thr Gly
            275                 280                 285

Ile Ser Ser Thr Met Gln Ser Glu Lys Gln Ala Ala Lys Pro Val Ala
            290                 295                 300

Ala Leu Asp Lys Asn Ile Ile Ile Lys Ala His Gly Gln Thr Asn Ala
305                 310                 315                 320

Leu Ile Val Thr Ala Ala Pro Asp Val Met Asn Asp Leu Glu Arg Val
            325                 330                 335

Ile Ala Gln Leu Asp Ile Arg Arg Pro Gln Val Leu Val Glu Ala Ile
            340                 345                 350

Ile Ala Glu Val Gln Asp Ala Asp Gly Leu Asn Leu Gly Ile Gln Trp
            355                 360                 365

Ala Asn Lys Asn Ala Gly Met Thr Gln Phe Thr Asn Ser Gly Leu Pro
            370                 375                 380

Ile Ser Thr Ala Ile Ala Gly Ala Asn Gln Tyr Asn Lys Asp Gly Thr
385                 390                 395                 400

Val Ser Ser Ser Leu Ala Ser Ala Leu Ser Ser Phe Asn Gly Ile Ala
                    405                 410                 415

Ala Gly Phe Tyr Gln Gly Asn Trp Ala Met Leu Leu Thr Ala Leu Ser
            420                 425                 430

Ser Ser Thr Lys Asn Asp Ile Leu Ala Thr Pro Ser Ile Val Thr Leu
            435                 440                 445

Asp Asn Met Glu Ala Thr Phe Asn Val Gly Gln Glu Val Pro Val Leu
            450                 455                 460

Thr Gly Ser Gln Thr Thr Ser Gly Asp Asn Ile Phe Asn Thr Val Glu
465                 470                 475                 480

Arg Lys Thr Val Gly Ile Lys Leu Lys Val Lys Pro Gln Ile Asn Glu
                    485                 490                 495

Gly Asp Ser Val Leu Leu Glu Ile Glu Gln Glu Val Ser Ser Val Ala
            500                 505                 510

Asp Ala Ala Ser Ser Thr Ser Ser Asp Leu Gly Ala Thr Phe Asn Thr
            515                 520                 525

Arg Thr Val Asn Asn Ala Val Leu Val Gly Ser Gly Glu Thr Val Val
            530                 535                 540

Val Gly Gly Leu Leu Asp Lys Ser Val Ser Asp Thr Ala Asp Lys Val
545                 550                 555                 560

Pro Leu Leu Gly Asp Ile Pro Val Ile Gly Ala Leu Phe Arg Ser Thr
                    565                 570                 575

Ser Lys Lys Val Ser Lys Arg Asn Leu Met Leu Phe Ile Arg Pro Thr
            580                 585                 590

Val Ile Arg Asp Arg Asp Glu Tyr Arg Gln Ala Ser Ser Gly Gln Tyr
            595                 600                 605

Thr Ala Phe Asn Asp Ala Gln Ser Lys Gln Arg Gly Lys Glu Asn Asn
            610                 615                 620

Asp Ala Met Leu Asn Gln Asp Leu Leu Glu Ile Tyr Pro Arg Gln Asp
625                 630                 635                 640

Thr Ala Ala Phe Arg Gln Val Ser Ala Ala Ile Asp Ala Phe Asn Leu
                    645                 650                 655

Gly Gly Asn Leu
            660
```

<210> SEQ ID NO 12
<211> LENGTH: 745
<212> TYPE: PRT
<213> ORGANISM: Neisseria meningitidis

<400> SEQUENCE: 12

Met Asn Thr Lys Leu Thr Lys Ile Ile Ser Gly Leu Phe Val Ala Thr
1               5                   10                  15

Ala Ala Phe Gln Thr Ala Ser Ala Gly Asn Ile Thr Asp Ile Lys Val
            20                  25                  30

Ser Ser Leu Pro Asn Lys Gln Lys Ile Val Lys Val Ser Phe Asp Lys
        35                  40                  45

Glu Ile Val Asn Pro Thr Gly Phe Val Thr Ser Ser Pro Ala Arg Ile
50                  55                  60

Ala Leu Asp Phe Glu Gln Thr Gly Ile Ser Met Asp Gln Gln Val Leu
65                  70                  75                  80

Glu Tyr Ala Asp Pro Leu Leu Ser Lys Ile Ser Ala Ala Gln Asn Ser
                85                  90                  95

Ser Arg Ala Arg Leu Val Leu Asn Leu Asn Lys Pro Gly Gln Tyr Asn
            100                 105                 110

Thr Glu Val Arg Gly Asn Lys Val Trp Ile Phe Ile Asn Glu Ser Asp
        115                 120                 125

Asp Thr Val Ser Ala Pro Ala Arg Pro Ala Val Lys Ala Ala Pro Ala
130                 135                 140

Ala Pro Ala Lys Gln Gln Ala Ala Pro Ser Thr Lys Ser Ala Val
145                 150                 155                 160

Ser Val Ser Glu Pro Phe Thr Pro Ala Lys Gln Gln Ala Ala Pro
                165                 170                 175

Phe Thr Glu Ser Val Val Ser Val Ser Ala Pro Phe Ser Pro Ala Lys
            180                 185                 190

Gln Gln Ala Ala Pro Ala Lys Gln Thr Asn Ile Asp Phe Arg Lys
        195                 200                 205

Asp Gly Lys Asn Ala Gly Ile Ile Glu Leu Ala Ala Leu Gly Phe Ala
210                 215                 220

Gly Gln Pro Asp Ile Ser Gln His Asp His Ile Ile Val Thr Leu
225                 230                 235                 240

Lys Asn His Thr Leu Pro Thr Thr Leu Gln Arg Ser Leu Asp Val Ala
                245                 250                 255

Asp Phe Lys Thr Pro Val Gln Lys Val Thr Leu Lys Arg Leu Asn Asn
            260                 265                 270

Asp Thr Gln Leu Ile Ile Thr Thr Ala Gly Asn Trp Glu Leu Val Asn
        275                 280                 285

Lys Ser Ala Ala Pro Gly Tyr Phe Thr Phe Gln Val Leu Pro Lys Lys
290                 295                 300

Gln Asn Leu Glu Ser Gly Gly Val Asn Asn Ala Pro Lys Thr Phe Thr
305                 310                 315                 320

Gly Arg Lys Ile Ser Leu Asp Phe Gln Asp Val Glu Ile Arg Thr Ile
                325                 330                 335

Leu Gln Ile Leu Ala Lys Glu Ser Gly Met Asn Ile Val Ala Ser Asp
            340                 345                 350

Ser Val Asn Gly Lys Met Thr Leu Ser Leu Lys Asp Val Pro Trp Asp
        355                 360                 365

Gln Ala Leu Asp Leu Val Met Gln Ala Arg Asn Leu Asp Met Arg Gln 370                 375                 380
Gln Gly Asn Ile Val Asn Ile Ala Pro Arg Asp Glu Leu Leu Ala Lys
385                 390                 395                 400

Asp Lys Ala Phe Leu Gln Ala Glu Lys Asp Ile Ala Asp Leu Gly Ala
                405                 410                 415

Leu Tyr Ser Gln Asn Phe Gln Leu Lys Tyr Lys Asn Val Glu Glu Phe
            420                 425                 430

Arg Ser Ile Leu Arg Leu Asp Asn Ala Asp Thr Thr Gly Asn Arg Asn
        435                 440                 445

Thr Leu Val Ser Gly Arg Gly Ser Val Leu Ile Asp Pro Ala Thr Asn
450                 455                 460

Thr Leu Ile Val Thr Asp Thr Arg Ser Val Ile Glu Lys Phe Arg Lys
465                 470                 475                 480

Leu Ile Asp Glu Leu Asp Val Pro Ala Gln Gln Val Met Ile Glu Ala
                485                 490                 495

Arg Ile Val Glu Ala Ala Asp Gly Phe Ser Arg Asp Leu Gly Val Lys
            500                 505                 510

Phe Gly Ala Thr Gly Lys Lys Lys Leu Lys Asn Asp Thr Ser Ala Phe
        515                 520                 525

Gly Trp Gly Val Asn Ser Gly Phe Gly Gly Asp Asp Lys Trp Gly Ala
530                 535                 540

Glu Thr Lys Ile Asn Leu Pro Ile Thr Ala Ala Ala Asn Ser Ile Ser
545                 550                 555                 560

Leu Val Arg Ala Ile Ser Ser Gly Ala Leu Asn Leu Glu Leu Ser Ala
                565                 570                 575

Ser Glu Ser Leu Ser Lys Thr Lys Thr Leu Ala Asn Pro Arg Val Leu
            580                 585                 590

Thr Gln Asn Arg Lys Glu Ala Lys Ile Glu Ser Gly Tyr Glu Ile Pro
        595                 600                 605

Phe Thr Val Thr Ser Ile Ala Asn Gly Gly Ser Ser Thr Asn Thr Glu
610                 615                 620

Leu Lys Lys Ala Val Leu Gly Leu Thr Val Thr Pro Asn Ile Thr Pro
625                 630                 635                 640

Asp Gly Gln Ile Ile Met Thr Val Lys Ile Asn Lys Asp Ser Pro Ala
                645                 650                 655

Gln Cys Ala Ser Gly Asn Gln Thr Ile Leu Cys Ile Ser Thr Lys Asn
            660                 665                 670

Leu Asn Thr Gln Ala Met Val Glu Asn Gly Thr Leu Ile Val Gly
        675                 680                 685

Gly Ile Tyr Glu Glu Asp Asn Gly Asn Thr Leu Thr Lys Val Pro Leu
690                 695                 700

Leu Gly Asp Ile Pro Val Ile Gly Asn Leu Phe Lys Thr Arg Gly Lys
705                 710                 715                 720

Lys Thr Asp Arg Arg Glu Leu Leu Ile Phe Ile Thr Pro Arg Ile Met
                725                 730                 735

Gly Thr Ala Gly Asn Ser Leu Arg Tyr
            740                 745

<210> SEQ ID NO 13
<211> LENGTH: 563
<212> TYPE: PRT
<213> ORGANISM: Salmonella enterica

<400> SEQUENCE: 13

```
Met Lys Thr His Ile Leu Leu Ala Arg Val Leu Ala Cys Ala Ala Leu
1               5                   10                  15

Val Leu Val Ala Pro Gly Tyr Ser Ser Glu Lys Ile Pro Val Thr Glu
            20                  25                  30

Ser Gly Phe Val Ala Lys Asp Asp Ser Leu Arg Thr Phe Phe Asp Ala
            35                  40                  45

Met Ala Leu Gln Leu Lys Glu Pro Val Ile Val Ser Lys Met Ala Ala
50                  55                  60

Arg Lys Lys Ile Thr Gly Asn Phe Glu Phe Asn Asp Pro Asn Ala Leu
65                  70                  75                  80

Leu Glu Lys Leu Ser Leu Gln Leu Gly Leu Ile Trp Tyr Phe Asp Gly
                85                  90                  95

Gln Ala Ile Tyr Ile Tyr Asp Ala Ser Glu Met Arg Asn Ala Val Val
            100                 105                 110

Ser Leu Arg Asn Val Ser Leu Asn Glu Phe Asn Asn Phe Leu Lys Arg
            115                 120                 125

Ser Gly Leu Tyr Asn Lys Asn Tyr Pro Leu Arg Gly Asp Asn Arg Lys
            130                 135                 140

Gly Thr Phe Tyr Val Ser Gly Pro Pro Val Tyr Val Asp Met Val Val
145                 150                 155                 160

Asn Ala Ala Thr Met Met Asp Lys Gln Asn Asp Gly Ile Glu Leu Gly
                165                 170                 175

Arg Gln Lys Ile Gly Val Met Arg Leu Asn Asn Thr Phe Val Gly Asp
            180                 185                 190

Arg Thr Tyr Asn Leu Arg Asp Gln Lys Met Val Ile Pro Gly Ile Ala
            195                 200                 205

Thr Ala Ile Glu Arg Leu Leu Gln Gly Glu Glu Gln Pro Leu Gly Asn
210                 215                 220

Ile Ala Ser Ser Glu Pro Val Pro Ala Met Pro Ala Phe Ser Ser Asn
225                 230                 235                 240

Gly Glu Lys Gly Lys Thr Ser Asn Tyr Pro Gly Gly Met Ser Leu Gln
                245                 250                 255

Glu Ala Leu Lys Gln Asn Ala Ala Gly Asp Ile Lys Ile Val Ala
            260                 265                 270

Tyr Pro Asp Thr Asn Ser Leu Leu Val Lys Gly Thr Ala Glu Gln Val
            275                 280                 285

His Phe Ile Glu Met Leu Val Lys Ala Leu Asp Val Ala Lys Arg His
            290                 295                 300

Val Glu Leu Ser Leu Trp Ile Val Asp Leu Asn Lys Ser Asp Leu Glu
305                 310                 315                 320

Arg Leu Gly Thr Ser Trp Ser Gly Ser Ile Thr Ile Gly Asp Lys Leu
                325                 330                 335

Gly Val Ser Leu Asn Gln Ser Ser Ile Ser Thr Leu Asp Gly Ser Arg
            340                 345                 350

Phe Ile Ala Ala Val Asn Ala Leu Glu Glu Lys Lys Gln Ala Thr Val
            355                 360                 365

Val Ser Arg Pro Val Leu Leu Thr Gln Glu Asn Val Pro Ala Ile Phe
            370                 375                 380

Asp Asn Asn Arg Thr Phe Tyr Thr Lys Leu Ile Gly Glu Arg Asn Val
385                 390                 395                 400

Ala Leu Glu His Val Thr Tyr Gly Thr Met Ile Arg Val Leu Pro Arg
                405                 410                 415

Phe Ser Ala Asp Gly Gln Ile Glu Met Ser Leu Asp Ile Glu Asp Gly
```

```
                420               425               430
Asn Asp Lys Thr Pro Gln Asn Asp Leu Thr Thr Ser Val Asp Ala Leu
            435                 440                 445

Pro Glu Val Gly Arg Thr Leu Ile Ser Thr Ile Ala Arg Val Pro His
    450                 455                 460

Gly Lys Ser Leu Leu Val Gly Gly Tyr Thr Arg Asp Ala Asn Thr Asp
465                 470                 475                 480

Thr Val Gln Ser Ile Pro Phe Leu Gly Lys Ile Pro Leu Ile Gly Ser
                485                 490                 495

Leu Phe Arg Tyr Ser Ser Lys Asn Lys Ser Asn Val Val Arg Val Phe
            500                 505                 510

Met Ile Glu Pro Lys Glu Ile Val Asp Pro Leu Met Pro Asp Ala Ser
            515                 520                 525

Glu Ser Val Asn Asn Ile Leu Lys Gln Ser Gly Ala Trp Ser Gly Asp
530                 535                 540

Asp Lys Leu Gln Lys Trp Val Arg Val Tyr Leu Asp Arg Gly Leu Glu
545                 550                 555                 560

Ala Thr Lys

<210> SEQ ID NO 14
<211> LENGTH: 563
<212> TYPE: PRT
<213> ORGANISM: Salmonella bongori

<400> SEQUENCE: 14

Met Lys Thr His Ile Leu Leu Ala Arg Val Leu Ala Cys Ala Ala Leu
1               5                   10                  15

Ile Leu Ala Ala Pro Gly Tyr Ser Ser Glu Lys Ile Pro Val Thr Gly
            20                  25                  30

Ser Gly Phe Val Ala Lys Asp Asp Ser Leu Arg Thr Phe Phe Asp Ala
        35                  40                  45

Met Ala Leu Gln Leu Lys Glu Pro Val Ile Val Ser Lys Met Ala Ala
    50                  55                  60

Arg Lys Lys Ile Thr Gly Asn Phe Glu Phe Asn Asp Pro Asn Ala Leu
65                  70                  75                  80

Leu Glu Lys Leu Ser Leu Gln Leu Gly Leu Ile Trp Tyr Phe Asp Gly
                85                  90                  95

Gln Ala Ile Tyr Ile Tyr Asp Ala Ser Glu Met Arg Asn Ala Val Val
            100                 105                 110

Ser Leu Arg Asn Val Ser Leu Asn Glu Phe Asn Phe Leu Lys Arg
        115                 120                 125

Ser Gly Leu Tyr Asn Lys Asn Tyr Pro Leu Arg Gly Asp Asn Arg Lys
    130                 135                 140

Gly Thr Phe Tyr Val Ser Gly Pro Pro Val Tyr Val Asp Met Val Val
145                 150                 155                 160

Asn Ala Ala Thr Met Met Asp Lys Gln Asn Asp Gly Ile Glu Leu Gly
                165                 170                 175

Arg Gln Lys Ile Gly Val Met Arg Leu Asn Asn Thr Phe Val Gly Asp
            180                 185                 190

Arg Thr Tyr Asn Leu Arg Asp Gln Lys Ile Val Ile Pro Gly Ile Ala
        195                 200                 205

Thr Ala Ile Glu Arg Leu Leu Gln Gly Glu Glu Lys Pro Leu Gly Asn
    210                 215                 220

Val Ala Ser Ser Glu Pro Val Pro Thr Met Pro Ala Phe Ser Ala Asn
```

```
                    225                 230                 235                 240

Gly Asp Lys Gly Lys Pro Ala Asn Tyr Ala Gly Gly Met Ser Leu Gln
                245                 250                 255

Glu Ala Leu Lys Gln Asn Ala Ala Gly Asp Ile Lys Ile Val Ala
            260                 265                 270

Tyr Pro Asp Thr Asn Ser Leu Val Lys Gly Thr Ala Glu Gln Val
        275                 280                 285

His Phe Ile Glu Met Leu Val Lys Val Leu Asp Val Ala Lys Arg His
    290                 295                 300

Val Glu Leu Ser Leu Trp Ile Val Asp Leu Asn Lys Ser Asp Leu Glu
305                 310                 315                 320

Arg Leu Gly Ala Ser Trp Ser Gly Ser Ile Thr Ile Gly Asp Lys Leu
                325                 330                 335

Gly Val Ser Leu Asn Gln Ser Ser Ile Ser Thr Leu Asp Gly Ser Arg
            340                 345                 350

Phe Ile Ala Ala Val Asn Ala Leu Glu Glu Lys Lys Gln Ala Thr Val
        355                 360                 365

Val Ser Arg Pro Val Leu Leu Thr Gln Glu Asn Val Pro Ala Ile Phe
    370                 375                 380

Asp Asn Asn Arg Thr Phe Tyr Thr Lys Leu Ile Gly Glu Arg Asn Val
385                 390                 395                 400

Ala Leu Glu His Val Thr Tyr Gly Thr Met Val Arg Val Leu Pro Arg
                405                 410                 415

Phe Ser Ala Asp Gly Gln Ile Glu Met Ser Leu Asp Ile Glu Asp Gly
            420                 425                 430

Asn Glu Thr Ile Pro Lys Thr Asp Ile Thr Ala Ser Val Asp Ala Leu
        435                 440                 445

Pro Glu Val Gly Arg Thr Leu Ile Ser Thr Ile Ala Arg Val Pro His
    450                 455                 460

Gly Lys Ser Leu Leu Val Gly Gly Tyr Thr Arg Asp Ala Asn Thr Asp
465                 470                 475                 480

Thr Val Gln Ser Val Pro Phe Leu Gly Lys Ile Pro Phe Ile Gly Gly
                485                 490                 495

Leu Phe Arg Tyr Ser Ser Lys Asn Lys Ser Asn Val Val Arg Val Phe
            500                 505                 510

Leu Ile Glu Pro Lys Glu Ile Val Asp Pro Leu Thr Pro Asp Ala Ser
        515                 520                 525

Glu Ser Val Asn Asn Ile Leu Lys Gln Ser Gly Thr Trp Ser Gly Asp
    530                 535                 540

Asp Lys Leu Gln Lys Trp Val Arg Val Tyr Leu Asp Arg Asn Gln Glu
545                 550                 555                 560

Thr Ile Lys

<210> SEQ ID NO 15
<211> LENGTH: 579
<212> TYPE: PRT
<213> ORGANISM: Chromobacterium haemolyticum

<400> SEQUENCE: 15

Met Asn Arg Ser Phe Leu Ser Ala Ala Leu Leu Ala Ala Leu Leu
1               5                   10                  15

Ala Ser Val Pro Ala Ala Ala Pro Glu Pro Ala Arg Ala Ala Asp
            20                  25                  30

Ser Ala Gly Tyr Val Ala Lys Lys Glu Gly Leu Arg Ser Phe Phe Asp
```

```
             35                  40                  45
Ala Ile Ser Ser Arg Leu Lys Lys Pro Val Ile Val Ser Lys Gln Ala
 50                  55                  60
Ala Arg Lys Gln Ile Ser Gly Asp Phe Asp Leu Ala Asn Pro Gln Ala
65                   70                  75                  80
Leu Leu Asp Lys Met Thr Gln Gln Leu Gly Leu Ile Trp Tyr His Asp
                 85                  90                  95
Gly Gln Ala Ile Tyr Val Tyr Asp Ala Ser Glu Thr Arg Asn Ala Val
                100                 105                 110
Val Ser Leu Arg Asn Val Ser Leu Ser Ala Phe Asn Asp Phe Leu Arg
            115                 120                 125
Lys Ser Gly Leu Tyr Asp Lys Arg Tyr Pro Leu Arg Gly Asp Asn Arg
        130                 135                 140
Ser Gly Thr Phe Tyr Val Ser Gly Pro Pro Val Phe Val Asp Leu Val
145                 150                 155                 160
Val Asn Ala Ala Gly Phe Met Asp Lys Gln Ser Asp Gly Ile Glu Leu
                165                 170                 175
Gly Arg Gln Lys Ile Gly Val Val Arg Leu Asn Asn Thr Phe Val Ser
            180                 185                 190
Asp Arg Ser Tyr Glu Leu Arg Asp Gln Lys Ile Val Ile Pro Gly Met
        195                 200                 205
Ala Thr Val Ile Glu Lys Leu Leu Gln Gly Asp Lys Pro Leu Gln
210                 215                 220
Thr Ala Gly Val Asn Pro Val Arg Pro Ala Arg Gly Ser Asp Ile
225                 230                 235                 240
Pro Ala Met Pro Asp Phe Pro Ala Ser Gly Glu Leu Lys Ala Pro Ala
                245                 250                 255
Tyr Gln Ala Gly Leu Ser Leu Pro Asp Ala Leu Lys Gln Asp Ala Ala
            260                 265                 270
Ala Gly Asp Ile Lys Val Ile Ala Tyr Pro Asp Thr Asn Ser Leu Leu
        275                 280                 285
Ile Lys Gly Thr Ala Glu Gln Val Arg Phe Ile Glu Asn Leu Ala Leu
290                 295                 300
Ala Leu Asp Val Ala Lys Arg His Val Glu Leu Ser Leu Trp Ile Ile
305                 310                 315                 320
Asp Leu Asp Lys Gly Asp Leu Asp Gln Leu Gly Val Asn Trp Ser Gly
                325                 330                 335
Ser Val Thr Val Gly Asn Lys Leu Gly Val Ala Leu Asn Pro Ser Ser
            340                 345                 350
Ser Ile Ser Thr Leu Asp Gly Thr Arg Phe Ile Ala Ser Val Met Ala
        355                 360                 365
Leu Ser Gln Lys Asn Lys Ala Asn Val Val Ser Arg Pro Val Val Leu
    370                 375                 380
Thr Gln Glu Asn Val Pro Ala Ile Phe Asp Asn Asn Arg Thr Phe Tyr
385                 390                 395                 400
Ala Lys Leu Val Gly Glu Arg Asn Ala Ser Leu Gln His Val Thr Tyr
                405                 410                 415
Gly Thr Leu Val Ser Val Leu Pro Arg Phe Ser Ala Asp Gly Gln Ile
            420                 425                 430
Glu Met Ser Leu Asn Ile Glu Asp Gly Arg Glu Ala Lys Thr Pro Asp
        435                 440                 445
Tyr Asp Arg Asp Pro Gln Asp Ala Leu Pro Glu Val Gly Arg Thr Arg
    450                 455                 460
```

```
Ile Ser Thr Val Ala Arg Val Pro Gln Gly Lys Ser Leu Leu Ile Gly
465                 470                 475                 480

Gly Tyr Thr Arg Asp Ala Asn Ile Glu Gln Asn Asn Lys Val Pro Phe
                485                 490                 495

Leu Gly Ser Leu Pro Leu Val Gly Gly Leu Phe Arg Tyr Arg Ser Gln
            500                 505                 510

Asn Gln Ser Asn Thr Val Arg Val Phe Leu Ile Gln Pro Arg Glu Ile
        515                 520                 525

Asp Asp Pro Leu Thr Pro Asp Ala Ser Asp Leu Ser Ala Ala Val Ala
    530                 535                 540

Lys Glu Gly Gly Ile Ala Ser Asp Pro Leu Gln Gln Trp Val Arg Asp
545                 550                 555                 560

Tyr Leu Asp Arg Glu Gln Arg Ala Glu Gly Ala Ala Lys Gly Ala Thr
                565                 570                 575

Arg Gly His

<210> SEQ ID NO 16
<211> LENGTH: 570
<212> TYPE: PRT
<213> ORGANISM: Burkholderia ubonensis

<400> SEQUENCE: 16

Met Lys Ile His His Leu Arg Ala Trp Phe Leu Val Cys Ala Val Leu
1               5                   10                  15

Leu Ala Pro Leu Ala Ala Arg Ala Val Gly Pro Met Ala Ser Ala Gly
            20                  25                  30

Ser Gly Tyr Val Ala Lys Asn Glu Ser Leu Arg Ser Phe Phe Asp Ala
        35                  40                  45

Leu Ala Ala Gln Leu Glu Lys Pro Val Ile Val Ser Lys Leu Ala Ala
    50                  55                  60

Arg Lys Gln Ile Ser Gly Glu Phe Asp Leu Asn Gly Ser Gln Ala Leu
65                  70                  75                  80

Leu Asp Lys Leu Ser Gln Gln Leu Gly Leu Ile Trp Tyr His Asp Gly
                85                  90                  95

Gln Ala Ile Tyr Ile Tyr Asp Ala Ser Glu Ile Arg Asn Ala Val Val
            100                 105                 110

Ser Leu Arg Asn Val Ser Leu Gly Ala Phe Asn Asp Phe Leu Arg Arg
        115                 120                 125

Ser Gly Leu Tyr Asp Arg Arg Tyr Pro Leu Arg Gly Asp Ala Arg Ser
    130                 135                 140

Gly Thr Phe Tyr Val Ser Gly Pro Ala Val Phe Val Asp Leu Val Val
145                 150                 155                 160

Asn Ala Ala Thr Phe Met Asp Lys Gln Ser Thr Gly Val Glu Leu Gly
                165                 170                 175

Arg Gln Lys Ile Gly Val Val Arg Leu Asn Asn Thr Phe Val Ser Asp
            180                 185                 190

Arg Thr Tyr Glu Leu Arg Asp Gln Lys Ile Val Ile Pro Gly Met Ala
        195                 200                 205

Thr Val Val Glu Lys Leu Leu Leu Gly Glu Gly Lys Pro Leu Gln Ser
    210                 215                 220

Ala Ala Ser Thr Ala Pro Leu His Pro Pro Ala Arg Arg Asp Asp Ile
225                 230                 235                 240

Pro Ala Met Pro Asp Phe Pro Ser Gly Gly Glu Ser Lys Ala Pro Ala
                245                 250                 255
```

```
Tyr Ser Gly Gly Leu Ser Leu Pro Glu Ala Leu Lys Gln Glu Val Ala
            260                 265                 270

Ala Gly Asp Ile Lys Val Ile Ala Tyr Pro Asp Thr Asn Ser Leu Leu
        275                 280                 285

Val Lys Gly Thr Thr Glu Gln Val Arg Phe Ile Glu Lys Leu Ala Ala
    290                 295                 300

Ala Leu Asp Val Pro Lys Arg His Val Glu Leu Ser Leu Trp Ile Ile
305                 310                 315                 320

Asp Leu Asp Lys Gly Asp Leu Asp Gln Leu Gly Val Lys Trp Ser Gly
            325                 330                 335

Ser Ala Thr Ile Gly Asp Lys Leu Gly Val Thr Leu Asn Gln Ala Gly
        340                 345                 350

Ser Val Ser Thr Leu Asp Gly Ser Arg Phe Ile Ala Tyr Val Met Ala
    355                 360                 365

Leu Glu Gln Lys Asp Lys Ala Gln Val Val Ser Arg Pro Val Val Leu
370                 375                 380

Thr Gln Glu Asn Val Pro Ala Leu Phe Asp Asn Asn Arg Thr Phe Tyr
385                 390                 395                 400

Ala Lys Leu Val Gly Glu Arg Thr Ala Ser Leu Gln Ser Val Thr Tyr
            405                 410                 415

Gly Thr Leu Ile Ser Val Leu Pro Arg Phe Ser Ala Asp Gly Gln Ile
        420                 425                 430

Glu Met Ser Leu Asn Ile Glu Asp Gly Arg Glu Ala Asn Ala Pro Asp
    435                 440                 445

Asp Glu Asn Ser Ser Phe Asp Ala Leu Pro Glu Val Gly Arg Thr His
450                 455                 460

Ile Ser Thr Val Ala Arg Val Pro Gln Gly Lys Ser Leu Leu Ile Gly
465                 470                 475                 480

Gly Tyr Thr Arg Asp Ser Ser Val Glu Arg Thr Ala Arg Ile Pro Gly
            485                 490                 495

Leu Arg Lys Leu Pro Leu Ile Gly Gly Leu Phe Arg Tyr Arg Ser Gln
        500                 505                 510

Asn Gln Ser Asn Thr Val Arg Val Phe Leu Ile Gln Pro Arg Glu Ile
    515                 520                 525

Ile Asp Pro Leu Thr Pro Asp Ala Ser Asp Leu Val Gly Glu Val Ala
530                 535                 540

Lys Gln Ala Gly Ile Gly Asn Asp Pro Leu Gln Gln Trp Val Arg Asp
545                 550                 555                 560

Tyr Leu Tyr His Gly Gly Arg Arg Gly Asp
            565                 570
```

<210> SEQ ID NO 17
<211> LENGTH: 575
<212> TYPE: PRT
<213> ORGANISM: Providencia alcalifaciens

<400> SEQUENCE: 17

```
Met Lys Thr Lys Val Ile Phe Ser Ala Leu Phe Leu Cys Leu Val Ser
1               5                   10                  15

Tyr Gly Ile Thr Ala Pro Gln Ala Glu Leu Ser Val Glu Leu Asn
                20                  25                  30

Ala Lys Gly Asp His Gly Tyr Val Ala Lys Asp Ser Leu Arg Ser
            35                  40                  45

Phe Phe Glu Ala Met Ala Ala Lys Leu Asn Glu Pro Val Ile Val Ser
```

-continued

```
                50                  55                  60
Lys Leu Ala Ala Arg Lys Lys Ile Thr Gly Thr Phe Asp Phe Ser Arg
 65                  70                  75                  80

Pro Lys Glu Leu Leu Asp Lys Leu Ser Phe Gln Leu Gly Leu Leu Trp
                 85                  90                  95

Tyr Phe Asp Gly Gln Ala Ile Tyr Ile Tyr Asp Ala Ser Glu Ile Arg
                100                 105                 110

Asn Ala Val Ile Ser Leu Gln Asn Ile Ser Leu Thr Ser Phe Asn Asp
                115                 120                 125

Phe Leu Arg Lys Ser Gly Leu Tyr Asp Gln Arg Tyr Pro Leu Arg Gly
            130                 135                 140

Asp Asn Asn Ser Asn Thr Phe Tyr Val Ser Gly Pro Pro Val Phe Val
145                 150                 155                 160

Glu Leu Ile Val Asn Thr Ala Thr Leu Ile Asp Lys Lys Asp Glu Gly
                165                 170                 175

Ile Gln Leu Gly Lys Gln Lys Ile Gly Val Ile Arg Leu Asn Asn Thr
                180                 185                 190

Phe Val Asn Asp Arg Val Tyr Lys Leu Arg Gly Gln Glu Ile Val Ile
            195                 200                 205

Pro Gly Met Ala Thr Val Ile Glu Asn Leu Leu Glu Gly Glu Lys Gln
            210                 215                 220

Pro Leu Ala Asn Ser Ile Leu Asn Lys Gln Ile Thr Glu Met Pro Asp
225                 230                 235                 240

Phe Val Ser Glu Met Asn Gly Met Ser Ser Val Pro Leu Asn Tyr Ser
                245                 250                 255

Ser Asn Val Ser Leu Pro Glu Ala Leu Lys Gln Thr Ala Ala Ala Gly
                260                 265                 270

Asp Ile Lys Val Ile Ala Tyr Pro Gly Thr Asn Ser Leu Leu Val Lys
            275                 280                 285

Gly Thr Ala Glu Gln Val Asp Phe Ile Glu Leu Leu Val Arg Thr Leu
            290                 295                 300

Asp Ile Thr Lys Arg His Val Glu Leu Ser Leu Trp Ile Ile Asp Leu
305                 310                 315                 320

Asn Lys Ser Asp Leu Asp Gln Leu Gly Val Glu Trp Ser Gly Gly Ile
                325                 330                 335

Asn Leu Gly Asp Lys Leu Ser Met Ser Phe Asn Gln Ser Thr Pro Ile
            340                 345                 350

Ser Thr Leu Asp Gly Gly Lys Phe Ile Ala Ser Val Tyr Ala Leu Glu
            355                 360                 365

Gln Lys Lys Gln Ala Thr Val Val Ser Arg Pro Val Ile Met Thr Gln
            370                 375                 380

Glu Asn Ile Pro Ala Ile Phe Asp Asn Asn Arg Thr Phe Tyr Thr Lys
385                 390                 395                 400

Leu Ile Gly Glu Arg Thr Ser Ser Leu Ala Asp Val Thr Tyr Gly Thr
                405                 410                 415

Leu Ile Ser Val Leu Pro Arg Phe Ser Ala Asp Gly Gln Ile Glu Met
            420                 425                 430

Leu Leu Asp Ile Glu Asp Gly Asn Glu Ala Arg Ser Val Asp Tyr Asn
            435                 440                 445

Asn Glu Glu Asn Val Asp Val Leu Pro Glu Val Gly Arg Thr His Ile
450                 455                 460

Ser Thr Ile Ala Arg Val Pro Gln Gly Lys Ser Leu Leu Ile Gly Gly
465                 470                 475                 480
```

```
Tyr Thr Arg Asp Ala Asn Ser Gln Asp Leu Gln Lys Val Pro Phe Leu
            485                 490                 495

Gly Asp Leu Pro Phe Val Gly Gly Leu Phe Arg Tyr Asn Asn Gln Asn
            500                 505                 510

Lys Ser Asn Thr Val Arg Val Phe Leu Ile Gln Pro Lys Glu Ile Val
            515                 520                 525

Glu Pro Leu Met Phe Asp Ala Asn Asp Val Ala Leu Lys Val Thr Lys
            530                 535                 540

Glu Gly Gly Ala Asp Ile Thr Asp Asp Pro Leu His Lys Trp Val Ile
545                 550                 555                 560

Ser Phe Leu Asn Arg Asp Thr Gly Leu Lys Leu Asn Asn Gly Asn
            565                 570                 575

<210> SEQ ID NO 18
<211> LENGTH: 576
<212> TYPE: PRT
<213> ORGANISM: Pseudogulbenkiania ferrooxidans

<400> SEQUENCE: 18

Met Ser Lys Cys Leu Ser Tyr Ala Leu Trp Leu Gly Cys Ala Leu Cys
1               5                   10                  15

Leu Ala Ala Gly Ala Leu Ala Ala Pro Glu Pro Gly Glu Ala Ala Asp
            20                  25                  30

Gly Ala Gly Tyr Val Ala Arg Lys Asp Ser Leu Arg Ser Phe Phe Asp
            35                  40                  45

Ala Ile Ser Ser Lys Leu Lys Lys Pro Val Ile Leu Ser Lys Gln Ala
        50                  55                  60

Ala Arg Lys Gln Val Ser Gly Glu Phe Asp Leu Ser Asn Pro Gln Ala
65                  70                  75                  80

Leu Leu Glu Arg Met Thr Gln Gln Leu Gly Leu Val Trp Tyr His Asp
                85                  90                  95

Gly Gln Ser Ile Tyr Val Tyr Asp Ala Ser Glu Thr Arg Asn Ala Val
            100                 105                 110

Val Ala Leu Arg Asn Val Ser Leu Ser Ala Phe Asn Gly Phe Leu Arg
            115                 120                 125

Lys Ser Gly Leu Tyr Asp Lys Arg Tyr Pro Leu Arg Gly Asp Ser Arg
            130                 135                 140

Ser Gly Ala Phe Tyr Val Ser Gly Pro Pro Met Tyr Val Asp Leu Val
145                 150                 155                 160

Ile Asn Ala Ala Gly Phe Met Asp Lys Gln Ser Glu Gly Met Asp Leu
                165                 170                 175

Gly Arg Leu Lys Ile Gly Val Ile Lys Leu Asn Asn Thr Phe Val Gly
            180                 185                 190

Asp Arg Ser Tyr Glu Leu Arg Asp Gln Lys Leu Val Ile Pro Gly Met
            195                 200                 205

Ala Thr Val Ile Glu Lys Leu Leu Thr Gly Glu Gly Lys Ser Val Arg
            210                 215                 220

Met Leu Pro Pro Ala Pro Ser Gln Pro Ser Pro Gly Leu Pro
225                 230                 235                 240

Ala Arg Ala Glu Asp Ala Ala Ser Gln Val Gly Leu Pro Pro Leu Pro
            245                 250                 255

Gly Leu Pro Leu Pro Ser Lys Ala Ala Leu Pro Glu Pro Pro Gln
            260                 265                 270

Asp Gly Pro Ala Gly Asp Ile Arg Val Ile Ala Tyr Pro Asp Thr Asn
```

-continued

```
                        275                 280                 285
Ser Leu Leu Val Lys Gly Ser Ala Glu Gln Val Arg Phe Ile Glu Asn
290                 295                 300

Leu Val Ser Ala Leu Asp Val Ala Lys Arg His Val Glu Leu Ser Leu
305                 310                 315                 320

Trp Ile Ile Asp Leu Gln Lys Glu Asp Leu Asn Arg Leu Gly Val Glu
                325                 330                 335

Trp Ser Gly Gln Leu Ala Val Gly Gly Leu Gly Val Ser Phe Asn
                340                 345                 350

Gly Ser Gly Ser Leu Ser Thr Leu Asp Gly Ser Arg Phe Ile Ala Ser
                355                 360                 365

Val Met Ala Leu Ser Gln Gln Asn Lys Ala Asn Val Val Ser Arg Pro
370                 375                 380

Val Leu Leu Thr Gln Glu Asn Val Pro Ala Val Phe Asp Asn Asn Arg
385                 390                 395                 400

Thr Phe Tyr Thr Lys Leu Glu Gly Glu Arg Ser Val Asp Leu Gln His
                405                 410                 415

Val Thr Tyr Gly Thr Leu Val Ser Val Leu Pro Arg Phe Ser Ala Asp
                420                 425                 430

Gly Gln Ile Glu Met Ser Leu Asn Ile Glu Asp Gly Ser Glu Ala Arg
                435                 440                 445

Ala Pro Asp Tyr Ser Lys Asp Asn Lys Asp Ala Ala Thr Pro Glu Val
450                 455                 460

Gly Arg Thr Arg Ile Ser Thr Val Ala Arg Val Pro Gln Gly Lys Ser
465                 470                 475                 480

Leu Leu Ile Gly Gly Phe Thr Arg Asp Ala Ser Ser Asp Asn Arg Ala
                485                 490                 495

Ala Val Pro Gly Leu Gly Gln Leu Pro Leu Val Gly Ser Leu Phe Arg
                500                 505                 510

Tyr Gln Arg Lys Asp Leu Ser Asn Ser Val Arg Val Phe Leu Ile Gln
                515                 520                 525

Pro Arg Glu Ile Asp Ser Pro Leu Thr Pro Asp Ala Ser Asp Leu Ala
530                 535                 540

Gly Gly Leu Ser Arg Gln Gly Gly Met Asp Met Asp Pro Leu Gln Gln
545                 550                 555                 560

Lys Leu Arg Arg Tyr Leu Glu Arg Arg Glu Gly Ala Gly His Gly Asp
                565                 570                 575
```

<210> SEQ ID NO 19
<211> LENGTH: 576
<212> TYPE: PRT
<213> ORGANISM: Chromobacterium vaccinii

<400> SEQUENCE: 19

```
Met Asn Lys Cys Leu Ser Tyr Ala Leu Trp Leu Gly Cys Ala Leu Cys
1               5                   10                  15

Leu Ala Ala Gly Ala Leu Ala Ala Pro Glu Pro Gly Glu Ala Ala Asp
                20                  25                  30

Gly Ala Gly Tyr Val Ala Arg Lys Asp Ser Leu Arg Ser Phe Phe Asp
                35                  40                  45

Ala Ile Ser Ser Lys Leu Lys Lys Pro Val Ile Leu Ser Lys Gln Ala
                50                  55                  60

Ala Arg Lys Gln Val Ser Gly Glu Phe Asp Leu Ser Asn Pro Gln Ala
65                  70                  75                  80
```

```
Leu Leu Glu Arg Met Thr Gln Gln Leu Gly Leu Val Trp Tyr His Asp
            85                  90                  95

Gly Gln Ser Ile Tyr Val Tyr Asp Ala Ser Glu Thr Arg Asn Ala Val
        100                 105                 110

Val Ala Leu Arg Asn Val Ser Leu Ser Ala Phe Asn Gly Phe Leu Arg
        115                 120                 125

Lys Ser Gly Leu Tyr Asp Lys Arg Tyr Pro Leu Arg Gly Asp Ser Arg
130                 135                 140

Ser Gly Ala Phe Tyr Val Ser Gly Pro Pro Met Tyr Val Asp Leu Val
145                 150                 155                 160

Ile Asn Ala Ala Gly Phe Met Asp Lys Gln Ser Glu Gly Met Asp Leu
                165                 170                 175

Gly Arg Leu Lys Ile Gly Val Ile Lys Leu Asn Asn Thr Phe Val Gly
            180                 185                 190

Asp Arg Ser Tyr Glu Leu Arg Asp Gln Lys Leu Val Ile Pro Gly Met
        195                 200                 205

Ala Thr Val Ile Glu Lys Leu Leu Thr Gly Gly Lys Ser Val Arg
        210                 215                 220

Met Leu Pro Pro Ala Pro Ser Leu Pro Pro Ser Ser Ala Leu Pro
225                 230                 235                 240

Ala Arg Ala Glu Asp Ala Ala Ser Gln Val Gly Leu Pro Pro Leu Pro
                245                 250                 255

Gly Leu Pro Leu Pro Ser Arg Thr Ala Leu Pro Glu Pro Pro Pro Gln
            260                 265                 270

Asp Gly Pro Ala Gly Asp Ile Arg Val Ile Ala Tyr Pro Asp Thr Asn
        275                 280                 285

Ser Leu Leu Val Lys Gly Ser Ala Glu Gln Val Arg Phe Ile Glu Asn
290                 295                 300

Leu Val Thr Ala Leu Asp Val Ala Lys Arg His Val Glu Leu Ser Leu
305                 310                 315                 320

Trp Ile Ile Asp Leu Gln Lys Glu Asp Leu Asn Arg Leu Gly Val Glu
                325                 330                 335

Trp Ser Gly Gln Leu Val Val Gly Gly Gly Leu Gly Val Ser Phe Asn
            340                 345                 350

Gly Ser Gly Ser Leu Ser Thr Leu Asp Gly Ser Arg Phe Ile Ala Ser
        355                 360                 365

Val Met Ala Leu Ser Gln Gln Asn Lys Ala Asn Val Val Ser Arg Pro
370                 375                 380

Val Leu Leu Thr Gln Glu Asn Val Pro Ala Val Phe Asp Asn Asn Arg
385                 390                 395                 400

Thr Phe Tyr Thr Lys Leu Glu Gly Glu Arg Ser Val Asp Leu Gln His
                405                 410                 415

Val Thr Tyr Gly Thr Leu Val Ser Val Leu Pro Arg Phe Ser Ala Asp
            420                 425                 430

Gly Gln Ile Glu Met Ser Leu Asn Ile Glu Asp Gly Ser Glu Ala Arg
        435                 440                 445

Ala Pro Asp Tyr Ser Lys Asp Asn Lys Asp Ala Ala Thr Pro Glu Val
450                 455                 460

Gly Arg Thr Arg Ile Ser Thr Val Ala Arg Val Pro Gln Gly Lys Ser
465                 470                 475                 480

Leu Leu Ile Gly Gly Phe Thr Arg Asp Ala Ser Ser Asp Asn Arg Ala
                485                 490                 495

Ala Val Pro Gly Leu Gly Gln Leu Pro Leu Val Gly Ser Leu Phe Arg
```

```
                    500                 505                 510
Tyr Gln Arg Lys Asp Leu Ser Asn Ser Val Arg Val Phe Leu Ile Gln
            515                 520                 525

Pro Arg Glu Ile Asp Ser Pro Leu Thr Pro Asp Ala Ser Asp Leu Ala
        530                 535                 540

Gly Gly Leu Ser Arg Gln Gly Gly Leu Asp Met Asp Pro Leu Gln Gln
545                 550                 555                 560

Lys Leu Arg Arg Tyr Leu Glu Arg Arg Glu Gly Ala Gly His Gly Asp
                565                 570                 575

<210> SEQ ID NO 20
<211> LENGTH: 569
<212> TYPE: PRT
<213> ORGANISM: Salmonella enterica

<400> SEQUENCE: 20

Met Asn Ile Ser Asn Val Cys Ala Lys Val Phe Ile Ile Phe Ser Ala
1               5                   10                  15

Val Met Cys Pro Tyr Ser Leu Ala Thr Gly Thr Glu Thr Val Ala Asp
            20                  25                  30

Ser Gly Tyr Val Ala Arg Asn Asp Ser Leu Gly Ser Phe Phe Glu Ala
        35                  40                  45

Met Ser Ala Arg Leu Asn Lys Ala Val Val Ser Lys Met Ala Ala
50                  55                  60

Arg Lys Lys Ile Asn Gly Asp Phe Asn Phe Arg Asp Pro Glu Ala Leu
65                  70                  75                  80

Leu Asn Arg Leu Ala Leu Gln Leu Gly Leu Ile Trp Tyr Ser Asp Gly
                85                  90                  95

Arg Thr Val Tyr Ile Tyr Asp Ala Ser Glu Ile Arg Asn Ala Val Val
            100                 105                 110

Ser Leu Gln Asn Thr Ser Leu Ser Ala Phe Asn Ala Phe Leu Lys Arg
        115                 120                 125

Ser Gly Leu Tyr Asp Ser Arg Tyr Pro Leu Arg Gly Asp Glu Gln Gly
    130                 135                 140

Gly Val Phe Tyr Val Ser Gly Pro Pro Val Phe Val Ser Leu Val Thr
145                 150                 155                 160

Arg Ala Ala Ala Leu Met Asp Lys Gln Asp Asn Asp Ile Arg Met Gly
                165                 170                 175

Arg Leu Lys Ile Gly Val Phe Arg Leu Asn Asn Thr Phe Val Asn Asp
            180                 185                 190

Arg Thr Tyr Gln Leu Arg Asp Gln Asn Ile Val Ile Pro Gly Ile Ser
        195                 200                 205

Thr Val Ile Asp Lys Leu Leu Ala Gly Glu Pro Gln Thr Leu Thr Gly
    210                 215                 220

Ile Pro Gly Arg Leu Leu Leu Pro Pro Gly Val Asp Pro Val Pro Gly
225                 230                 235                 240

Val Ala Pro Glu Asp Gly Ile Ala Asp Ser Asp Met Ser Val Asp Arg
                245                 250                 255

Ala Gly Glu Ala Ser Ala Ala Pro Ala Gly Val Pro Ala Gly Asp Ile
            260                 265                 270

Arg Val Ile Ser Tyr Pro Asp Thr Asn Ser Leu Leu Val Lys Gly Thr
        275                 280                 285

Ala Glu Gln Val Asp Phe Ile Gly Ser Leu Ile Arg Val Leu Asp Val
    290                 295                 300
```

```
Ala Lys Arg His Val Glu Leu Ser Leu Trp Ile Ile Asp Leu Asn Lys
305                 310                 315                 320

Asn Asp Leu Glu Gln Leu Gly Ala Ser Trp Gly Gly Ala Ala Gly Val
            325                 330                 335

Gly Asn Arg Leu Asp Val Thr Leu Asn Gln Thr Leu Val Ser Thr Leu
            340                 345                 350

Asp Gly Val His Phe Leu Ala Ser Val Tyr Ala Leu Glu Lys Lys Asn
            355                 360                 365

Gln Ala Arg Ile Val Ser Lys Pro Val Leu Met Thr Gln Glu Asn Val
    370                 375                 380

Pro Ala Ile Phe Asp Asn Asn Arg Thr Phe Tyr Thr Lys Leu Ile Gly
385                 390                 395                 400

Glu Arg Asn Ser Ser Leu Ala His Val Thr Tyr Gly Thr Met Ile Ser
                405                 410                 415

Val Leu Pro Arg Phe Ser Glu Asp Gly Glu Ile Glu Met Ser Leu Asp
            420                 425                 430

Ile Glu Asp Gly Asn Glu Lys Gln Ser Val Thr Gly Asn Glu Glu
            435                 440                 445

Glu Thr Val Leu Pro Glu Val Gly Arg Thr His Ile Ser Thr Val Ala
    450                 455                 460

Arg Val Pro Gln Gly Lys Ser Leu Leu Ile Gly Gly Tyr Thr Arg Asp
465                 470                 475                 480

Thr Arg Thr Glu Asp Val Gln Lys Ile Pro Leu Leu Gly Asp Ile Pro
                485                 490                 495

Leu Ile Gly Gly Leu Phe Arg Tyr Glu Asn Gln Asn Ser Asn Val
            500                 505                 510

Val Arg Val Phe Leu Ile Gln Pro Lys Glu Ile Ser Asp Pro Leu Thr
    515                 520                 525

Pro Asp Ala Asp Val Phe Ala Ala Glu Leu Met Gln Asn Ser Gly Ile
530                 535                 540

Glu Ser Asn Arg Asp Pro Leu Asp Lys Trp Val Leu Ser Tyr Leu Asn
545                 550                 555                 560

Arg Gly Gln Ala Leu Asn His Gly Lys
                565

<210> SEQ ID NO 21
<211> LENGTH: 566
<212> TYPE: PRT
<213> ORGANISM: Escherichia coli

<400> SEQUENCE: 21

Met Lys Leu Ser Asn Ile Ile Val Ile Phe Ile Ile Leu Leu Phe Gly
1               5                   10                  15

Ile Ser Pro Phe Ser Ile Ala Thr Gly Ser Glu Thr Leu Phe Asp Asn
            20                  25                  30

Gly Tyr Val Ala Arg Asn Asp Ser Leu Asn Ser Phe Phe Glu Ala Met
        35                  40                  45

Ser Thr Lys Leu Asn Lys Thr Val Val Ser Lys Ser Ala Ser Arg
    50                  55                  60

Lys Lys Ile Asn Gly Asn Phe Asn Phe Arg Glu Pro Glu Ala Leu Leu
65                  70                  75                  80

Asp Arg Leu Ala Ser Gln Leu Gly Val Ile Trp Tyr Ser Asp Gly Gln
                85                  90                  95

Thr Ile Tyr Ile Tyr Asp Ala Glu Glu Ile Arg Asn Ser Val Ile Ser
            100                 105                 110
```

-continued

```
Leu Gln Asn Val Ser Leu Ser Ala Phe Lys Ser Phe Leu Lys Glu Ala
            115                 120                 125

Gly Leu Tyr Asp Ser Arg Tyr Pro Leu Lys Gly Asp Glu Gln Asn Gly
        130                 135                 140

Ile Val Tyr Ile Ser Gly Pro Pro Ile Phe Val Ser Ile Val Thr Lys
145                 150                 155                 160

Thr Ala Ala Leu Ile Asp Lys Gln Asn Asn Asp Ile Glu Met Gly Arg
                165                 170                 175

Leu Lys Ile Gly Val Phe Arg Leu His Asn Thr Phe Val Asn Asp Arg
            180                 185                 190

Thr Tyr Gln Leu Arg Asp Gln Asn Ile Val Ile Pro Gly Ile Ala Thr
        195                 200                 205

Val Ile Glu Lys Leu Leu Ala Gly Glu Gln Gln Asn Leu Thr Glu Val
210                 215                 220

Gln Gly Arg Met Phe Arg Ala Ser Gly Ser Asn Ile Ala Ser Glu Thr
225                 230                 235                 240

Leu Ser Gly Asn Ser Ser Thr Asp Asn Glu Met Tyr Ile Asp Glu Thr
                245                 250                 255

Arg Asp Ser Thr Thr Ser Ser Ser Thr Pro Ile Ser Asp Ile Lys Val
            260                 265                 270

Ile Ser Tyr Pro Asp Thr Asn Ser Leu Leu Val Lys Gly Thr Ala Glu
        275                 280                 285

Gln Val Asp Phe Ile Gly Ala Leu Val Arg Leu Leu Asp Val Ala Lys
    290                 295                 300

Arg His Val Glu Leu Ser Leu Trp Ile Ile Asp Leu Asn Lys Asn Asp
305                 310                 315                 320

Leu Glu Gln Leu Gly Val Ala Trp Gly Gly Ser Ala Ser Phe Ser Asn
                325                 330                 335

Lys Leu Asp Ile Ala Leu Asn Gln Thr Leu Val Ser Thr Leu Asp Gly
            340                 345                 350

Val His Phe Leu Ala Ser Val Tyr Ala Leu Glu Lys Lys Asn Gln Ala
        355                 360                 365

Arg Ile Val Ser Lys Pro Val Leu Met Thr Gln Glu Asn Val Pro Ala
    370                 375                 380

Ile Phe Asp Asn Asn Arg Thr Phe Tyr Thr Lys Leu Ile Gly Glu Arg
385                 390                 395                 400

Asn Ser Ser Leu Ala His Val Thr Tyr Gly Thr Met Ile Ser Val Leu
                405                 410                 415

Pro Arg Phe Ser Ala Asp Gly Glu Ile Glu Met Ser Leu Asn Ile Glu
            420                 425                 430

Asp Gly Asn Glu Glu Lys Gln Ser Val Ser Gly Asn Gly Asp Ser Val
        435                 440                 445

Leu Pro Glu Val Gly Arg Thr His Ile Ser Thr Val Ala Arg Val Pro
    450                 455                 460

Gln Gly Lys Ser Leu Leu Ile Gly Gly Tyr Thr Arg Asp Ser Arg Thr
465                 470                 475                 480

Lys Asp Val Gln Lys Ile Pro Leu Leu Gly Asp Ile Pro Leu Ile Gly
                485                 490                 495

Gly Leu Phe Arg Tyr Glu Asn Gln Asn Gln Asn Val Val Arg Val
            500                 505                 510

Phe Leu Ile Gln Pro Lys Glu Ile Leu Asp Pro Leu Met Pro Asp Ala
        515                 520                 525
```

```
Asp Val Phe Ala Ala Glu Leu Met Gln Asp Ser Gly Ile Glu Asn Asn
            530                 535                 540

Arg Asp Pro Leu Asp Lys Trp Val Leu Ser Tyr Leu Asn Arg Gly Gln
545                 550                 555                 560

Ala Leu Asn His Gly Lys
                565

<210> SEQ ID NO 22
<211> LENGTH: 567
<212> TYPE: PRT
<213> ORGANISM: Shigella dysenteriae

<400> SEQUENCE: 22

Met Lys Ile Lys Leu Arg Ile Thr Ile Ile Leu Ile Ser Val Leu Cys
1               5                   10                  15

Ile Phe Asn Gly Leu Leu Thr Pro Gly Ala Tyr Ala Ala Ala Ala Asn
            20                  25                  30

Gly Tyr Val Ala Asn Lys Asp Asn Leu Arg Ser Phe Phe Glu Thr Val
        35                  40                  45

Ser Ser Tyr Ala Gly Lys Pro Thr Ile Val Ser Lys Leu Ala Met Lys
50                  55                  60

Lys Gln Ile Ser Gly Asn Phe Asp Leu Thr Glu Pro Tyr Ala Leu Ile
65                  70                  75                  80

Glu Arg Leu Ser Ala Gln Met Gly Leu Ile Trp Tyr Asp Asp Gly Lys
                85                  90                  95

Ala Ile Tyr Ile Tyr Asp Ser Ser Glu Met Arg Asn Ala Leu Ile Asn
            100                 105                 110

Leu Arg Lys Val Ser Thr Asn Glu Phe Asn Asn Phe Leu Lys Lys Ser
        115                 120                 125

Gly Leu Tyr Asn Ser Arg Tyr Glu Ile Lys Gly Gly Asn Gly Thr
130                 135                 140

Phe Tyr Val Ser Gly Pro Pro Val Tyr Val Asp Leu Val Val Asn Ala
145                 150                 155                 160

Ala Lys Leu Met Glu Gln Asn Ser Asp Gly Ile Glu Ile Gly Arg Asn
                165                 170                 175

Lys Val Gly Ile Ile His Leu Val Asn Thr Phe Val Asn Asp Arg Thr
            180                 185                 190

Tyr Glu Leu Arg Gly Glu Lys Ile Val Ile Pro Gly Met Ala Lys Ile
        195                 200                 205

Leu Ser Thr Leu Leu Asn Asn Asn Ile Lys Gln Ser Thr Gly Val Asn
210                 215                 220

Val Leu Ser Glu Ile Ser Ser Arg Gln Gln Leu Lys Asn Val Ser Arg
225                 230                 235                 240

Met Pro Pro Phe Pro Gly Ala Glu Glu Asp Asp Asp Leu Gln Val Glu
                245                 250                 255

Lys Ile Ile Ser Thr Ala Gly Ala Pro Glu Thr Asp Asp Ile Gln Ile
            260                 265                 270

Ile Ala Tyr Pro Asp Thr Asn Ser Leu Leu Val Lys Gly Thr Val Ser
        275                 280                 285

Gln Val Asp Phe Ile Glu Lys Leu Val Ala Thr Leu Asp Ile Pro Lys
290                 295                 300

Arg His Ile Glu Leu Ser Leu Trp Ile Asp Ile Asp Lys Thr Asp
305                 310                 315                 320

Leu Glu Gln Leu Gly Ala Asp Trp Ser Gly Thr Ile Lys Ile Gly Ser
                325                 330                 335
```

Ser Leu Ser Ala Ser Phe Asn Asn Ser Gly Ser Ile Ser Thr Leu Asp
            340                 345                 350

Gly Thr Gln Phe Ile Ala Thr Ile Gln Ala Leu Ala Gln Lys Arg Arg
        355                 360                 365

Ala Ala Val Val Ala Arg Pro Val Val Leu Thr Gln Glu Asn Ile Pro
370                 375                 380

Ala Ile Phe Asp Asn Asn Arg Thr Phe Tyr Thr Lys Leu Val Gly Glu
385                 390                 395                 400

Arg Thr Ala Glu Leu Asp Glu Val Thr Tyr Gly Thr Met Ile Ser Val
            405                 410                 415

Leu Pro Arg Phe Ala Ala Arg Asn Gln Ile Glu Leu Leu Asn Ile
            420                 425                 430

Glu Asp Gly Asn Glu Ile Asn Ser Asp Lys Thr Asn Val Asp Asp Leu
            435                 440                 445

Pro Gln Val Gly Arg Thr Leu Ile Ser Thr Ile Ala Arg Val Pro Gln
450                 455                 460

Gly Lys Ser Leu Leu Ile Gly Gly Tyr Thr Arg Asp Thr Asn Thr Tyr
465                 470                 475                 480

Glu Ser Arg Lys Ile Pro Ile Leu Gly Ser Ile Pro Phe Ile Gly Lys
            485                 490                 495

Leu Phe Gly Tyr Glu Gly Thr Asn Ala Asn Asn Ile Val Arg Val Phe
            500                 505                 510

Leu Ile Glu Pro Arg Glu Ile Asp Glu Arg Met Met Asn Asn Ala Asn
            515                 520                 525

Glu Ala Ala Val Asp Ala Arg Ala Ile Thr Gln Gln Met Ala Lys Asn
            530                 535                 540

Lys Glu Ile Asn Asp Glu Leu Leu Gln Lys Trp Ile Lys Thr Tyr Leu
545                 550                 555                 560

Asn Arg Glu Val Val Gly Gly
            565

<210> SEQ ID NO 23
<211> LENGTH: 567
<212> TYPE: PRT
<213> ORGANISM: Escherichia coli

<400> SEQUENCE: 23

Met Lys Ile Lys Leu Arg Ile Thr Ile Ile Leu Ile Ser Ala Leu Cys
1               5                   10                  15

Ile Phe Asn Gly Leu Leu Thr Pro Gly Ala Tyr Ala Ala Thr Ala Asn
            20                  25                  30

Gly Tyr Val Ala Asn Lys Glu Asn Leu Arg Ser Phe Phe Glu Thr Val
        35                  40                  45

Ser Ser Tyr Ala Gly Lys Pro Thr Ile Val Ser Lys Leu Ala Met Lys
    50                  55                  60

Lys Gln Ile Ser Gly Asn Phe Asp Leu Thr Glu Pro Tyr Ala Leu Ile
65                  70                  75                  80

Glu Arg Leu Ser Ala Gln Met Gly Leu Ile Trp Tyr Asp Asp Gly Lys
                85                  90                  95

Ala Ile Tyr Ile Tyr Asp Ser Ser Glu Met Arg Asn Ala Leu Ile Asn
            100                 105                 110

Leu Arg Lys Val Ser Thr Asn Glu Phe Asn Asn Phe Leu Lys Lys Ser
            115                 120                 125

Gly Leu Tyr Asn Ser Arg Tyr Glu Ile Lys Gly Gly Gly Asn Gly Thr

-continued

```
            130                 135                 140
Phe Tyr Val Ser Gly Pro Pro Val Tyr Val Asp Leu Val Asn Ala
145                 150                 155                 160

Ala Lys Leu Met Glu Gln Asn Ser Asp Gly Ile Glu Ile Gly Arg Asn
                    165                 170                 175

Lys Val Gly Ile Ile His Leu Val Asn Thr Phe Val Asn Asp Arg Thr
                180                 185                 190

Tyr Glu Leu Arg Gly Glu Lys Ile Val Ile Pro Gly Met Ala Lys Val
                195                 200                 205

Leu Ser Thr Leu Leu Asn Asn Asn Ile Lys Gln Ser Thr Gly Val Asn
210                 215                 220

Val Leu Ser Glu Ile Ser Ser Arg Gln Gln Leu Lys Asn Val Ser Arg
225                 230                 235                 240

Met Pro Pro Phe Pro Gly Ala Glu Glu Asp Asp Leu Gln Val Glu
                    245                 250                 255

Lys Ile Ile Ser Thr Ala Gly Ala Pro Glu Thr Asp Asp Ile Gln Ile
                260                 265                 270

Ile Ala Tyr Pro Asp Thr Asn Ser Leu Leu Val Lys Gly Thr Val Ser
                275                 280                 285

Gln Val Asp Phe Ile Glu Lys Leu Val Ala Thr Leu Asp Ile Pro Lys
                290                 295                 300

Arg His Ile Glu Leu Ser Leu Trp Ile Ile Asp Ile Asp Lys Thr Asp
305                 310                 315                 320

Leu Glu Gln Leu Gly Ala Asp Trp Ser Gly Thr Ile Lys Ile Gly Ser
                    325                 330                 335

Ser Leu Ser Ala Ser Phe Asn Asn Ser Gly Ser Ile Ser Thr Leu Asp
                340                 345                 350

Gly Thr Gln Phe Ile Ala Thr Ile Gln Ala Leu Ala Gln Lys Arg Arg
                355                 360                 365

Ala Ala Val Val Ala Arg Pro Val Val Leu Thr Gln Glu Asn Ile Pro
370                 375                 380

Ala Ile Phe Asp Asn Asn Arg Thr Phe Tyr Thr Lys Leu Val Gly Glu
385                 390                 395                 400

Arg Thr Ala Glu Leu Asp Glu Val Thr Tyr Gly Thr Met Ile Ser Val
                    405                 410                 415

Leu Pro Arg Phe Ala Ala Arg Asn Gln Ile Glu Leu Leu Asn Ile
                420                 425                 430

Glu Asp Gly Asn Glu Ile Asn Ser Asp Lys Thr Asn Val Asp Asp Leu
                435                 440                 445

Pro Gln Val Gly Arg Thr Leu Ile Ser Thr Ile Ala Arg Val Pro Gln
450                 455                 460

Gly Lys Ser Leu Leu Ile Gly Gly Tyr Thr Arg Asp Thr Asn Thr Tyr
465                 470                 475                 480

Glu Ser Arg Lys Ile Pro Ile Leu Gly Ser Ile Pro Phe Ile Gly Lys
                    485                 490                 495

Leu Phe Gly Tyr Glu Gly Thr Asn Ala Asn Asn Ile Val Arg Val Phe
                500                 505                 510

Leu Ile Glu Pro Arg Glu Ile Asp Glu Arg Met Met Asn Asn Ala Asn
                515                 520                 525

Glu Ala Ala Val Asp Ala Arg Ala Ile Thr Gln Gln Met Ala Lys Asn
530                 535                 540

Lys Glu Ile Asn Asp Glu Leu Leu Gln Lys Trp Ile Lys Thr Tyr Leu
545                 550                 555                 560
```

Asn Arg Glu Val Val Gly Gly
              565

<210> SEQ ID NO 24
<211> LENGTH: 519
<212> TYPE: PRT
<213> ORGANISM: Stenotrophomonas rhizophila

<400> SEQUENCE: 24

Met Ala Arg Gln Glu Gly Leu Arg Thr Phe Phe Asp Ala Leu Ser Ala
1               5                   10                  15

Ser Leu Asp Lys Pro Val Ile Leu Ser Lys Ala Ala Arg Arg Thr
            20                  25                  30

Ile Ser Gly Asp Phe Ser Met Val Ala Pro Gln Gln Thr Leu Glu Arg
        35                  40                  45

Val Val Arg Gln Met Gly Leu Val Trp Tyr Ser Asp Gly Gln Thr Leu
    50                  55                  60

Tyr Ile Tyr Glu Ala Ala Glu Val Lys Ser Ala Val Ile Ser Leu Asn
65                  70                  75                  80

Thr Ile Thr Val His Lys Leu Asp Ala Phe Leu Arg Ser Ser Gly Leu
                85                  90                  95

Arg Asp Thr Arg Tyr Pro Leu Arg His Asp Gly Leu Arg Thr Phe Tyr
            100                 105                 110

Ile Ser Gly Pro Pro Ile Tyr Val Asp Leu Val Ala Gln Ala Ala Gln
        115                 120                 125

Phe Met Asp Asn Gln Ser Ala Ser Leu Gln Leu Gly Gln Gln Arg Ile
    130                 135                 140

Gly Val Ile Asn Leu Arg Asn Thr Phe Val Ala Asp Arg Thr Tyr Glu
145                 150                 155                 160

Leu Arg Glu Gln Ser Ile Thr Val Pro Gly Ile Ala Thr Ala Ile Glu
                165                 170                 175

Thr Leu Leu Lys Gly Glu Gly Arg Gly Ala Asp Ala Val Ile His Lys
            180                 185                 190

Asp Ala Glu Gly His Pro Gly Gly Met Pro Ser Phe Pro Leu Glu Glu
        195                 200                 205

Leu Gly Ala His Glu Ala Ala Ser Gly Asp Asn Thr Ser Arg Gln Ile
    210                 215                 220

Ile Ala Arg Asp Leu Ala Ala Gly Asn Ile Arg Val Val Ala Tyr Pro
225                 230                 235                 240

Asp Thr Asn Ser Leu Leu Val Lys Gly Leu Pro Glu Gln Val Gln Phe
                245                 250                 255

Ile Glu Asn Leu Val Ala Ala Leu Asp Glu Pro Lys Arg His Val Glu
            260                 265                 270

Leu Ser Leu Trp Ile Ile Asp Leu His Lys Asp Asp Leu Asn Glu Leu
        275                 280                 285

Gly Val Asp Trp Arg Gly Ser Phe Lys Val Gly Ser Lys Val Ala Ala
    290                 295                 300

Ser Leu Asn Gly Gly Ser Leu Ser Thr Leu Asp Ser Ala Ser Phe Met
305                 310                 315                 320

Ala Ala Ile Ser Ala Leu Glu Thr Asp Asn Arg Ala Arg Val Val Ser
                325                 330                 335

Arg Pro Val Val Leu Thr Gln Glu Asn Val Pro Ala Ile Phe Asp Asn
            340                 345                 350

Asn Arg Thr Phe Tyr Ala Arg Leu Ile Gly Glu Arg Ser Val Gln Leu

```
                355                 360                 365
Glu His Val Thr Tyr Gly Thr Leu Val Ser Val Leu Pro Arg Leu Ser
370                 375                 380

Pro Ser Gly Glu Val Glu Met Ala Leu Asn Ile Glu Asp Gly Ser Val
385                 390                 395                 400

Val Glu Ser Ala Arg Glu Gln Ser Ser Gly Ala Asp Thr Leu Pro Thr
                405                 410                 415

Val Gly Arg Thr Arg Ile Ser Thr Val Ala Arg Val Pro Gln Gly Lys
                420                 425                 430

Ser Leu Leu Val Gly Gly Phe Thr Arg Asp Glu Arg Ala Glu Val Ile
                435                 440                 445

Lys Arg Ile Pro Leu Leu Gly His Ile Pro Tyr Leu Gly Arg Val Phe
                450                 455                 460

Ser Tyr Arg Gln Thr Arg Gln Ala Asn Thr Val Arg Val Phe Leu Ile
465                 470                 475                 480

Gln Pro Arg Glu Leu Asp Ser Pro Leu Glu Pro Gly Ala Met Gln Thr
                485                 490                 495

Gly Ser Gln Val Ile Gly Asn Val Val Arg Asp Pro Ala Glu Arg Ala
                500                 505                 510

Val Leu Arg Val Leu Glu Arg
                515

<210> SEQ ID NO 25
<211> LENGTH: 519
<212> TYPE: PRT
<213> ORGANISM: Pseudomonas putida

<400> SEQUENCE: 25

Met Ala Arg Gln Glu Gly Leu Arg Thr Phe Phe Asp Ala Leu Ser Ala
1               5                   10                  15

Ser Leu Asp Lys Pro Val Ile Leu Ser Lys Ala Ala Ala Arg Arg Thr
                20                  25                  30

Ile Ser Gly Asp Phe Ser Met Val Ala Pro Gln Gln Thr Leu Glu Arg
            35                  40                  45

Val Val Arg Gln Met Gly Leu Val Trp Tyr Ser Asp Gly Gln Thr Leu
        50                  55                  60

Tyr Ile Tyr Glu Ala Ala Glu Ala Lys Ser Ala Val Ile Ser Leu Asn
65                  70                  75                  80

Thr Ile Thr Val His Lys Leu Asp Ala Phe Leu Arg Ser Ser Gly Leu
                85                  90                  95

Arg Asp Thr Arg Tyr Pro Leu Arg His Asp Gly Leu Arg Thr Phe Tyr
                100                 105                 110

Ile Ser Gly Pro Pro Ile Tyr Val Asp Leu Val Ala Gln Ala Ala Gln
            115                 120                 125

Phe Met Asp Asn Gln Ser Ala Ser Leu Gln Leu Gly Gln Gln Arg Ile
130                 135                 140

Gly Val Ile Asn Leu Arg Asn Thr Phe Val Ala Asp Arg Thr Tyr Glu
145                 150                 155                 160

Leu Arg Glu Gln Ser Ile Thr Val Pro Gly Ile Ala Thr Ala Ile Glu
                165                 170                 175

Thr Leu Leu Lys Gly Glu Gly Arg Gly Ala Asp Ala Val Ile His Lys
                180                 185                 190

Asp Ala Glu Gly His Pro Gly Gly Met Pro Ser Phe Pro Leu Glu Glu
                195                 200                 205
```

```
Leu Gly Ala His Glu Ala Ala Ser Gly Asp Asn Thr Ser Arg Gln Ile
    210                 215                 220
Ile Ala Arg Asp Leu Ala Ala Gly Asn Ile Arg Val Val Ala Tyr Pro
225                 230                 235                 240
Asp Thr Asn Ser Leu Leu Val Lys Gly Leu Pro Glu Gln Val Gln Phe
                245                 250                 255
Ile Glu Asn Leu Val Ala Ala Leu Asp Glu Pro Lys Arg His Val Glu
            260                 265                 270
Leu Ser Leu Trp Ile Ile Asp Leu His Lys Asp Asp Leu Asn Glu Leu
        275                 280                 285
Gly Val Asp Trp Arg Gly Ser Phe Lys Val Gly Ser Lys Val Ala Ala
    290                 295                 300
Ser Leu Asn Gly Gly Ser Leu Ser Thr Leu Asp Ser Ala Ser Phe Met
305                 310                 315                 320
Ala Ala Ile Ser Ala Leu Glu Thr Asp Asn Arg Ala Arg Val Val Ser
                325                 330                 335
Arg Pro Val Val Leu Thr Gln Glu Asn Val Pro Ala Ile Phe Asp Asn
            340                 345                 350
Asn Arg Thr Phe Tyr Ala Arg Leu Ile Gly Glu Arg Ser Val Gln Leu
        355                 360                 365
Glu His Val Thr Tyr Gly Thr Leu Val Ser Val Leu Pro Arg Leu Ser
    370                 375                 380
Pro Ser Gly Glu Val Glu Met Ala Leu Asn Ile Glu Asp Gly Ser Val
385                 390                 395                 400
Val Glu Ser Ala Arg Glu Gln Ser Ser Gly Ala Asp Thr Leu Pro Thr
                405                 410                 415
Val Gly Arg Thr Arg Ile Ser Thr Val Ala Arg Val Pro Gln Gly Lys
            420                 425                 430
Ser Leu Leu Val Gly Gly Phe Thr Arg Asp Glu Arg Ala Glu Val Ile
        435                 440                 445
Lys Arg Ile Pro Leu Leu Gly His Ile Pro Tyr Leu Gly Arg Val Phe
    450                 455                 460
Ser Tyr Arg Gln Thr Arg Gln Ala Asn Thr Val Arg Val Phe Leu Ile
465                 470                 475                 480
Gln Pro Arg Glu Leu Asp Ser Pro Leu Glu Pro Gly Ala Met Gln Ile
                485                 490                 495
Gly Ser Gln Val Ile Gly Asn Val Ala Arg Asp Pro Ala Glu Arg Ala
            500                 505                 510
Val Leu Arg Val Leu Glu Arg
        515

<210> SEQ ID NO 26
<211> LENGTH: 549
<212> TYPE: PRT
<213> ORGANISM: Yersinia entomophaga

<400> SEQUENCE: 26

Met Leu Gly Val Val Leu Ala Gly Met Pro Glu Lys Ala Phe Ser
1               5                   10                  15

Glu Glu Asn Ser Ser Leu Ser Gly Tyr Val Ala Arg Gln Asn Asp
                20                  25                  30

Ile Lys Gly Leu Ile Asp Ala Leu Ser Ser Arg Met Asn Lys Pro Ile
            35                  40                  45

Ile Ile Ser Lys Ala Val Ala Arg Lys Lys Ile Ser Gly Glu Phe Asp
        50                  55                  60
```

```
Leu Asn Asn Pro Gln Arg Leu Ile Asp Asn Ile Ser Ala Gln Leu Gly
 65                  70                  75                  80

Leu Ile Trp Tyr His Asp Gly Gln Ala Ile Tyr Ile Tyr Asp Ala Ser
                 85                  90                  95

Glu Met Arg Asn Ala Val Val Val Leu Arg Asn Thr Ser Phe Ser Ala
                100                 105                 110

Val Ser Asn Phe Leu Arg Lys Ser Gly Leu Tyr Asp Gln Arg Tyr Pro
                115                 120                 125

Leu Arg Ser Asp Ser Val Ser Ser Thr Phe Tyr Val Ser Gly Pro Pro
            130                 135                 140

Ile Tyr Val Glu Leu Val Thr Asn Thr Ala Lys Phe Leu Asp Glu Lys
145                 150                 155                 160

Asn Asn Asp Leu Asp Gly Arg Ser Lys Val Ala Ser Ile Pro Leu Phe
                165                 170                 175

Asn Thr Phe Val Gln Asp Arg Asp Phe Lys Tyr Arg Asp Asp Arg Ile
                180                 185                 190

Ile Ile Pro Gly Ala Ala Ser Ile Val Gln Gln Leu Leu Asn Gly Asn
            195                 200                 205

Glu Ser Gly Gly Asp Val Met Val Pro Ala Pro Ala Thr Asp Thr Ile
210                 215                 220

Ala Thr Asp Leu Pro Pro Arg Leu Asp Glu Phe Pro Gly Val Ser Gln
225                 230                 235                 240

Ala Lys Pro Lys Leu Pro Phe Ala Asp Leu Thr Thr Ala Ile Arg Gly
                245                 250                 255

Arg Pro Ser Ala Ser Gly Phe Gln Ile Val Ala Asn Pro Gly Thr Asn
                260                 265                 270

Ser Leu Leu Val Lys Gly Ser Ala Glu Gln Val Ser Tyr Val Gln Asn
            275                 280                 285

Ile Val Ser Val Leu Asp Leu Pro Lys Arg His Ile Glu Leu Ser Val
            290                 295                 300

Trp Ile Val Asp Leu Gln Lys Asp Ala Leu Glu Gln Met Gly Val Glu
305                 310                 315                 320

Trp Asn Gly Gly Val Asn Val Gly Gly Lys Leu Gly Ile Ser Phe Asn
                325                 330                 335

Gly Gly Ala Ser Ser Thr Val Asp Gly Ala Thr Phe Met Ala Ser Val
                340                 345                 350

Leu Ala Leu Ser Gln Lys Asn Gln Ala Asn Ile Val Ser Arg Pro Met
            355                 360                 365

Val Leu Thr Gln Glu Asn Ile Pro Ala Ile Phe Asp Asn Ser Arg Thr
370                 375                 380

Phe Tyr Thr Gln Leu Ile Gly Glu Arg Ser Val Glu Leu Gln His Ile
385                 390                 395                 400

Thr Tyr Gly Thr Ser Val Asn Val Leu Pro Arg Phe Thr Asp Gly Asn
                405                 410                 415

Glu Ile Glu Met Met Leu Asn Val Glu Asp Gly Ser Gln Val Pro Val
                420                 425                 430

Ser Ser Asp Thr Pro Asn Gly Leu Pro Glu Val Gly Arg Thr Asn Ile
            435                 440                 445

Ser Thr Ile Ala Arg Val Pro Arg Gly Lys Ser Leu Leu Ile Gly Gly
            450                 455                 460

Tyr Thr Arg Asp Glu Ser Thr Asp Gly Glu Ala Lys Val Pro Leu Leu
465                 470                 475                 480
```

Gly Asp Ile Pro Leu Ile Gly Gly Leu Phe Arg Tyr Lys Lys Ser Arg
                485             490             495

Asn Ser Asn Thr Val Arg Val Phe Leu Ile Gln Pro Arg Glu Ile Glu
            500             505             510

Ser Pro Leu Gln Pro Asp Ala Ser Asn Leu Ile Ala Asp Met Gln Lys
        515             520             525

Asn Leu Ala Asn Pro Ala Leu Gln Asp Trp Met Arg Asn Tyr Val Asp
    530             535             540

Ser Gln Lys Trp Leu
545

<210> SEQ ID NO 27
<211> LENGTH: 562
<212> TYPE: PRT
<213> ORGANISM: Yersinia nurmii

<400> SEQUENCE: 27

Met Asn Tyr Val Ile Gly Phe Lys Arg Thr Cys Val Cys Ile Leu Gly
1               5                   10                  15

Val Val Val Leu Ala Gly Met Pro Glu Lys Ala Phe Ser Glu Glu Asp
            20                  25                  30

Ser Ser Ser Ile Ser Gly Tyr Ile Ala Arg Gln Asn Asp Ile Lys Gly
        35                  40                  45

Leu Ile Asp Ala Leu Ser Ser Arg Met Asn Lys Pro Ile Ile Ile Ser
    50                  55                  60

Lys Ala Ala Ala Arg Lys Lys Ile Ser Gly Glu Phe Asp Leu Asn Asn
65                  70                  75                  80

Pro Gln Arg Leu Ile Asp Asn Ile Ser Ala Gln Leu Gly Leu Ile Trp
                85                  90                  95

Tyr His Asp Gly Gln Ala Ile Tyr Ile Tyr Asp Ala Ser Glu Met Arg
            100                 105                 110

Asn Ala Val Val Leu Arg Asn Thr Ser Phe Ser Ala Val Ser Asn
        115                 120                 125

Phe Leu Arg Lys Ser Gly Leu Tyr Asp Gln Arg Tyr Pro Leu Arg Ser
    130                 135                 140

Asp Ser Val Ser Ser Thr Phe Tyr Val Ser Gly Pro Pro Ile Tyr Val
145                 150                 155                 160

Glu Leu Val Thr Asn Thr Ala Lys Phe Leu Asp Glu Lys Asn Asn Asp
                165                 170                 175

Leu Asp Gly Arg Ser Lys Val Ala Ser Ile Pro Leu Phe Asn Thr Phe
            180                 185                 190

Val Gln Asp Arg Asp Phe Lys Tyr Arg Asp Arg Ile Ile Ile Pro
        195                 200                 205

Gly Ala Ala Ser Ile Val Gln Gln Leu Leu Asn Gly Asn Glu Ser Gly
    210                 215                 220

Gly Asp Val Met Val Pro Ala Pro Val Thr Asp Ala Ile Ala Thr Asp
225                 230                 235                 240

Leu Pro Pro Arg Leu Asp Glu Phe Pro Gly Val Ser Gln Ala Lys Pro
                245                 250                 255

Lys Leu Pro Phe Ala Asp Leu Thr Thr Ala Ile Arg Ser Arg Pro Ser
            260                 265                 270

Ala Ser Gly Phe Gln Ile Val Ala Asn Pro Gly Thr Asn Ser Leu Leu
        275                 280                 285

Val Lys Gly Ser Ala Glu Gln Val Ser Tyr Val Gln Asn Ile Val Ser
    290                 295                 300

Val Leu Asp Leu Pro Lys Arg His Ile Glu Leu Ser Val Trp Ile Val
305                 310                 315                 320

Asp Leu Gln Lys Asp Ala Leu Glu Gln Met Gly Val Glu Trp Asn Gly
            325                 330                 335

Gly Val Asn Val Gly Gly Lys Leu Gly Ile Ser Phe Asn Gly Gly Ala
            340                 345                 350

Ser Ser Thr Val Asp Gly Ala Thr Phe Met Ala Ser Val Leu Ala Leu
            355                 360                 365

Ser Gln Lys Asn Gln Ala Asn Ile Val Ser Arg Pro Met Val Leu Thr
370                 375                 380

Gln Glu Asn Ile Pro Ala Ile Phe Asp Asn Ser Arg Thr Phe Tyr Thr
385                 390                 395                 400

Gln Leu Ile Gly Glu Arg Ser Val Glu Leu Gln His Ile Thr Tyr Gly
                405                 410                 415

Thr Ser Val Asn Val Leu Pro Arg Phe Thr Asp Gly Asn Glu Ile Glu
            420                 425                 430

Met Met Leu Asn Val Glu Asp Gly Ser Gln Val Pro Val Ser Ser Asp
            435                 440                 445

Thr Pro Asn Gly Leu Pro Glu Val Gly Arg Thr Asn Ile Ser Thr Ile
450                 455                 460

Ala Arg Val Pro Arg Gly Lys Ser Leu Leu Ile Gly Gly Tyr Thr Arg
465                 470                 475                 480

Asp Glu Ser Thr Asp Gly Glu Ala Lys Val Pro Leu Leu Gly Asp Ile
                485                 490                 495

Pro Leu Ile Gly Gly Leu Phe Arg Tyr Lys Lys Ser Arg Asn Ser Asn
            500                 505                 510

Thr Val Arg Val Phe Leu Ile Gln Pro Arg Glu Ile Glu Ser Pro Leu
            515                 520                 525

Gln Pro Asp Ala Ser Asn Leu Ile Ala Asp Met Gln Lys Asn Leu Ala
530                 535                 540

Asn Pro Ala Leu Gln Asp Trp Met Arg Asn Tyr Val Asp Ser Gln Lys
545                 550                 555                 560

Trp Leu

<210> SEQ ID NO 28
<211> LENGTH: 539
<212> TYPE: PRT
<213> ORGANISM: Arsenophonus nasoniae

<400> SEQUENCE: 28

Met Lys Arg Leu Gln Ile Arg Lys Asp Ser Ser Ile Leu Ile Phe Phe
1               5                   10                  15

Met Phe Leu Asn Phe Ile Leu Leu Ser Ser Lys Ala Val Ser Glu
            20                  25                  30

Gln Thr Ile Glu Ser Gly Tyr Ile Ala Lys Asn Glu Thr Ile Arg Gly
            35                  40                  45

Val Phe Asp Ala Leu Ser Ser Val Ile Asn Lys Pro Ile Ile Val Ser
50                  55                  60

Gln Leu Ala Ile Lys Lys Lys Ile Thr Gly Asp Phe Asp Leu Lys Tyr
65                  70                  75                  80

Pro Leu Asp Thr Leu Arg Asp Ile Thr Gln Gln Leu Asn Leu Met Trp
                85                  90                  95

Tyr Asp Asn Gly Gln Val Ile Tyr Ile Cys Asp Ala Ile Glu Met Arg
            100                 105                 110

```
Asn Thr Val Ile Thr Leu Asn Thr Thr Ile Gln Glu Ile Lys Asn
        115                 120                 125

Phe Leu Lys Asp Ser Gly Leu Tyr Asp Glu Arg Tyr Pro Leu Arg Ser
130                 135                 140

Gly Ser Asn Asn Arg Leu Phe Tyr Ile Ser Gly Pro Pro Val Tyr Ile
145                 150                 155                 160

Glu Thr Ile Ile Asn Thr Thr Gln Phe Leu Asp Glu Thr Thr Thr Glu
                165                 170                 175

Phe Asp Gly Arg Glu Lys Ile Ala Ile Val Pro Leu Tyr Asn Thr Phe
            180                 185                 190

Val Glu Asp Arg His Tyr Gln Tyr Arg Phe Asn Asp Ile Ile Ile Pro
        195                 200                 205

Gly Met Ala Ser Ile Ile Asn Lys Leu Met Asp Ala Ser Ser Asn Asn
    210                 215                 220

Ile Ser Lys Leu Lys Asn His Ile Gln Lys Lys Asn Gln Asp Glu Leu
225                 230                 235                 240

Val Asn Gln Ser Asn Asn Ser Ser Leu Ile Glu Asn Ser Pro Leu Asn
                245                 250                 255

Lys Gly Leu Val Ser Ile Ile Ser Asn Pro Gly Asn Asn Ser Leu Leu
            260                 265                 270

Ile Lys Gly Asn Lys Glu Gln Val Asn Tyr Leu Arg Lys Ile Val Glu
        275                 280                 285

Gln Leu Asp Ile Thr Lys Arg His Ile Glu Leu Ser Val Trp Ile Ile
    290                 295                 300

Asp Ile Glu Lys Lys Ala Leu Asp Gln Leu Gly Ile Lys Trp Ser Gly
305                 310                 315                 320

Gly Ala Lys Ile Gly Gln Lys Leu Gly Val Ser Leu Asn Ala Gly Thr
                325                 330                 335

Ser Thr Ile Asp Gly Ala Ser Phe Met Thr Ala Ile Phe Ala Leu Thr
            340                 345                 350

Arg Asn Asp Lys Ala Asn Ile Val Ser Arg Pro Met Val Leu Thr Gln
        355                 360                 365

Glu Asn Ile Pro Ala Ile Phe Asp Asn Asn Arg Thr Phe Tyr Thr Lys
    370                 375                 380

Leu Ile Gly Glu Arg Ala Thr Asp Leu Lys Asn Val Thr Tyr Gly Thr
385                 390                 395                 400

Ala Ile Ser Val Leu Pro Arg Phe Thr Ile Asn Asn Gln Ile Glu Met
                405                 410                 415

Met Ile Thr Val Glu Asp Gly Ser Arg Ala Gly Gln Ile Thr Asp His
            420                 425                 430

Leu Pro Glu Ile Gly Arg Thr Asn Ile Ser Thr Ile Ala Arg Val Pro
        435                 440                 445

Gln Asn Lys Ser Leu Leu Ile Gly Gly Tyr Thr Arg Asp Glu His Arg
    450                 455                 460

Asn Ile Glu Glu Lys Ile Pro Leu Leu Gly Asp Ile Pro Tyr Leu Gly
465                 470                 475                 480

Ser Leu Phe Arg Tyr Asn Ile Glu Lys Lys Asp Ser Leu Val Arg Val
                485                 490                 495

Phe Leu Ile Gln Pro Arg Glu Ile Ile Asn Pro Leu Ser Thr Ser Ala
            500                 505                 510

Glu Asn Ile Ala Lys Lys Val Lys Glu Asp Lys Phe Asp Asn Lys Leu
        515                 520                 525
```

-continued

```
Glu Asp Trp Met Ser Asn Phe Leu Ser Asn His
    530                 535
```

<210> SEQ ID NO 29
<211> LENGTH: 587
<212> TYPE: PRT
<213> ORGANISM: Pantoea stewartii

<400> SEQUENCE: 29

```
Met Asn Glu Phe Val Arg Lys Thr Leu Lys Ser Arg Val Pro Cys Phe
1               5                   10                  15

Leu Leu Thr Val Leu Ser Cys Ala Pro Ala Gly Ala Asn Met Leu Asn
            20                  25                  30

Thr Ser Ser Ala Pro Ala Arg Ser Met Gln Ser Thr Val Glu Asn Thr
        35                  40                  45

Tyr Val Ala Ser Asn Asn Ser Val Gln Gln Leu Phe Phe Val Val Gly
    50                  55                  60

Gly Ala Leu His Lys Pro Phe Ile Val Ser Val Glu Ala Ala Lys Lys
65                  70                  75                  80

Arg Val Ser Gly Asn Phe Asp Leu Asn Asp Pro Lys Ser Val Leu Asp
                85                  90                  95

Thr Val Ala Ala Arg Thr Gly Leu Ile Trp Tyr Asp Asp Gly Ser Ser
            100                 105                 110

Val Tyr Ile Tyr Asp Thr Ser Glu Ile Gln Ser Ser Val Val Arg Leu
        115                 120                 125

Ala Phe Ala Pro Tyr Asp Arg Leu Val Ala Tyr Leu Gln Ser Ser Gly
    130                 135                 140

Leu Tyr Asp Pro Arg Phe Pro Leu Arg Ser Asp Gly Arg Ser Gly Ser
145                 150                 155                 160

Phe Tyr Val Ser Gly Pro Pro Val Tyr Val Glu Leu Val Ser Ala Ala
                165                 170                 175

Ala Lys Tyr Ile Asp Ala Thr Tyr Ala Lys Pro Gly Thr Gly Glu Thr
            180                 185                 190

Thr Ile Arg Val Ile Lys Leu Lys Asn Thr Phe Val Asn Asp Arg Asn
        195                 200                 205

Tyr Thr Gln Arg Asp Val Pro Ile Ser Val Pro Gly Val Ala Thr Val
    210                 215                 220

Leu Asn Gln Leu Leu Asn Asn Thr Ser Cys Arg Glu Gly Gly Arg Ser
225                 230                 235                 240

Ala Pro Ala Gly Ala Ile Ile Thr Val Asp Asn Asp Thr Arg Ser Ala
                245                 250                 255

Leu Glu Ala Ala Ser Ala Thr Gln Lys Gly Asn Phe Pro Pro Leu Pro
            260                 265                 270

Ser Phe Asn Ala Ala Pro Ala Arg Gly Arg Ala Val Asp Arg Asp
        275                 280                 285

Ile Pro Ser Gln Gln Thr Ile Asn Ile Val Gly Tyr Ser Asp Thr Asn
    290                 295                 300

Ser Leu Leu Ile Gln Gly Ser Glu Arg Gln Val Ser Phe Val Glu Asp
305                 310                 315                 320

Leu Val Asn Ala Ile Asp Ile Pro Lys Gln Gln Ile Gln Leu Ser Leu
                325                 330                 335

Trp Ile Ile Asp Ile Ser Lys Asp Asp Ile Asn Glu Leu Gly Ile Arg
            340                 345                 350

Trp Gln Gly Ala Ala Lys Met Gly Asn Thr Gly Val Thr Phe Asn Thr
        355                 360                 365
```

-continued

```
Ser Ser Leu Thr Pro Glu Ser Ser Leu His Phe Leu Ala Asp Val Ser
    370                 375                 380
Ala Leu Ala Lys Lys Gly Ser Ala Gln Val Val Ser Arg Pro Glu Ile
385                 390                 395                 400
Leu Thr Gln Glu Asn Val Pro Ala Leu Phe Asp Asn Asn Ser Ser Phe
                405                 410                 415
Tyr Ala Lys Leu Ile Gly Glu Arg Thr Ser Ser Leu Glu Lys Ile Thr
                420                 425                 430
Tyr Gly Thr Met Ile Ser Val Leu Pro Arg Leu Ala Gln Arg Gln Gln
                435                 440                 445
Glu Ile Glu Met Ile Leu Asn Ile Gln Asp Gly Gly Leu Leu Leu Asn
    450                 455                 460
Ala Asp Gly Ser Thr Glu Asn Ile Asp Ser Leu Pro Met Val Asn Asn
465                 470                 475                 480
Thr Gln Ile Ser Thr Glu Ala Arg Val Pro Val Gly Tyr Ser Leu Leu
                485                 490                 495
Val Gly Gly Tyr Ser Arg Asp Gln Asp Glu His His Arg Leu Gly Ile
                500                 505                 510
Pro Leu Leu Arg Asp Ile Pro Phe Val Gly Lys Leu Phe Asp Tyr Ser
    515                 520                 525
Tyr Thr Ser His Lys Lys Met Val Arg Leu Phe Leu Ile Gln Pro Gly
                530                 535                 540
Leu Leu Thr Ser Gly Glu Thr Trp Gln Gly Arg Thr Glu Asn Asn Pro
545                 550                 555                 560
Val Met Gly Arg Thr Trp Thr Ser Asn Glu Val Thr Leu Lys Ser Thr
                565                 570                 575
Val Ser Met Leu Arg Glu Thr Met Lys Asp Asn
                580                 585

<210> SEQ ID NO 30
<211> LENGTH: 586
<212> TYPE: PRT
<213> ORGANISM: Enterobacter aerogenes

<400> SEQUENCE: 30

Met Asn Leu Arg Asn Cys Pro Leu Cys Cys Leu Leu Leu Gly Ala Leu
1                   5                   10                  15
Thr Cys Met Pro Ala Lys Ala Ala Leu Leu Asp Lys Gln Asp Met Arg
                20                  25                  30
Asn Thr Ser Gly Leu Thr Gln Thr Ser Ser Phe Asp Ser Glu Asn Ile
            35                  40                  45
Tyr Val Ala Ser Asn Asn Ser Val Gln Gln Phe Phe Phe Val Ile Gly
        50                  55                  60
Gly Ala Leu His Lys Pro Phe Ile Val Ser Thr Glu Ala Ala Lys Lys
65                  70                  75                  80
Lys Val Ser Gly Asn Phe Asp Leu Thr Lys Pro Lys Glu Leu Phe Asn
                85                  90                  95
Thr Leu Ala Ala Arg Thr Gly Leu Ile Trp Tyr Asp Asp Gly Ser Ser
                100                 105                 110
Val Tyr Val Tyr Asp Ser Ser Glu Leu Gln Ser Arg Val Val Arg Leu
            115                 120                 125
Ala Tyr Ala Pro Phe Asp Arg Leu Leu Ala Tyr Leu Arg Ser Ser Asp
        130                 135                 140
Leu Tyr Asp Ser Arg Phe Pro Leu Arg Ser Asp Gly His Ser Gly Ser
```

```
            145                 150                 155                 160

Phe Tyr Val Ser Gly Pro Pro Val Tyr Val Glu Leu Val Ala Ser Ala
                        165                 170                 175

Ala Lys Tyr Ile Asp Ala Thr Tyr Ala His Pro Gly Thr Gly Glu Ser
                        180                 185                 190

Thr Ile Arg Val Ile Lys Leu Lys Asn Thr Phe Val Asn Asp Arg Ile
                        195                 200                 205

Tyr Thr Gln Arg Asp Thr Pro Leu Thr Val Pro Gly Val Ala Thr Val
                        210                 215                 220

Leu Asn Gln Leu Leu Asn Asp Gly Ser Asn Lys Ser Gly Gly Arg Ser
        225                 230                 235                 240

Thr Pro Ser Gly Ala Thr Ile Ser Ile Asp Asn Asp Thr Arg Gly Ala
                        245                 250                 255

Leu Met Ala Ala Ser Ala Met Gln Lys Gly Asn Phe Pro Pro Leu Pro
                        260                 265                 270

Ala Phe Asn Val Arg Ser Thr Ala Glu His Pro Ser Phe His Asp Asp
                        275                 280                 285

Pro Gly Gln Gln Gly Ile Asn Ile Val Gly Tyr Ser Asp Thr Asn Ser
                        290                 295                 300

Leu Leu Ile Gln Gly Ala Glu Arg Gln Val Ser Phe Val Glu Asp Leu
        305                 310                 315                 320

Val Ser Ala Ile Asp Ile Pro Lys His Gln Ile Gln Leu Ser Leu Trp
                        325                 330                 335

Ile Ile Asp Ile Ser Lys Asp Asp Ile Asn Glu Leu Gly Ile Arg Trp
                        340                 345                 350

Gln Gly Ala Gly Lys Phe Gly Asn Thr Gly Val Thr Phe Asn Thr Ser
                        355                 360                 365

Ser Leu Thr Pro Glu Asn Ser Leu His Phe Leu Ala Asp Val Ser Ala
                        370                 375                 380

Leu Ala Lys Arg Gly Asn Ala Gln Val Val Ser Arg Pro Glu Ile Leu
        385                 390                 395                 400

Thr Gln Glu Asn Val Pro Ala Leu Phe Asp Asn Asn Ser Ser Phe Tyr
                        405                 410                 415

Ala Lys Leu Val Gly Glu Arg Thr Ser Ser Leu Glu Lys Ile Thr Tyr
                        420                 425                 430

Gly Thr Met Ile Ser Val Leu Pro Arg Leu Ala Gln Arg His Gln Glu
                        435                 440                 445

Ile Glu Met Ile Leu Asn Ile Gln Asp Gly Gly Leu Pro Leu Asn Ala
                        450                 455                 460

Ser Gly Glu Val Glu Asn Val Asp Ser Leu Pro Met Val Asn Asn Thr
        465                 470                 475                 480

Gln Ile Ser Thr Glu Ala Arg Val Pro Val Gly Tyr Ser Leu Leu Val
                        485                 490                 495

Gly Gly Tyr Ser Arg Asp Gln Asp Glu His His Ser Ile Gly Ile Pro
                        500                 505                 510

Leu Leu Arg Asp Ile Pro Phe Leu Gly Lys Leu Phe Asp Tyr Ser Tyr
                        515                 520                 525

Thr Asn His Lys Lys Met Val Arg Met Phe Leu Ile Gln Pro Arg Leu
                        530                 535                 540

Leu Asn Ser Gly Glu Thr Trp Gln Gly Arg Asp Glu Arg Asn Pro Val
        545                 550                 555                 560

Leu Gly Arg Thr Leu Ser Gly Asp Asn Val Thr Leu Lys Ser Thr Val
                        565                 570                 575
```

-continued

Ser Met Leu Arg Asp Thr Met Lys Arg His
            580                 585

<210> SEQ ID NO 31
<211> LENGTH: 674
<212> TYPE: PRT
<213> ORGANISM: Vibrio cholerae

<400> SEQUENCE: 31

Met Lys Tyr Trp Leu Lys Lys Ser Ser Trp Leu Leu Ala Gly Ser Leu
1               5                   10                  15

Leu Ser Thr Pro Leu Ala Met Ala Asn Glu Phe Ser Ala Ser Phe Lys
            20                  25                  30

Gly Thr Asp Ile Gln Glu Phe Ile Asn Ile Val Gly Arg Asn Leu Glu
        35                  40                  45

Lys Thr Ile Ile Val Asp Pro Ser Val Arg Gly Lys Val Asp Val Arg
    50                  55                  60

Ser Phe Asp Thr Leu Asn Glu Glu Gln Tyr Tyr Ser Phe Phe Leu Ser
65                  70                  75                  80

Val Leu Glu Val Tyr Gly Phe Ala Val Val Glu Met Asp Asn Gly Val
                85                  90                  95

Leu Lys Val Ile Lys Ser Lys Asp Ala Lys Thr Ser Ala Ile Pro Val
            100                 105                 110

Leu Ser Gly Glu Glu Arg Ala Asn Gly Asp Glu Val Ile Thr Gln Val
        115                 120                 125

Val Ala Val Lys Asn Val Ser Val Arg Glu Leu Ser Pro Leu Leu Arg
130                 135                 140

Gln Leu Ile Asp Asn Ala Gly Ala Gly Asn Val Val His Tyr Asp Pro
145                 150                 155                 160

Ala Asn Ile Ile Leu Ile Thr Gly Arg Ala Ala Val Val Asn Arg Leu
                165                 170                 175

Ala Glu Ile Ile Arg Arg Val Asp Gln Ala Gly Asp Lys Glu Ile Glu
            180                 185                 190

Val Val Glu Leu Asn Asn Ala Ser Ala Ala Glu Met Val Arg Ile Val
        195                 200                 205

Glu Ala Leu Asn Lys Thr Thr Asp Ala Gln Asn Thr Pro Glu Phe Leu
    210                 215                 220

Lys Pro Lys Phe Val Ala Asp Glu Arg Thr Asn Ser Ile Leu Ile Ser
225                 230                 235                 240

Gly Asp Pro Lys Val Arg Glu Arg Leu Lys Arg Leu Ile Lys Gln Leu
                245                 250                 255

Asp Val Glu Met Ala Ala Lys Gly Asn Asn Arg Val Val Tyr Leu Lys
            260                 265                 270

Tyr Ala Lys Ala Glu Asp Leu Val Glu Val Leu Lys Gly Val Ser Glu
        275                 280                 285

Asn Leu Gln Ala Glu Lys Gly Thr Gly Gln Pro Thr Thr Ser Lys Arg
    290                 295                 300

Asn Glu Val Met Ile Ala Ala His Ala Asp Thr Asn Ser Leu Val Leu
305                 310                 315                 320

Thr Ala Pro Gln Asp Ile Met Asn Ala Met Leu Glu Val Ile Gly Gln
                325                 330                 335

Leu Asp Ile Arg Arg Ala Gln Val Leu Ile Glu Ala Leu Ile Val Glu
            340                 345                 350

Met Ala Glu Gly Asp Gly Ile Asn Leu Gly Val Gln Trp Gly Ser Leu

```
                355                 360                 365
Glu Ser Gly Ser Val Ile Gln Tyr Gly Asn Thr Gly Ala Ser Ile Gly
            370                 375                 380

Asn Val Met Ile Gly Leu Glu Ala Lys Asp Thr Thr Gln Thr Lys
385                 390                 395                 400

Ala Val Tyr Asp Thr Asn Asn Asn Phe Leu Arg Asn Glu Thr Thr Thr
                405                 410                 415

Thr Lys Gly Asp Tyr Thr Lys Leu Ala Ser Ala Leu Ser Ser Ile Gln
            420                 425                 430

Gly Ala Ala Val Ser Ile Ala Met Gly Asp Trp Thr Ala Leu Ile Asn
        435                 440                 445

Ala Val Ser Asn Asp Ser Ser Ser Asn Ile Leu Ser Ser Pro Ser Ile
    450                 455                 460

Thr Val Met Asp Asn Gly Glu Ala Ser Phe Ile Val Gly Glu Glu Val
465                 470                 475                 480

Pro Val Ile Thr Gly Ser Thr Ala Gly Ser Asn Asn Asp Asn Pro Phe
                485                 490                 495

Gln Thr Val Asp Arg Lys Glu Val Gly Ile Lys Leu Lys Val Val Pro
            500                 505                 510

Gln Ile Asn Glu Gly Asn Ser Val Gln Leu Asn Ile Glu Gln Glu Val
        515                 520                 525

Ser Asn Val Leu Gly Ala Asn Gly Ala Val Asp Val Arg Phe Ala Lys
    530                 535                 540

Arg Gln Leu Asn Thr Ser Val Met Val Gln Asp Gly Gln Met Leu Val
545                 550                 555                 560

Leu Gly Gly Leu Ile Asp Glu Arg Ala Leu Glu Ser Glu Ser Lys Val
                565                 570                 575

Pro Leu Leu Gly Asp Ile Pro Leu Leu Gly Gln Leu Phe Arg Ser Thr
            580                 585                 590

Ser Ser Gln Val Glu Lys Lys Asn Leu Met Val Phe Ile Lys Pro Thr
        595                 600                 605

Ile Ile Arg Asp Gly Val Thr Ala Asp Gly Ile Thr Gln Arg Lys Tyr
    610                 615                 620

Asn Tyr Ile Arg Ala Glu Gln Leu Phe Arg Ala Glu Lys Gly Leu Arg
625                 630                 635                 640

Leu Leu Asp Asp Ala Ser Val Pro Val Leu Pro Lys Phe Gly Asp Asp
                645                 650                 655

Arg Arg His Ser Pro Glu Ile Gln Ala Phe Ile Glu Gln Met Glu Ala
            660                 665                 670

Lys Gln

<210> SEQ ID NO 32
<211> LENGTH: 650
<212> TYPE: PRT
<213> ORGANISM: Vibrio cholerae

<400> SEQUENCE: 32

Asn Glu Phe Ser Ala Ser Phe Lys Gly Thr Asp Ile Gln Glu Phe Ile
1               5                   10                  15

Asn Ile Val Gly Arg Asn Leu Glu Lys Thr Ile Ile Val Asp Pro Ser
            20                  25                  30

Val Arg Gly Lys Val Asp Val Arg Ser Phe Asp Thr Leu Asn Glu Glu
        35                  40                  45

Gln Tyr Tyr Ser Phe Phe Leu Ser Val Leu Glu Val Tyr Gly Phe Ala
```

```
            50                  55                  60
Val Val Glu Met Asp Asn Gly Val Leu Lys Val Ile Lys Ser Lys Asp
 65                  70                  75                  80

Ala Lys Thr Ser Ala Ile Pro Val Leu Ser Gly Glu Arg Ala Asn
                 85                  90                  95

Gly Asp Glu Val Ile Thr Gln Val Val Ala Val Lys Asn Val Ser Val
                100                 105                 110

Arg Glu Leu Ser Pro Leu Leu Arg Gln Leu Ile Asp Asn Ala Gly Ala
                115                 120                 125

Gly Asn Val Val His Tyr Asp Pro Ala Asn Ile Ile Leu Ile Thr Gly
130                 135                 140

Arg Ala Ala Val Val Asn Arg Leu Ala Glu Ile Ile Arg Arg Val Asp
145                 150                 155                 160

Gln Ala Gly Asp Lys Glu Ile Glu Val Val Glu Leu Asn Asn Ala Ser
                165                 170                 175

Ala Ala Glu Met Val Arg Ile Val Glu Ala Leu Asn Lys Thr Thr Asp
                180                 185                 190

Ala Gln Asn Thr Pro Glu Phe Leu Lys Pro Lys Phe Val Ala Asp Glu
                195                 200                 205

Arg Thr Asn Ser Ile Leu Ile Ser Gly Asp Pro Lys Val Arg Glu Arg
210                 215                 220

Leu Lys Arg Leu Ile Lys Gln Leu Asp Val Glu Met Ala Ala Lys Gly
225                 230                 235                 240

Asn Asn Arg Val Val Tyr Leu Lys Tyr Ala Lys Ala Glu Asp Leu Val
                245                 250                 255

Glu Val Leu Lys Gly Val Ser Glu Asn Leu Gln Ala Glu Lys Gly Thr
                260                 265                 270

Gly Gln Pro Thr Thr Ser Lys Arg Asn Glu Val Met Ile Ala Ala His
                275                 280                 285

Ala Asp Thr Asn Ser Leu Val Leu Thr Ala Pro Gln Asp Ile Met Asn
290                 295                 300

Ala Met Leu Glu Val Ile Gly Gln Leu Asp Ile Arg Arg Ala Gln Val
305                 310                 315                 320

Leu Ile Glu Ala Leu Ile Val Glu Met Ala Glu Gly Asp Gly Ile Asn
                325                 330                 335

Leu Gly Val Gln Trp Gly Ser Leu Glu Ser Gly Ser Val Ile Gln Tyr
                340                 345                 350

Gly Asn Thr Gly Ala Ser Ile Gly Asn Val Met Ile Gly Leu Glu Glu
                355                 360                 365

Ala Lys Asp Thr Thr Gln Thr Lys Ala Val Tyr Asp Thr Asn Asn Asn
370                 375                 380

Phe Leu Arg Asn Glu Thr Thr Thr Lys Gly Asp Tyr Thr Lys Leu
385                 390                 395                 400

Ala Ser Ala Leu Ser Ser Ile Gln Gly Ala Ala Val Ser Ile Ala Met
                405                 410                 415

Gly Asp Trp Thr Ala Leu Ile Asn Ala Val Ser Asn Asp Ser Ser Ser
                420                 425                 430

Asn Ile Leu Ser Ser Pro Ser Ile Thr Val Met Asp Asn Gly Glu Ala
                435                 440                 445

Ser Phe Ile Val Gly Glu Glu Val Pro Val Ile Thr Gly Ser Thr Ala
450                 455                 460

Gly Ser Asn Asn Asp Asn Pro Phe Gln Thr Val Asp Arg Lys Glu Val
465                 470                 475                 480
```

```
Gly Ile Lys Leu Lys Val Val Pro Gln Ile Asn Glu Gly Asn Ser Val
                485                 490                 495

Gln Leu Asn Ile Glu Gln Glu Val Ser Asn Val Leu Gly Ala Asn Gly
            500                 505                 510

Ala Val Asp Val Arg Phe Ala Lys Arg Gln Leu Asn Thr Ser Val Met
            515                 520                 525

Val Gln Asp Gly Gln Met Leu Val Leu Gly Leu Ile Asp Glu Arg
        530                 535                 540

Ala Leu Glu Ser Glu Ser Lys Val Pro Leu Leu Gly Asp Ile Pro Leu
545                 550                 555                 560

Leu Gly Gln Leu Phe Arg Ser Thr Ser Ser Gln Val Glu Lys Lys Asn
                565                 570                 575

Leu Met Val Phe Ile Lys Pro Thr Ile Ile Arg Asp Gly Val Thr Ala
                580                 585                 590

Asp Gly Ile Thr Gln Arg Lys Tyr Asn Tyr Ile Arg Ala Glu Gln Leu
                595                 600                 605

Phe Arg Ala Glu Lys Gly Leu Arg Leu Leu Asp Asp Ala Ser Val Pro
            610                 615                 620

Val Leu Pro Lys Phe Gly Asp Asp Arg Arg His Ser Pro Glu Ile Gln
625                 630                 635                 640

Ala Phe Ile Glu Gln Met Glu Ala Lys Gln
                645                 650

<210> SEQ ID NO 33
<211> LENGTH: 411
<212> TYPE: PRT
<213> ORGANISM: Vibrio cholerae

<400> SEQUENCE: 33

Gly Asn Asn Arg Val Val Tyr Leu Lys Tyr Ala Lys Ala Glu Asp Leu
1               5                   10                  15

Val Glu Val Leu Lys Gly Val Ser Glu Asn Leu Gln Ala Glu Lys Gly
            20                  25                  30

Thr Gly Gln Pro Thr Thr Ser Lys Arg Asn Glu Val Met Ile Ala Ala
        35                  40                  45

His Ala Asp Thr Asn Ser Leu Val Leu Thr Ala Pro Gln Asp Ile Met
    50                  55                  60

Asn Ala Met Leu Glu Val Ile Gly Gln Leu Asp Ile Arg Arg Ala Gln
65                  70                  75                  80

Val Leu Ile Glu Ala Leu Ile Val Glu Met Ala Glu Gly Asp Gly Ile
                85                  90                  95

Asn Leu Gly Val Gln Trp Gly Ser Leu Glu Ser Gly Ser Val Ile Gln
            100                 105                 110

Tyr Gly Asn Thr Gly Ala Ser Ile Gly Asn Val Met Ile Gly Leu Glu
        115                 120                 125

Glu Ala Lys Asp Thr Thr Gln Thr Lys Ala Val Tyr Asp Thr Asn Asn
    130                 135                 140

Asn Phe Leu Arg Asn Glu Thr Thr Thr Lys Gly Asp Tyr Thr Lys
145                 150                 155                 160

Leu Ala Ser Ala Leu Ser Ser Ile Gln Gly Ala Ala Val Ser Ile Ala
                165                 170                 175

Met Gly Asp Trp Thr Ala Leu Ile Asn Ala Val Ser Asn Asp Ser Ser
            180                 185                 190

Ser Asn Ile Leu Ser Ser Pro Ser Ile Thr Val Met Asp Asn Gly Glu
```

```
                195                 200                 205
Ala Ser Phe Ile Val Gly Glu Glu Val Pro Val Ile Thr Gly Ser Thr
210                 215                 220

Ala Gly Ser Asn Asn Asp Asn Pro Phe Gln Thr Val Asp Arg Lys Glu
225                 230                 235                 240

Val Gly Ile Lys Leu Lys Val Val Pro Gln Ile Asn Glu Gly Asn Ser
                245                 250                 255

Val Gln Leu Asn Ile Glu Gln Glu Val Ser Asn Val Leu Gly Ala Asn
            260                 265                 270

Gly Ala Val Asp Val Arg Phe Ala Lys Arg Gln Leu Asn Thr Ser Val
        275                 280                 285

Met Val Gln Asp Gly Gln Met Leu Val Leu Gly Gly Leu Ile Asp Glu
290                 295                 300

Arg Ala Leu Glu Ser Glu Ser Lys Val Pro Leu Leu Gly Asp Ile Pro
305                 310                 315                 320

Leu Leu Gly Gln Leu Phe Arg Ser Thr Ser Ser Gln Val Glu Lys Lys
                325                 330                 335

Asn Leu Met Val Phe Ile Lys Pro Thr Ile Ile Arg Asp Gly Val Thr
            340                 345                 350

Ala Asp Gly Ile Thr Gln Arg Lys Tyr Asn Tyr Ile Arg Ala Glu Gln
        355                 360                 365

Leu Phe Arg Ala Glu Lys Gly Leu Arg Leu Leu Asp Asp Ala Ser Val
370                 375                 380

Pro Val Leu Pro Lys Phe Gly Asp Asp Arg Arg His Ser Pro Glu Ile
385                 390                 395                 400

Gln Ala Phe Ile Glu Gln Met Glu Ala Lys Gln
                405                 410

<210> SEQ ID NO 34
<211> LENGTH: 396
<212> TYPE: PRT
<213> ORGANISM: Vibrio cholerae

<400> SEQUENCE: 34

Gly Asn Asn Arg Val Val Tyr Leu Lys Tyr Ala Lys Ala Glu Asp Leu
1               5                   10                  15

Val Glu Val Leu Lys Gly Val Ser Glu Ser Gly Ser Val Met Ile Ala
                20                  25                  30

Ala His Ala Asp Thr Asn Ser Leu Val Leu Thr Ala Pro Gln Asp Ile
            35                  40                  45

Met Asn Ala Met Leu Glu Val Ile Gly Gln Leu Asp Ile Arg Arg Ala
        50                  55                  60

Gln Val Leu Ile Glu Ala Leu Ile Val Glu Met Ala Glu Gly Asp Gly
65                  70                  75                  80

Ile Asn Leu Gly Val Gln Trp Gly Ser Leu Glu Ser Gly Ser Val Ile
                85                  90                  95

Gln Tyr Gly Asn Thr Gly Ala Ser Ile Gly Asn Val Met Ile Gly Leu
            100                 105                 110

Glu Glu Ala Lys Asp Thr Thr Gln Thr Lys Ala Val Tyr Asp Thr Asn
        115                 120                 125

Asn Asn Phe Leu Arg Asn Glu Thr Thr Thr Lys Gly Asp Tyr Thr
    130                 135                 140

Lys Leu Ala Ser Ala Leu Ser Ser Ile Gln Gly Ala Ala Val Ser Ile
145                 150                 155                 160
```

Ala Met Gly Asp Trp Thr Ala Leu Ile Asn Ala Val Ser Asn Asp Ser
                165                 170                 175

Ser Ser Asn Ile Leu Ser Ser Pro Ser Ile Thr Val Met Asp Asn Gly
            180                 185                 190

Glu Ala Ser Phe Ile Val Gly Glu Val Pro Val Ile Thr Gly Ser
        195                 200                 205

Thr Ala Gly Ser Asn Asn Asp Asn Pro Phe Gln Thr Val Asp Arg Lys
        210                 215                 220

Glu Val Gly Ile Lys Leu Lys Val Val Pro Gln Ile Asn Glu Gly Asn
225                 230                 235                 240

Ser Val Gln Leu Asn Ile Glu Gln Glu Val Ser Asn Val Leu Gly Ala
                245                 250                 255

Asn Gly Ala Val Asp Val Arg Phe Ala Lys Arg Gln Leu Asn Thr Ser
            260                 265                 270

Val Met Val Gln Asp Gly Gln Met Leu Val Leu Gly Leu Ile Asp
        275                 280                 285

Glu Arg Ala Leu Glu Ser Glu Ser Lys Val Pro Leu Leu Gly Asp Ile
        290                 295                 300

Pro Leu Leu Gly Gln Leu Phe Arg Ser Thr Ser Ser Gln Val Glu Lys
305                 310                 315                 320

Lys Asn Leu Met Val Phe Ile Lys Pro Thr Ile Ile Arg Asp Gly Val
                325                 330                 335

Thr Ala Asp Gly Ile Thr Gln Arg Lys Tyr Asn Tyr Ile Arg Ala Glu
            340                 345                 350

Gln Leu Phe Arg Ala Glu Lys Gly Leu Arg Leu Leu Asp Asp Ala Ser
        355                 360                 365

Val Pro Val Leu Pro Lys Phe Gly Asp Asp Arg Arg His Ser Pro Glu
        370                 375                 380

Ile Gln Ala Phe Ile Glu Gln Met Glu Ala Lys Gln
385                 390                 395

<210> SEQ ID NO 35
<211> LENGTH: 334
<212> TYPE: PRT
<213> ORGANISM: Vibrio cholerae

<400> SEQUENCE: 35

Arg Ala Gln Val Leu Ile Glu Ala Leu Ile Val Glu Met Ala Glu Gly
1               5                   10                  15

Asp Gly Ile Asn Leu Gly Val Gln Trp Gly Ser Leu Glu Ser Gly Ser
            20                  25                  30

Val Ile Gln Tyr Gly Asn Thr Gly Ala Ser Ile Gly Asn Val Met Ile
        35                  40                  45

Gly Leu Glu Glu Ala Lys Asp Thr Thr Gln Thr Lys Ala Val Tyr Asp
    50                  55                  60

Thr Asn Asn Asn Phe Leu Arg Asn Glu Thr Thr Thr Lys Gly Asp
65                  70                  75                  80

Tyr Thr Lys Leu Ala Ser Ala Leu Ser Ser Ile Gln Gly Ala Ala Val
                85                  90                  95

Ser Ile Ala Met Gly Asp Trp Thr Ala Leu Ile Asn Ala Val Ser Asn
            100                 105                 110

Asp Ser Ser Ser Asn Ile Leu Ser Ser Pro Ser Ile Thr Val Met Asp
        115                 120                 125

Asn Gly Glu Ala Ser Phe Ile Val Gly Glu Glu Val Pro Val Ile Thr
    130                 135                 140

```
Gly Ser Thr Ala Gly Ser Asn Asn Asp Asn Pro Phe Gln Thr Val Asp
145                 150                 155                 160

Arg Lys Glu Val Gly Ile Lys Leu Lys Val Val Pro Gln Ile Asn Glu
                165                 170                 175

Gly Asn Ser Val Gln Leu Asn Ile Glu Gln Glu Val Ser Asn Val Leu
            180                 185                 190

Gly Ala Asn Gly Ala Val Asp Val Arg Phe Ala Lys Arg Gln Leu Asn
        195                 200                 205

Thr Ser Val Met Val Gln Asp Gly Gln Met Leu Val Leu Gly Gly Leu
    210                 215                 220

Ile Asp Glu Arg Ala Leu Glu Ser Glu Ser Lys Val Pro Leu Leu Gly
225                 230                 235                 240

Asp Ile Pro Leu Leu Gly Gln Leu Phe Arg Ser Thr Ser Ser Gln Val
                245                 250                 255

Glu Lys Lys Asn Leu Met Val Phe Ile Lys Pro Thr Ile Ile Arg Asp
            260                 265                 270

Gly Val Thr Ala Asp Gly Ile Thr Gln Arg Lys Tyr Asn Tyr Ile Arg
        275                 280                 285

Ala Glu Gln Leu Phe Arg Ala Glu Lys Gly Leu Arg Leu Leu Asp Asp
    290                 295                 300

Ala Ser Val Pro Val Leu Pro Lys Phe Gly Asp Asp Arg Arg His Ser
305                 310                 315                 320

Pro Glu Ile Gln Ala Phe Ile Glu Gln Met Glu Ala Lys Gln
                325                 330

<210> SEQ ID NO 36
<211> LENGTH: 272
<212> TYPE: PRT
<213> ORGANISM: Vibrio cholerae

<400> SEQUENCE: 36

Arg Ala Gln Val Leu Ile Glu Ala Leu Ile Val Glu Met Ala Glu Gly
1               5                   10                  15

Asp Gly Ile Asn Leu Gly Val Gln Trp Gly Ser Leu Glu Ser Gly Ser
            20                  25                  30

Val Ile Gln Tyr Gly Asn Thr Gly Ala Ser Ile Gly Asn Val Met Ile
        35                  40                  45

Gly Leu Glu Glu Ala Lys Asp Thr Thr Gln Thr Lys Ala Val Tyr Asp
    50                  55                  60

Thr Asn Asn Asn Phe Leu Arg Asn Glu Thr Thr Thr Lys Gly Asp
65                  70                  75                  80

Tyr Thr Lys Leu Ala Ser Ala Leu Ser Ser Ile Gln Gly Ala Ala Val
                85                  90                  95

Ser Ile Ala Met Gly Asp Trp Thr Ala Leu Ile Asn Ala Val Ser Asn
            100                 105                 110

Asp Ser Ser Ser Asn Ile Leu Ser Ser Pro Ser Ile Thr Val Met Asp
        115                 120                 125

Asn Gly Glu Ala Ser Phe Ile Val Gly Glu Glu Val Pro Val Ile Thr
    130                 135                 140

Gly Ser Thr Ala Gly Ser Asn Asn Asp Asn Pro Phe Gln Thr Val Asp
145                 150                 155                 160

Arg Lys Glu Val Gly Ile Lys Leu Lys Val Val Pro Gln Ile Asn Glu
                165                 170                 175

Gly Asn Ser Val Gln Leu Asn Ile Glu Gln Glu Val Ser Asn Val Leu
```

```
                180                 185                 190
Gly Ala Asn Gly Ala Val Asp Val Arg Phe Ala Lys Arg Gln Leu Asn
            195                 200                 205

Thr Ser Val Met Val Gln Asp Gly Gln Met Leu Val Leu Gly Gly Leu
        210                 215                 220

Ile Asp Glu Arg Ala Leu Glu Ser Glu Ser Lys Val Pro Leu Leu Gly
225                 230                 235                 240

Asp Ile Pro Leu Leu Gly Gln Leu Phe Arg Ser Thr Ser Ser Gln Val
                245                 250                 255

Glu Lys Lys Asn Leu Met Val Phe Ile Lys Pro Thr Ile Ile Arg Asp
            260                 265                 270

<210> SEQ ID NO 37
<211> LENGTH: 686
<212> TYPE: PRT
<213> ORGANISM: Escherichia coli

<400> SEQUENCE: 37

Met Phe Trp Arg Asp Ile Thr Leu Ser Val Trp Arg Lys Lys Thr Thr
1               5                   10                  15

Gly Leu Lys Thr Lys Arg Leu Leu Pro Leu Val Leu Ala Ala Ala
            20                  25                  30

Leu Cys Ser Ser Pro Val Trp Ala Glu Glu Ala Thr Phe Thr Ala Asn
        35                  40                  45

Phe Lys Asp Thr Asp Leu Lys Ser Phe Ile Glu Thr Val Gly Ala Asn
    50                  55                  60

Leu Asn Lys Thr Ile Ile Met Gly Pro Gly Val Gln Gly Lys Val Ser
65                  70                  75                  80

Ile Arg Thr Met Thr Pro Leu Asn Glu Arg Gln Tyr Tyr Gln Leu Phe
                85                  90                  95

Leu Asn Leu Leu Glu Ala Gln Gly Tyr Ala Val Val Pro Met Glu Asn
            100                 105                 110

Asp Val Leu Lys Val Val Lys Ser Ser Ala Ala Lys Val Glu Pro Leu
        115                 120                 125

Pro Leu Val Gly Glu Gly Ser Asp Asn Tyr Ala Gly Asp Glu Met Val
    130                 135                 140

Thr Lys Val Val Pro Val Arg Asn Val Ser Val Arg Glu Leu Ala Pro
145                 150                 155                 160

Ile Leu Arg Gln Met Ile Asp Ser Ala Gly Ser Gly Asn Val Val Asn
                165                 170                 175

Tyr Asp Pro Ser Asn Val Ile Met Leu Thr Gly Arg Ala Ser Val Val
            180                 185                 190

Glu Arg Leu Thr Glu Val Ile Gln Arg Val Asp His Ala Gly Asn Arg
        195                 200                 205

Thr Glu Glu Val Ile Pro Leu Asp Asn Ala Ser Ala Ser Glu Ile Ala
    210                 215                 220

Arg Val Leu Glu Ser Leu Thr Lys Asn Ser Gly Glu Asn Gln Pro Ala
225                 230                 235                 240

Thr Leu Lys Ser Gln Ile Val Ala Asp Glu Arg Thr Asn Ser Val Ile
                245                 250                 255

Val Ser Gly Asp Pro Ala Thr Arg Asp Lys Met Arg Arg Leu Ile Arg
            260                 265                 270

Arg Leu Asp Ser Glu Met Glu Arg Ser Gly Asn Ser Gln Val Phe Tyr
        275                 280                 285
```

```
Leu Lys Tyr Ser Lys Ala Glu Asp Leu Val Asp Val Leu Lys Gln Val
290                 295                 300

Ser Gly Thr Leu Thr Ala Ala Lys Glu Glu Ala Glu Gly Thr Val Gly
305                 310                 315                 320

Ser Gly Arg Glu Ile Val Ser Ile Ala Ala Ser Lys His Ser Asn Ala
            325                 330                 335

Leu Ile Val Thr Ala Pro Gln Asp Ile Met Gln Ser Leu Gln Ser Val
        340                 345                 350

Ile Glu Gln Leu Asp Ile Arg Arg Ala Gln Val His Val Glu Ala Leu
    355                 360                 365

Ile Val Glu Val Ala Glu Gly Ser Asn Ile Asn Phe Gly Val Gln Trp
370                 375                 380

Ala Ser Lys Asp Ala Gly Leu Met Gln Phe Ala Asn Gly Thr Gln Ile
385                 390                 395                 400

Pro Ile Gly Thr Leu Gly Ala Ala Ile Ser Gln Ala Lys Pro Gln Lys
            405                 410                 415

Gly Ser Thr Val Ile Ser Glu Asn Gly Ala Thr Thr Ile Asn Pro Asp
        420                 425                 430

Thr Asn Gly Asp Leu Ser Thr Leu Ala Gln Leu Leu Ser Gly Phe Ser
    435                 440                 445

Gly Thr Ala Val Gly Val Val Lys Gly Asp Trp Met Ala Leu Val Gln
450                 455                 460

Ala Val Lys Asn Asp Ser Ser Asn Val Leu Ser Thr Pro Ser Ile
465                 470                 475                 480

Thr Thr Leu Asp Asn Gln Glu Ala Phe Phe Met Val Gly Gln Asp Val
            485                 490                 495

Pro Val Leu Thr Gly Ser Thr Val Gly Ser Asn Asn Ser Asn Pro Phe
        500                 505                 510

Asn Thr Val Glu Arg Lys Lys Val Gly Ile Met Leu Lys Val Thr Pro
    515                 520                 525

Gln Ile Asn Glu Gly Asn Ala Val Gln Met Val Ile Glu Gln Glu Val
530                 535                 540

Ser Lys Val Glu Gly Gln Thr Ser Leu Asp Val Val Phe Gly Glu Arg
545                 550                 555                 560

Lys Leu Lys Thr Thr Val Leu Ala Asn Asp Gly Glu Leu Ile Val Leu
            565                 570                 575

Gly Gly Leu Met Asp Asp Gln Ala Gly Glu Ser Val Ala Lys Val Pro
        580                 585                 590

Leu Leu Gly Asp Ile Pro Leu Ile Gly Asn Leu Phe Lys Ser Thr Ala
    595                 600                 605

Asp Lys Lys Glu Lys Arg Asn Leu Met Val Phe Ile Arg Pro Thr Ile
610                 615                 620

Leu Arg Asp Gly Met Ala Ala Asp Gly Val Ser Gln Arg Lys Tyr Asn
625                 630                 635                 640

Tyr Met Arg Ala Glu Gln Ile Tyr Arg Asp Glu Gln Gly Leu Ser Leu
            645                 650                 655

Met Pro His Thr Ala Gln Pro Val Leu Pro Ala Gln Asn Gln Ala Leu
        660                 665                 670

Pro Pro Glu Val Arg Ala Phe Leu Asn Ala Gly Arg Thr Arg
    675                 680                 685

<210> SEQ ID NO 38
<211> LENGTH: 678
<212> TYPE: PRT
```

<213> ORGANISM: Aeromonas hydrophila

<400> SEQUENCE: 38

```
Met Ile Asn Lys Gly Lys Gly Trp Arg Leu Ala Thr Val Ala Ala Ala
1               5                   10                  15

Leu Met Met Ala Gly Ser Ala Trp Ala Thr Glu Tyr Ser Ala Ser Phe
            20                  25                  30

Lys Asn Ala Asp Ile Glu Glu Phe Ile Asn Thr Val Gly Lys Asn Leu
        35                  40                  45

Ser Lys Thr Ile Ile Glu Pro Ser Val Arg Gly Lys Ile Asn Val
    50                  55                  60

Arg Ser Tyr Asp Leu Leu Asn Glu Glu Gln Tyr Tyr Gln Phe Phe Leu
65                  70                  75                  80

Ser Val Leu Asp Val Tyr Gly Phe Ala Val Pro Met Asp Asn Gly
                85                  90                  95

Val Leu Lys Val Val Arg Ser Lys Asp Ala Lys Thr Ser Ala Ile Pro
            100                 105                 110

Val Val Asp Glu Thr Asn Pro Gly Ile Gly Asp Glu Met Val Thr Arg
        115                 120                 125

Val Val Pro Val Arg Asn Val Ser Val Arg Glu Leu Ala Pro Leu Leu
    130                 135                 140

Arg Gln Leu Asn Asp Asn Ala Gly Gly Gly Asn Val Val His Tyr Asp
145                 150                 155                 160

Pro Ser Asn Val Leu Leu Ile Thr Gly Arg Ala Ala Val Val Asn Arg
                165                 170                 175

Leu Val Glu Val Val Arg Arg Val Asp Lys Ala Gly Asp Gln Glu Val
            180                 185                 190

Asp Ile Ile Lys Leu Lys Tyr Ala Ser Ala Gly Glu Met Val Arg Leu
        195                 200                 205

Val Thr Asn Leu Asn Lys Asp Gly Asn Ser Gln Gly Gly Asn Thr Ser
    210                 215                 220

Leu Leu Leu Ala Pro Lys Val Val Ala Asp Glu Arg Thr Asn Ser Val
225                 230                 235                 240

Val Val Ser Gly Glu Pro Lys Ala Arg Ala Arg Ile Ile Gln Met Val
                245                 250                 255

Arg Gln Leu Asp Arg Asp Leu Gln Ser Gln Gly Asn Thr Arg Val Phe
            260                 265                 270

Tyr Leu Lys Tyr Gly Lys Ala Lys Asp Met Val Glu Val Leu Lys Gly
        275                 280                 285

Val Ser Ser Ile Glu Ala Asp Lys Lys Gly Gly Thr Ala Thr
    290                 295                 300

Thr Ala Gly Gly Gly Ala Ser Ile Gly Gly Lys Leu Ala Ile Ser
305                 310                 315                 320

Ala Asp Glu Thr Thr Asn Ala Leu Val Ile Thr Ala Gln Pro Asp Val
                325                 330                 335

Met Ala Glu Leu Glu Gln Val Val Ala Lys Leu Asp Ile Arg Arg Ala
            340                 345                 350

Gln Val Leu Val Glu Ala Ile Ile Val Glu Ile Ala Asp Gly Asp Gly
        355                 360                 365

Leu Asn Leu Gly Val Gln Trp Ala Asn Thr Asn Gly Gly Thr Gln
    370                 375                 380

Phe Thr Asn Ala Gly Pro Gly Ile Gly Ser Val Ala Ile Ala Ala Lys
385                 390                 395                 400
```

```
Asp Tyr Lys Asp Asn Gly Thr Thr Gly Leu Ala Lys Leu Ala Glu
            405                 410                 415

Asn Phe Asn Gly Met Ala Ala Gly Phe Tyr Gln Gly Asn Trp Ala Met
        420                 425                 430

Leu Val Thr Ala Leu Ser Thr Asn Thr Lys Ser Asp Ile Leu Ser Thr
    435                 440                 445

Pro Ser Ile Val Thr Met Asp Asn Lys Glu Ala Ser Phe Asn Val Gly
450                 455                 460

Gln Glu Val Pro Val Gln Thr Gly Thr Gln Asn Ser Thr Ser Gly Asp
465                 470                 475                 480

Thr Thr Phe Ser Thr Ile Glu Arg Lys Thr Val Gly Thr Lys Leu Val
            485                 490                 495

Val Thr Pro Gln Ile Asn Glu Gly Asp Ser Val Leu Leu Thr Ile Glu
        500                 505                 510

Gln Glu Val Ser Ser Val Gly Lys Gln Ala Thr Gly Thr Asp Gly Leu
    515                 520                 525

Gly Pro Thr Phe Asp Thr Arg Thr Val Lys Asn Ala Val Leu Val Lys
530                 535                 540

Ser Gly Glu Thr Val Val Leu Gly Gly Leu Met Asp Glu Gln Thr Lys
545                 550                 555                 560

Glu Glu Val Ser Lys Val Pro Leu Leu Gly Asp Ile Pro Val Leu Gly
            565                 570                 575

Tyr Leu Phe Arg Ser Thr Ser Asn Asn Thr Ser Lys Arg Asn Leu Met
        580                 585                 590

Val Phe Ile Arg Pro Thr Ile Leu Arg Asp Ala Asn Val Tyr Ser Gly
    595                 600                 605

Ile Ser Ser Asn Lys Tyr Thr Leu Phe Arg Ala Gln Gln Leu Asp Ala
610                 615                 620

Val Ala Gln Glu Gly Tyr Ala Thr Ser Pro Asp Arg Gln Val Leu Pro
625                 630                 635                 640

Glu Tyr Gly Gln Asp Val Thr Met Ser Pro Glu Ala Lys Gln Ile
            645                 650                 655

Glu Leu Met Lys Thr His Gln Gln Ala Thr Ala Asp Gly Val Gln Pro
        660                 665                 670

Phe Val Gln Gly Asn Lys
        675

<210> SEQ ID NO 39
<211> LENGTH: 658
<212> TYPE: PRT
<213> ORGANISM: Pseudomonas aeruginosa

<400> SEQUENCE: 39

Met Ser Gln Pro Leu Leu Arg Ala Leu Phe Ala Pro Ser Ser Arg Ser
1               5                   10                  15

Tyr Val Pro Ala Val Leu Leu Ser Leu Ala Leu Gly Ile Gln Ala Ala
            20                  25                  30

His Ala Glu Asn Ser Gly Gly Asn Ala Phe Val Pro Ala Gly Asn Gln
        35                  40                  45

Gln Glu Ala His Trp Thr Ile Asn Leu Lys Asp Ala Asp Ile Arg Glu
    50                  55                  60

Phe Ile Asp Gln Ile Ser Glu Ile Thr Gly Glu Thr Phe Val Val Asp
65                  70                  75                  80

Pro Arg Val Lys Gly Gln Val Ser Val Val Ser Lys Ala Gln Leu Ser
            85                  90                  95
```

```
Leu Ser Glu Val Tyr Gln Leu Phe Leu Ser Val Met Ser Thr His Gly
            100                 105                 110

Phe Thr Val Val Ala Gln Gly Asp Gln Ala Arg Ile Val Pro Asn Ala
        115                 120                 125

Glu Ala Lys Thr Glu Ala Gly Gly Gln Ser Ala Pro Asp Arg Leu
    130                 135                 140

Glu Thr Arg Val Ile Gln Val Gln Gln Ser Pro Val Ser Glu Leu Ile
145                 150                 155                 160

Pro Leu Ile Arg Pro Leu Val Pro Gln Tyr Gly His Leu Ala Ala Val
                165                 170                 175

Pro Ser Ala Asn Ala Leu Ile Ile Ser Asp Arg Ser Ala Asn Ile Ala
            180                 185                 190

Arg Ile Glu Asp Val Ile Arg Gln Leu Asp Gln Lys Gly Ser His Asp
        195                 200                 205

Tyr Ser Val Ile Asn Leu Arg Tyr Gly Trp Val Met Asp Ala Ala Glu
    210                 215                 220

Val Leu Asn Asn Ala Met Ser Arg Gly Gln Ala Lys Gly Ala Ala Gly
225                 230                 235                 240

Ala Gln Val Ile Ala Asp Ala Arg Thr Asn Arg Leu Ile Ile Leu Gly
                245                 250                 255

Pro Pro Gln Ala Arg Ala Lys Leu Val Gln Leu Ala Gln Ser Leu Asp
            260                 265                 270

Thr Pro Thr Ala Arg Ser Ala Asn Thr Arg Val Ile Arg Leu Arg His
        275                 280                 285

Asn Asp Ala Lys Thr Leu Ala Glu Thr Leu Gly Gln Ile Ser Glu Gly
    290                 295                 300

Met Lys Asn Asn Gly Gly Gln Gly Gly Glu Gln Thr Gly Gly Gly Arg
305                 310                 315                 320

Pro Ser Asn Ile Leu Ile Arg Ala Asp Glu Ser Thr Asn Ala Leu Val
                325                 330                 335

Leu Leu Ala Asp Pro Asp Thr Val Asn Ala Leu Glu Asp Ile Val Arg
            340                 345                 350

Gln Leu Asp Val Pro Arg Ala Gln Val Leu Val Glu Ala Ala Ile Val
        355                 360                 365

Glu Ile Ser Gly Asp Ile Gln Asp Ala Val Gly Val Gln Trp Ala Ile
    370                 375                 380

Asn Lys Gly Gly Met Gly Gly Thr Lys Thr Asn Phe Ala Asn Thr Gly
385                 390                 395                 400

Leu Ser Ile Gly Thr Leu Leu Gln Ser Leu Glu Ser Asn Lys Ala Pro
                405                 410                 415

Glu Ser Ile Pro Asp Gly Ala Ile Val Gly Ile Gly Ser Ser Ser Phe
            420                 425                 430

Gly Ala Leu Val Thr Ala Leu Ser Ala Asn Thr Lys Ser Asn Leu Leu
        435                 440                 445

Ser Thr Pro Ser Leu Leu Thr Leu Asp Asn Gln Lys Ala Glu Ile Leu
    450                 455                 460

Val Gly Gln Asn Val Pro Phe Gln Thr Gly Ser Tyr Thr Thr Asn Ser
465                 470                 475                 480

Glu Gly Ser Ser Asn Pro Phe Thr Thr Val Glu Arg Lys Asp Ile Gly
                485                 490                 495

Val Ser Leu Lys Val Thr Pro His Ile Asn Asp Gly Ala Ala Leu Arg
            500                 505                 510
```

```
Leu Glu Ile Glu Gln Glu Ile Ser Ala Leu Pro Asn Ala Gln Gln
    515                 520                 525

Arg Asn Asn Thr Asp Leu Ile Thr Ser Lys Arg Ser Ile Lys Ser Thr
    530                 535                 540

Ile Leu Ala Glu Asn Gly Gln Val Ile Val Gly Gly Leu Ile Gln
545                 550                 555                 560

Asp Asp Val Ser Gln Ala Glu Ser Lys Val Pro Leu Leu Gly Asp Ile
                565                 570                 575

Pro Leu Leu Gly Arg Leu Phe Arg Ser Thr Lys Asp Thr His Thr Lys
                580                 585                 590

Arg Asn Leu Met Val Phe Leu Arg Pro Thr Val Val Arg Asp Ser Ala
    595                 600                 605

Gly Leu Ala Ala Leu Ser Gly Lys Lys Tyr Ser Asp Ile Arg Val Ile
    610                 615                 620

Asp Gly Thr Arg Gly Pro Glu Gly Arg Pro Ser Ile Leu Pro Thr Asn
625                 630                 635                 640

Ala Asn Gln Leu Phe Asp Gly Gln Ala Val Asp Leu Arg Glu Leu Met
                645                 650                 655

Thr Glu

<210> SEQ ID NO 40
<211> LENGTH: 638
<212> TYPE: PRT
<213> ORGANISM: Klebsiella oxytoca

<400> SEQUENCE: 40

Met Lys Lys Phe Pro Trp Ala Cys Val Ala Leu Thr Ala Leu Ser Leu
1               5                   10                  15

Tyr Ala Ser Ser Leu Leu Ala Ala Asn Phe Ser Ala Ser Phe Lys Asn
                20                  25                  30

Thr Asp Ile Arg Glu Phe Ile Asp Thr Val Gly Arg Asn Leu Asn Lys
            35                  40                  45

Thr Ile Leu Val Asp Pro Ser Val Gln Gly Thr Val Ser Val Arg Thr
50                  55                  60

Tyr Asn Val Leu Thr Glu Asp Glu Tyr Tyr Gln Phe Phe Leu Ser Val
65                  70                  75                  80

Leu Asp Leu Tyr Gly Leu Ser Val Ile Pro Met Asp Asn Gly Met Val
                85                  90                  95

Lys Val Val Arg Ser Ser Val Ala Arg Thr Ala Gly Ala Pro Leu Ala
                100                 105                 110

Asp Ser Lys Asn Pro Gly Lys Gly Asp Glu Ile Ile Thr Arg Val Val
            115                 120                 125

Arg Met Glu Asn Val Pro Val Arg Glu Leu Ala Pro Leu Leu Arg Gln
130                 135                 140

Leu Asn Asp Ala Thr Gly Ile Gly Asn Val Val His Phe Glu Pro Ser
145                 150                 155                 160

Asn Val Leu Leu Leu Thr Gly Lys Ala Ser Val Val Asn Arg Leu Val
                165                 170                 175

Asp Leu Val Gln Arg Val Asp Lys Asp Gly Ile Gln Arg Arg Glu Ile
            180                 185                 190

Ile Pro Leu Arg Phe Ala Ser Ala Lys Glu Leu Ser Asp Met Leu Asn
            195                 200                 205

Asn Leu Asn Asn Glu Glu Gln Lys Gly Gln Asn Ala Pro Gln Leu Ala
    210                 215                 220
```

```
Thr Lys Val Val Ala Asp Asp Glu Thr Asn Ser Leu Val Ile Ser Gly
225                 230                 235                 240

Ser Glu Asp Ala Arg Ala Arg Thr Arg Ser Leu Ile His Gln Leu Asp
            245                 250                 255

Arg Glu Gln Asn Asn Glu Gly Asn Thr Arg Val Phe Tyr Leu Lys Tyr
        260                 265                 270

Ala Ser Ala Thr Lys Val Val Pro Val Leu Thr Gly Ile Gly Glu Gln
    275                 280                 285

Leu Lys Asp Lys Pro Gly Ala Lys Ala Lys Thr Ala Ser Ala Ser
290                 295                 300

Thr Asp Leu Asn Ile Thr Ala Asp Ser Thr Asn Ser Leu Val Ile
305                 310                 315                 320

Thr Ala Gln Pro Asn Val Met Asn Ser Leu Glu Lys Val Ile Asp Lys
            325                 330                 335

Leu Asp Ile Arg Arg Pro Gln Val Leu Val Glu Ala Ile Ile Ala Glu
            340                 345                 350

Val Gln Asp Gly Asn Gly Leu Asp Leu Gly Val Gln Trp Thr Ser Lys
    355                 360                 365

His Gly Gly Val Gln Phe Gly Ala Thr Gly Leu Pro Ile Ser Gln Ile
370                 375                 380

Lys Asn Gly Thr Met Lys Gly Ala Ser Phe Thr Gly Leu Ala Thr Gly
385                 390                 395                 400

Phe Phe Asn Gly Asp Phe Gly Ala Leu Val Thr Ala Leu Ser Thr Asp
            405                 410                 415

Gly Lys Asn Asp Ile Leu Ser Thr Pro Ser Val Val Thr Leu Asp Asn
        420                 425                 430

Lys Glu Ala Ser Phe Asn Val Gly Gln Asp Val Pro Val Leu Ser Gly
        435                 440                 445

Ser Gln Thr Thr Ser Gly Asp Asn Val Phe Asn Ser Val Glu Arg Lys
    450                 455                 460

Thr Val Gly Thr Lys Leu Lys Ile Val Pro Gln Ile Asn Asp Gly Asp
465                 470                 475                 480

Met Ile His Leu Lys Ile Glu Gln Glu Val Ser Ser Val Asp Asn Ser
            485                 490                 495

Ala Thr Glu Asp Ser Ser Leu Gly Pro Thr Phe Asn Thr Arg Thr Ile
        500                 505                 510

Asn Asn Glu Val Met Val His Ser Gly Gln Thr Val Val Leu Gly Gly
        515                 520                 525

Leu Met Glu Asn Val Thr Lys Gln Ser Val Ser Lys Val Pro Leu Leu
530                 535                 540

Gly Asp Ile Pro Leu Val Gly Gln Leu Phe Arg Tyr Thr Ser Gln Asp
545                 550                 555                 560

Thr Ser Lys Arg Asn Leu Met Val Phe Ile His Thr Thr Val Leu Arg
            565                 570                 575

Asp Asp Asp Asn Tyr Ser Ala Ala Ser Lys Glu Lys Tyr Asp Gln Ile
            580                 585                 590

Arg Val Arg Gln Met Gln Arg Val Glu Glu Lys Lys Leu Gly Ile Val
    595                 600                 605

Glu Pro Ser Asp Asn Ala Val Leu Pro Ala Phe Pro Ala Ala Ser Thr
    610                 615                 620

Ala Pro Val Lys Thr His Ala Ala Arg Asn Pro Phe Lys Glu
625                 630                 635
```